United States Patent
Kuo et al.

(10) Patent No.: US 10,308,596 B2
(45) Date of Patent: Jun. 4, 2019

(54) HDAC8 INHIBITORS FOR TREATING CANCER

(71) Applicants: City of Hope, Duarte, CA (US); Taipei Medical University, Taipei (TW); Academia Sinica, Taipei (TW)

(72) Inventors: Ya-Huei Kuo, Duarte, CA (US); Wei-Jan Huang, Taipei (TW); Chung-I Chang, Taipei (TW)

(73) Assignees: CITY OF HOPE, Duarte, CA (US); TAIPEI MEDICAL UNIVERSITY, Taipei (TW); ACADEMIA SINICA, Taipei (TW)

(*) Notice: Subject to any disclaimer, the term of this patent is extended or adjusted under 35 U.S.C. 154(b) by 26 days.

(21) Appl. No.: 15/042,012

(22) Filed: Feb. 11, 2016

(65) Prior Publication Data

US 2016/0237027 A1 Aug. 18, 2016
US 2017/0050922 A2 Feb. 23, 2017

Related U.S. Application Data

(63) Continuation of application No. PCT/US2014/051876, filed on Aug. 20, 2014.

(60) Provisional application No. 61/868,073, filed on Aug. 20, 2013.

(51) Int. Cl.

| | |
|---|---|
| C07C 259/06 | (2006.01) |
| C07D 213/56 | (2006.01) |
| C07D 307/91 | (2006.01) |
| C07D 209/08 | (2006.01) |
| C07D 209/18 | (2006.01) |
| C07D 213/74 | (2006.01) |
| C07D 215/14 | (2006.01) |
| C07D 217/16 | (2006.01) |
| C07D 217/20 | (2006.01) |
| C07D 317/60 | (2006.01) |
| C07D 333/24 | (2006.01) |

(52) U.S. Cl.
CPC .......... *C07C 259/06* (2013.01); *C07D 209/08* (2013.01); *C07D 209/18* (2013.01); *C07D 213/56* (2013.01); *C07D 213/74* (2013.01); *C07D 215/14* (2013.01); *C07D 217/16* (2013.01); *C07D 217/20* (2013.01); *C07D 307/91* (2013.01); *C07D 317/60* (2013.01); *C07D 333/24* (2013.01)

(58) Field of Classification Search
CPC ... C07C 259/06; C07C 209/08; C07C 209/18; C07C 213/56; C07C 213/74; C07C 215/14; C07C 217/16; C07C 217/20; C07C 307/91; C07C 317/60; C07D 333/24
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,028,629 A * | 7/1991 | Hite ...................... | C07C 259/06 514/575 |
| 5,212,162 A | 5/1993 | Missel et al. | |
| 5,403,841 A | 4/1995 | Lang et al. | |
| 2012/0322769 A1 | 12/2012 | Yang et al. | |

FOREIGN PATENT DOCUMENTS

| | | |
|---|---|---|
| WO | WO-01/42437 A2 | 6/2001 |
| WO | WO-01/42437 A3 | 6/2001 |
| WO | WO-2008/101186 A1 | 8/2008 |
| WO | WO-2013/101600 A1 | 7/2013 |

OTHER PUBLICATIONS

Adya, N. et al. (Dec. 1998). "The leukemic protein core binding factor beta (CBFbeta)-smooth-muscle myosin heavy chain sequesters CBFalpha2 into cytoskeletal filaments and aggregates," *Mol Cell Biol* 18(12):7432-7443.

Appelbaum, F.R., et al. (Oct. 2006). "The clinical spectrum of adult acute myeloid leukaemia associated with core binding factor translocations," *Br J Haematol* 135(2):165-173.

Balasubramanian, S.et al. (May 2008, e-published Feb. 7, 2008). "A novel histone deacetylase 8 (HDAC8)-specific inhibitor PCI-34051 induces apoptosis in T-cell lymphomas," *Leukemia* 22(5):1026-1034.

Ben-Ami, O., et al. (Sep. 26, 2013, e-published Sep. 19, 2013). "Addiction of t(8;21) and inv(16) acute myeloid leukemia to native RUNX1," *Cell Rep* 4(6):1131-1143.

Britos-Bray, M., et al. (Dec. 1998). "CBFbeta-SMMHC, expressed in M4eo acute myeloid leukemia, reduces p53 induction and slows apoptosis in hematopoietic cells exposed to DNA-damaging agents" *Blood* 92(11):4344-4352.

Buggy, J.J. et al. (Aug. 15, 2000). "Cloning and characterization of a novel human histone deacetylase, HDAC8," *Biochem J* 350 Pt 1:199-205.

Castilla, L.H. et al. (Nov. 15, 1996). "Failure of embryonic hematopoiesis and lethal hemorrhages in mouse embryos heterozygous for a knocked-in leukemia gene CBFB-MYH11," *Cell* 87(4):687-696.

Dai, C. et al. (Nov. 2010). "p53 post-translational modification: deregulated in tumorigenesis ," *Trends Mol Med* 16(11):528-536.

Deardorff, M.A., et al. (Sep. 13, 2012). "HDAC8 mutations in Cornelia de Lange syndrome affect the cohesin acetylation cycle," *Nature* 489(7415):313-317.

Durst, K.L. et al. (Jan. 2003). "The inv(16) fusion protein associates with corepressors via a smooth muscle myosin heavy-chain domain," *Mol Cell Biol* 23(2):607-619.

European Search Report dated Mar. 17, 2017, for EP Application No. 14837390.5, Aug. 20, 2014, 10 pages.

Galletti, P. et al. (Dec. 2009). "Azetidinones as zinc-binding groups to design selective HDAC8 inhibitors," *ChemMedChem* 4(12):1991-2001.

(Continued)

*Primary Examiner* — Sreenivasan Padmanabhan
*Assistant Examiner* — Jody L Karol
(74) *Attorney, Agent, or Firm* — Mintz; Irina Britva; Kenneth Jenkins

(57) ABSTRACT

Provided herein, inter alia, are compound and methods of treating cancer by inhibiting HDAC8.

9 Claims, 44 Drawing Sheets

Specification includes a Sequence Listing.

(56) References Cited

OTHER PUBLICATIONS

Goyama, S. et al. (Sep. 2013). "Transcription factor RUNX1 promotes survival of acute myeloid leukemia cells," *J Clin Invest* 123(9):3876-3888.

Grimwade, D. et al. (2009). "Independent prognostic factors for AML outcome," *Hematology Am Soc Hematol Educ Program* 385-395.

Grimwade, D. et al. (Jul. 22, 2010, e-published Apr. 12, 2010). "Refinement of cytogenetic classification in acute myeloid leukemia: determination of prognostic significance of rare recurring chromosomal abnormalities among 5876 younger adult patients treated in the United Kingdom Medical Research Council trials," *Blood* 116(3):354-365.

Haberland, M. et al. (Jul. 15, 2009). "Epigenetic control of skull morphogenesis by histone deacetylase 8," *Genes Dev* 23(14):1625-1630.

Haferlach, C. et al. (Aug. 2008). "Mutations of the TP53 gene in acute myeloid leukemia are strongly associated with a complex aberrant karyotype," *Leukemia* 22(8):1539-1541.

Hu, E. et al. (May 19, 2000). "Cloning and characterization of a novel human class I histone deacetylase that functions as a transcription repressor," *J Biol Chem* 275(20):15254-15264.

Hu, E. et al. (Nov. 2003, e-published Sep. 15, 2003). "Identification of novel isoform-selective inhibitors within class I histone deacetylases," *J Pharmacol Exp Ther* 307(2):720-728.

Huang, G. et al. (Feb. 15 2001). "Dimerization with PEBP2beta protects RUNX1/AML1 from ubiquitin-proteasome-mediated degradation," *Embo J* 20(4):723-733.

Huang, W.J. et al. (Oct. 2012, e-published Aug. 20, 2012). "Synthesis and biological evaluation of ortho-aryl N-hydroxycinnamides as potent histone deacetylase (HDAC) 8 isoform-selective inhibitors," *ChemMedChem* 7(10):1815-1824.

International Search Report dated Jan. 21, 2015, for PCT Application No. PCT/US2014/051876, filed Aug. 20, 2014, 5 pages.

Ito, A. et al. (Nov. 15, 2002). "MDM2-HDAC1-mediated deacetylation of p53 is required for its degradation," *EMBO J* 21(22):6236-6245.

Jeannet, R., et al. (Mar. 2013). "Alcam Regulates Long-term Hematopoietic Stem Cell Engraftment and Self-Renewal," *Stem Cells* 31(3): 26 pages.

Juan, L.J. et al. (Jul. 7, 2000). "Histone deacetylases specifically down-regulate p53-dependent gene activation," *J Biol Chem* 275(27):20436-20443.

Kamikubo, Y. et al. (May 18, 2010). "Accelerated leukemogenesis by truncated CBF beta-SMMHC defective in high-affinity binding with RUNX1," *Cancer Cell* 17(5):455-468.

Kanno, Y. et al. (Jul. 1998). "Cytoplasmic sequestration of the polyomavirus enhancer binding protein 2 (PEBP2)/core binding factor alpha (CBFalpha) subunit by the leukemia-related PEBP2/CBFbeta-SMMHC fusion protein inhibits PEBP2/CBF-mediated transactivation," *Mol Cell Biol* 18(7):4252-4261.

Khan, N. et al. (Jan. 15, 2008). "Determination of the class and isoform selectivity of small-molecule histone deacetylase inhibitors," *Biochem J* 409(2):581-589.

Kojima, K. et al. (Nov. 1, 2005). "MDM2 antagonists induce p53-dependent apoptosis in AML: implications for leukemia therapy," *Blood* 106(9):3150-3159.

Krennhrubec, K. et al. (May 15, 2007, e-published Feb. 25, 2007). "Design and evaluation of 'Linkerless' hydroxamic acids as selective HDAC8 inhibitors," *Bioorg Med Chem Lett* 17(10):2874-2878.

Kühn, R. et al. (Sep. 8, 1995). "Inducible gene targeting in mice," *Science* 269(5229):1427-1429.

Kuo, Y.-H. et al. (Jan. 2006). "Cbf beta-SMMHC induces distinct abnormal myeloid progenitors able to develop acute myeloid leukemia," *Cancer Cell* 9(1):57-68.

Kuo, Y.-H. et al. (Feb. 1, 2008). "Cbfbeta-SMMHC impairs differentiation of common lymphoid progenitors and reveals an essential role for RUNX in early B-cell development," *Blood* 111(3):1543-1551.

Kuo, Y.-H., et al. (Apr. 2, 2009, e-published Jan. 28, 2009). "Runx2 induces acute myeloid leukemia in cooperation with Cbfbeta-SMMHC in mice," *Blood* 113(14):3323-3332.

Kurosawa, S. et al. (Oct. 2013, e-published May 28, 2013). "Prognosis of patients with core binding factor acute myeloid leukemia after first relapse," *Haematologic* 98(10):1525-1531.

Lee, H., et al. (Jul. 2006). "Histone deacetylase 8 safeguards the human ever-shorter telomere 1B (hEST1B) protein from ubiquitin-mediated degradation," *Mol Cell Biol* 26(14):5259-5269.

Li, L. et al. (Feb. 14, 2012). "Activation of p53 by SIRT1 inhibition enhances elimination of CML leukemia stem cell in combination with imatinib," *Cancer Cell* 21(2):266-281.

Liu, P. et al. (Aug. 20, 1993), "Fusion between transcription factor CBF β/PEBP2β and a myosin heavy chain in acute myeloid leukemia," *Science* 261(5124):1041-1044.

Liu, P.P. et al. (May 1, 1995). "Molecular pathogenesis of the chromosome 16 inversion in the M4Eo subtype of acute myeloid leukemia," *Blood* 85(9):2289-2302.

Lo, H.-L. et al. (Nov. 2007, e-published Sep. 6, 2007). "Inhibition of HIV-1 replication with designed miRNAs expressed from RNA polymerase II promoters," *Gene Ther* 14(21)1 503-1512.

Long, J. et al. (Jul. 8, 2010, e-published Apr. 19, 2010). "Multiple distinct molecular mechanisms influence sensitivity and resistance to MDM2 inhibitors in adult acute myelogenous leukemia," Blood 116(1):71-80.

Look, A.T. (Nov. 7, 1997). "Oncogenic transcription factors in the human acute leukemias," *Science* 278(5340):1059-1064.

Lukasik, S.M. et al. (Sep. 2002). "Altered affinity of CBFβ-SMMHC for Runx1 explains its role in leukemogenesis," *Nat Struct Biol* 9(9):674-679.

Luo, J. et al. (Nov. 16, 2000). "Deacetylation of p53 modulates its effect on cell growth and apoptosis," *Nature* 408(6810):377-381.

Luo, J. et al. (Oct. 19, 2001). "Negative control of p53 by Sir2alpha promotes cell survival under stress," *Cell* 107(2):137-148.

Lutterbach, B. et al. (Oct. 26, 1999). "The inv(16) encodes an acute myeloid leukemia 1 transcriptional corepressor," *Proc Natl Acad Sci U S A* 96(22):12822-12827.

Mandoli, A. et al. (Apr. 2014, e-published Sep. 4, 2013). "CBFB-MYH11/RUNX1 together with a compendium of hematopoietic regulators, chromatin modifiers and basal transcription factors occupies self-renewal genes in inv(16) acute myeloid leukemia," 28(4):77-778.

Moreno, D.A. et al. (Sep. 2010). "Differential expression of HDAC3, HDAC7 and HDAC9 is associated with prognosis and survival in childhood acute lymphoblastic leukaemia," *Br J Haematol* 150(6):665-673.

Mrózek, K. et al. (Jun. 2004). Cytogenetics in acute leukemia, *Blood Rev* 18(2):115-136.

Mrózek, K. et al. (Dec. 20, 2012). "Prognostic significance of the European LeukemiaNet standardized system for reporting cytogenetic and molecular alterations in adults with acute myeloid leukemia," *J Clin Oncol* 30(36):4515-4523.

Nahi, H et al. (Mar. 2008). "Chromosomal aberrations in 17p predict in vitro drug resistance and short overall survival in acute myeloid leukemia," *Leuk Lymphoma* 49(3):508-516.

Oehme, I. et al. (Jan. 1, 2009). "Histone deacetylase 8 in neuroblastoma tumorigenesis," *Clin Cancer Res* 15(1):91-99.

Oehme, I. et al. (Nov. 2009). "Targeting of HDAC8 and investigational inhibitors in neuroblastoma," *Expert Opin Investig Drugs* 18(11)1605-1617.

Ogawa, E. et al. (May 1993). "Molecular cloning and characterization of PEBP2 beta, the heterodimeric partner of a novel *Drosophila* runt-related DNA binding protein PEBP2 alpha," *Virology* 194(1):314-331.

Okuda, T. et al. (Jan. 26, 1996). "AML1, the target of multiple chromosomal translocations in human leukemia, is essential for normal fetal liver hematopoiesis," *Cell* 84(2):321-330.

Prébet, T. et al. (Oct. 1, 2009, e-published Aug. 31, 2009). "Acute myeloid leukemia with translocation (8;21) or inversion (16) in elderly patients treated with conventional chemotherapy: a collaborative study of the French CBF-AML intergroup," *J Clin Oncol* 27(28):4747-4753.

(56) References Cited

OTHER PUBLICATIONS

PUBCHEM CID 11687004, create date: Oct. 26, 2006, located at <https://pubchem.ncbi.nlm.nih.gov/compound/11687004> last visited Jun. 20, 2017, 13 pages.

Rücker, F.G. et al. (Mar. 1, 2012, e-published Dec. 20, 2011). "TP53 alterations in acute myeloid leukemia with complex karyotype correlate with specific copy number alterations, monosomal karyotype, and dismal outcome," *Blood* 119(9):2114-2121.

Speck, N.A. (Jul. 2002). "Core-binding factors in haematopoiesis and leukaemia," *Nat Rev Cancer* 2(7):502-513.

Suzuki, T. et al. (Mar. 2014, e-published Jan. 8, 2014). "Design, synthesis, and biological activity of NCC149 derivatives as histone deacetylase 8-selective inhibitors," *ChemMedChem* 9(3):657-664.

Tang, W. et al. (May 2011, e-published Feb. 2, 2011). "Discovery of histone deacetylase 8 selective inhibitors," *Bioorg Med Chem Lett* 21(9):2601-2605.

Van Den Wyngaert, I., et al. (Jul. 28, 2000). "Cloning and characterization of human histone deacetylase 8," *FEBS Lett* 478(1-2):77-83.

Von Neuhoff, C., et al. (Jun. 1, 2010). "Prognostic impact of specific chromosomal aberrations in a large group of pediatric patients with acute myeloid leukemia treated uniformly according to trial AML-BFM 98," *J Clin Oncol* 28(16):2682-2689.

Waltregny, D., et al. (Jun. 19, 2005). "Histone deacetylase HDAC8 associates with.smooth muscle α-actin and is essential for smooth muscle cell contractility," *FASEB J* 19(8):966-968.

Wang, S. et al. (Jun. 1993). "Cloning and characterization of subunits of the T-cell receptor and murine leukemia virus enhancer core-binding factor," *Mol Cell Biol* 13(6):3324-3339.

Wang, Q., et al. (Nov. 15, 1996). "The CBFbeta subunit is essential for CBFalpha2 (AML1) function in vivo," *Cell* 87(4):697-708.

Whitehead, L. et al. (Aug. 1, 2011, e-published Jun. 15, 2011). "Human HDAC isoform selectivity achieved via exploitation of the acetate release channel with structurally unique small molecule inhibitors," *Bioorg Med Chem* 19(15):4626-4634.

Written Opinion dated Jan. 21, 2015, for PCT Application No. PCT/US2014/051876, filed Aug. 20, 2014, 5 pages.

Yan, W. et al. (Jan. 31, 2013, e-published Mar. 5, 2012). "Histone deacetylase inhibitors suppress mutant p53 transcription via histone deacetylase 8," *Oncogene* 32(5):599-609.

Zhao, L., et al. (Apr. 15, 2007, e-published Dec. 21, 2006). "CBFB-MYH11 hinders early T-cell development and induces massive cell death in the thymus," *Blood* 109(8):3432-3440.

Zhao, Z., et al. (Jul. 1, 2010). "p53 loss promotes acute myeloid leukemia by enabling aberrant self-renewal," *Genes Dev* 24(13):1389-1402.

\* cited by examiner

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
gcggctgttt ttcttggtag                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
agacgaggaa agcagttcca                                               20

<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3
ttagtggctg taagtcagca aga                                           23

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
ccttcagatc actcccacct                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 5
gtgagcggct gcttgtct                                                 18

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic polynucleotide

<400> SEQUENCE: 6
ggtcccgaag taggagagga                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 7
gacagctagc cgcacagtt                                                19

<210> SEQ ID NO 8
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 8
ggccaggcag ttcctttt                                                 18

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 9
ttctccggag tgttcatgc                                                19

<210> SEQ ID NO 10
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 10
tacagcggag ggcatcag                                                 18

<210> SEQ ID NO 11
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 11
tcctcctcag accgctttt                                                19

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 12
cctggttcat catcgctaat c                                             21
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
ggtgacgtgt ctgatgttgg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
gacacttgcc aattcccact                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
tacccttgtg cctcgctcag                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 16
cggcgtttgg agtggtaga                                               19

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
ccttcgtgag aattggcttc                                              20

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 18
caacacatga ctctctggaa tca                                          23

<210> SEQ ID NO 19
<211> LENGTH: 21
<212> TYPE: DNA
<213> ORGANISM: Artificial Sequence
<220> FEATURE:
<223> OTHER INFORMATION: Synthetic polynucleotide
```

```
<400> SEQUENCE: 19
ctctcctgcg aagagcgaaa c                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 20
cctcgttgct tttctgctca a                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 21
gacctcaacg cacagtacga g                                              21

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 22
aggagtccca tgatgagatt gt                                             22

<210> SEQ ID NO 23
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 23
gtggatcagc aagcaggag                                                 19

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
tttgtcaaga aagggtgtaa cg                                             22
```

HDAC8 INHIBITORS FOR TREATING CANCER

CROSS-REFERENCES TO RELATED APPLICATIONS

This application is a continuation of International Application No. PCT/US2014/051876, filed Aug. 20, 2014, which claims the benefit of U.S. Provisional Application No. 61/868,073, filed Aug. 20, 2013. The disclosure of each of the prior applications is considered part of and is incorporated by reference in the disclosure of this application

STATEMENT AS TO RIGHTS TO INVENTIONS MADE UNDER FEDERALLY SPONSORED RESEARCH AND DEVELOPMENT

This invention was made with Government support under grant number P30 CA033572 awarded by the National Cancer Institute. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48440_535N01US_ST25.TXT, created Apr. 28, 2016, 5.160 bytes, machine format IBM-PC, MS-Windows operating system, is hereby incorporated by reference.

BACKGROUND OF THE INVENTION

Histone deacetylases (HDACs) play a role in the reversible acetylation of histones, transcription factors, and other proteins, which are associated with chromatin remodeling and regulation of gene expression. Acute myeloid leukemia (AML) arises, in part, from disordered hematopoiesis as a consequence of multiple cooperative mutations or alternations disrupting differentiation, proliferation and survival programs in hematopoietic progenitors. Recurrent chromosomal abnormalities in AML frequently involve transcription factor fusion proteins that contribute to unique etiology and prognosis (1). Chromosomal 16 inversion, inv(16) (p13.1q22) or t(16;16)(p13.1;q22) is found in approximately 5-12% of AML patients and is associated with dismal prognosis. Accordingly, new treatments for AML patients are necessary. Provided herein are solutions to these and other problems in the art.

BRIEF SUMMARY OF THE INVENTION

It has been discovered herein, inter alia, that HDAC8 activity is linked to cancer. Thus, provided herein are compounds and methods for treating cancer with HDAC8 inhibitors. In a first aspect is a compound having the formula:

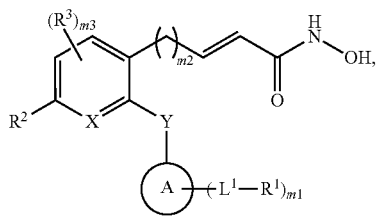

A is cycloalkyl, heterocycloalkyl, aryl, or heteroaryl. X is —C($R^4$)= or —N=. Y is a bond, —N($R^5$)—, —O—, or —S—. $L^1$ is a bond, —C(O)—, —C(O)O—, —O—, —S—, —N($R^6$)—, —C(O)N($R^6$)—, —S(O)$_{n6}$—, —S(O)N($R^6$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is halogen, —$N_3$, —$CF_3$, —$CCl_3$, —$CBr_3$, —$CI_3$, —CN, —$OR^{1A}$, —C(O)$R^{1A}$, —$NR^{1A}R^{1B}$, —C(O)$OR^{1A}$, —C(O)$NR^{1A}R^{1B}$, —$NO_2$, —$SR^{1A}$, —S(O)$_{n1}R^{1A}$, —S(O)$_{n1}OR^{1A}$, —S(O)$_{n1}NR^{1A}R^{1B}$, —$NHNR^{1A}R^{1B}$, —$ONR^{1A}R^{1B}$, —NHC(O)$NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is halogen, —$N_3$, —$CF_3$, —$CCl_3$, —$CBr_3$, —$CI_3$, —CN, —$OR^{2A}$, —C(O)$R^{2A}$, —$NR^{2A}R^{2B}$, —C(O)$OR^{2A}$, —C(O)$NR^{2A}R^{2B}$, —$NO_2$, —$SR^{2A}$, —S(O)$_{n2}R^{2A}$, —S(O)$_{n2}OR^{2A}$, —S(O)$_{n2}NR^{2A}R^{2B}$, —$NHNR^{2A}R^{2B}$, —$ONR^{2A}R^{2B}$, —NHC(O)$NHNR^{2A}R^{2B}$, substituted or unsubstituted $C_1$-$C_5$ alkyl, or substituted or unsubstituted 2 to 5 membered heteroalkyl. $R^3$ is independently halogen, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —S, —S(O)$_2$H, —$NHNH_2$, —$ONH_2$, —NHC(O)$NHNH_2$, substituted or unsubstituted $C_1$-$C_5$ alkyl, or substituted or unsubstituted 2 to 5 membered heteroalkyl. $R^4$ is hydrogen, halogen, —$N_3$, —$CF_3$, —$CCl_3$, —$CBr_3$, —$CI_3$, —CN, —$OR^{4A}$, —C(O)$R^{4A}$, —$NR^{4A}R^{4B}$, —C(O)$OR^{4A}$, —C(O)$NR^{4A}R^{4B}$, —$NO_2$, —$SR^{4A}$, —S(O)$_{n4}R^{4A}$, —S(O)$_{n4}OR^{4A}$, —S(O)$_{n4}NR^{4A}R^{4B}$, —$NHNR^{4A}R^{4B}$, —$ONR^{4A}R^{4B}$, —NHC(O)$NHNR^{4A}R^{4B}$, substituted or unsubstituted $C_1$-$C_5$ alkyl, or substituted or unsubstituted 2 to 5 membered heteroalkyl. $R^5$ is hydrogen, halogen, —$N_3$, —$CF_3$, —$CCl_3$, —$CBr_3$, —$CI_3$, —CN, —$OR^{5A}$, —C(O)$R^{5A}$, —$NR^{5A}R^{5B}$, —C(O)$OR^{5A}$, —C(O)$NR^{5A}R^{5B}$, —$NO_2$, —$SR^{5A}$, —S(O)$_{n5}R^{5A}$, —S(O)$_{n5}OR^{5A}$, —S(O)$_{n5}NR^{5A}R^{5B}$, —$NHNR^{5A}R^{5B}$, —$ONR^{5A}R^{5B}$, —NHC(O)$NHNR^{5A}R^{5B}$, substituted or unsubstituted $C_1$-$C_5$ alkyl, or substituted or unsubstituted 2 to 5 membered heteroalkyl. $R^6$ is hydrogen, halogen, —$N_3$, —$CF_3$, —$CCl_3$, —$CBr_3$, —$CI_3$, —CN, —$OR^{6A}$, —C(O)$R^{6A}$, —$NR^{6A}R^{6B}$, —C(O)$OR^{6A}$, —C(O)$NR^{6A}R^{6B}$, —$NO_2$, —$SR^{6A}$, —S(O)$_{n6}R^{6A}$, —S(O)$_{n6}OR^{6A}$, —S(O)$_{n6}NR^{6A}R^{6B}$, —$NHNR^{6A}R^{6B}$, —$ONR^{6A}R^{6B}$, —NHC(O)$NHNR^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{2A}$, $R^{2B}$, $R^{4A}$, $R^{4B}$, $R^{5A}$, $R^{5B}$, $R^{6A}$, and $R^{6B}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n4, n5, and n6 are independently 1, 2, or 3. The symbol m1 is 0, 1, 2, 3, or 4. The symbol m2 is 0, 1, 2, 3, 4, 5, or 6. The symbol m3 is 0, 1, or 2.

Also provided herein are methods of treating cancer. In one aspect is a method of treating cancer in a subject in need thereof by administering an effective amount of an HDAC8 inhibitor to said subject.

Further provided herein are methods of inhibiting HDAC8 mediated deacetylation of p53. In one aspect is a method of inhibiting HDAC8 mediated deacetylation of p53 by contacting HDAC8 with a HDAC8 inhibitor in the presence of p53, thereby inhibiting HDAC8 deacetylation of p53.

BRIEF DESCRIPTION OF THE DRAWINGS

FIG. 1A: Relative expression of p53 target genes including (in order left to right, top to bottom) p21, Mdm2, Bax, Bid, Puma, Gadd45b, LincRNA-p21 and Stag1 in 32D-CM or 32D-CBFβ cells, determined by qRT-PCR. Shown are fold induction 24 h after 3 Gy IR relative to non-IR (mean+/−SD) performed in replicate and three independent experiments. FIG. 1B: Western blot analysis of Ac-p53, p53, CM, CBFβ and HDAC8 at indicated time points (2, 4, 6 and 12 h) after IR in 32D-CM or 32D-CBFβ cells. β-actin served as loading control. FIG. 1C: Western blot time course analysis (2, 4, 6 and 12 h) of Ac-p53, p53, CM, CBFβ after IR in BM progenitor cells isolated from CM-expressing pre-leukemic or control mice. β-actin served as loading control. FIG. 1D: Western blot of Ac-p53, p53, CM, CBFβ in Cbfb$^{56M/+}$ BM progenitor cells transduced with MIG-Cre and IR (3 Gy, 6 h). β-actin served as loading control. FIG. 1E: Western blot of Ac-p53, p53, CM, CBFβ in 32D-CM cells expressing control (Ctrl)-shRNA or CM shRNA (A3, D4) 6 h after 3 Gy IR. β-actin served as loading control. FIG. 1F: Western blot of CM and β-actin in sorted leukemic BM cells transduced with non-silencing ctrl-shRNA or CM shRNA (A3, D4). FIG. 1G: Histogram depicting relative expression of p53 target genes including (in order left to right) p21, Gadd45b, LincRNA-p21 Bax, Puma, and Bid in sorted leukemic BM cells transduced with non-silencing ctrl-shRNA or CM shRNA (A3, D4). Shown are fold change (mean+/−SD) relative to ctrl-shRNA expressing cells, performed in triplicate. Ordering (left to right for p53 target): ctrl, A3, A4.

FIG. 2A: Co-IP and immunoblot (IB) analysis in 32D-CM (top) or 32D-CBFβ (bottom) cells using anti-p53 or anti-mouse IgG for IP, and anti-p53 (left) or anti-CBFβ (right) for IB. Shown are representative of more than three independent experiments. FIG. 2B: Co-IP (anti-FLAG) and IB (anti-p53) analysis in 32D-Flag, 32D-CBFβ or 32D-CM cells. Input of CBFβ or CM are shown using anti-FLAG (IP, IB). FIG. 2C: Co-IP and IB analysis in control BM progenitor cells (lane 1 from left), CM-expressing pre-leukemic or leukemic BM cells without IR (left) or pre-leukemic BM cells after IR (right). IP was performed with anti-CBFβ and IB was performed with anti-p53 (top) or anti-CBFβ (middle). Bottom panel shows western blot using anti-p53. FIG. 2D: Co-IP (anti-FLAG) and IB (anti-p53) analysis in nuclear and cytoplasmic fractions prepared from the indicated cell lines. Western blot analyses for CM, p53, and Histone H3 for each fraction are shown. FIG. 2E: DUOLINK® in situ proximity ligation assay (PLA) using mouse anti-CBFβ antibody plus rabbit anti-p53 antibody and PLA probes. Punctuate red fluorescent spots indicate intermolecular protein interactions (left). DAPI-stained nuclei are shown in blue (center) and GFP reporter indicates transduced cells (right). Shown are representative images. FIG. 2F. Co-IP and IB in inv(16)$^+$ AML (163, 987) or non-inv(16) AML (467, 865) CD34$^+$ cells 3 h after IR. Co-IP was performed using anti-p53 (DO-1) or anti-mouse IgG, and IB was performed with anti-CBF β (top) or anti-p53 antibodies (bottom).

FIG. 3A: Sequential co-IP and IB analysis in 32D-CBFβ or 32D-CM cells using anti-HDAC8 for the primary IP, followed by IP using anti-CBFβ, and IB with anti-p53. Cells were either not IR (left panel) or received 3 Gy IR (right panel). FIG. 3B: Sequential co-IP and IB analysis in 32D-CBFβ or 32D-CM cells using anti-p53 for the primary IP, followed by IP using anti-CBFβ, and IB with anti-HDAC8. FIG. 3C: Illustration of CM deletion variants (left) used in Co-IP (anti-p53) and IB (anti-CBFβ or anti-p53) analysis (right). Arrows correspond to the expected size of CM variants. FIG. 3D: DUOLINK® in situ PLA in 32D cells expressing FL-CM or deletion mutants d134, d179 or DC95 using mouse anti-CBFβ plus rabbit anti-p53 and PLA probes. Red fluorescent spots indicate CM-p53 protein interactions (top), DAPI staining is in blue (center) and GFP reporter indicates transduced cells (bottom). Shown are representative images. FIG. 3E: Western blotting of Hdac8 in 32D-CM cells expressing non-silencing control shRNA or Hdac8-shRNA (sh1 or sh2) (left). Co-IP (IgG or anti-p53) and IB (anti-CBFβ or anti-p53) analysis in shRNA (control, sh1 or sh2) expressing cells (right). FIG. 3F: In situ PLA in 32D-CM cells expressing control shRNA or Hdac8-shRNA (sh1 or sh2) using mouse anti-CBFβ plus rabbit anti-p53 and PLA probes. Spots indicate CM-p53 protein interactions (left), DAPI staining (center) and GFP reporter indicates transduced cells (right). Representative images are shown.

FIG. 4A: Western blotting of Hdac8, Ac-p53 (K379), and total p53 levels after shRNA-mediated knock-down in 32D-CM cells in response to IR (3 Gy). Levels of β-actin were detected as loading control. FIG. 4B: Western blotting of Ac-p53 (K379), p53 and Hdac8 in 32D-CM cells treated with HDAC8 inhibitor PCI-34051, 22d or Nutlin-3 at doses indicated for 6 h. FIG. 4C: Western blotting of Ac-p53 (K379), p53 in CM, ΔC95 compared to CBFβ or FLAG expressing 32D cells at 2 h or 4 h after IR (3 Gy). FIG. 4D: Fold induction of p53 target genes including p21, Mdm2, Bax, Bid, Puma, Gadd45b, LincRNA-p21 and Stag1 in 32D-CBFβ, CM or CM-ΔC95 expressing cells, determined by qRT-PCR. Shown are fold induction 24 h after 3 Gy IR relative to non-IR (mean+/−SD) performed in triplicate and two independent experiments. FIG. 4E: Fold activation of p53 target genes, Bax, Puma, p21, Gadd45b and LincRNA-p21 in 32D-CM cells treated with HDAC8i PCI-34051 (10 μM) or 22d (10 μM) for 16 h, determined by qRT-PCR. Relative expression of each target gene was normalized to levels of Hprt. Shown are fold activation compared to levels in vehicle treated cells (dashed line). Results represent the mean±SD of triplicated assays.

FIG. 5A: Relative expression level of HDAC8 in normal (NL) PBSC (n=7) or inv(16)$^+$ AML (n=7) CD34$^+$ cells determined by qRT-PCR. Levels of HDAC8 expression were normalized to levels of ACTB in each sample. Dashed line indicates the average of all NL PBSC samples (set to an arbitrary value of 1). Each dot represents average of triplicated result from an individual patient and line indicates mean±SEM (standard error the mean) of each all samples (p=0.0003). FIG. 5B: Relative proliferation of inv(16)$^+$ AML CD34$^+$ (n=7) or normal CD34$^+$ (n=7) cells treated with indicated dose of 22d HDAC8i for 48 h, as determined by Cell Titer-Glo Luminescent Cell Viability Assay and normalized to vehicle treated controls. Each dot represents an individual subject and lines indicate mean±SEM. * P<0.05;  P<0.01; * P<0.001. FIG. 5C: Percent apoptosis determined by Annexin V labeling of inv(16)$^+$ AML CD34$^+$ (n=6) or normal CD34$^+$ (n=5) cells treated with indicated doses of 22d for 48 h, and normalized to vehicle treated controls. Each dot represents an individual patient and lines indicate mean±SEM. * P<0.05;  P<0.01; * P<0.001. FIG. 5D: Western blotting of Ac-p53 (K382), and p53 levels in inv(16)$^+$ AML CD34$^+$ cells treated with 22d (10 μM) or Nutlin-3 (2.5 μM) for 6 h. Levels of β-actin were detected as loading control. Shown are representative results from four patients. FIG. 5E: Fold induction of p53 target genes in inv(16)$^+$ AML CD34$^+$ (n=9) or normal CD34$^+$ (n=7) cells treated with 22d (10 μM) for 16 h, determined by qRT-PCR. Relative expression of each target gene was normalized to levels of ACTB. Each dot represents an individual subject and lines indicate mean±SEM. Dash line indicates levels in vehicle treated cells. * P <0.05;  P<0.01; * P<0.001. FIG. 5F: Representative FACS plot of Annexin V/DAPI labeling in inv(16)$^+$ AML CD34$^+$ cells transduced with a pLKO-GFP vector expressing p53 shRNA (GFP$^+$) and treated with 22d for 48 h. FIG. 5G: Relative survival of sorted GFP+ inv(16)$^+$ AML CD34$^+$ cells expressing p53 shRNA (open diamond) or non-silencing control (solid dot) and treated with indicated doses of 22d for 48 h. Each dot represents an individual patient and lines indicate mean±SEM.

FIG. 6A: Schematic illustration of experimental design. Cbfb$^{+/56M}$Mx1Cre or Cbfb$^{+/56M}$Mx1Cre/tdTomato$^+$ mice were induced with pIpC and AML cells were isolated from bone marrow of moribund mice, treated with 22d or vehicle for 48 or 72 h and transplanted into sub-lethally irradiated (6.5 Gy) C57Bl/6 congenic mice. Progression of AML was monitored by engraftment of AML cells in peripheral blood (PB) over time (4, 8 weeks) and engraftment in bone marrow and spleen was analyzed 8 weeks after transplantation. A cohort of mice was monitored for AML development and disease-free survival. FIG. 6B: Engraftment of dTomato$^+$ AML cells in the PB 4 weeks (n=7; p=0.0006) or 8 weeks (vehicle, n=5; 22d, n=7; p=0.0025) after transplantation. Results represent mean±SD. FIG. 6C: Representative images of spleens from mice transplanted with vehicle treated cells (top) or 22d treated cells (bottom) 8 weeks after transplantation. FIG. 6D: Representative FACS plots of engrafted dTomato$^+$/cKit$^+$ AML cells in the bone marrow or spleen 8 weeks after transplantation. Shown are representative frequencies of dTomato$^+$/cKit$^+$ cells in individual transplanted mice. FIG. 6E: Frequency of AML cells (dTomato$^+$/cKit$^+$) in the bone marrow of mice transplanted with vehicle treated (n=5) or 22d treated cells (n=7). Each dot represent results from individual mouse and line indicate median. p=0.0025. FIG. 6F: Frequency of AML cells (dTomato$^+$/cKit$^+$) in the spleen of mice transplanted with vehicle treated (n=5) or 22d treated cells (n=7). Each dot represent results from an individual mouse and lines indicate median. p=0.0025. FIG. 6G: Survival curve of mice transplanted with AML cells treated with 22d (n=10) or vehicle (n=1). **p=0.0025

FIG. 7A: Schematic illustration of experimental design. Cbfb$^{+/56M}$Mx1Cre/tdTomato$^+$ mice were induced with pIpC and AML cells were isolated from bone marrow of moribund mice and transplanted into sub-lethally irradiated (6.5 Gy) C57Bl/6 congenic mice. After 5-6 weeks, mice were randomized into two groups, one group was treated with vehicle and the other treated with 22d by intraperitoneal injection (50 mg/kg/dose) twice a day for 2 weeks. AML engraftment was analyzed at the end of the treatment period, and transplanted into 2$^{nd}$ recipients. Recipients were analyzed for engraftment at 8 weeks or monitored for leukemia onset and survival. FIG. 7B: Representative FACS plots of engrafted dTomato+/cKit+ AML cells in the bone marrow after the 2-week treatment with vehicle (top) or 22d (bottom). FIG. 7C: Frequency of AML cells (dTomato$^+$/cKit$^+$) in the bone marrow of mice treated with vehicle (n=13) or 22d (n=13) for 2 weeks. Each dot represent results from an individual mouse and lines indicate median±SEM. **p=0.0097. FIG. 7D: Total number of AML cells (dTomato$^+$/cKit$^+$) in the bone marrow of mice treated with vehicle (n=13) or 22d (n=13) for 2 weeks. Each dot represent results from an individual mouse and lines indicate median±SEM. *p=0.01. FIG. 7E: Representative FACS plots of dTomato$^+$/cKit$^+$ AML cells in the bone marrow of 2$^{nd}$ transplant recipients whom received BM from vehicle treated (top) or 22d treated (bottom) mice. Mice were analyzed 8 weeks after transplantation. FIG. 7F: Frequency of AML cells in the bone marrow of 2$^{nd}$ transplant recipients received BM from vehicle treated (n=5) or 22d treated (n=4) mice. *p<0.0001. FIG. 7G. Total number of AML cells in the bone marrow of 2$^{nd}$ transplant recipients received BM from vehicle treated (n=5) or 22d treated (n=4) mice. *p=0.0006. FIG. 7H: Spleen weight of 2$^{nd}$ transplant recipient who received BM from vehicle treated (n=5) or 22d treated (n=4) mice, 8 weeks after transplantation. *p=0.0159. FIG. 7I: Survival curve of 2$^{nd}$ transplant recipients of vehicle treated (n=5) or 22d treated (n=4) BM.

Figure 12A:
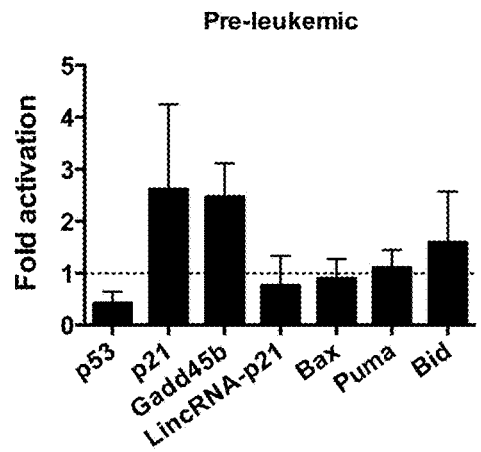
Figure 12B:
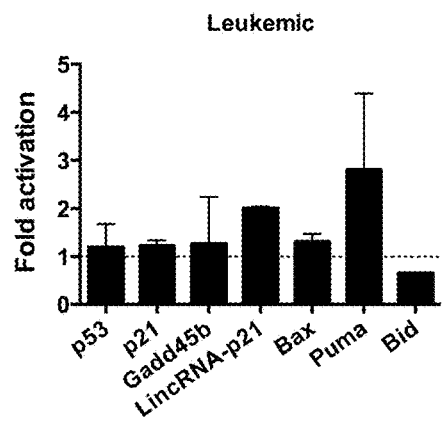

FIGS. 12A-12B. HDAC8i induces activation of p53 targets in progenitor cells expressing endogenous levels of CM. Fold activation of p53 target genes in pre-leukemic (FIG. 12A, n=4) or leukemic (FIG. 12B, n=4) progenitor cells expressing CM, treated with HDAC8i 22d (10 µM) for 16 h, determined by qRT-PCR. Relative expression of each target gene was normalized to levels of Hprt. Shown are fold activation compared to levels in vehicle treated cells (dashed line). Results represent the mean±SD.

Figure 13A:
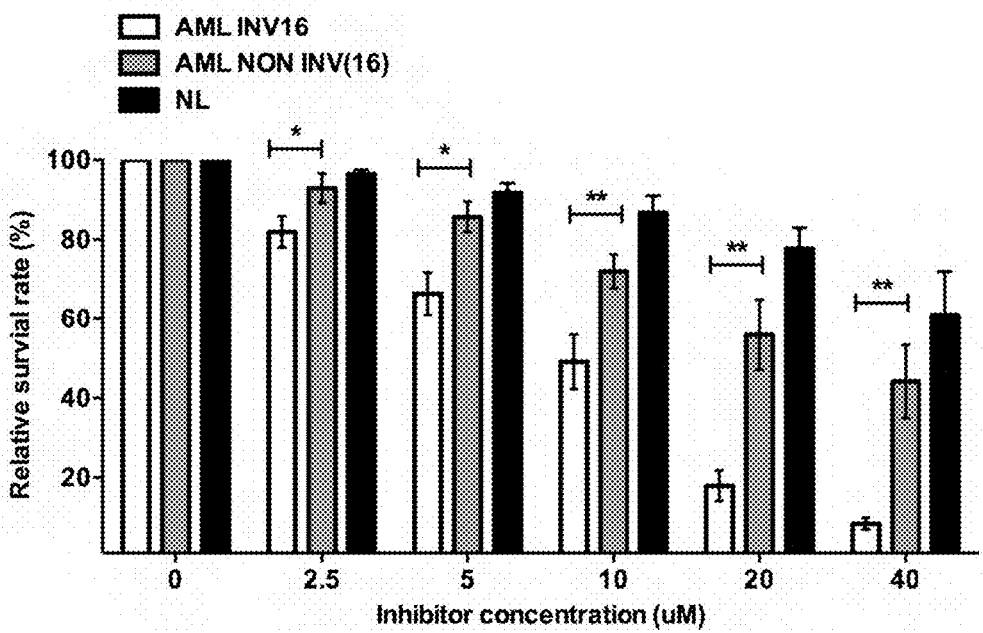
Figure 13B:
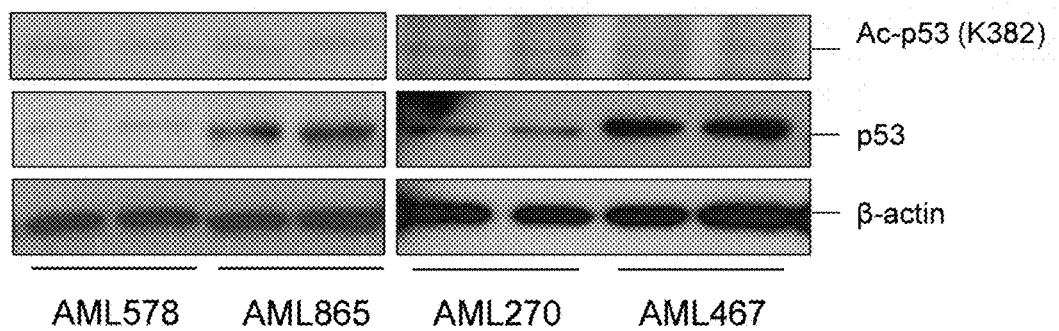

FIGS. 13A-13B. HDAC8i treatment selectively induce of apoptosis and p53 acetylation in inv(16)$^+$ AML CD34$^+$ cells. FIG. 12A: Percent survival determined by Annexin V labeling of inv(16)$^+$ AML CD34$^+$ (n=6), non-inv(16) AML (n=4) or normal CD34$^+$ (n=5) cells treated with indicated doses of 22d for 48 h, and normalized to vehicle treated controls. Shown are mean±SEM. * P<0.05;  P<0.01; * P<0.001. FIG. 12B: Western blotting of Ac-p53 (K382), and p53 levels in non-inv(16) AML CD34$^+$ cells treated with 22d (10 mM) for 6 h. Levels of β-actin were detected as loading control.

Figure 14A:
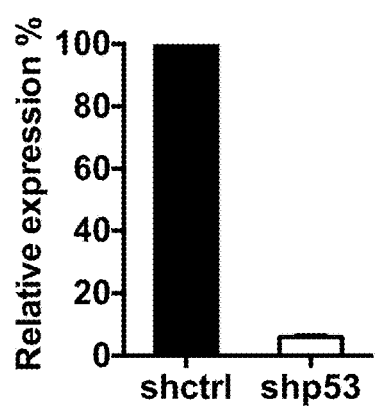
Figure 14B:
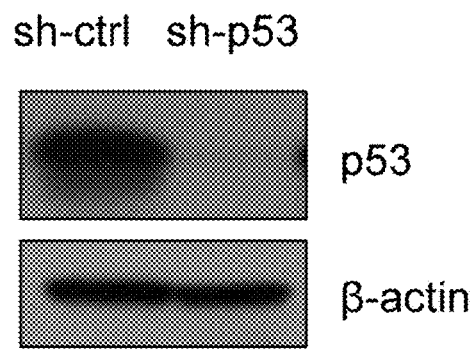

FIG. 14A-14B. Confirmation of p53 knock-down by lentivirus expressing shRNA. FIG. 14A: Change in p53 expression level in GFP sorted MV4-11 cells transduced with pLKO.1-GFP lentivirus expressing sh-p53 or non-silencing control (sh-ctrl) normalized to levels of b-actin. Shown are mean±SEM. FIG. 14B: Western blot analysis of p53 in GFP sorted MV4-11 cells transduced with pLKO.1-GFP lentivirus expressing sh-p53 or sh-ctrl. Levels of b-actin serve as loading control.

Figure 15A:
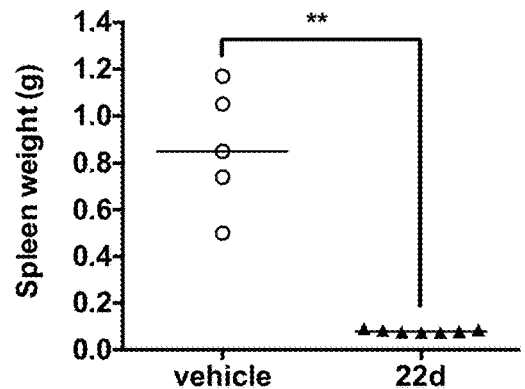
Figure 15B:
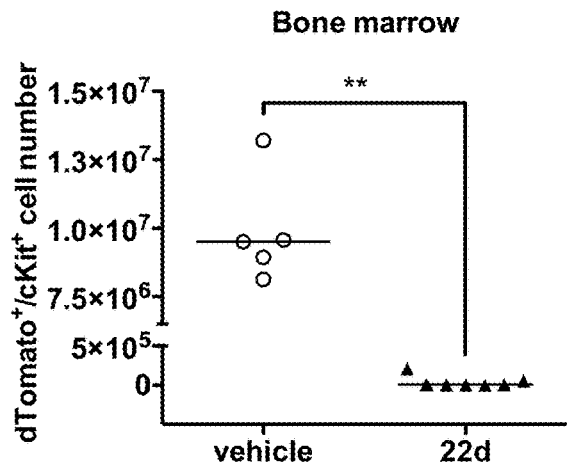
Figure 15C:
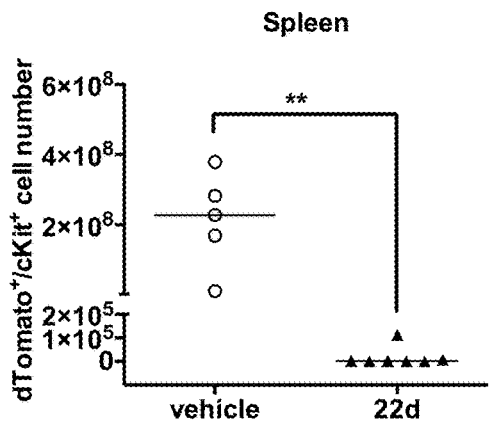
Figure 15D:
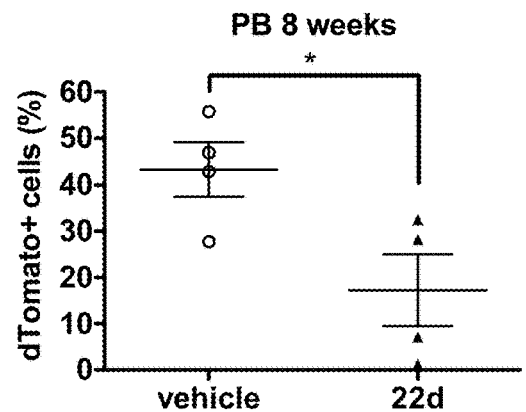
Figure 15E:
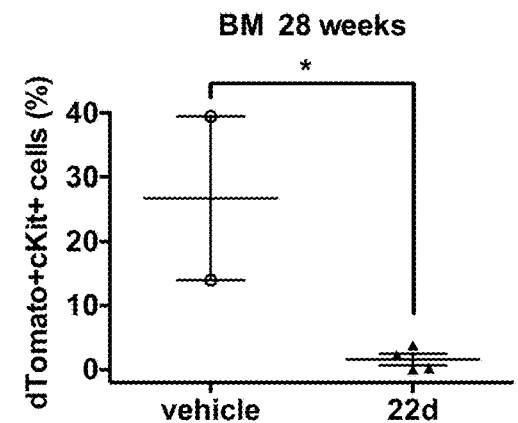
Figure 15F:
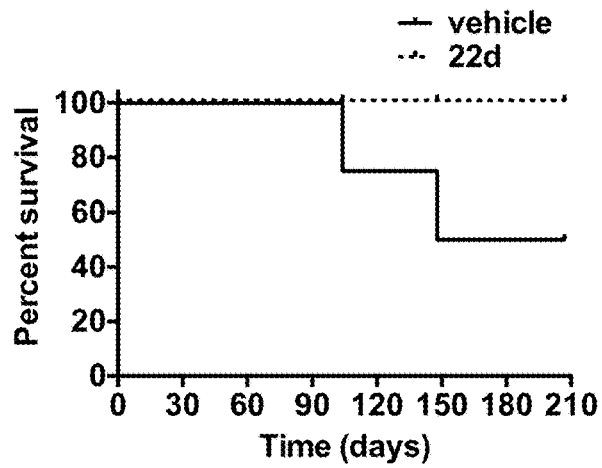

FIGS. 15A-15F. HDAC8i 22d treatment significantly reduces engraftment and progression of AML. FIG. 15A. Weight of spleens isolated mice transplanted with vehicle treated (n=5) or 22d treated cells (n=7). Each dot represent results from individual mice and line indicate median. p=0.0025. FIG. 15B. Total number of AML cells (dTomato$^+$/cKit$^+$) in the bone marrow (2 femurs and 2 tibia) of mice transplanted with vehicle treated (n=5) or 22d treated cells (n=7). Each dot represent results from individual mice and line indicate median. p=0.0025. FIG. 15C. Total number of AML cells (dTomato$^+$/cKit$^+$) in the spleen of mice transplanted with vehicle treated (n=5) or 22d treated cells (n=7). Each dot represent results from individual mice and line indicate median. p=0.0025. FIG. 15D. The frequency of dTomato+ cells in the PB 8 weeks after transplantation of 2×10$^6$ AML cells treated with 22d or vehicle ex vivo for 48 h (n=4). Each dot represent results from individual mice and line indicate mean±SEM. p=0.0357. FIG. 15E. The frequency of dTomato+/ckit+ cells in the BM 28 weeks after transplantation of 2×10$^6$ cells treated with 22d (n=4) or vehicle (n=2; 2 had succumbed to AML) ex vivo for 48 h (n=4). Each dot represent results from individual mice and line indicate mean±SEM. FIG. 15F. Survival curve of mice transplanted with 2×10$^6$ AML cells treated with 22d or vehicle (n=4).

Figure 16A:
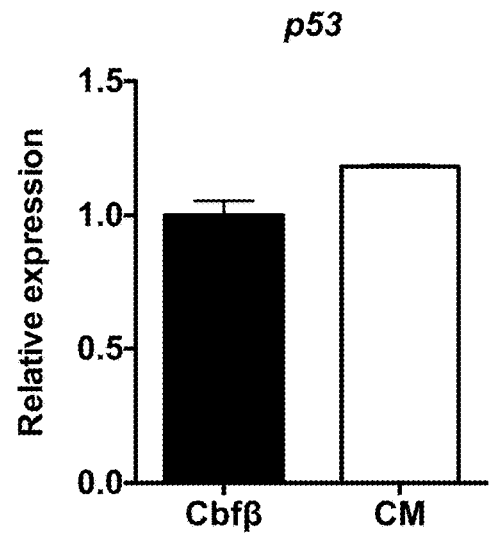
Figure 16B:
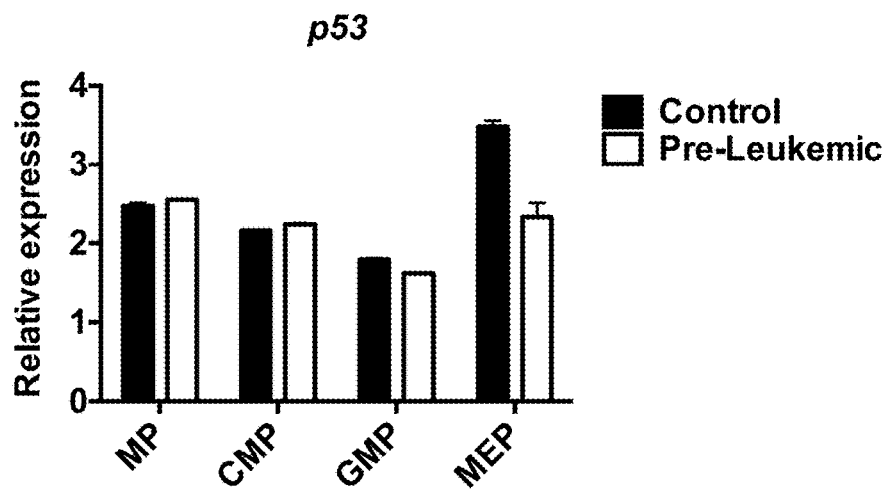

FIGS. 16A-16B. CBFb-SMMHC does not affect p53 mRNA expression. FIG. 16A: Relative expression of p53 mRNA in 32D-Cbfb or 32D-CM cells as determined by qRT-PCR. Shown are mean±SD. FIG. 16B: Relative expression of p53 mRNA in pre-leukemic progenitor subsets sorted from induced Cbfb$^{+/56M}$Mx1Cre, analyzed by qRT-PCR. Phenotypic progenitor subsets are defined as myeloid progenitors (MPs) (Lin$^-$/ckit$^+$/Sca1$^-$), common myeloid progenitors (CMPs) (Lin$^-$/ckit$^+$/Sca1$^-$/CD34$^+$/FcgR$^{lo}$), granulocyte-macrophage progenitors (GMPs) (Lin$^-$/ckit$^+$/Sca1$^-$/CD34$^+$/FcgR$^{hi}$), and megakaryocyte-erythroid progenitors (MEPs) (Lin$^-$/ckit$^+$/Sca1$^-$/CD34$^+$/FcgR$^{hi}$).

Figure 17A:
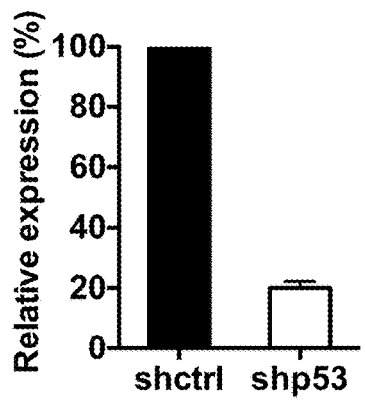
Figure 17B:
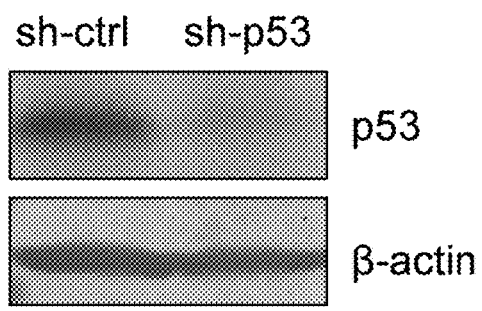
Figure 17C:
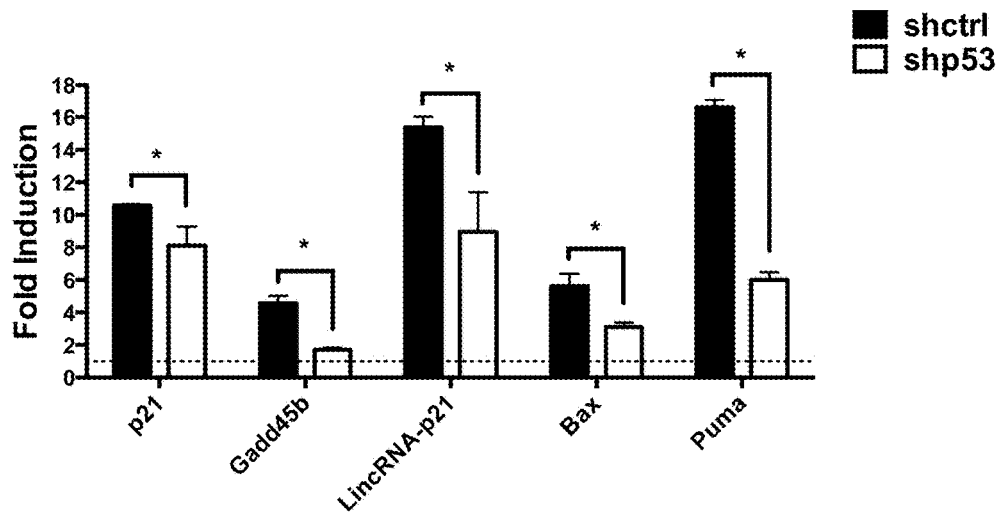
Figure 18A:
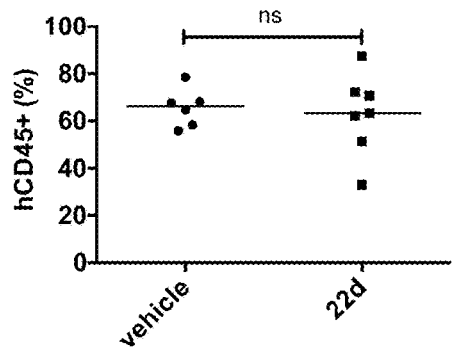
Figure 18B:
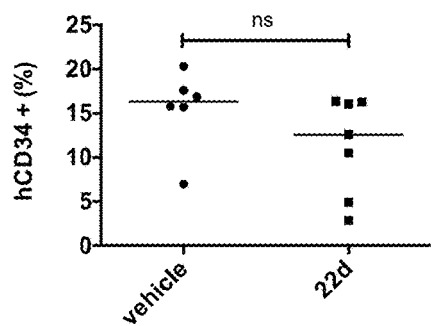
Figure 18C:
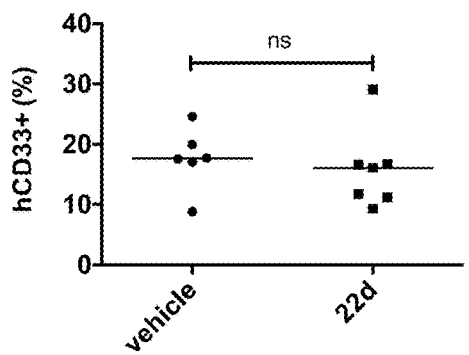
Figure 18D:
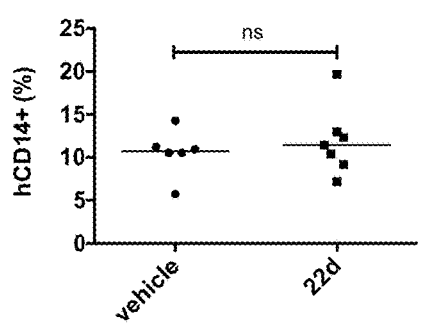
Figure 18E:
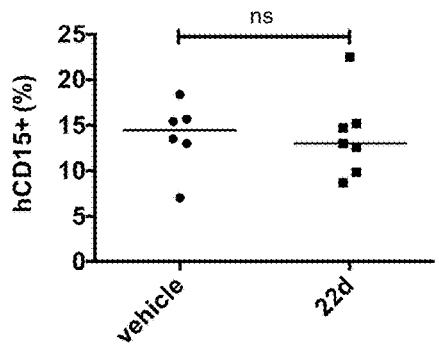
Figure 18F:
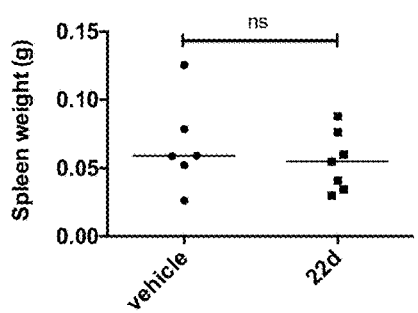

FIGS. 17A-17C. Effects of 22d on p53 targets are p53-dependent. FIG. 17A: Change in p53 expression level in 32D-CM cells transduced with pLKO.1 lentivirus expressing sh-p53 or non-silencing control (sh-Ctrl) normalized to levels of b-actin. Shown are mean±SEM. FIG. 17B: Western blotting of p53 levels in 32D-CM cells expressing sh-p53 or sh-Ctrl. Levels of 3-actin were detected as loading control. FIG. 17C: Fold activation of p53 target genes treated with 22d (10 mM) for 16 h, determined by qRT-PCR. Relative expression of each target gene was normalized to levels of ACTB. * P<0.05.

FIGS. 18A-18F. Treatment of HDAC8i 22d does not affect normal HSC engraftment. Engraftment of normal CB CD34$^+$ cells treated with 22d (10 µM) or vehicle for 48 h into sub-lethally irradiated NOD/SCID/interleukin-2 receptor-g chain deficient (NSG) mice. Shown are engraftment levels of each population (CD45+, CD34+, CD33+, CD14+, CD15+) in the bone marrow and spleen weight at 16 weeks after transplantation. Each dot represents result from an individual mouse and line indicates medium. ns, not significant. FIGS. 18A-18F (in order): CD45+, CD34+, CD33+, CD14+, CD15+, and spleen.

Figure 19:
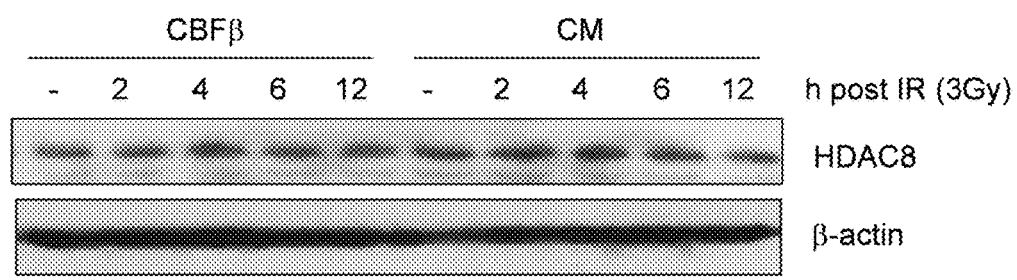

FIG. 19 CBFb-SMMHC does not affect HDAC8 expression. Western blot analysis of HDAC8 in 32D-CM or 32D-CBFβ cells before and at various time points after IR (3 Gy). Levels of β-actin serve as loading control.

Figure 20:
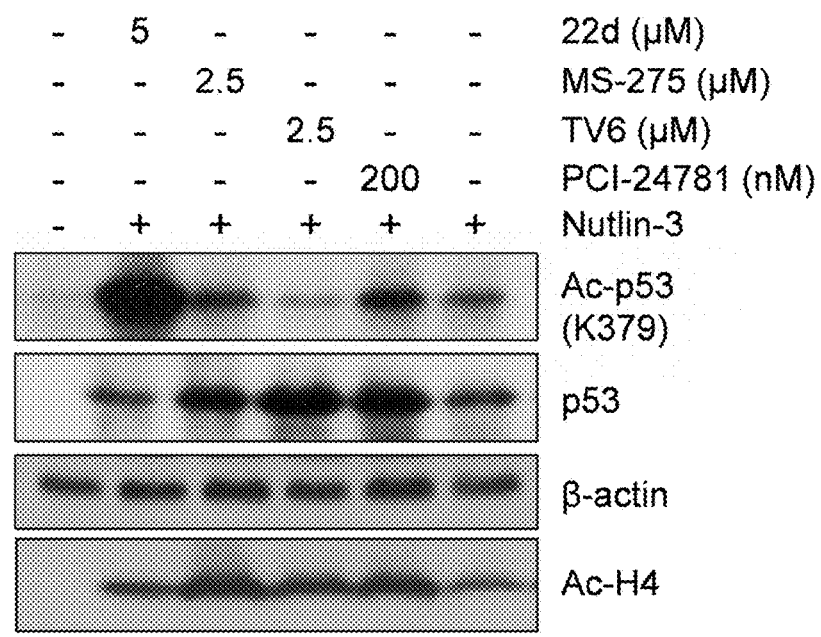

FIG. 20. HDAC8i selectively induce acetylated p53 in CM-expressing cells. Western blot analysis of Ac-p53, p53, acetylated histone H4 (Ac-H4) in 32D-CM cells treated with indicated inhibitors. Levels of β-actin serve as loading control.

Figure 21A:
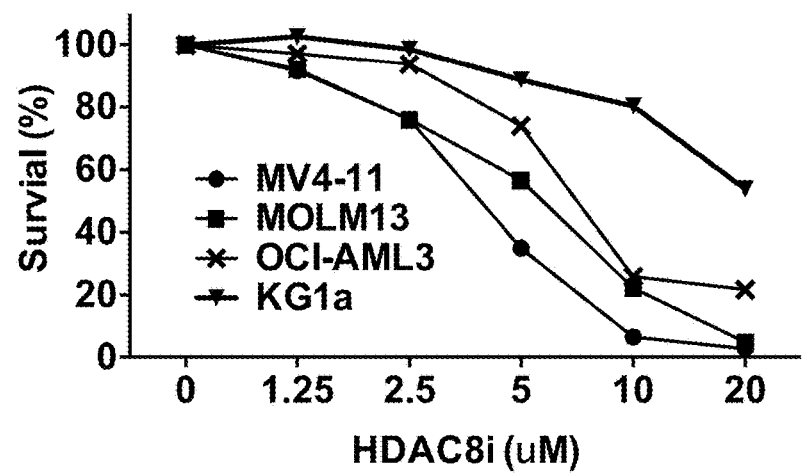
Figure 21B:
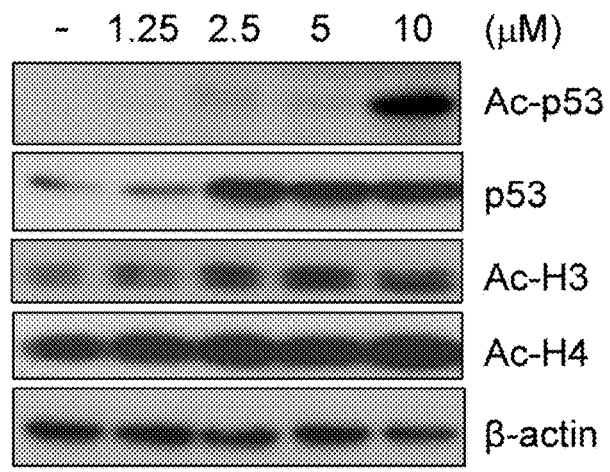
Figure 21C:
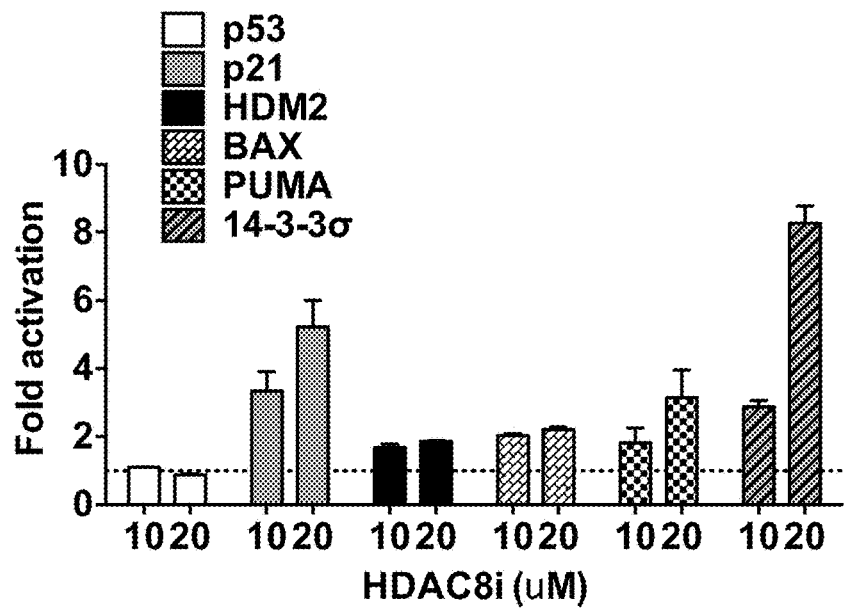
Figure 21D:
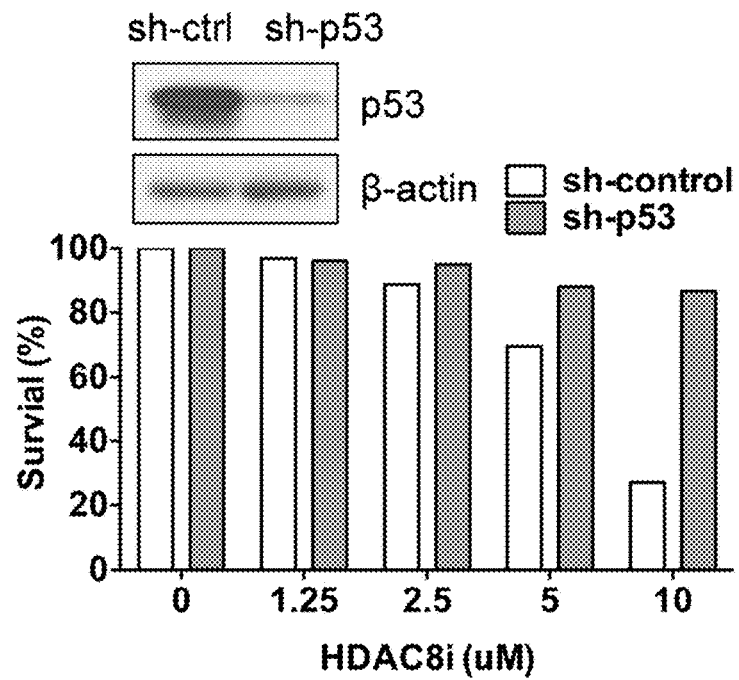

FIGS. 21A-21D. HDAC8 inhibition activates p53 and induces p53-dependent apoptosis in human AML cells. FIG. 21A: Relative survival of human AML cells treated with HDAC8i (Cmpd 22d) for 48 h, as determined by Annexin V labeling and normalized to vehicle-treated controls. FIG. 21B: Western blot analysis of Ac-p53, total p53, Ac-H3, Ac-H4, β-actin in MV4-11 cells treated with indicated doses of HDAC8i for 6 h. FIG. 21C: Fold change in mRNA levels of p53 targets after treatment with PCI-48012 (10 mM or 20 mM) for 16 h. FIG. 21D: Western blot analysis of p53, β-actin in MV4-11 cells transduced with control or sh-p53 (top). Relative survival of control or sh-p53 transduced MV4-11 cells treated with HDAC8i (bottom).

Figure 22A:
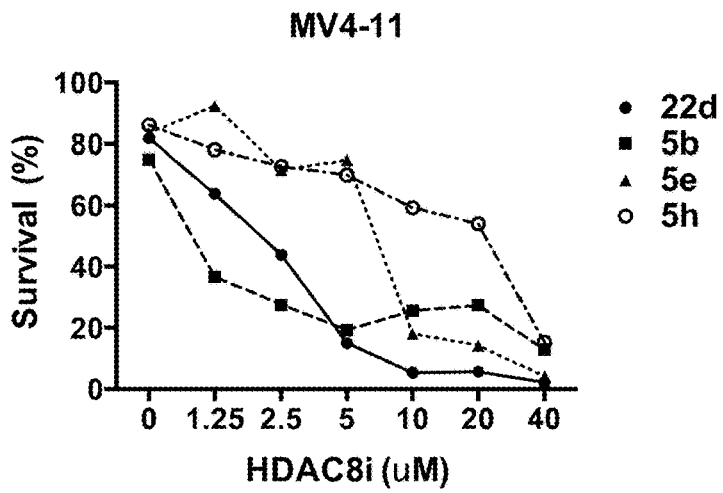
Figure 22B:
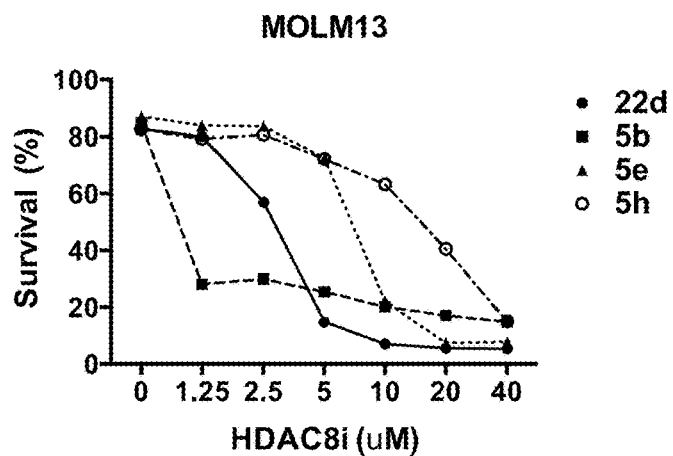
Figure 22C:
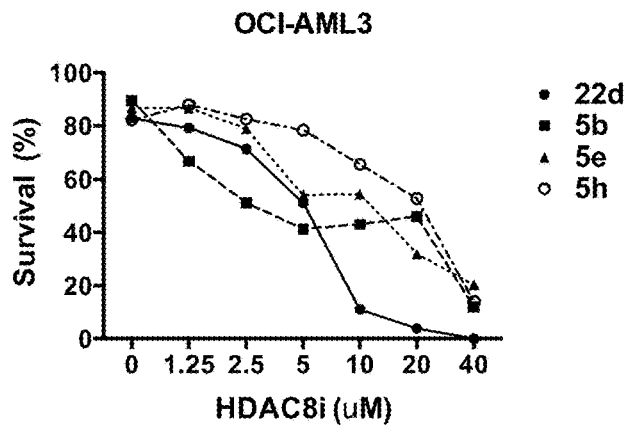
Figure 22D:
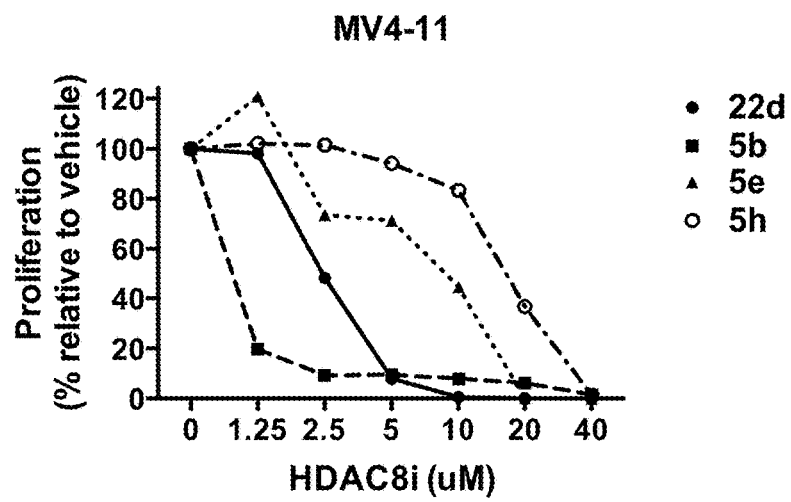
Figure 22E:
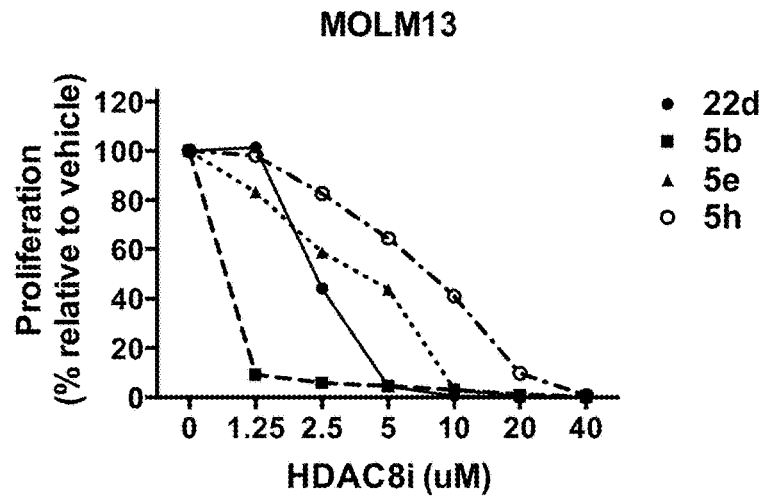

FIGS. 22A-22E. Activity of HDAC8i compounds on AML cell proliferation and survival. FIGS. 22A-22C. Relative survival of non-p53-mutated AML cell lines (Mv4-11, MOLM13, OCI-AML3; FIGS. 22A-22C, respectively) treated with various HDAC8i (22d, 5b, 5e, 5 h) for 48 h, as determined by Annexin V labeling and normalized to vehicle-treated controls. FIGS. 22D-22E: Relative proliferation of AML cell lines (Mv4-11, MOLM13, FIGS. 22D,22E, respectively) treated with various HDAC8i (22d, 5b, 5e, 5h) for 48 h, as determined by Cell Titer-Glo Luminescent Cell Viability Assay and normalized to vehicle treated controls.

Figure 23:
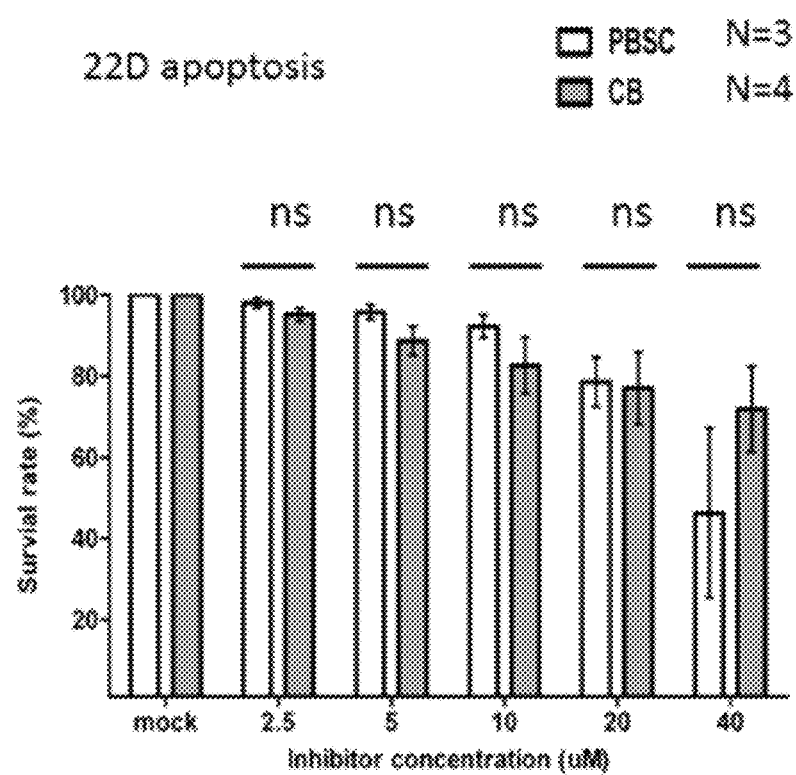

FIG. 23. Figure depicts histogram of survival rate of PBSC and CB cells showing no significant difference based on cell origin upon contact with Cmpd 22d.

Figure 24A:
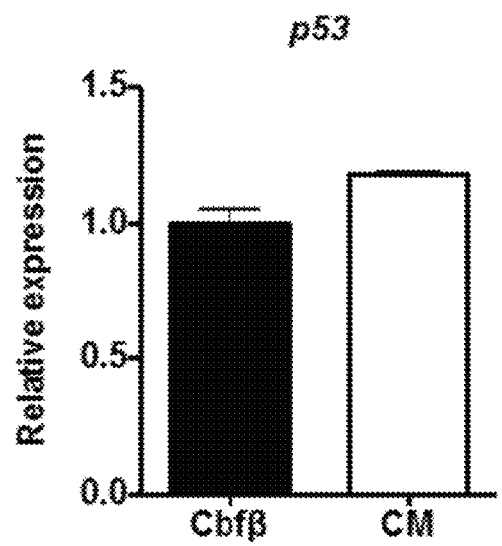
Figure 24B:
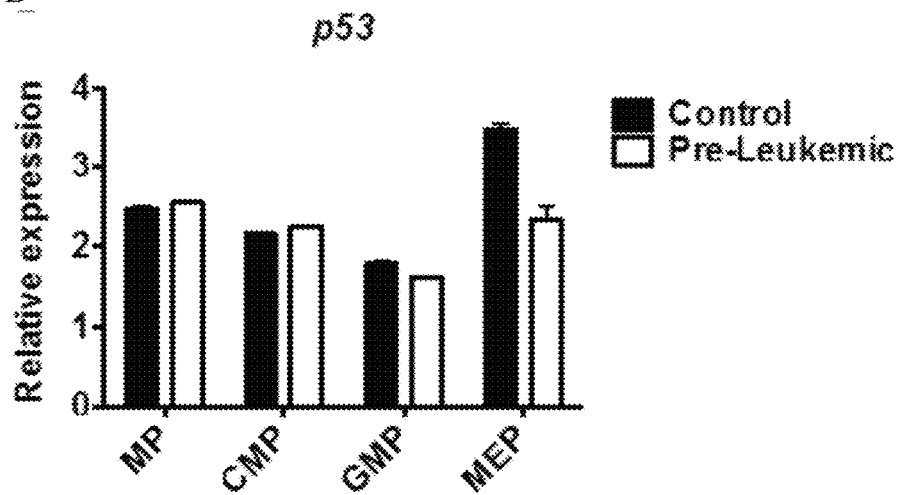

FIGS. 24A-24B. Histograms demonstrating no significant changes in p53 mRNA or protein levels by CBFβ-SMMHC expression in 32D myeloid progenitor cell line (FIG. 24A) or in primary myeloid progenitor cells (FIG. 24B). Legend: y-axis: relative expression of indicated proteins. Legend (FIG. 24B): Control (filled), pre-leukemic (open).

Figure 25:
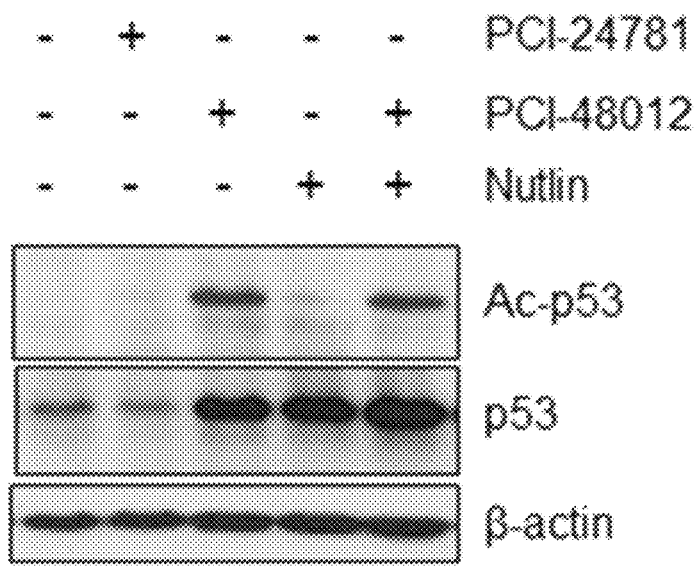

FIG. 25. The figure depicts the effect of agents PCI-24781, PCI-48012 and Nutlin on protein expression for Ac-p53, p53 and β-actin.

Figure 26A:
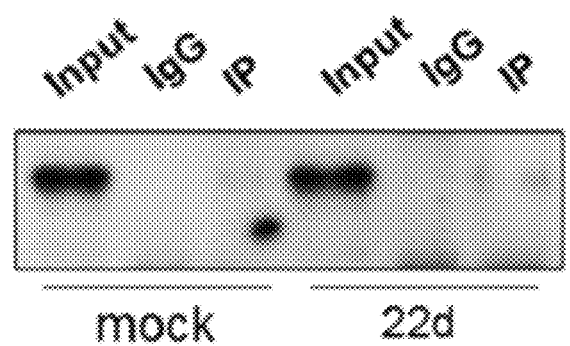
Figure 26B:
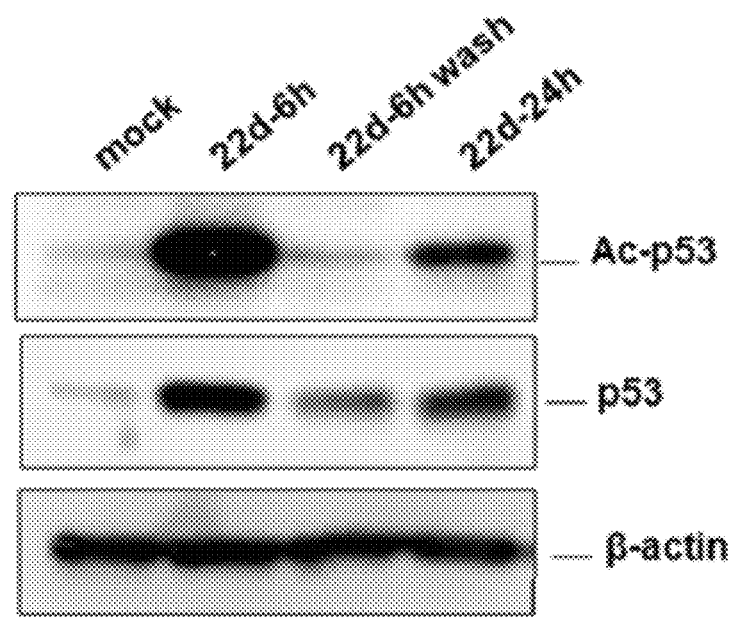
Figure 26C:
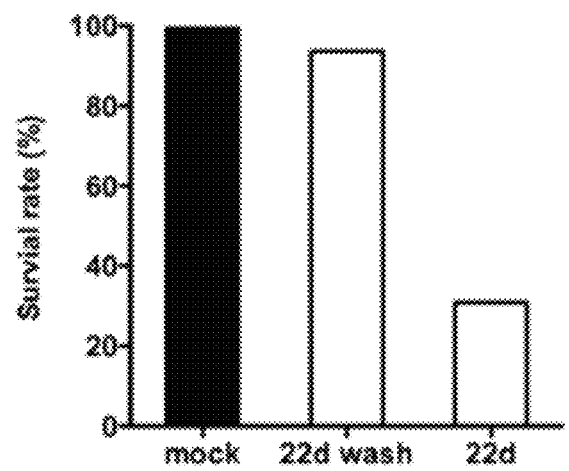

FIGS. 26A-26C. Effects of HDAC8 inhibitors on interaction between p53 and CM. FIG. 26A: Figure depicts effects of Cmpd 22d on IgG and IP expression. FIG. 26B: Figure depicts protein expression levels after contact with Cmpd 22d on Ac-p53, p53 and Jβ-actin under the indicated timing and wash conditions. FIG. 26C: Histogram depicting survival rate with and without wash of Cmpd 22d.

Figure 27A:
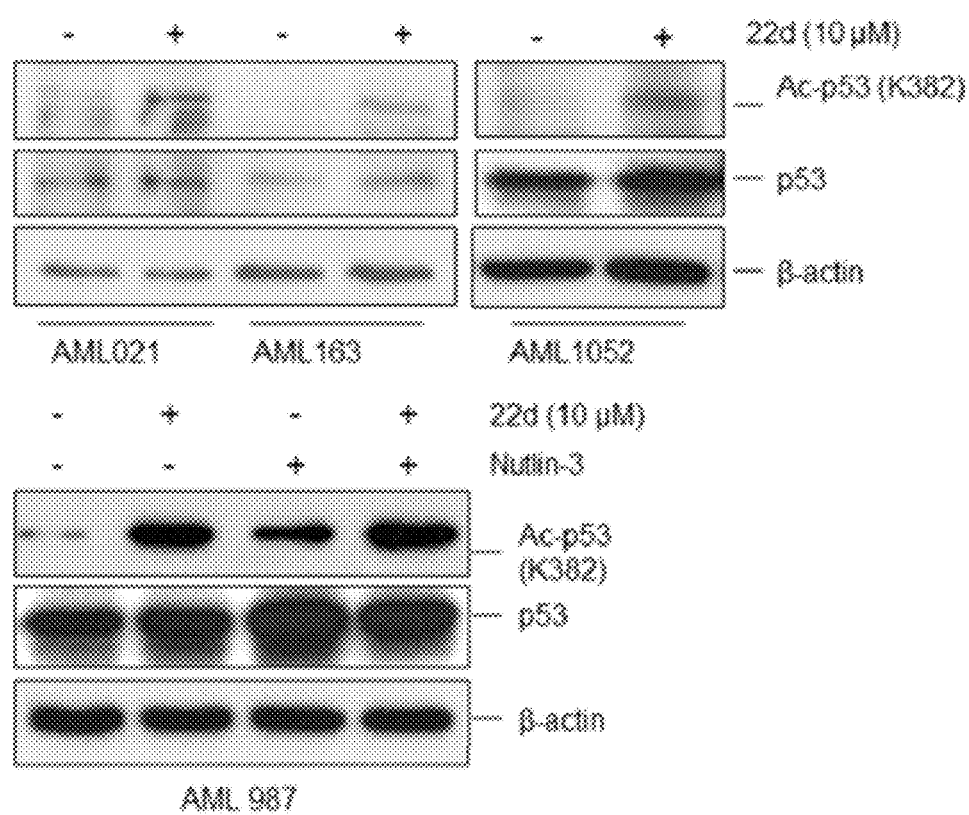
Figure 27B:
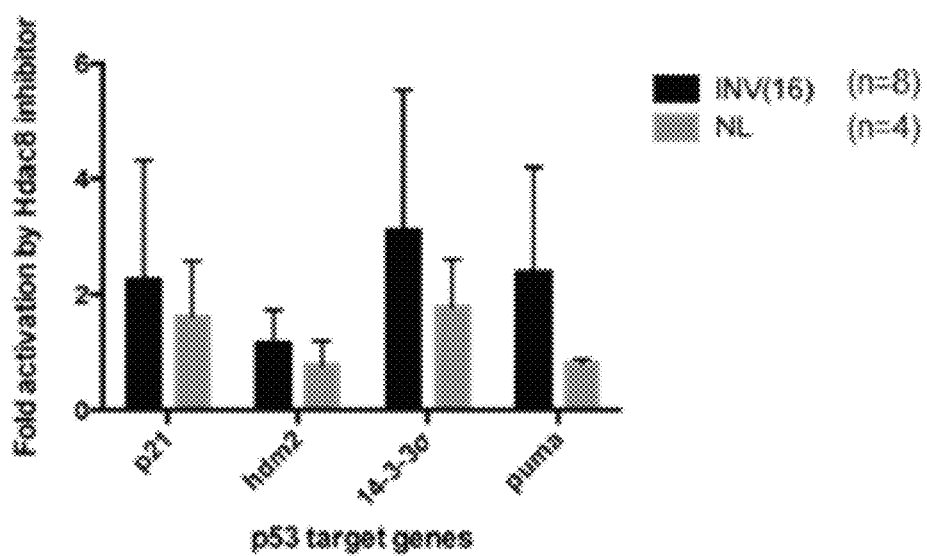

FIGS. 27A-27B. Inhibition of HDAC8 selectively activate p53 in inv(16)+ AML CD34+ cells. FIG. 27A: Figure depicts Western blotting of Ac-p53, (K382), and p53 levels in inv(16)+ AML CD34+ cells upon contact with Cmpd 22d. FIG. 27B: Histogram depicts the fold activation of the indicated p53 target genes (in order left to right: p21, hdm2, 14-3-3σ, puma) in inv(16)+ AML CD34+ and normal CD34+ cells. Legend: inv(16)+ AML CD34+ (black filled); normal CD34+ cells (gray filled).

DETAILED DESCRIPTION

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, S, Se and Si, and wherein the nitrogen, selenium, and sulfur atoms may optionally be oxidized, and the nitrogen heteroatom may optionally be quaternized. Heteroalkyl is not cyclized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. The ring-forming substituents may be attached to adjacent members of the base structure. For example, two ring-forming substituents attached to adjacent members of a cyclic base structure create a fused ring structure. The ring-forming substituents may be attached to a single member of the base structure. For example, two ring-forming substituents attached to a single member of a cyclic base structure create a spirocyclic structure. The ring-forming substituents may be attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_3$-$C_8$ aryl, and each substituted or unsubstituted heteroaryl is a substituted or unsubstituted $C_3$-$C_{85}$ heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_3$-$C_7$ aryl, and each substituted or unsubstituted heteroaryl is a substituted or unsubstituted $C_3$-$C_7$ heteroaryl.

Each substituted group described in the compounds herein may be substituted with at least one substituent group. More specifically, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein may be substituted with at least one substituent group. At least one or all of these groups may be substituted with at least one size-limited substituent group. At least one or all of these groups may be substituted with at least one lower substituent group.

Each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl may be a substituted or unsubstituted $C_3$-$C_8$ cycloalkyl, and/or each substituted or unsubstituted heterocycloalkyl may be a substituted or unsubstituted 3 to 8 membered heterocycloalkyl. Each substituted or unsubstituted alkylene may be a substituted or unsubstituted $C_1$-$C_{20}$ alkylene, each substituted or unsubstituted heteroalkylene may be a substituted or unsubstituted 2 to 20 membered heteroalkylene, each substituted or unsubstituted cycloalkylene may be a substituted or unsubstituted $C_3$-$C_8$ cycloalkylene, each substituted or unsubstituted heterocycloalkylene may be a substituted or unsubstituted 3 to 8 membered heterocycloalkylene, each substituted or unsubstituted arylene may be a substituted or unsubstituted $C_3$-$C_8$ arylene, and/or each substituted or unsubstituted heteroaryl may be a substituted or unsubstituted $C_3$-$C_8$ heteroarylene.

Each substituted or unsubstituted alkyl may be a substituted or unsubstituted $C_1$-$C_8$ alkyl, each substituted or unsubstituted heteroalkyl may be a substituted or unsubstituted 2 to 8 membered heteroalkyl, each substituted or unsubstituted cycloalkyl may be a substituted or unsubstituted $C_3$-$C_7$ cycloalkyl, each substituted or unsubstituted heterocycloalkyl may be a substituted or unsubstituted 3 to 7 membered heterocycloalkyl, each substituted or unsubstituted aryl may be a substituted or unsubstituted $C_3$-$C_7$ aryl, and/or each substituted or unsubstituted heteroaryl may be a substituted or unsubstituted $C_3$-$C_7$ heteroaryl. Each substituted or unsubstituted alkylene may be a substituted or unsubstituted $C_1$-$C_8$ alkylene, each substituted or unsubstituted heteroalkylene may be a substituted or unsubstituted 2 to 8 membered heteroalkylene, each substituted or unsubstituted cycloalkylene may be a substituted or unsubstituted $C_3$-$C_7$ cycloalkylene, each substituted or unsubstituted heterocycloalkylene may be a substituted or unsubstituted 3 to 7 membered heterocycloalkylene, each substituted or unsubstituted arylene may be a substituted or unsubstituted $C_3$-$C_7$ arylene, and/or each substituted or unsubstituted heteroarylene may be a substituted or unsubstituted $C_3$-$C_7$ heteroarylene.

Certain compounds described herein possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the compounds described herein. The compounds described herein do not include those that are known in art to be too unstable to synthesize and/or isolate. Compounds described herein include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds described herein may exist in tautomeric forms, all such tautomeric forms of the compounds being within the scope described herein.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope described herein.

Unless otherwise stated, structures depicted herein are also meant to include compounds which differ only in the presence of one or more isotopically enriched atoms. For example, compounds described herein include the present structures except for the replacement of a hydrogen by a deuterium or tritium, or the replacement of a carbon by $^{13}$C- or $^{14}$C-enriched carbon.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). Compounds described herein further include all isotopic variations thereof, whether radioactive or not.

The symbol "~~~" denotes the point of attachment of a chemical moiety to the remainder of a molecule or chemical formula.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently.

Description of compounds described herein are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "DNA" and "RNA" refer to deoxyribonucleic acid and ribonucleic acid, respectively.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as naturally occurring nucleic acids. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide, is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles described herein.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V);

6) Phenylalanine (F), Tyrosine (Y), Tryptophan (W); 7) Serine (S), Threonine (T); and 8) Cysteine (C), Methionine (M) (see. e.g., Creighton, *Proteins* (1984)).

The term "pharmaceutically acceptable salts" is meant to include salts of the active compounds that are prepared with relatively nontoxic acids or bases, depending on the particular substituents found on the compounds described herein. When compounds described herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds described herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfiuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds described herein contain both basic and acidic functionalities that allow the compounds to be converted into either base or acid addition salts.

Thus, the compounds described herein may exist as salts, such as with pharmaceutically acceptable acids. The compounds described herein include such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the compounds described herein may be provided in a prodrug form. Prodrugs of the compounds described herein are those compounds that readily undergo chemical changes under physiological conditions to provide their respective active forms. Prodrugs of the compounds described herein may be converted in vivo after administration. Additionally, prodrugs can be converted to the compounds described herein by chemical or biochemical methods in an ex vivo environment, such as, for example, when contacted with a suitable enzyme or chemical reagent.

Certain compounds described herein can exist in unsolvated forms as well as solvated forms, including hydrated forms. In general, the solvated forms compounds described herein are equivalent to unsolvated forms. Certain compounds described herein may exist in multiple crystalline or amorphous forms. In general, all physical forms compounds described herein are equivalent for their uses described herein.

"Pharmaceutically acceptable excipient" and "pharmaceutically acceptable carrier" refer to a substance that aids the administration of an active agent to and absorption by a subject and can be included in the compositions described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein. One of skill in the art will recognize that other pharmaceutical excipients are useful in the compositions described herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds and complexes described herein can be used in combination with one another, with other active drugs known to be useful in treating a disease (e.g. anticancer drugs) or with adjunctive agents that may not be effective alone, but may contribute to the efficacy of the active agent.

By "co-administer" it is meant that a composition described herein is administered at the same time, just prior to, or just after the administration of one or more additional therapies, for example an anticancer agent as described herein. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds and complexes described herein may be combined with treatments for cancer such as chemotherapy or radiation therapy.

The terms "HDAC8 inhibitor" and "HDAC8i" are used interchangeably herein and refer a composition (e.g. compound, peptide, protein, nucleic acid, or antibody) which reduces the activity of HDAC8 (Histone Deacetylase 8) relative to the activity of HDAC8 in the absence of the inhibitor. HDAC8 inhibitors may be selective for HDAC8 as described herein. The HDAC8 inhibitor may be a HDAC8 inhibitor compound (e.g. a compound having a molecular weight (MW) of less than about 1000 Da). The HDAC8 inhibitor compound may be a compound described herein. HDAC8 inhibitor compounds further include compounds known to selectively inhibit HDAC8 expression or activity including one or more of those exemplified in, for example, U.S. Pat. No. 7,820,711; PCT/JP2011/050647; and/or PCT/US2014/012968.

HDAC8 inhibitor compounds include one or more of the compounds described herein, and further includes, for example, one or more of the compounds described by K. Krennhrubec, et al., *Bioorg. Med. Chem. Lett.* 2007, 17, 2874-2878; P. Galletti, et al., *ChemMedChem.* 2009, 4, 1991-2001; E. Hu, et al., *J. Pharmacol. Exp. Ther.* 2003, 307, 720-728; W. Tang, et al., *Bioorg. Med. Chem. Lett.* 2011, 21, 2601-2605; S. Balasubramanian, et al., *Leukemia* 2008, 22, 1026-1034; L. Whitehead, et al., Bioorg. Med. Chem. 2011, 19, 4626-4634; and T. Suzuki, et al., ChemMedChem. 2014, 9, 657-664.

The HDAC8 inhibitor may be a HDAC8 inhibitor antibody (e.g. those described by PCT/US2000/033622). The HDAC8 inhibitor may be a HDAC8 inhibitor polynucleotide. The HDAC8 inhibitor polynucleotide may be a mdRNA as described by, for example, PCT/US2008/055612. The HDAC8 inhibitor polynucleotide may be RNA (e.g. a HDAC8 inhibitor RNA), siRNA (e.g. a HDAC8 inhibitor siRNA), shRNA (e.g. a HDAC8 inhibitor shRNA) or a miRNA (e.g. a HDAC8 inhibitor miRNA). The HDAC8 inhibitor may be a HDAC8 inhibitor protein.

"Selective", "selectivity" or the like of a compound refers to the compound's ability to discriminate between molecular targets. A selective HDAC8 inhibitor described herein may have an $IC_{50}$ for HDAC8 activity that is at least about 1, 2, 3, 4, 5, 6, 7, 8, 9, or 10 fold lower than the $IC_{50}$ for one or more of HDAC1, HDAC2, HDAC3, HDAC6, HDAC10, and/or HDAC 11. A selective HDAC8 inhibitor may have an $IC_{50}$ for HDAC8 acetyltransferase activity that is about 5, 10, 50, 150, 200, 250, 300, 350, 400, 450 or more than about 500 fold lower than the $IC_{50}$ for acetyltransferase activity of another HDAC (e.g. HDAC1, HDAC2, HDAC3, HDAC6, HDAC10, or HDAC 11).

"Specific", "specifically", "specificity", or the like of a compound refers to the compound's ability to cause a particular action, such as inhibition, to a particular molecular target with minimal or no action to other proteins in the cell.

"HDAC8" is used herein and according to its common, ordinary meaning and refers to proteins of the same or similar names and functional fragments and homologs thereof. The term includes any recombinant or naturally occurring form of HDAC8 (e.g. Histone deacetylase 8; GI No: 8132878), or variants or fragments thereof that maintain HDAC8 activity (e.g. within at least 30%, 40%, 50%, 60%, 70%, 80%, 90%, 95%, or 100% activity compared to HDAC8).

"p53" is used herein and according to its common, ordinary meaning and refers to proteins of the same or similar names and functional fragments and homologs thereof. The term includes any recombinant or naturally occurring form of p53 (e.g. GI No: 23491729), or variants or fragments thereof that maintain p53 activity (e.g. within at least 30%, 40%, 50%, 60%, 70%, 80%, 90%, 95%, or 100% activity compared to p53). A "mutated p53" is a p53 variant that is aberrantly acetylated or deacetylated resulting from a mutation to the wildtype p53 amino acid sequence. The phrase "non-mutated p53" refers to p53 variants which are correctly acetylated or deacetylated. A non-mutated p53 may include mutations so long as those mutations impart no effect on p53 acetylation or deacetylation. Thus, a "non-mutated p53 cancer" refers to a cancer characterized by correctly acetylated or deacetylated p53. Likewise, a "mutated p53 cancer" refers to a cancer characterized by incorrectly acetylated or deacetylated p53.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. A control may be the measurement of the activity of a protein in the absence of a compound as described herein.

A "test compound" as used herein refers to an experimental compound used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. A patient may be human.

"Disease" or "condition" or "disorder" refers to a state of being or health status of a patient or subject capable of being treated with the compounds, drugs, pharmaceutical compositions, or methods provided herein. The disease may be a disease related to (e.g. caused by) an abnormal cell growth or abnormal protein activity (e.g. cancer).

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-azaepothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-10, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

I. COMPOSITIONS

Provided herein are compounds for treating cancer. The compound has formula (I):

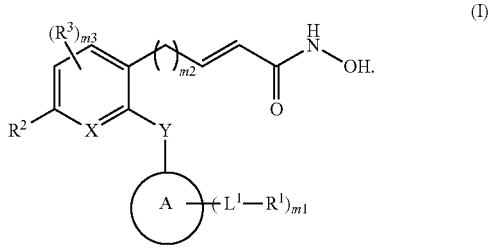

In the compound of formula (I), A is cycloalkyl, heterocycloalkyl, aryl, or heteroaryl. X is —C(R$^4$)═ or —N═. Y is a bond, —N(R$^5$)—, —O—, or —S—. L$^1$ is a bond, —C(O)—, —C(O)O—, —O—, —S—, —N(R$^6$)—, —C(O)N(R$^6$)—, —S(O)$_{n6}$—, —S(O)N(R$^6$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. R$^1$ is halogen, —N$_3$, —CF$_3$, —CCl$_3$, —CBr$_3$, —CI$_3$, —CN, —OR$^{1A}$, —C(O)R$^{1A}$, —NR$^{1A}$R$^{1B}$, —C(O)OR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is halogen, —N$_3$, —CF$_3$, —CCl$_3$, —CBr$_3$, —CI$_3$, —CN, —OR$^{2A}$, —C(O)R$^{2A}$, —NR$^{2A}$R$^{2B}$, —C(O)OR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted C$_1$-C$_5$ alkyl, or substituted or unsubstituted 2 to 5 membered heteroalkyl. R$^3$ is independently hydrogen, halogen, —N$_3$, —CF$_3$, —CCl$_3$, —CBr$_3$, —CI$_3$, —CN, —C(O)H, —OCH$_3$, —OCH$_2$CH$_3$, —NH$_2$, —COOH, —CONH$_2$, —NO$_2$, —SH, —S(O)$_2$H, —NHNH$_2$, —ONH$_2$, —NHC(O)NHNH$_2$, substituted or unsubstituted C$_1$-C$_5$ alkyl, or substituted or unsubstituted 2 to 5 membered heteroalkyl. R$^4$ is hydrogen, halogen, —N$_3$, —CF$_3$, —CCl$_3$, —CBr$_3$, —CI$_3$, —CN, —OR$^{4A}$, —C(O)R$^{4A}$, —NR$^{4A}$R$^{4B}$, —C(O)OR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted C$_1$-C$_5$ alkyl, or substituted or unsubstituted 2 to 5 membered heteroalkyl. R$^5$ is hydrogen, halogen, —N$_3$, —CF$_3$, —CCl$_3$, —CBr$_3$, —CI$_3$, —CN, —OR$^{5A}$, —C(O)R$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted C$_1$-C$_5$ alkyl, or substituted or unsubstituted 2 to 5 membered heteroalkyl. R$^6$ is hydrogen, halogen, —N$_3$, —CF$_3$, —CCl$_3$, —CBr$_3$, —CI$_3$, —CN, —OR$^{6A}$, —C(O)R$^{6A}$, —NR$^{6A}$R$^{6B}$, —C(O)OR$^{6A}$, —C(O)NR$^{6A}$R$^{6B}$, —NO$_2$, —SR$^{6A}$, —S(O)R$^{6A}$, —S(O)$_{n6}$OR$^{6A}$, —S(O)$_{n6}$NR$^{6A}$R$^{6B}$, —NHNR$^{6A}$R$^{6B}$, —ONR$^{6A}$R$^{6B}$, —NHC(O)NHNR$^{6A}$R$^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$, R$^{1B}$, R$^{2A}$, R$^{2B}$, R$^{4A}$, R$^{4B}$, R$^{5A}$, R$^{5B}$, R$^{6A}$, and R$^{6B}$ are independently hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n1, n2, n4, n5, and n6 are independently 1, 2, or 3. The symbol m1 is 0, 1, 2, 3, or 4. The symbol m2 is 0, 1, 2, 3, 4, 5, or 6. The symbol m3 is 0, 1, or 2.

Ring A may be heterocycloalkyl, aryl, or heteroaryl. Ring A may be heterocycloalkyl or aryl. Ring A may be aryl or heteroaryl. Ring A may be heterocycloalkyl or heteroaryl.

Ring A may be cycloalkyl. Ring A may be a 3 to 10 membered cycloalkyl. Ring A may be 3 to 8 membered cycloalkyl. Ring A may be 3 to 6 membered cycloalkyl. Ring A may be cyclopropanyl. Ring A may be cyclopropenyl. Ring A may be cyclobutanyl. Ring A may be cyclobutenyl. Ring A may be cyclopentanyl. Ring A may be cyclopentenyl. Ring A may be cyclohexanyl. Ring A may be cyclohexenyl. Ring A may be cyclopentanyl, cyclopentenyl, cyclohexanyl, or cyclohexenyl.

Ring A may be heterocycloalkyl or heteroaryl. Ring A may be heterocycloalkyl. Ring A may be 3 to 10 membered heterocycloalkyl. Ring A may be 3 to 8 membered heterocycloalkyl. Ring A may be 3 to 6 membered heterocycloalkyl. Ring A may be 3 membered heterocycloalkyl. Ring A may be 4 membered heterocycloalkyl. Ring A may be aziridinyl, azirinyl, oxiranyl, oxirenyl, thiiranyl, thiirenyl, azetidinyl, azetyl, oxetanyl, oxetyl, thietanyl, or thietyl.

Ring A may be 5 membered heterocycloalkyl. Ring A may be 6 membered heterocycloalkyl. Ring A may be tetrahydrofuranyl, tetrahydropyranyl, tetrahydrothiopyranyl, pyranyl, thianyl, dioxanyl, piperidinyl, piperazinyl, oxathianyl, morpholinyl, trioxanyl, pyrrolinyl, pyrrolidinyl, pyrrolidonyl, pyrrolidionyl, pyrazolidinyl, imidazolinyl, imidazolidinyl, isoxazolinyl, isoxazolidinyl, oxazolinyl, oxazolidinyl, oxazolidinonyl, or thiazolidinyl Ring A may be aryl. Ring A may be 5 to 10 membered aryl. Ring A may be 5 or 6 membered aryl. Ring A may be 5 membered aryl. Ring A may be 6 membered aryl. Ring A may be phenylene. Ring A may be heteroaryl. Ring A may be 5 to 10 membered heteroaryl. Ring A may be 5 or 6 membered heteroaryl. Ring A may be 5 membered heteroaryl. Ring A may be 6 membered heteroaryl. Ring A may be pyrroyl, furanyl, thiophenyl, imidazolyl, oxazolyl, isoxazolyl, thiazolyl, pyrazoyl, furyl, thienyl, triazolyl, tetrazolyl, pyridinyl, pyrimidinyl, pyrazinyl, or pyridazinyl.

Ring A may be a 5,6-, 6,5-, or 6,6-fused ring aryl or 5,6-, 6,5-, or 6,6-fused ring heteroaryl as described herein. Ring A may be a 5,6-fused ring aryl. Ring A may be a 5,6-fused ring heteroaryl. Ring A may be a 6,5-fused ring aryl. Ring A may be a 6,5-fused ring heteroaryl. Ring A may be 6,6-fused ring aryl. Ring A may be a 6,6-fused ring heteroaryl. Ring A may indenyl, indolyl, isoindolyl, indolizinyl, purinyl, benzothiazolyl, benzoxazoyl, benzoimidazoyl, benzofuranyl, isobenzofuranyl indazolyl, pyrrollopyridinyl, pyrrollopyrimidinyl, pyrazolopyridinyl, imidazopyridinyl, benzotriazolyl, benzothiophenyl, quinolyl, quinolinyl, isoquinolyl, naphthalenyl, cinnolinyl, phthalazinyl, isoquinolinyl, quinoxalinyl, or quinazolinyl.

The symbol m2 may be 0. The symbol m2 may be 1. The symbol m2 may be 1, 2, 3, 4, 5, or 6. The symbol m2 may be 1, 2, or 3. The symbols n1, n2, n4, n5, and n6 may independently be 1. The symbols n1, n2, n4, n5, and n6 may independently be 2. The symbols n1, n2, n4, n5, and n6 may independently be 3.

$R^1$ may be halogen, —$N_3$, —$CF_3$, —$CCl_3$, —$CBr_3$, —$CI_3$, —CN, —$OR^{1A}$, —$C(O)R^{1A}$, —$NR^{1A}R^{1B}$, —$C(O)OR^{1A}$, —$C(O)NR^{1A}R^{1B}$, —$NO_2$, —$SR^{1A}$, —$S(O)_{n1}R^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —$NHC(O)NHNR^{1A}R^{1B}$. $R^1$ may be halogen, —$N_3$, —$CF_3$, —$CCl_3$, —$CBr_3$, —$CI_3$, —CN, —$OR^{1A}$, —$C(O)R^{1A}$, —$NR^{1A}R^{1B}$, —$C(O)OR^{1A}$, —$C(O)NR^{1A}R^{1B}$, —$NO_2$, —$SR^{1A}$. $R^1$ may be halogen, —$N_3$, —$CF_3$, —$CCl_3$, —$CBr_3$, —$CI_3$, —CN, —$OR^{1A}$, —$NH_2$, —C(O)OH, —$C(O)NH_2$, —$NO_2$, or —SH. $R^1$ may be halogen, —$CF_3$, —$NO_2$, —$NH_2$, —$OR^{1A}$. $R^1$ may be halogen. $R^1$ may be F. $R^1$ may be Cl. $R^1$ may be Br. $R^1$ may be I. $R^1$ may be —$CF_3$. $R^1$ may be —$NH_2$. $R^1$ may be —$OR^{1A}$, where $R^{1A}$ is as defined herein. $R^1$ may be —$OR^{1A}$ where $R^{1A}$ is substituted or unsubstituted alkyl, substituted or unsubstituted heteroalkyl, or substituted or unsubstituted aryl. $R^1$ may be —$OR^{1A}$ where $R^{1A}$ is substituted or unsubstituted alkyl. $R^1$ may be —$OR^{1A}$ where $R^{1A}$ is unsubstituted alkyl. $R^1$ may be —$OR^{1A}$ where $R^{1A}$ is substituted $C_1$-$C_5$ alkyl. $R^1$ may be —$OR^{1A}$ where $R^{1A}$ is unsubstituted $C_1$-$C_3$ alkyl. $R^1$ may be —$OR^{1A}$ where $R^{1A}$ is methyl (e.g. —$OCH_3$). $R^1$ may be halogen, —$CF_3$, —$NO_2$, —$NH_2$, —$OR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ may be substituted or unsubstituted alkyl. $R^1$ may be substituted alkyl. $R^1$ may be unsubstituted alkyl. $R^1$ may be substituted or unsubstituted $C_1$-$C_{20}$ alkyl. $R^1$ may be substituted $C_1$-$C_{20}$ alkyl. $R^1$ may be unsubstituted $C_1$-$C_{20}$ alkyl. $R^1$ may be substituted or unsubstituted $C_1$-$C_{10}$ alkyl. $R^1$ may be substituted $C_1$-$C_{10}$ alkyl. $R^1$ may be unsubstituted $C_1$-$C_{10}$ alkyl. $R^1$ may be substituted or unsubstituted $C_1$-$C_5$ alkyl. $R^1$ may be substituted $C_1$-$C_5$ alkyl. $R^1$ may be unsubstituted $C_1$-$C_5$ alkyl. $R^1$ may be substituted or unsubstituted $C_1$-$C_3$ alkyl. $R^1$ may be substituted $C_1$-$C_3$ alkyl. $R^1$ may be unsubstituted $C_1$-$C_3$ alkyl. $R^1$ may be methyl. $R^1$ may be ethyl. $R^1$ may be propyl.

$R^1$ may be $R^{10}$-substituted or unsubstituted alkyl. $R^1$ may be $R^{10}$-substituted alkyl. $R^1$ may be $R^{10}$-substituted or unsubstituted $C_1$-$C_{20}$ alkyl. $R^1$ may be substituted $C_1$-$C_{20}$ alkyl. $R^1$ may be $R^{10}$-substituted or unsubstituted $C_1$-$C_{10}$ alkyl. $R^1$ may be $R^{10}$-substituted $C_1$-$C_{10}$ alkyl. $R^1$ may be $R^{10}$-substituted or unsubstituted $C_1$-$C_5$ alkyl. $R^1$ may be $R^{10}$-substituted $C_1$-$C_5$ alkyl. $R^1$ may be $R^{10}$-substituted or unsubstituted $C_1$-$C_3$ alkyl. $R^1$ may be $R^{10}$-substituted $C_1$-$C_3$ alkyl.

$R^1$ may be substituted or unsubstituted 2 to 20 membered heteroalkyl. $R^1$ may be substituted 2 to 20 membered heteroalkyl. $R^1$ may be unsubstituted 2 to 20 membered heteroalkyl. $R^1$ may be substituted or unsubstituted 2 to 10 membered heteroalkyl. $R^1$ may be substituted 2 to 10 membered heteroalkyl. $R^1$ may be unsubstituted 2 to 10 membered heteroalkyl. $R^1$ may be substituted or unsubstituted 2 to 6 membered heteroalkyl. $R^1$ may be substituted 2 to 6 membered heteroalkyl. $R^1$ may be unsubstituted 2 to 6 membered heteroalkyl. $R^1$ may be substituted or unsubstituted 2 to 5 membered heteroalkyl. $R^1$ may be substituted 2 to 5 membered heteroalkyl. $R^1$ may be unsubstituted 2 to 5 membered heteroalkyl.

$R^1$ may be $R^{10}$-substituted or unsubstituted 2 to 20 membered heteroalkyl. $R^1$ may be $R^{10}$-substituted 2 to 20 membered heteroalkyl. $R^1$ may be $R^{10}$-substituted or unsubstituted 2 to 10 membered heteroalkyl. $R^1$ may be $R^{10}$-substituted 2 to 10 membered heteroalkyl. $R^1$ may be $R^{10}$-substituted or unsubstituted 2 to 6 membered heteroalkyl. $R^1$ may be $R^{10}$-substituted 2 to 6 membered heteroalkyl. $R^1$ may be $R^{10}$-substituted or unsubstituted 2 to 5 membered heteroalkyl. $R^1$ may be $R^{10}$-substituted 2 to 5 membered heteroalkyl.

$R^1$ may be substituted or unsubstituted 3 to 10 membered cycloalkyl. $R^1$ may be substituted 3 to 10 membered cycloalkyl. $R^1$ may be unsubstituted 3 to 10 membered cycloalkyl. $R^1$ may be substituted or unsubstituted 3 to 6 membered cycloalkyl. $R^1$ may be substituted 3 to 6 membered cycloalkyl. $R^1$ may be unsubstituted 3 to 6 membered cycloalkyl. $R^1$ may be substituted or unsubstituted 3 to 5 membered cycloalkyl. $R^1$ may be substituted 3 to 5 membered cycloalkyl. $R^1$ may be unsubstituted 3 to 5 membered cycloalkyl. $R^1$ may be substituted or unsubstituted 3 membered cycloalkyl. $R^1$ may be substituted 3 membered cycloalkyl. $R^1$ may be unsubstituted 3 membered cycloalkyl. $R^1$ may be substituted or unsubstituted 4 membered cycloalkyl. $R^1$ may be substituted 4 membered cycloalkyl. $R^1$ may be unsubstituted 4 membered cycloalkyl. $R^1$ may be substituted or unsubstituted 5 membered cycloalkyl. $R^1$ may be substituted 5 membered cycloalkyl. $R^1$ may be unsubstituted 5 membered cycloalkyl. $R^1$ may be substituted or unsubstituted 6 membered cycloalkyl. $R^1$ may be substituted 6 membered cycloalkyl. $R^1$ may be unsubstituted 6 membered cycloalkyl.

$R^1$ may be $R^{10}$-substituted or unsubstituted 3 to 10 membered cycloalkyl. $R^1$ may be $R^{10}$-substituted 3 to 10 membered cycloalkyl. $R^1$ may be $R^{10}$-substituted or unsubstituted 3 to 6 membered cycloalkyl. $R^1$ may be $R^{10}$-substituted 3 to 6 membered cycloalkyl. $R^1$ may be $R^{10}$-substituted or unsubstituted 3 to 5 membered cycloalkyl. $R^1$ may be $R^{10}$-substituted 3 to 5 membered cycloalkyl. $R^1$ may be $R^{10}$-substituted or unsubstituted 3 membered cycloalkyl. $R^1$ may be $R^{10}$-substituted 3 membered cycloalkyl. $R^1$ may be $R^{10}$-substituted or unsubstituted 4 membered cycloalkyl. $R^1$ may be $R^{10}$-substituted 4 membered cycloalkyl. $R^1$ may be $R^{10}$-substituted or unsubstituted 5 membered cycloalkyl. $R^1$ may be $R^{10}$-substituted 5 membered cycloalkyl. $R^1$ may be $R^{10}$-substituted or unsubstituted 6 membered cycloalkyl. $R^1$ may be $R^{10}$-substituted 6 membered cycloalkyl.

$R^1$ may be substituted or unsubstituted 3 to 10 membered heterocycloalkyl. $R^1$ may be substituted 3 to 10 membered heterocycloalkyl. $R^1$ may be unsubstituted 3 to 10 membered heterocycloalkyl. $R^1$ may be substituted or unsubstituted 3 to 6 membered heterocycloalkyl. $R^1$ may be substituted 3 to 6 membered heterocycloalkyl. $R^1$ may be unsubstituted 3 to 6 membered heterocycloalkyl. $R^1$ may be substituted or unsubstituted 3 to 5 membered heterocycloalkyl. $R^1$ may be substituted 3 to 5 membered heterocycloalkyl. $R^1$ may be unsubstituted 3 to 5 membered heterocycloalkyl. $R^1$ may be substituted or unsubstituted 3 membered heterocycloalkyl. $R^1$ may be substituted 3 membered heterocycloalkyl. $R^1$ may be unsubstituted 3 membered heterocycloalkyl. $R^1$ may be substituted or unsubstituted 4 membered heterocycloalkyl. $R^1$ may be substituted 4 membered heterocycloalkyl. $R^1$ may be unsubstituted 4 membered heterocycloalkyl. $R^1$ may be substituted or unsubstituted 5 membered heterocycloalkyl. $R^1$ may be substituted 5 membered heterocycloalkyl. $R^1$ may be unsubstituted 5 membered heterocycloalkyl. $R^1$ may be substituted or unsubstituted 6 membered heterocycloalkyl. $R^1$ may be substituted 6 membered heterocycloalkyl. $R^1$ may be unsubstituted 6 membered heterocycloalkyl.

$R^1$ may be $R^{10}$-substituted or unsubstituted 3 to 10 membered heterocycloalkyl. $R^1$ may be $R^{10}$-substituted 3 to 10 membered heterocycloalkyl. $R^1$ may be $R^{10}$-substituted or unsubstituted 3 to 6 membered heterocycloalkyl. $R^1$ may be $R^{10}$-substituted 3 to 6 membered heterocycloalkyl. $R^1$ may be $R^{10}$-substituted or unsubstituted 3 to 5 membered heterocycloalkyl. $R^1$ may be $R^{10}$-substituted 3 to 5 membered heterocycloalkyl. $R^1$ may be $R^{10}$-substituted or unsubstituted 3 membered heterocycloalkyl. $R^1$ may be $R^{10}$-substituted 3 membered heterocycloalkyl. $R^1$ may be $R^{10}$-substituted or unsubstituted 4 membered heterocycloalkyl. $R^1$ may be $R^{10}$-substituted 4 membered heterocycloalkyl. $R^1$ may be $R^{10}$-substituted or unsubstituted 5 membered heterocycloalkyl. $R^1$ may be $R^{10}$-substituted 5 membered heterocycloalkyl. $R^1$ may be $R^{10}$-substituted or unsubstituted 6 membered heterocycloalkyl. $R^1$ may be $R^{10}$-substituted 6 membered heterocycloalkyl.

$R^1$ may be substituted or unsubstituted aryl. $R^1$ may be substituted aryl. $R^1$ may be unsubstituted aryl. $R^1$ may be substituted or unsubstituted 5 to 10 membered aryl. $R^1$ may be substituted 5 to 10 membered aryl. $R^1$ may be unsubstituted 5 to 10 membered aryl. $R^1$ may be substituted or unsubstituted 5 or 6 membered aryl. $R^1$ may be substituted 5 or 6 membered aryl. $R^1$ may be unsubstituted 5 or 6 membered aryl. $R^1$ may be substituted or unsubstituted 5 membered aryl. $R^1$ may be substituted 5 membered aryl. $R^1$ may be unsubstituted 5 membered aryl. $R^1$ may be substituted or unsubstituted 6 membered aryl. $R^1$ may be substituted 6 membered aryl. $R^1$ may be unsubstituted 6 membered aryl.

$R^1$ may be $R^{10}$-substituted or unsubstituted aryl. $R^1$ may be $R^{10}$-substituted aryl. $R^1$ may be $R^{10}$-substituted or unsubstituted 5 to 10 membered aryl. $R^1$ may be $R^{10}$-substituted 5 to 10 membered aryl. $R^1$ may be $R^{10}$-substituted or unsubstituted 5 or 6 membered aryl. $R^1$ may be $R^{10}$-substituted 5 or 6 membered aryl. $R^1$ may be $R^{10}$-substituted or unsubstituted 5 membered aryl. $R^1$ may be $R^{10}$-substituted 5 membered aryl. $R^1$ may be $R^{10}$-substituted or unsubstituted 6 membered aryl. $R^1$ may be $R^{10}$-substituted 6 membered aryl.

$R^1$ may be substituted or unsubstituted heteroaryl. $R^1$ may be substituted heteroaryl. $R^1$ may be unsubstituted heteroaryl. $R^1$ may be substituted or unsubstituted 5 to 10 membered heteroaryl. $R^1$ may be substituted 5 to 10 membered heteroaryl. $R^1$ may be unsubstituted 5 to 10 membered heteroaryl. $R^1$ may be substituted or unsubstituted 5 or 6 membered heteroaryl. $R^1$ may be substituted 5 or 6 membered heteroaryl. $R^1$ may be unsubstituted 5 or 6 membered heteroaryl. $R^1$ may be substituted or unsubstituted 5 membered heteroaryl. $R^1$ may be substituted 5 membered heteroaryl. $R^1$ may be unsubstituted 5 membered heteroaryl. $R^1$ may be substituted or unsubstituted 6 membered heteroaryl. $R^1$ may be substituted 6 membered heteroaryl. $R^1$ may be unsubstituted 6 membered heteroaryl.

$R^1$ may be $R^{10}$-substituted or unsubstituted heteroaryl. $R^1$ may be $R^{10}$-substituted heteroaryl. $R^1$ may be $R^{10}$-substituted or unsubstituted 5 to 10 membered heteroaryl. $R^1$ may be $R^{10}$-substituted 5 to 10 membered heteroaryl. $R^1$ may be $R^{10}$-substituted or unsubstituted 5 or 6 membered heteroaryl. $R^1$ may be $R^{10}$-substituted 5 or 6 membered heteroaryl. $R^1$ may be $R^{10}$-substituted or unsubstituted 5 membered heteroaryl. $R^1$ may be $R^{10}$-substituted 5 membered heteroaryl. $R^1$ may be $R^{10}$-substituted or unsubstituted 6 membered heteroaryl. $R^1$ may be $R^{10}$-substituted 6 membered heteroaryl.

$R^{10}$ is hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, $R^{11}$-substituted or unsubstituted (e.g. $C_1$-$C_5$) alkyl, $R^{11}$-substituted or unsubstituted (e.g. 2 to 5 membered) heteroalkyl, $R^{11}$-substituted or unsubstituted (e.g. $C_3$-$C_8$) cycloalkyl, $R^{11}$-substituted or unsubstituted (e.g. 3 to 8 membered) heterocycloalkyl, $R^{11}$-substituted or unsubstituted aryl (e.g. phenyl or naphthyl), or $R^1$-substituted or unsubstituted (e.g. 5 or 6 membered or fused ring) heteroaryl. $R^{10}$ may be hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, substituted or unsubstituted (e.g. $C_1$-$C_5$) alkyl, substituted or unsubstituted (e.g. 2 to 5 membered) heteroalkyl, substituted or unsubstituted (e.g. $C_3$-$C_8$) cycloalkyl, substituted or unsubstituted (e.g. 3 to 8 membered) heterocycloalkyl, substituted or unsubstituted aryl (e.g. phenyl or naphthyl), or substituted or unsubstituted (e.g. 5 or 6 membered or fused ring) heteroaryl. $R^{10}$ may be hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^{11}$ is hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, $R^{12}$-substituted or unsubstituted (e.g. $C_1$-$C_5$) alkyl, $R^{12}$-substituted or unsubstituted (e.g. 2 to 5 membered) heteroalkyl, $R^{12}$-substituted or unsubstituted (e.g. $C_3$-$C_8$) cycloalkyl, $R^{12}$-substituted or unsubstituted (e.g. 3 to 8 membered) heterocycloalkyl, $R^{12}$-substituted or unsubstituted aryl (e.g. phenyl or naphthyl), or $R^{12}$-substituted or unsubstituted (e.g. 5 or 6 membered or fused ring) heteroaryl.

$R^{12}$ is hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, $R^{13}$-substituted or unsubstituted (e.g. $C_1$-$C_5$) alkyl, $R^{13}$-substituted or unsubstituted (e.g. 2 to 5 membered) heteroalkyl, $R^{13}$-substituted or unsubstituted (e.g. $C_3$-$C_8$) cycloalkyl, $R^{13}$-substituted or unsubstituted (e.g. 3 to 8 membered) heterocycloalkyl, $R^{13}$-substituted or unsubstituted aryl (e.g. phenyl or naphthyl), or $R^{13}$-substituted or unsubstituted (e.g. 5 or 6 membered or fused ring) heteroaryl.

$R^{13}$ is hydrogen, halogen, oxo, $—N_3$, $—CF_3$, $—CCl_3$, $—CBr_3$, $—CI_3$, $—CN$, $—C(O)H$, $—OCH_3$, $—OCH_2CH_3$, $—NH_2$, $—COOH$, $—CONH_2$, $—NO_2$, $—SH$, $—S(O)_2H$, $—NHNH_2$, $—ONH_2$, $—NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

The symbol m1 may be 0, 1, 2, or 3. The symbol m1 may be 0. The symbol m1 may be 1. The symbol m1 may be 2. The symbol m1 may be 3. The symbol m1 may be 1, 2, or 3. When $R^1$ is halogen, the symbol m1 may be 1. When $R^1$ is —$CF_3$ the symbol m1 may be 1, 2, or 3. $R^1$ may independently be halogen or —$CF_3$ and the symbol m1 is 2 or 3. When $R^1$ is —$OR^{1A}$, the symbol m1 may be 1, 2, or 3. When $R^1$ is —$OCH_3$ the symbol m1 may be 1, 2, or 3. When $R^1$ is —$OCH_3$ the symbol m1 may be 1. When $R^1$ is —$OCH_3$ the symbol m1 may be 2. When $R^1$ is —$OCH_3$ the symbol m1 may be 3.

$R^{1A}$ and $R^{1B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —$NHC(O)NHNH_2$, $R^{10}$-substituted or unsubstituted (e.g. $C_1$-$C_5$) alkyl, $R^{10}$-substituted or unsubstituted (e.g. 2 to 5 membered) heteroalkyl, $R^{10}$-substituted or unsubstituted (e.g. $C_3$-$C_8$) cycloalkyl, $R^{10}$-substituted or unsubstituted (e.g. 3 to 8 membered) heterocycloalkyl, $R^{10}$-substituted or unsubstituted aryl (e.g. phenyl or naphthyl), or $R^{10}$-substituted or unsubstituted (e.g. 5 or 6 membered or fused ring) heteroaryl.

$R^{1A}$ and $R^{1B}$ may independently be hydrogen, oxo, halogen, —$CF_3$, —CN, —OH, —$NH_2$, —COOH, —$CONH_2$, —$NO_2$, —SH, —$S(O)_3H$, or —$ONH_2$. $R^{1A}$ and $R^{1B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ may independently be $R^{1C}$-substituted or unsubstituted (e.g. $C_1$-$C_5$) alkyl, $R^{1C}$-substituted or unsubstituted (e.g. 2 to 5 membered) heteroalkyl, $R^{1C}$-substituted or unsubstituted (e.g. $C_3$-$C_8$) cycloalkyl, $R^{1C}$-substituted or unsubstituted (e.g. 3 to 8 membered) heterocycloalkyl, $R^{1C}$-substituted or unsubstituted aryl (e.g. phenyl or naphthyl), or $R^{1C}$-substituted or unsubstituted (e.g. 5 or 6 membered or fused ring) heteroaryl.

$R^{1C}$ is hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —$NHC(O)H$, —$NHC(O)$—OH, —NHOH, —$OCF_3$, —$OCHF_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^2$ may be halogen, —$N_3$, —$CF_3$, —$CCl_3$, —$CBr_3$, —$CI_3$, —CN, —$OR^{2A}$, —$C(O)R^{2A}$, —$NR^{2A}R^{2B}$, —$C(O)OR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, or —$NHC(O)NHNR^{2A}R^{2B}$. $R^2$ may be halogen, —$N_3$, —$CF_3$, —$CCl_3$, —$CBr_3$, —$CI_3$, —CN, —$OR^{2A}$, —$NR^{2A}R^{2B}$, —$NO_2$, or —$SR^{2A}$. $R^2$ may be halogen, —$N_3$, —$CF_3$, —$CCl_3$, —$CBr_3$, —$CI_3$, —CN, —$OR^{2A}$, —$C(O)R^{2A}$, —$NR^{2A}R^{2B}$, —$C(O)OH$, —$NO_2$, or —SH. $R^2$ may be halogen, —$CF_3$, —$CCl_3$, —$CBr_3$, —$CI_3$, —$OR^{2A}$, —$NH_2$, —$N(CH_3)_2$—$NO_2$. $R^2$ may be halogen, —$CF_3$, —$OR^{2A}$, or —$NO_2$. $R^2$ may be halogen. $R^2$ may be —$CF_3$. $R^2$ may be —$OR^{2A}$. $R^2$ may be —$NO_2$. $R^2$ may be —$OR^{2A}$, where $R^{2A}$ is substituted or unsubstituted alkyl, substituted or unsubstituted heteroalkyl, or substituted or unsubstituted aryl. $R^2$ may be —$OR^{2A}$, where $R^{2A}$ is substituted or unsubstituted alkyl. $R^2$ may be —$OR^{2A}$, where $R^{2A}$ is substituted or unsubstituted $C_1$-$C_5$ alkyl. $R^2$ may be —$OR^{2A}$, where $R^{2A}$ is substituted or unsubstituted $C_1$-$C_3$ alkyl. $R^2$ may be —$OR^{2A}$, where $R^{2A}$ is methyl. $R^2$ may be halogen, —$CF_3$, —$OR^{2A}$, —$NO_2$, substituted or unsubstituted $C_1$-$C_5$ alkyl, or substituted or unsubstituted 2 to 5 membered heteroalkyl.

$R^2$ may be substituted or unsubstituted $C_1$-$C_5$ alkyl, or substituted or unsubstituted 2 to 5 membered heteroalkyl. $R^2$ may be substituted or unsubstituted $C_1$-$C_5$ alkyl. $R^2$ may be substituted $C_1$-$C_5$ alkyl. $R^2$ may be unsubstituted $C_1$-$C_5$ alkyl. $R^2$ may be substituted or unsubstituted $C_1$-$C_3$ alkyl. $R^2$ may be substituted $C_1$-$C_3$ alkyl. $R^2$ may be unsubstituted $C_1$-$C_3$ alkyl. $R^2$ may be methyl. $R^2$ may be ethyl. $R^2$ may be propyl.

$R^2$ may be $R^{20}$-substituted or unsubstituted $C_1$-$C_5$ alkyl. $R^2$ may be $R^{20}$-substituted or unsubstituted $C_1$-$C_5$ alkyl. $R^2$ may be $R^{20}$-substituted $C_1$-$C_5$ alkyl. $R^2$ may be $R^{20}$-substituted or unsubstituted $C_1$-$C_3$ alkyl. $R^2$ may be $R^{20}$-substituted $C_1$-$C_3$ alkyl.

$R^2$ may be substituted or unsubstituted 2 to 5 membered heteroalkyl. $R^2$ may be substituted 2 to 5 membered heteroalkyl. $R^2$ may be unsubstituted 2 to 5 membered heteroalkyl. $R^2$ may be $R^{20}$-substituted or unsubstituted 2 to 5 membered heteroalkyl. $R^2$ may be $R^{20}$-substituted 2 to 5 membered heteroalkyl.

$R^{20}$ is hydrogen, halogen, oxo, —$N_3$, —$CF_3$, —$CCl_3$, —$CBr_3$, —$CI_3$, —CN, —$C(O)H$, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^{2A}$ and $R^{2B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —$NHC(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ and $R^{2B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —$NHC(O)NHNH_2$, $R^{20}$-substituted or unsubstituted (e.g. $C_1$-$C_5$) alkyl, $R^{20}$-substituted or unsubstituted (e.g. 2 to 5 membered) heteroalkyl, $R^{20}$-substituted or unsubstituted (e.g. $C_3$-$C_8$) cycloalkyl, $R^{20}$-substituted or unsubstituted (e.g. 3 to 8 membered) heterocycloalkyl, $R^{20}$-substituted or unsubstituted aryl (e.g. phenyl or naphthyl), or $R^{20}$-substituted or unsubstituted (e.g. 5 or 6 membered or fused ring) heteroaryl.

$R^{2A}$ and $R^{2B}$ may independently be hydrogen, oxo, halogen, —$CF_3$, —CN, —OH, —$NH_2$, —COOH, —$CONH_2$, —$NO_2$, —SH, —$S(O)_3H$, or —$ONH_2$. $R^{2A}$ and $R^{2B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ and $R^{2B}$ may independently be $R^{2C}$-substituted or unsubstituted (e.g. $C_1$-$C_5$) alkyl, $R^{2C}$-substituted or unsubstituted (e.g. 2 to 5 membered) heteroalkyl, $R^{2C}$-substituted or unsubstituted (e.g. $C_3$-$C_8$) cycloalkyl, $R^{2C}$-substituted or unsubstituted (e.g. 3 to 8 membered) heterocycloalkyl, $R^{2C}$-substituted or unsubstituted aryl (e.g. phenyl or naphthyl), or $R^{2C}$-substituted or unsubstituted (e.g. 5 or 6 membered or fused ring) heteroaryl.

$R^{2C}$ is hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —$OCHF_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^3$ may be hydrogen, halogen, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, or —$NHC(O)NHNH_2$. $R^3$ may be hydrogen, halogen, —$N_3$, —$CF_3$, —$CCl_3$, —$CBr_3$, —$CI_3$, —CN, —$OCH_3$, —$OCH_2CH_3$, —$NH_2$, —COOH, —$CONH_2$, —$NO_2$, —SH, —$S(O)_2H$, —$NHNH_2$, or —$ONH_2$. $R^3$ may be hydrogen, halogen, —$N_3$, —$CF_3$, —$CCl_3$, —$CBr_3$, —$CI_3$, —CN, —$OCH_3$, —$OCH_2CH_3$, —$NH_2$, —COOH, —$CONH_2$, —$NO_2$, or —SH. $R^3$ may be hydrogen, halogen, —$N_3$, —$CF_3$, —$CCl_3$, —$CBr_3$, —$CI_3$, —CN, —$OCH_3$, —$OCH_2CH_3$, —$NH_2$, or —$NO_2$. $R^3$ may be hydrogen, halogen, or —$OR^{3A}$. $R^3$ may be hydrogen, halogen, —$CF_3$, —$OCH_3$, —$OCH_2CH_3$, —$NH_2$, or —$NO_2$. $R^3$ may be halogen. $R^3$ may be hydrogen. $R^3$ may be —$CF_3$. $R^3$ may be —$OCH_3$. $R^3$ may be —$OCH_2CH_3$. $R^3$ may be —$NH_2$. $R^3$ may be —$NO_2$.

$R^3$ may be substituted or unsubstituted $C_1$-$C_5$ alkyl, or substituted or unsubstituted 2 to 5 membered heteroalkyl. $R^3$ may be substituted or unsubstituted $C_1$-$C_5$ alkyl. $R^3$ may be substituted $C_1$-$C_5$ alkyl. $R^3$ may be unsubstituted $C_1$-$C_5$ alkyl. $R^3$ may be substituted or unsubstituted $C_1$-$C_3$ alkyl. $R^3$ may be substituted $C_1$-$C_3$ alkyl. $R^3$ may be unsubstituted $C_1$-$C_3$ alkyl. $R^3$ may be methyl. $R^3$ may be ethyl. $R^3$ may be propyl.

$R^3$ may be $R^{30}$-substituted or unsubstituted $C_1$-$C_5$ alkyl. $R^3$ may be $R^{30}$-substituted or unsubstituted $C_1$-$C_5$ alkyl. $R^3$ may be $R^{30}$-substituted $C_1$-$C_5$ alkyl. $R^3$ may be $R^{30}$-substituted or unsubstituted $C_1$-$C_3$ alkyl. $R^3$ may be $R^{30}$-substituted $C_1$-$C_3$ alkyl.

$R^3$ may be substituted or unsubstituted 2 to 5 membered heteroalkyl. $R^3$ may be substituted 2 to 5 membered heteroalkyl. $R^3$ may be unsubstituted 2 to 5 membered heteroalkyl. $R^3$ may be $R^{30}$-substituted or unsubstituted 2 to 5 membered heteroalkyl. $R^3$ may be $R^{30}$-substituted 2 to 5 membered heteroalkyl.

$R^{30}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

The symbol m3 may be 1. The symbol m3 may be 2. When $R^3$ is halogen, the symbol m3 may be 1. When $R^3$ is —$CF_3$, the symbol m3 may be 1. When $R^3$ is —$OCH_3$ or —$OCH_2CH_3$, the symbol m3 may be 1. When $R^3$ is —$OCH_3$ or —$OCH_2CH_3$, the symbol m3 may be 2. $R^3$ may independently be halogen and —$OCH_3$ and the symbol m3 is 2.

X may be —$C(R^4)$=. X may be —N=.

When X is —$C(R^4)$=, $R^4$ may be hydrogen, halogen, —$N_3$, —$CF_3$, —$CCl_3$, —$CBr_3$, —$CI_3$, —CN, —$OR^{4A}$, —$C(O)R^{4A}$, —$NR^{4A}R^{4B}$, —$C(O)OR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_{n4}NR^{4A}R^{4B}$, —$NHNR^{4A}R^{4B}$, —$ONR^{4A}R^{4B}$, or —NHC(O)$NHNR^{4A}R^4$. $R^4$ may be hydrogen, halogen, —$OR^{4A}$, or —$C(O)R^{4A}$. $R^4$ may be hydrogen or halogen. $R^4$ may be hydrogen. $R^4$ may be halogen.

$R^4$ may be substituted or unsubstituted $C_1$-$C_5$ alkyl, or substituted or unsubstituted 2 to 5 membered heteroalkyl. $R^4$ may be substituted or unsubstituted $C_1$-$C_5$ alkyl. $R^4$ may be substituted $C_1$-$C_5$ alkyl. $R^4$ may be unsubstituted $C_1$-$C_5$ alkyl. $R^4$ may be substituted or unsubstituted $C_1$-$C_3$ alkyl. $R^4$ may be substituted $C_1$-$C_3$ alkyl. $R^4$ may be unsubstituted $C_1$-$C_3$ alkyl. $R^4$ may be methyl. $R^4$ may be ethyl. $R^4$ may be propyl.

$R^4$ may be $R^{40}$-substituted or unsubstituted $C_1$-$C_5$ alkyl. $R^4$ may be $R^{40}$-substituted or unsubstituted $C_1$-$C_5$ alkyl. $R^4$ may be $R^{40}$-substituted $C_1$-$C_5$ alkyl. $R^4$ may be $R^{40}$-substituted or unsubstituted $C_1$-$C_3$ alkyl. $R^4$ may be $R^{40}$-substituted $C_1$-$C_3$ alkyl.

$R^4$ may be substituted or unsubstituted 2 to 5 membered heteroalkyl. $R^4$ may be substituted 2 to 5 membered heteroalkyl. $R^4$ may be unsubstituted 2 to 5 membered heteroalkyl. $R^4$ may be $R^{40}$-substituted or unsubstituted 2 to 5 membered heteroalkyl. $R^4$ may be $R^{40}$-substituted 2 to 5 membered heteroalkyl.

$R^{40}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl. $R^{4A}$ and $R^{4B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —$NHC(O)NHNH_2$, $R^{40}$-substituted or unsubstituted (e.g. $C_1$-$C_5$) alkyl, $R^{40}$-substituted or unsubstituted (e.g. 2 to 5 membered) heteroalkyl, $R^{40}$-substituted or unsubstituted (e.g. $C_3$-$C_8$) cycloalkyl, $R^{40}$-substituted or unsubstituted (e.g. 3 to 8 membered) heterocycloalkyl, $R^{40}$-substituted or unsubstituted aryl (e.g. phenyl or naphthyl), or $R^{40}$-substituted or unsubstituted (e.g. 5 or 6 membered or fused ring) heteroaryl.

$R^{4A}$ and $R^{4B}$ may independently be hydrogen, oxo, halogen, —$CF_3$, —CN, —OH, —$NH_2$, —COOH, —$CONH_2$, —$NO_2$, —SH, —$S(O)_3H$, or —$ONH_2$. $R^{4A}$ and $R^{4B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{4A}$ and $R^{4B}$ may independently be $R^{4C}$-substituted or unsubstituted (e.g. $C_1$-$C_5$) alkyl, $R^{4C}$-substituted or unsubstituted (e.g. 2 to 5 membered) heteroalkyl, $R^{4C}$-substituted or unsubstituted (e.g. $C_3$-$C_8$) cycloalkyl, $R^{4C}$-substituted or unsubstituted (e.g. 3 to 8 membered) heterocycloalkyl, $R^{4C}$-substituted or unsubstituted aryl (e.g. phenyl or naphthyl), or $R^{4C}$-substituted or unsubstituted (e.g. 5 or 6 membered or fused ring) heteroaryl.

$R^{4C}$ is hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —$NHC(O)NHNH_2$, —$NHC(O)NH_2$, —$NHS(O)_2H$, —NHC(O)H, —NHC(O)—OH, —NHOH, —$OCF_3$, —OCHF$_2$, unsubstituted (e.g. C$_1$-C$_5$) alkyl, unsubstituted (e.g. 2 to 5 membered) heteroalkyl, unsubstituted (e.g. C$_3$-C$_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

Y may be a bond or —N(R$^5$)—. Y may be a bond or —O—. Y may be a bond or —S—. Y may be a bond, —N(R$^5$)—, or —S—. Y may be a bond. Y may be —O—. Y may be —S—. Y may be —N(R$^5$)—.

When Y is —N(R$^5$)—, R$^5$ may be hydrogen, halogen, —N$_3$, —CF$_3$, —CCl$_3$, —CBr$_3$, —CI$_3$, —CN, —OR$^{5A}$, —C(O)R$^{5A}$, —NR$^{5A}$R$^{5B}$, —C(O)OR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, or —NHC(O)NHNR$^{5A}$R$^{5B}$. R$^5$ may be hydrogen, halogen, —N$_3$, —CF$_3$, —CCl$_3$, —CBr$_3$, —CI$_3$, —CN, —OR$^{5A}$, —NR$^{5A}$R$^{5B}$, —C(O)OR$^{5A}$, —C(O)NR$^{5A}$R$^{5B}$, —NO$_2$, or —SR$^{5A}$. R$^5$ may be hydrogen, halogen, —N$_3$, —CF$_3$, —CCl$_3$, —CBr$_3$, —CI$_3$, —CN, —OR$^{5A}$, —NR$^{5A}$R$^{5B}$, —C(O)OR$^{5A}$, —NO$_2$, or —SR$^{5A}$. R$^5$ may be hydrogen, halogen, —CF$_3$, —CN, —OR$^{5A}$, —NR$^{5A}$R$^{5B}$, —NO$_2$, or —SR$^{5A}$. R$^5$ may be hydrogen, halogen, —CF$_3$, —CN, —OR$^{5A}$, —NH$_2$, —NO$_2$, or —SH. R$^5$ may be hydrogen. R$^5$ may be halogen. R$^5$ may be —CF$_3$. R$^5$ may be —CN. R$^5$ may be —OR$^{5A}$. R$^5$ may be —NR$^{5A}$R$^{5B}$. R$^5$ may be, —NO$_2$. R$^5$ may be —SR$^{5A}$.

R$^5$ may be substituted or unsubstituted C$_1$-C$_5$ alkyl, or substituted or unsubstituted 2 to 5 membered heteroalkyl. R$^5$ may be substituted or unsubstituted C$_1$-C$_5$ alkyl. R$^5$ may be substituted C$_1$-C$_5$ alkyl. R$^5$ may be unsubstituted C$_1$-C$_5$ alkyl. R$^5$ may be substituted or unsubstituted C$_1$-C$_3$ alkyl. R$^5$ may be substituted C$_1$-C$_3$ alkyl. R$^5$ may be unsubstituted C$_1$-C$_3$ alkyl. R$^5$ may be methyl. R$^5$ may be ethyl. R$^5$ may be propyl.

R$^5$ may be R$^{50}$-substituted or unsubstituted C$_1$-C$_5$ alkyl. R$^5$ may be R$^{50}$-substituted or unsubstituted C$_1$-C$_5$ alkyl. R$^5$ may be R$^{50}$-substituted C$_1$-C$_5$ alkyl. R$^5$ may be R$^{50}$-substituted or unsubstituted C$_1$-C$_3$ alkyl. R$^5$ may be R$^{50}$-substituted C$_1$-C$_3$ alkyl.

R$^5$ may be substituted or unsubstituted 2 to 5 membered heteroalkyl. R$^5$ may be substituted 2 to 5 membered heteroalkyl. R$^5$ may be unsubstituted 2 to 5 membered heteroalkyl. R$^5$ may be R$^{50}$-substituted or unsubstituted 2 to 5 membered heteroalkyl. R$^5$ may be R$^5$-substituted 2 to 5 membered heteroalkyl.

R$^{50}$ is hydrogen, halogen, oxo, —N$_3$, —CF$_3$, —CCl$_3$, —CBr$_3$, —CI$_3$, —CN, —C(O)H, —OCH$_3$, —OCH$_2$CH$_3$, —NH$_2$, —COOH, —CONH$_2$, —NO$_2$, —SH, —S(O)$_2$H, —NHNH$_2$, —ONH$_2$, —NHC(O)NHNH$_2$, unsubstituted (e.g. C$_1$-C$_5$) alkyl, unsubstituted (e.g. 2 to 5 membered) heteroalkyl, unsubstituted (e.g. C$_3$-C$_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

R$^{5A}$ and R$^{5B}$ may independently be hydrogen, oxo, halogen, —CF$_3$, —CN, —OH, —NH$_2$, —COOH, —CONH$_2$, —NO$_2$, —SH, —S(O)$_3$H, or —ONH$_2$. R$^{5A}$ and R$^{5B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{5A}$ and R$^{5B}$ may independently be hydrogen, oxo, halogen, —CF$_3$, —CN, —OH, —NH$_2$, —COOH, —CONH$_2$, —NO$_2$, —SH, —S(O)$_3$H, —ONH$_2$, —NHC(O)NHNH$_2$, R$^{50}$-substituted or unsubstituted (e.g. C$_1$-C$_5$) alkyl, R$^{50}$-substituted or unsubstituted (e.g. 2 to 5 membered) heteroalkyl, R$^{50}$-substituted or unsubstituted (e.g. C$_3$-C$_8$) cycloalkyl, R$^{50}$-substituted or unsubstituted (e.g. 3 to 8 membered) heterocycloalkyl, R$^5$-substituted or unsubstituted aryl (e.g. phenyl or naphthyl), or R$^{50}$-substituted or unsubstituted (e.g. 5 or 6 membered or fused ring) heteroaryl.

R$^{5A}$ and R$^{5B}$ may independently be R$^{5C}$-substituted or unsubstituted (e.g. C$_1$-C$_5$) alkyl, R$^{5C}$-substituted or unsubstituted (e.g. 2 to 5 membered) heteroalkyl, R$^{5C}$-substituted or unsubstituted (e.g. C$_3$-C$_8$) cycloalkyl, R$^{5C}$-substituted or unsubstituted (e.g. 3 to 8 membered) heterocycloalkyl, R$^{5C}$-substituted or unsubstituted aryl (e.g. phenyl or naphthyl), or R$^{5C}$-substituted or unsubstituted (e.g. 5 or 6 membered or fused ring) heteroaryl.

R$^{5C}$ is hydrogen, oxo, halogen, —CF$_3$, —CN, —OH, —NH$_2$, —COOH, —CONH$_2$, —NO$_2$, —SH, —S(O)$_2$Cl, —S(O)$_3$H, —S(O)$_4$H, —S(O)$_2$NH$_2$, —NHNH$_2$, —ONH$_2$, —NHC(O)NHNH$_2$, —NHC(O)NH$_2$, —NHS(O)$_2$H, —NHC(O)H, —NHC(O)—OH, —NHOH, —OCF$_3$, —OCHF$_2$, unsubstituted (e.g. C$_1$-C$_5$) alkyl, unsubstituted (e.g. 2 to 5 membered) heteroalkyl, unsubstituted (e.g. C$_3$-C$_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

L$^1$ may be a bond, —C(O)—, —O—, —S—, —N(R$^6$)—, —C(O)N(R$^6$)—, —S(O)$_{n6}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. L$^1$ may be a bond, —C(O)—, —O—, —S—, —NH—, —C(O)NH—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. L$^1$ may be a bond, —C(O)—, —O—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

L$^1$ may be a bond, —C(O)—, —O—, —S—, —N(R$^6$)—, —C(O)N(R$^6$)—, or —S(O)$_{n6}$—. L$^1$ may be a bond, —C(O)—, —O—, —S—, —NH—, —C(O)NH—, or —S(O)$_2$—. L$^1$ may be a bond. L$^1$ may be —C(O). L$^1$ may be —O—. L$^1$ may be —S—. L$^1$ may —N(R$^6$)—. L$^1$ may be —C(O)N(R$^6$). L$^1$ may be —S(O)$_{n6}$—.

L$^1$ may be substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

L$^1$ may be substituted or unsubstituted alkylene. L$^1$ may be substituted alkylene. L$^1$ may be unsubstituted alkylene. L$^1$ may be substituted or unsubstituted C$_1$-C$_{20}$ alkylene. L$^1$ may be substituted C$_1$-C$_{20}$ alkylene. L$^1$ may be substituted or unsubstituted C$_1$-C$_{10}$ alkylene. L$^1$ may be substituted C$_1$-C$_{10}$ alkylene. L$^1$ may be unsubstituted C$_1$-C$_{10}$ alkylene. L$^1$ may be substituted or unsubstituted C$_1$-C$_5$ alkylene. L$^1$ may be substituted C$_1$-C$_5$ alkylene. L$^1$ may be unsubstituted C$_1$-C$_5$ alkylene.

L$^1$ may be R$^{14}$-substituted or unsubstituted alkylene. L$^1$ may be R$^{14}$-substituted alkylene. L$^1$ may be R$^{14}$-substituted or unsubstituted C$_1$-C$_{20}$ alkylene. L$^1$ may be R$^{14}$-substituted C$_1$-C$_{20}$ alkylene. L$^1$ may be R$^{14}$-substituted or unsubstituted C$_1$-C$_{10}$ alkylene. L$^1$ may be R$^{14}$-substituted C$_1$-C$_{10}$ alkylene.

$L^1$ may be $R^{14}$-substituted or unsubstituted $C_1$-$C_5$ alkylene. $L^1$ may be $R^{14}$-substituted $C_1$-$C_5$ alkylene.

$L^1$ may be substituted or unsubstituted heteroalkylene. $L^1$ may be substituted heteroalkylene. $L^1$ may be unsubstituted heteroalkylene. $L^1$ may be substituted or unsubstituted 2 to 20 membered heteroalkylene. $L^1$ may be substituted 2 to 20 membered heteroalkylene. $L^1$ may be unsubstituted 2 to 20 membered heteroalkylene. $L^1$ may be substituted or unsubstituted 2 to 10 membered heteroalkylene. $L^1$ may be substituted 2 to 10 membered heteroalkylene. $L^1$ may be unsubstituted 2 to 10 membered heteroalkylene. $L^1$ may be substituted or unsubstituted 2 to 5 membered heteroalkylene. $L^1$ may be substituted 2 to 5 membered heteroalkylene. $L^1$ may be unsubstituted 2 to 5 membered heteroalkylene.

$L^1$ may be $R^{14}$-substituted or unsubstituted heteroalkylene. $L^1$ may be $R^{14}$-substituted heteroalkylene. $L^1$ may be $R^{14}$-substituted or unsubstituted 2 to 20 membered heteroalkylene. $L^1$ may be $R^{14}$-substituted 2 to 20 membered heteroalkylene. $L^1$ may be $R^{14}$-substituted or unsubstituted 2 to 10 membered heteroalkylene. $L^1$ may be $R^{14}$-substituted 2 to 10 membered heteroalkylene. $L^1$ may be $R^{14}$-substituted or unsubstituted 2 to 5 membered heteroalkylene. $L^1$ may be $R^{14}$-substituted 2 to 5 membered heteroalkylene.

$L^1$ may be substituted or unsubstituted cycloalkylene. $L^1$ may be substituted cycloalkylene. $L^1$ may be unsubstituted cycloalkylene. $L^1$ may be substituted or unsubstituted 3 to 10 membered cycloalkylene. $L^1$ may be substituted 3 to 10 membered cycloalkylene. $L^1$ may be unsubstituted 3 to 10 membered cycloalkylene. $L^1$ may be substituted or unsubstituted 3 to 6 membered cycloalkylene. $L^1$ may be substituted 3 to 6 membered cycloalkylene. $L^1$ may be unsubstituted 3 to 6 membered cycloalkylene. $L^1$ may be substituted or unsubstituted 3 membered cycloalkylene. $L^1$ may be substituted or unsubstituted 4 membered cycloalkylene. $L^1$ may be substituted or unsubstituted 5 membered cycloalkylene. $L^1$ may be substituted or unsubstituted 6 membered cycloalkylene.

$L^1$ may be $R^{14}$-substituted or unsubstituted cycloalkylene. $L^1$ may be $R^{14}$-substituted cycloalkylene. $L^1$ may be $R^{14}$-substituted or unsubstituted 3 to 10 membered cycloalkylene. $L^1$ may be $R^{14}$-substituted 3 to 10 membered cycloalkylene. $L^1$ may be $R^{14}$-substituted or unsubstituted 3 to 6 membered cycloalkylene. $L^1$ may be $R^{14}$-substituted 3 to 6 membered cycloalkylene. $L^1$ may be $R^{14}$-substituted or unsubstituted 3 membered cycloalkylene. $L^1$ may be $R^{14}$-substituted or unsubstituted 4 membered cycloalkylene. $L^1$ may be $R^{14}$-substituted or unsubstituted 5 membered cycloalkylene. $L^1$ may be $R^{14}$-substituted or unsubstituted 6 membered cycloalkylene.

$L^1$ may be substituted or unsubstituted heterocycloalkylene. $L^1$ may be substituted heterocycloalkylene. $L^1$ may be unsubstituted heterocycloalkylene. $L^1$ may be substituted or unsubstituted 3 to 10 membered heterocycloalkylene. $L^1$ may be substituted 3 to 10 membered heterocycloalkylene. $L^1$ may be unsubstituted 3 to 10 membered heterocycloalkylene. $L^1$ may be substituted or unsubstituted 3 to 6 membered heterocycloalkylene. $L^1$ may be substituted 3 to 6 membered heterocycloalkylene. $L^1$ may be unsubstituted 3 to 6 membered heterocycloalkylene. $L^1$ may be substituted or unsubstituted 3 membered heterocycloalkylene. $L^1$ may be substituted or unsubstituted 4 membered heterocycloalkylene. $L^1$ may be substituted or unsubstituted 5 membered heterocycloalkylene. $L^1$ may be substituted or unsubstituted 6 membered heterocycloalkylene.

$L^1$ may be $R^{14}$-substituted or unsubstituted heterocycloalkylene. $L^1$ may be $R^{14}$-substituted heterocycloalkylene. $L^1$ may be $R^{14}$-substituted 3 to 10 membered heterocycloalkylene. $L^1$ may be $R^{14}$-substituted 3 to 10 membered heterocycloalkylene. $L^1$ may be $R^{14}$-substituted or unsubstituted 3 to 6 membered heterocycloalkylene. $L^1$ may be $R^{14}$-substituted 3 to 6 membered heterocycloalkylene. $L^1$ may be $R^{14}$-substituted or unsubstituted 3 membered heterocycloalkylene. $L^1$ may be $R^{14}$-substituted or unsubstituted 4 membered heterocycloalkylene. $L^1$ may be $R^{14}$-substituted or unsubstituted 5 membered heterocycloalkylene. $L^1$ may be $R^{14}$-substituted or unsubstituted 6 membered heterocycloalkylene.

$L^1$ may be substituted or unsubstituted arylene. $L^1$ may be substituted arylene. $L^1$ may be unsubstituted arylene. $L^1$ may be substituted or unsubstituted 5 to 10 membered arylene. $L^1$ may be substituted 5 to 10 membered arylene. $L^1$ may be unsubstituted 5 to 10 membered arylene. $L^1$ may be substituted or unsubstituted 5 membered arylene. $L^1$ may be substituted 5 membered arylene. $L^1$ may be unsubstituted 5 membered arylene. $L^1$ may be substituted or unsubstituted 6 membered arylene. $L^1$ may be substituted 6 membered arylene. $L^1$ may be unsubstituted 6 membered arylene (e.g. phenylene).

$L^1$ may be $R^{14}$-substituted or unsubstituted arylene. $L^1$ may be $R^{14}$-substituted arylene. $L^1$ may be $R^{14}$-substituted or unsubstituted 5 to 10 membered arylene. $L^1$ may be $R^{14}$-substituted 5 to 10 membered arylene. $L^1$ may be $R^{14}$-substituted or unsubstituted 5 membered arylene. $L^1$ may be $R^{14}$-substituted 5 membered arylene. $L^1$ may be $R^{14}$-substituted or unsubstituted 6 membered arylene. $L^1$ may be $R^{14}$-substituted 6 membered arylene.

$L^1$ may be substituted or unsubstituted heteroarylene. $L^1$ may be substituted heteroarylene. $L^1$ may be unsubstituted heteroarylene. $L^1$ may be substituted or unsubstituted 5 to 10 membered heteroarylene. $L^1$ may be substituted 5 to 10 membered heteroarylene. $L^1$ may be unsubstituted 5 to 10 membered heteroarylene. $L^1$ may be substituted or unsubstituted 5 membered heteroarylene. $L^1$ may be substituted 5 membered heteroarylene. $L^1$ may be unsubstituted 5 membered heteroarylene. $L^1$ may be substituted or unsubstituted 6 membered heteroarylene. $L^1$ may be substituted 6 membered heteroarylene. $L^1$ may be unsubstituted 6 membered heteroarylene.

$L^1$ may be $R^{14}$-substituted or unsubstituted heteroarylene. $L^1$ may be $R^{14}$-substituted heteroarylene. $L^1$ may be $R^{14}$-substituted or unsubstituted 5 to 10 membered heteroarylene. $L^1$ may be $R^{14}$-substituted 5 to 10 membered heteroarylene. $L^1$ may be $R^{14}$-substituted or unsubstituted 5 membered heteroarylene. $L^1$ may be $R^{14}$-substituted 5 membered heteroarylene. $L^1$ may be $R^{14}$-substituted or unsubstituted 6 membered heteroarylene. $L^1$ may be $R^{14}$-substituted 6 membered heteroarylene.

$R^{14}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, $R^{15}$-substituted or unsubstituted (e.g. $C_1$-$C_5$) alkyl, $R^{15}$-substituted or unsubstituted (e.g. 2 to 5 membered) heteroalkyl, $R^{15}$-substituted or unsubstituted (e.g. $C_3$-$C_8$) cycloalkyl, $R^{15}$-substituted or unsubstituted (e.g. 3 to 8 membered) heterocycloalkyl, $R^{s1}$-substituted or unsubstituted aryl (e.g. phenyl or naphthyl), or $R^{15}$-substituted or unsubstituted (e.g. 5 or 6 membered or fused ring) heteroaryl. $R^{14}$ may be hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, substituted or unsubstituted (e.g. $C_1$-$C_5$) alkyl, substituted or unsubstituted (e.g. 2 to 5 membered) heteroalkyl, substituted or unsubstituted (e.g. $C_3$-$C_8$)

cycloalkyl, substituted or unsubstituted (e.g. 3 to 8 membered) heterocycloalkyl, substituted or unsubstituted aryl (e.g. phenyl or naphthyl), or substituted or unsubstituted (e.g. 5 or 6 membered or fused ring) heteroaryl. $R^{14}$ may be hydrogen, halogen, oxo, $-N_3$, $-CF_3$, $-CCl_3$, $-CBr_3$, $-CI_3$, $-CN$, $-C(O)H$, $-OCH_3$, $-OCH_2CH_3$, $-NH_2$, $-COOH$, $-CONH_2$, $-NO_2$, $-SH$, $-S(O)_2H$, $-NHNH_2$, $-ONH_2$, $-NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^{15}$ is hydrogen, halogen, oxo, $-N_3$, $-CF_3$, $-CCl_3$, $-CBr_3$, $-CI_3$, $-CN$, $-C(O)H$, $-OCH_3$, $-OCH_2CH_3$, $-NH_2$, $-COOH$, $-CONH_2$, $-NO_2$, $-SH$, $-S(O)_2H$, $-NHNH_2$, $-ONH_2$, $-NHC(O)NHNH_2$, $R^{16}$-substituted or unsubstituted (e.g. $C_1$-$C_5$) alkyl, $R^{16}$-substituted or unsubstituted (e.g. 2 to 5 membered) heteroalkyl, $R^{16}$-substituted or unsubstituted (e.g. $C_3$-$C_8$) cycloalkyl, $R^{16}$-substituted or unsubstituted (e.g. 3 to 8 membered) heterocycloalkyl, $R^{16}$-substituted or unsubstituted aryl (e.g. phenyl or naphthyl), or $R^{16}$-substituted or unsubstituted (e.g. 5 or 6 membered or fused ring) heteroaryl.

$R^{16}$ is hydrogen, halogen, oxo, $-N_3$, $-CF_3$, $-CCl_3$, $-CBr_3$, $-CI_3$, $-CN$, $-C(O)H$, $-OCH_3$, $-OCH_2CH_3$, $-NH_2$, $-COOH$, $-CONH_2$, $-NO_2$, $-SH$, $-S(O)_2H$, $-NHNH_2$, $-ONH_2$, $-NHC(O)NHNH_2$, $R^{17}$-substituted or unsubstituted (e.g. $C_1$-$C_5$) alkyl, $R^{17}$-substituted or unsubstituted (e.g. 2 to 5 membered) heteroalkyl, $R^{17}$-substituted or unsubstituted (e.g. $C_3$-$C_8$) cycloalkyl, $R^{17}$-substituted or unsubstituted (e.g. 3 to 8 membered) heterocycloalkyl, $R^{17}$-substituted or unsubstituted aryl (e.g. phenyl or naphthyl), or $R^{17}$-substituted or unsubstituted (e.g. 5 or 6 membered or fused ring) heteroaryl.

$R^{17}$ is hydrogen, halogen, oxo, $-N_3$, $-CF_3$, $-CCl_3$, $-CBr_3$, $-CI_3$, $-CN$, $-C(O)H$, $-OCH_3$, $-OCH_2CH_3$, $-NH_2$, $-COOH$, $-CONH_2$, $-NO_2$, $-SH$, $-S(O)_2H$, $-NHNH_2$, $-ONH_2$, $-NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

When $L^1$ is $-N(R^6)-$, $-C(O)N(R^6)-$, or $-S(O)N(R^6)-$, $R^6$ may be hydrogen, halogen, $-N_3$, $-CF_3$, $-CCl_3$, $-CBr_3$, $-CI_3$, $-CN$, $-OR^{6A}$, $-C(O)R^{6A}$, $-NR^{6A}R^{6B}$, $-C(O)OR^{6A}$, $-C(O)NR^{6A}R^{6B}$, $-NO_2$, $-SR^{6A}$, $-S(O)_{n6}R^{6A}$, $-S(O)_{n6}OR^{6A}$, $-S(O)_{n6}NR^{6A}R^{6B}$, $-NHNR^{6A}R^{6B}$, $-ONR^{6A}R^{6B}$, or $-NHC(O)NHNR^{6A}R^{6B}$. $R^6$ may be hydrogen, halogen, $-N_3$, $-CF_3$, $-CCl_3$, $-CBr_3$, $-CI_3$, $-CN$, $-OR^{6A}$, $-C(O)R^{6A}$, $-NR^{6A}R^{6B}$, $-C(O)OR^{6A}$, $-C(O)NR^{6A}R^{6B}$, $-NO_2$, $-SR^{6A}$, or $-S(O)_{n6}R^{6A}$. $R^6$ may be hydrogen, halogen, $-N_3$, $-CF_3$, $-CCl_3$, $-CBr_3$, $-CI_3$, $-CN$, $-OR^{6A}$, $-NR^{6A}R^{6B}$, $-C(O)OR^{6A}$, $-C(O)NR^{6A}R^{6B}$, $-NO_2$, or $-SR^{6A}$. $R^6$ may be hydrogen, halogen, $-N_3$, $-CF_3$, $-CCl_3$, $-CBr_3$, $-CI_3$, $-CN$, $-OR^{6A}$, $-NR^{6A}R^{6B}$, $-C(O)OR^{6A}$, $-NO_2$, or $-SR^{6A}$. $R^6$ may be hydrogen, halogen, $-N_3$, $-CF_3$, $-CCl_3$, $-CBr_3$, $-CI_3$, $-CN$, $-OR^{6A}$, $-NR^{6A}R^{6B}$, or $-NO_2$. $R^6$ may be hydrogen, halogen, $-N_3$, $-CF_3$, $-CCl_3$, $-CBr_3$, $-CI_3$, $-CN$, $-OR^{6A}$, or $-NH_2$. $R^6$ may be hydrogen. $R^6$ may be halogen. $R^6$ may be $-N_3$. $R^6$ may be $-CF_3$. $R^6$ may be $-CN$. $R^6$ may be $-OR^{6A}$. $R^6$ may be $-NH_2$. $R^6$ may be $-NO_2$.

$R^6$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ may be substituted or unsubstituted alkyl. $R^6$ may be substituted alkyl. $R^6$ may be unsubstituted alkyl. $R^6$ may be substituted or unsubstituted $C_1$-$C_{20}$ alkyl. $R^6$ may be substituted $C_1$-$C_{20}$ alkyl. $R^6$ may be unsubstituted $C_1$-$C_{20}$ alkyl. $R^6$ may be substituted or unsubstituted $C_1$-$C_{10}$ alkyl. $R^6$ may be substituted $C_1$-$C_{10}$ alkyl. $R^6$ may be unsubstituted $C_1$-$C_{10}$ alkyl. $R^6$ may be substituted or unsubstituted $C_1$-$C_5$ alkyl. $R^6$ may be substituted $C_1$-$C_5$ alkyl. $R^6$ may be unsubstituted $C_1$-$C_5$ alkyl. $R^6$ may be substituted or unsubstituted $C_1$-$C_3$ alkyl. $R^6$ may be substituted $C_1$-$C_3$ alkyl. $R^6$ may be unsubstituted $C_1$-$C_3$ alkyl. $R^6$ may be methyl. $R^6$ may be ethyl. $R^6$ may be propyl.

$R^6$ may be $R^{60}$-substituted or unsubstituted alkyl. $R^6$ may be $R^{60}$-substituted alkyl. $R^6$ may be $R^{60}$-substituted or unsubstituted $C_1$-$C_{20}$ alkyl. $R^6$ may be $R^{60}$-substituted $C_1$-$C_{20}$ alkyl. $R^6$ may be $R^{60}$-substituted or unsubstituted $C_1$-$C_{10}$ alkyl. $R^6$ may be $R^{60}$-substituted $C_1$-$C_{10}$ alkyl $R^6$ may be $R^{60}$-substituted or unsubstituted $C_1$-$C_5$ alkyl. $R^6$ may be $R^{60}$-substituted $C_1$-$C_5$ alkyl. $R^6$ may be $R^{60}$-substituted or unsubstituted $C_1$-$C_3$ alkyl. $R^6$ may be $R^{60}$-substituted $C_1$-$C_3$ alkyl.

$R^6$ may be substituted or unsubstituted 2 to 20 membered heteroalkyl. $R^6$ may be substituted 2 to 20 membered heteroalkyl. $R^6$ may be unsubstituted 2 to 20 membered heteroalkyl. $R^6$ may be substituted or unsubstituted 2 to 10 membered heteroalkyl. $R^6$ may be substituted 2 to 10 membered heteroalkyl. $R^6$ may be unsubstituted 2 to 10 membered heteroalkyl. $R^6$ may be substituted or unsubstituted 2 to 6 membered heteroalkyl. $R^6$ may be substituted 2 to 6 membered heteroalkyl. $R^6$ may be unsubstituted 2 to 6 membered heteroalkyl. $R^6$ may be substituted or unsubstituted 2 to 5 membered heteroalkyl. $R^6$ may be substituted 2 to 5 membered heteroalkyl. $R^6$ may be unsubstituted 2 to 5 membered heteroalkyl.

$R^6$ may be $R^{60}$-substituted or unsubstituted 2 to 20 membered heteroalkyl. $R^6$ may be $R^{60}$-substituted 2 to 20 membered heteroalkyl. $R^6$ may be $R^{60}$-substituted or unsubstituted 2 to 10 membered heteroalkyl. $R^6$ may be $R^{60}$-substituted 2 to 10 membered heteroalkyl. $R^6$ may be $R^{60}$-substituted or unsubstituted 2 to 6 membered heteroalkyl. $R^6$ may be $R^{60}$-substituted 2 to 6 membered heteroalkyl. $R^6$ may be $R^{60}$-substituted or unsubstituted 2 to 5 membered heteroalkyl. $R^6$ may be $R^{60}$-substituted 2 to 5 membered heteroalkyl.

$R^6$ may be substituted or unsubstituted 3 to 10 membered cycloalkyl. $R^6$ may be substituted 3 to 10 membered cycloalkyl. $R^6$ may be unsubstituted 3 to 10 membered cycloalkyl. $R^6$ may be substituted or unsubstituted 3 to 6 membered cycloalkyl. $R^6$ may be substituted 3 to 6 membered cycloalkyl. $R^6$ may be unsubstituted 3 to 6 membered cycloalkyl. $R^6$ may be substituted or unsubstituted 3 to 5 membered cycloalkyl. $R^6$ may be substituted 3 to 5 membered cycloalkyl. $R^6$ may be unsubstituted 3 to 5 membered cycloalkyl. $R^6$ may be substituted or unsubstituted 3 membered cycloalkyl. $R^6$ may be substituted 3 membered cycloalkyl. $R^6$ may be unsubstituted 3 membered cycloalkyl. $R^6$ may be substituted or unsubstituted 4 membered cycloalkyl. $R^6$ may be substituted 4 membered cycloalkyl. $R^6$ may be unsubstituted 4 membered cycloalkyl. $R^6$ may be substituted or unsubstituted 5 membered cycloalkyl. $R^6$ may be substituted 5 membered cycloalkyl. $R^6$ may be unsubstituted 5 membered cycloalkyl. $R^6$ may be substituted or unsubstituted 6 membered cycloalkyl. $R^6$ may be substituted 6 membered cycloalkyl. $R^6$ may be unsubstituted 6 membered cycloalkyl.

$R^6$ may be $R^{60}$-substituted or unsubstituted 3 to 10 membered cycloalkyl. $R^6$ may be $R^{60}$-substituted 3 to 10 membered cycloalkyl. $R^6$ may be $R^{60}$-substituted or unsubstituted 3 to 6 membered cycloalkyl. $R^6$ may be $R^{60}$-substituted 3 to 6 membered cycloalkyl. $R^6$ may be $R^{60}$-substituted or unsubstituted 3 to 5 membered cycloalkyl. $R^6$ may be $R^{60}$-substituted 3 to 5 membered cycloalkyl. $R^6$ may be $R^{60}$-substituted or unsubstituted 3 membered cycloalkyl. $R^6$ may be $R^{60}$-substituted 3 membered cycloalkyl. $R^6$ may be $R^{60}$-substituted or unsubstituted 4 membered cycloalkyl. $R^6$ may be $R^{60}$-substituted 4 membered cycloalkyl. $R^6$ may be $R^{60}$-substituted or unsubstituted 5 membered cycloalkyl. $R^6$ may be $R^{60}$-substituted 5 membered cycloalkyl. $R^6$ may be $R^{60}$-substituted or unsubstituted 6 membered cycloalkyl. $R^6$ may be $R^{60}$ substituted 6 membered cycloalkyl.

$R^6$ may be substituted or unsubstituted 3 to 10 membered heterocycloalkyl. $R^6$ may be substituted 3 to 10 membered heterocycloalkyl. $R^6$ may be unsubstituted 3 to 10 membered heterocycloalkyl. $R^6$ may be substituted or unsubstituted 3 to 6 membered heterocycloalkyl. $R^6$ may be substituted 3 to 6 membered heterocycloalkyl. $R^6$ may be unsubstituted 3 to 6 membered heterocycloalkyl. $R^6$ may be substituted or unsubstituted 3 to 5 membered heterocycloalkyl. $R^6$ may be substituted 3 to 5 membered heterocycloalkyl. $R^6$ may be unsubstituted 3 to 5 membered heterocycloalkyl. $R^6$ may be substituted or unsubstituted 3 membered heterocycloalkyl. $R^6$ may be substituted 3 membered heterocycloalkyl. $R^6$ may be unsubstituted 3 membered heterocycloalkyl. $R^6$ may be substituted or unsubstituted 4 membered heterocycloalkyl. $R^6$ may be substituted 4 membered heterocycloalkyl. $R^6$ may be unsubstituted 4 membered heterocycloalkyl. $R^6$ may be substituted or unsubstituted 5 membered heterocycloalkyl. $R^6$ may be substituted 5 membered heterocycloalkyl. $R^6$ may be unsubstituted 5 membered heterocycloalkyl. $R^6$ may be substituted or unsubstituted 6 membered heterocycloalkyl. $R^6$ may be substituted 6 membered heterocycloalkyl. $R^6$ may be unsubstituted 6 membered heterocycloalkyl.

$R^6$ may be $R^{60}$-substituted or unsubstituted 3 to 10 membered heterocycloalkyl. $R^6$ may be $R^{60}$-substituted 3 to 10 membered heterocycloalkyl. $R^6$ may be $R^{60}$-substituted or unsubstituted 3 to 6 membered heterocycloalkyl. $R^6$ may be $R^{60}$-substituted 3 to 6 membered heterocycloalkyl. $R^6$ may be $R^{60}$-substituted or unsubstituted 3 to 5 membered heterocycloalkyl. $R^6$ may be $R^{60}$-substituted 3 to 5 membered heterocycloalkyl. $R^6$ may be $R^{60}$-substituted or unsubstituted 3 membered heterocycloalkyl. $R^6$ may be $R^{60}$-substituted 3 membered heterocycloalkyl. $R^6$ may be $R^{60}$-substituted or unsubstituted 4 membered heterocycloalkyl. $R^6$ may be $R^{60}$-substituted 4 membered heterocycloalkyl. $R^6$ may be $R^{60}$-substituted or unsubstituted 5 membered heterocycloalkyl. $R^6$ may be $R^{60}$-substituted 5 membered heterocycloalkyl. $R^6$ may be $R^{60}$-substituted or unsubstituted 6 membered heterocycloalkyl. $R^6$ may be $R^{60}$-substituted 6 membered heterocycloalkyl.

$R^6$ may be substituted or unsubstituted aryl. $R^6$ may be substituted aryl. $R^6$ may be unsubstituted aryl. $R^6$ may be substituted or unsubstituted 5 to 10 membered aryl. $R^6$ may be substituted 5 to 10 membered aryl. $R^6$ may be unsubstituted 5 to 10 membered aryl. $R^6$ may be substituted or unsubstituted 5 or 6 membered aryl. $R^6$ may be substituted 5 or 6 membered aryl. $R^6$ may be unsubstituted 5 or 6 membered aryl. $R^6$ may be substituted 5 membered aryl. $R^6$ may be substituted 5 membered aryl. $R^6$ may be unsubstituted 5 membered aryl. $R^6$ may be substituted or unsubstituted 6 membered aryl. $R^6$ may be substituted 6 membered aryl. $R^6$ may be unsubstituted 6 membered aryl.

$R^6$ may be $R^{60}$-substituted or unsubstituted aryl. $R^6$ may be $R^{60}$-substituted aryl. $R^6$ may be $R^{60}$-substituted or unsubstituted 5 to 10 membered aryl. $R^6$ may be $R^{60}$-substituted 5 to 10 membered aryl. $R^6$ may be $R^{60}$-substituted or unsubstituted 5 or 6 membered aryl. $R^6$ may be $R^{60}$-substituted 5 or 6 membered aryl. $R^6$ may be $R^{60}$-substituted or unsubstituted 5 membered aryl. $R^6$ may be $R^{60}$-substituted 5 membered aryl. $R^6$ may be $R^{60}$-substituted or unsubstituted 6 membered aryl. $R^6$ may be $R^{60}$-substituted 6 membered aryl.

$R^6$ may be substituted or unsubstituted heteroaryl. $R^6$ may be substituted heteroaryl. $R^6$ may be unsubstituted heteroaryl. $R^6$ may be substituted or unsubstituted 5 to 10 membered heteroaryl. $R^6$ may be substituted 5 to 10 membered heteroaryl. $R^6$ may be unsubstituted 5 to 10 membered heteroaryl. $R^6$ may be substituted or unsubstituted 5 or 6 membered heteroaryl. $R^6$ may be substituted 5 or 6 membered heteroaryl. $R^6$ may be unsubstituted 5 or 6 membered heteroaryl. $R^6$ may be substituted or unsubstituted 5 membered heteroaryl. $R^6$ may be substituted 5 membered heteroaryl. $R^6$ may be unsubstituted 5 membered heteroaryl. $R^6$ may be substituted or unsubstituted 6 membered heteroaryl. $R^6$ may be substituted 6 membered heteroaryl. $R^6$ may be unsubstituted 6 membered heteroaryl.

$R^6$ may be $R^{60}$-substituted or unsubstituted heteroaryl. $R^6$ may be $R^{60}$-substituted heteroaryl. $R^6$ may be $R^{60}$-substituted or unsubstituted 5 to 10 membered heteroaryl. $R^6$ may be $R^{60}$-substituted 5 to 10 membered heteroaryl. $R^6$ may be $R^{60}$-substituted or unsubstituted 5 or 6 membered heteroaryl. $R^6$ may be $R^{60}$-substituted 5 or 6 membered heteroaryl. $R^6$ may be $R^{60}$-substituted or unsubstituted 5 membered heteroaryl. $R^6$ may be $R^{60}$-substituted 5 membered heteroaryl. $R^6$ may be $R^{60}$-substituted or unsubstituted 6 membered heteroaryl. $R^6$ may be $R^{60}$-substituted 6 membered heteroaryl.

$R^{60}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, $R^{61}$-substituted or unsubstituted (e.g. $C_1$-$C_5$) alkyl, $R^{61}$-substituted or unsubstituted (e.g. 2 to 5 membered) heteroalkyl, $R^{61}$-substituted or unsubstituted (e.g. $C_3$-$C_8$) cycloalkyl, $R^{61}$-substituted or unsubstituted (e.g. 3 to 8 membered) heterocycloalkyl, $R^{61}$-substituted or unsubstituted aryl (e.g. phenyl or naphthyl), or $R^{61}$-substituted or unsubstituted (e.g. 5 or 6 membered or fused ring) heteroaryl. $R^{60}$ may be hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, substituted or unsubstituted (e.g. $C_1$-$C_5$) alkyl, substituted or unsubstituted (e.g. 2 to 5 membered) heteroalkyl, substituted or unsubstituted (e.g. $C_3$-$C_8$) cycloalkyl, substituted or unsubstituted (e.g. 3 to 8 membered) heterocycloalkyl, substituted or unsubstituted aryl (e.g. phenyl or naphthyl), or substituted or unsubstituted (e.g. 5 or 6 membered or fused ring) heteroaryl. $R^{60}$ may be hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —$NHC(O)NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^{61}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —NHC(O)$NHNH_2$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{62}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —NHC(O)$NHNH_2$, $R^{63}$-substituted or unsubstituted (e.g. $C_1$-$C_5$) alkyl, $R^{63}$-substituted or unsubstituted (e.g. 2 to 5 membered) heteroalkyl, $R^{63}$-substituted or unsubstituted (e.g. $C_3$-$C_8$) cycloalkyl, $R^{63}$-substituted or unsubstituted (e.g. 3 to 8 membered) heterocycloalkyl, $R^{63}$-substituted or unsubstituted e.g. phenyl or naphthyl), or $R^{63}$-substituted or unsubstituted (e.g. 5 or 6 membered or fused ring) heteroaryl.

$R^{63}$ is hydrogen, halogen, oxo, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —$S(O)_2H$, —$NHNH_2$, —$ONH_2$, —NHC(O)$NHNH_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

$R^{6A}$ and $R^{6B}$ may independently be hydrogen, oxo, halogen, —$CF_3$, —CN, —OH, —$NH_2$, —COOH, —$CONH_2$, —$NO_2$, —SH, —$S(O)_3H$, or —$ONH_2$. $R^{6A}$ and $R^{6B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{6A}$ and $R^{6B}$ may independently be hydrogen, oxo, halogen, —$CF_3$, —CN, —OH, —$NH_2$, —COOH, —$CONH_2$, —$NO_2$, —SH, —$S(O)_3H$, —$ONH_2$, —NHC(O)$NHNH_2$, $R^{60}$-substituted or unsubstituted (e.g. $C_1$-$C_5$) alkyl, $R^{60}$-substituted or unsubstituted (e.g. 2 to 5 membered) heteroalkyl, $R^{60}$-substituted or unsubstituted (e.g. $C_3$-$C_8$) cycloalkyl, $R^{60}$-substituted or unsubstituted (e.g. 3 to 8 membered) heterocycloalkyl, $R^{60}$-substituted or unsubstituted aryl (e.g. phenyl or naphthyl), or $R^{60}$-substituted or unsubstituted (e.g. 5 or 6 membered or fused ring) heteroaryl.

$R^{6A}$ and $R^{6B}$ may independently be $R^{6C}$-substituted or unsubstituted (e.g. $C_1$-$C_5$) alkyl, $R^{6C}$-substituted or unsubstituted (e.g. 2 to 5 membered) heteroalkyl, $R^{6C}$-substituted or unsubstituted (e.g. $C_3$-$C_8$) cycloalkyl, $R^{6C}$-substituted or unsubstituted (e.g. 3 to 8 membered) heterocycloalkyl, $R^{6C}$-substituted or unsubstituted aryl (e.g. phenyl or naphthyl), or $R^{6C}$-substituted or unsubstituted (e.g. 5 or 6 membered or fused ring) heteroaryl.

$R^{6C}$ is hydrogen, oxo, halogen, —$CF_3$, —CN, —OH, —$NH_2$, —COOH, —$CONH_2$, —$NO_2$, —SH, —$S(O)_2Cl$, —$S(O)_3H$, —$S(O)_4H$, —$S(O)_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, unsubstituted (e.g. $C_1$-$C_5$) alkyl, unsubstituted (e.g. 2 to 5 membered) heteroalkyl, unsubstituted (e.g. $C_3$-$C_8$) cycloalkyl, unsubstituted (e.g. 3 to 8 membered) heterocycloalkyl, unsubstituted aryl (e.g. phenyl or naphthyl), or unsubstituted (e.g. 5 or 6 membered or fused ring) heteroaryl.

The compound of formula (I) may have the formula:

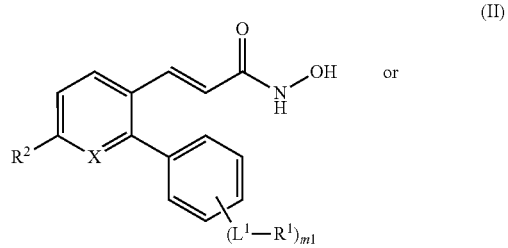

or

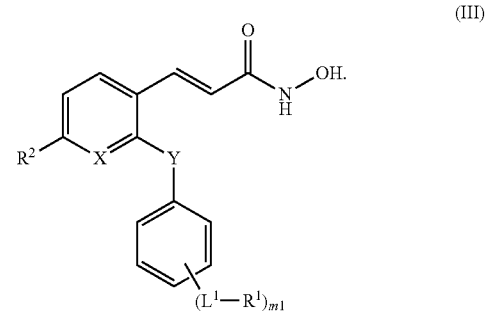

$L^1$, $R^1$, $R^2$, X, Y, and m1 are as described herein. $R^2$ of the compounds of formula (II) or (III) may be halogen or —$OR^{2A}$, where $R^{2A}$ is hydrogen or unsubstituted $C_1$-$C_5$ alkyl compounds. X of formula (II) or (III) may be —$CH_2$— or —N—. Y of formula (II) or (III) may be —NH— or —O—. $L^1$ of formula (II) or (III) may be a bond. $R^1$ of formula (II) or (III) may be halogen, —$NO_2$, —$NH_2$, —$OR^{1A}$, where $R^{1A}$ is hydrogen or unsubstituted $C_1$-$C_5$ alkyl, where the symbol m1 is 1, 2, or 3.

The compound of formula (I) may have the formula:

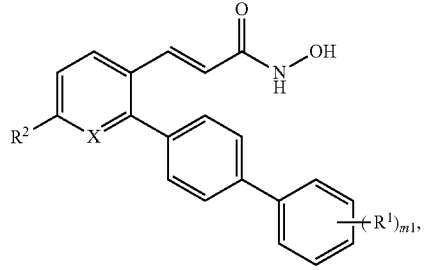

where $R^1$, m1, $R^2$, and X are as described herein. $R^1$ may be —$OR^{1A}$, where $R^{1A}$ is as described herein (e.g. substituted or unsubstituted alkyl) and m1 is 1, 2, or 3. $R^1$ may be halogen. $R^1$ may be —$CF_3$. $R^1$ may be —$NO_2$. $R^1$ may be —$NH_2$. $R^1$ may be substituted at the 2, 3, or 4 positions with one or more of be —$OR^{1A}$, where $R^{1A}$ is as described herein (e.g. substituted or unsubstituted alkyl), halogen, —$CF_3$, —$NO_2$, or —$NH_2$. The symbol m1 may be 1, 2, or 3.

The compound of formula (I) may have the formula:

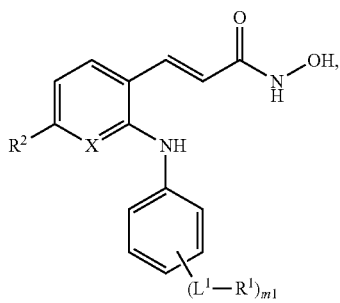

where $L^1$, $R^1$, m1, $R^2$ and X are as described herein. $L^1$ may be a bond and $R^1$ may be —$OR^{1A}$, where $R^{1A}$ is as defined herein (e.g. substituted or unsubstituted alkyl) and m1 is 1, 2, or 3. $R^1$ may be halogen. $R^1$ may be —$CF_3$. $R^1$ may be —$NO_2$. $R^1$ may be —$NH_2$. $R^1$ may be substituted at the 2, 3, or 4 positions with one or more of be —$OR^{1A}$, where $R^{1A}$ is as described herein (e.g. substituted or unsubstituted alkyl), halogen, —$CF_3$, —$NO_2$, or —$NH_2$. The symbol m1 may be 1, 2, or 3.

The compound of formula (I) may have formula:

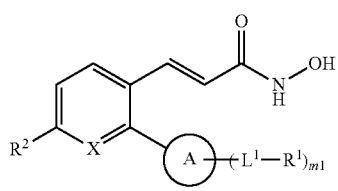

(IV)

or

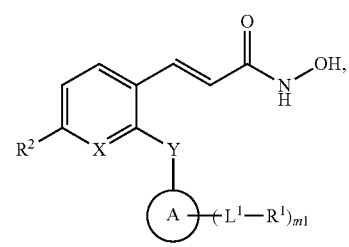

(V)

where A is 5,6-fused ring heteroaryl, 6,5-fused ring heteroaryl, or 6,6-fused ring heteroaryl. $L^1$, $R^1$, m1, $R^2$, X and Y are as described herein. $R^2$ of the compounds of formula (IV) or formula (V) may be halogen or —$OR^{2A}$, where $R^{2A}$ is hydrogen or unsubstituted $C_1$-$C_5$ alkyl. X of the compounds of formula (IV) or formula (V) may be —$CH_2$— or —N—. Y of the compounds of formula (IV) or formula (V) may be —NH— or —O—. $L^1$ of the compounds of formula (IV) or formula (V) may be a bond. $R^1$ of the compounds of formula (IV) or formula (V) may be halogen, —$NO_2$, —$NH_2$, —$OR^{1A}$, where $R^{1A}$ is hydrogen or unsubstituted $C_1$-$C_5$ alkyl where the symbol m1 is 1, 2, or 3.

The compound of formula (I) may be a compound having the structure set forth in Table 1, 2, or 3, or in the examples provided herein.

TABLE 1

Compounds and inhibition of HDAC8 (relative potency) and HeLa nuclear HDACs (IC$_{50}$, nM)

| Compound | R | IC$_{50}$ PCI34051/IC$_{50}$ compound | HeLa HDAC |
|---|---|---|---|
| 5a | MeO, MeO, OMe (3,4,5-trimethoxyphenyl) | 0.29 | >10000 |
| 5b | thiophene | 1.43 | >10000 |
| 5c | phenyl | 1.17 | >10000 |
| 5d | 4-fluorophenyl | 1.90 | >10000 |
| 5e | benzo[d][1,3]dioxole | 1.86 | 8550 ± 0.12 |
| 5f | indole | 0.64 | >10000 |
| 5g | isoquinoline | 0.28 | 798.4 ± 0.3 |

TABLE 1-continued

Compounds and inhibition of HDAC8 (relative potency) and HeLa nuclear HDACs (IC$_{50}$, nM)

| Compound | R | IC$_{50}$ PCI34051/IC$_{50}$ compound | HeLa HDAC |
|---|---|---|---|
| 5h | quinolin-3-yl | 0.63 | 836.0 ± 9.1 |
| PCI34051 | | 1 | >10000 |
| X1 | pyridyl (2-, 3-, or 4-) | | |
| X2 | indol-2-yl | | |
| X3 | benzo-fused 5-ring (X = N, O, S) | | |
| X4 | benzo-fused 5-ring (X = N, O, S) | | |
| X5 | 5-membered heterocycle (X = N, O) | | |

TABLE 2

Compounds and inhibition of HDAC8 (relative potency) and HeLa nuclear HDACs (IC$_{50}$, nM) and cytotoxicity (IC$_{50}$, µM)

| Compound | R | IC$_{50}$ PCI34051/IC$_{50}$ compound | HeLa HDAC |
|---|---|---|---|
| 6a | H | 0.40 | >10000 |
| 6b | 2-OMe | 0.17 | >10000 |
| 6c | 3-OMe | 0.44 | >10000 |
| 6d | 4-OMe | 0.30 | >10000 |
| 6e | 3,4-diOMe | 0.44 | >10000 |
| 6f | 3,4,5-triOMe | 0.24 | >10000 |
| PCI34051 | | 1 | >10000 |
| X6 | 2- or 3- or 4-R (R = F, Cl, Br) | | |
| X7 | 2- or 3- or 4-R (R = NO$_2$) | | |
| X8 | 2- or 3- or 4-R (R = NH$_2$) | | |
| X9 | 2- or 3- or 4-CF$_3$ | | |

TABLE 3

Compounds and inhibition of HDAC 8 (relative potency) and HeLa nuclear HDACs (IC$_{50}$, nM)

15a-e

TABLE 3-continued

Compounds and inhibition of HDAC 8 (relative potency) and HeLa nuclear HDACs (IC$_{50}$, nM)

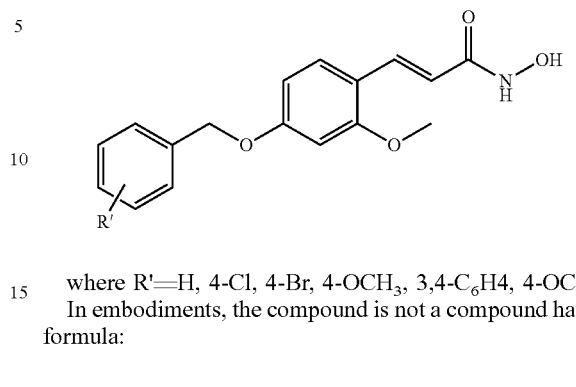

25

| Compound | R | IC$_{50}$ PCI34051/IC$_{50}$ compound | HeLa HDAC |
|---|---|---|---|
| 15a | 4-F | 0.38 | >10000 |
| 15b | 4-CF$_3$ | 0.55 | >10000 |
| 15c | 5-OMe | 0.06 | >10000 |
| 15d | 3,4-OMe | 0.44 | >10000 |
| 15e | 3,4,5-OMe | 0.02 | >10000 |
| 21 |  | 0.68 | >10000 |
| 25 |  | 0.49 | >10000 |
| PCI-34051 |  | 1 |  |
| X10 | 3- or 5- or 6-R, (R = F) |  |  |
| X11 | 3- or 4-or 5- or 6-R (R = Cl, Br) |  |  |
| X12 | 3- or 4-or 5- or 6-R (R = NO$_2$) |  |  |
| X13 | 3- or 4-or 5- or 6-R (R = NH$_2$) |  |  |
| X14 | 3- or 4-or 5- or 6-R CF$_3$ |  |  |

In embodiments, $R^1$ and $R^2$ of the compound of formula (I) are not unsubstituted aryl. In embodiments $R^1$ and $R^2$ of the compound of formula (I) are not unsubstituted phenyl. In embodiments, when $L^1$ is a bond, $R^1$ is not unsubstituted aryl or unsubstituted heteroaryl. In embodiments, when $L^1$ is a bond, $R^1$ is not substituted or unsubstituted aryl (e.g. phenyl). In embodiments, when $L^1$ is a bond, $R^1$ is not —OR$^{14}$, where $R^{14}$ is methyl or substituted or unsubstituted benzyl. In embodiments, when $L^1$ is a bond, $R^1$ is not —OR$^{14}$, where $R^{14}$ is methyl or substituted or unsubstituted benzyl and $R^2$ is not —OCH$_3$. In embodiments, when $L^1$ is substituted or unsubstituted arylene, $R^1$ is not substituted or unsubstituted aryl. In embodiments, when $L^1$ is unsubstituted arylene (e.g. phenyl), $R^1$ is not substituted or unsubstituted aryl. In embodiments when $L^1$ is unsubstituted arylene, $R^1$ is not unsubstituted aryl (e.g. phenyl). In embodiments the compound is not a compound as set forth in Scheme 1. In embodiments the compound is not a compound as set forth in Scheme 2. In embodiments the compound is not a compound as set forth in Scheme 3. In embodiments the compound is not a compound as set forth in Scheme 4. In embodiments the compound is not a compound as set forth in Scheme 5. In embodiments the compound is not a compound as set forth in Scheme 6. In embodiments the compound is not a compound as set forth in Table 1. In embodiments the compound is not a compound as set forth in Table 4. In embodiments the compound is not a compound as set forth in Table 5. In embodiments the compound is not a compound as set forth in Table 6.

In embodiments, the compound is not a compound having formula:

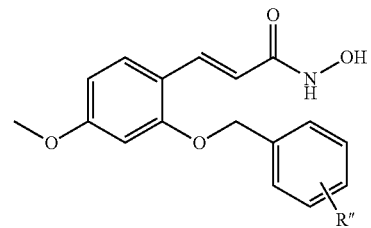

where R'=H, 4-Cl, 4-Br, 4-OCH$_3$, 3,4-C$_6$H4, 4-OCF$_3$.

In embodiments, the compound is not a compound having formula:

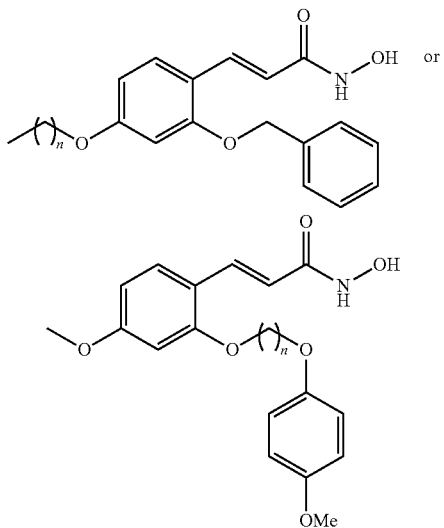

where R"=H, 4-Cl, 4-Br, 4-OCH$_3$, 3,4-C$_6$H4.

In embodiments, the compound is not a compound having formula:

where n is 2-5.

In embodiments, the compound is not a compound having formula:

where R''' is:

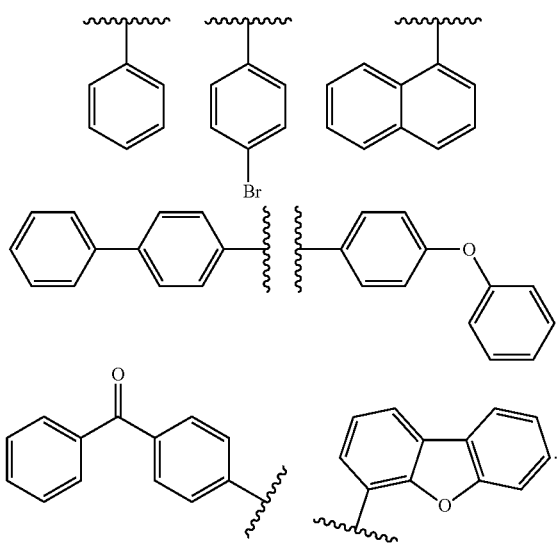

In embodiments, the compound is not a compound having formula:

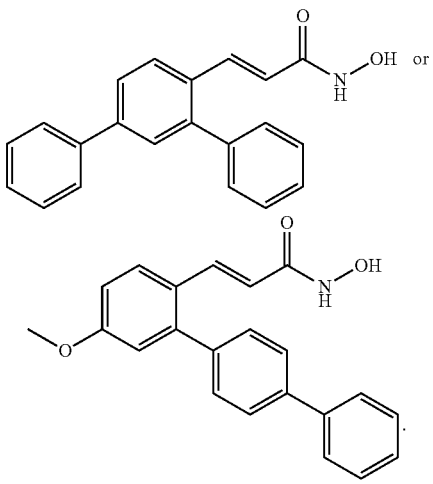

II. METHODS OF TREATING

Provided herein are methods of treating cancer with a HDAC8 inhibitor. In one aspect, the method is a method of treating cancer by administering to a subject in need thereof an effective amount of a HDAC8 inhibitor as described herein. The HDAC8 inhibitor is as described herein. The HDAC8 inhibitor may be a compound of formula (I) as described herein including one or more compounds set forth in Tables 1-3 and/or one or more of those set forth in the Examples. The HDAC8 inhibitor may be an HDAC8 inhibitor antibody. The HDAC8 inhibitor may be a HDAC8 inhibitor polynucleotide. The HDAC8 inhibitor may be a HDAC8 inhibitor protein. The inhibitor may block the active site of HDAC8.

The cancer may be a non-mutated p53 cancer. The non-mutated p53 cancer may be a blood cancer (e.g. a non-mutated p53 blood cancer) or a solid tumor cancer (e.g. a non-mutated p53 solid tumor cancer). The non-mutated p53 cancer may be acute myeloid leukemia (AML), acute lymphoblastic leukemia (ALL), lymphoma, neuroblastoma, glioma, bladder cancer, lung cancer, non-small cell lung cancer, or breast cancer (including triple-negative breast cancer).

The non-mutated p53 cancer may be acute myeloid leukemia (AML), acute lymphoblastic leukemia (ALL), lymphoma, neuroblastoma, glioma, bladder cancer, or lung cancer. The non-mutated p53 cancer may be acute myeloid leukemia (AML), acute lymphoblastic leukemia (ALL), lymphoma, neuroblastoma, or glioma. The non-mutated p53 cancer may be acute myeloid leukemia (AML), acute lymphoblastic leukemia (ALL), or lymphoma. The non-mutated p53 cancer may be acute myeloid leukemia (AML) or acute lymphoblastic leukemia (ALL).

The non-mutated p53 cancer may be acute myeloid leukemia (AML). The non-mutated p53 cancer may be acute lymphoblastic leukemia (ALL). The non-mutated p53 cancer may be lymphoma. The non-mutated p53 cancer may be neuroblastoma. The non-mutated p53 cancer may be glioma. The non-mutated p53 cancer may be bladder cancer. The non-mutated p53 cancer may be lung cancer. The non-mutated p53 cancer may be non-small cell lung cancer. The non-mutated p53 cancer may be breast cancer (including triple-negative breast cancer).

The cancer may have increased HDAC8 activity or expression when compared to a non-cancerous cell. The cancer may have increased HDAC8 activity and expression when compared to a non-cancerous cell. The cancer may have increased HDAC8 activity when compared to a non-cancerous cell. The cancer may have increased HDAC8 expression when compared to a non-cancerous cell.

The non-mutated p53 cancer may have increased HDAC8 activity or expression when compared to a mutated p53 cancer. The non-mutated p53 cancer may have increased HDAC8 activity and expression when compared to a mutated p53 cancer. The non-mutated p53 cancer may have increased HDAC8 activity when compared to a mutated p53 cancer. The non-mutated p53 cancer may have increased HDAC8 expression when compared to a mutated p53 cancer. p53 may be deacetylated in the non-mutated cancer. p53 may be deacetylated in a non-mutated cancer having increased HDAC8 activity or expression. The non-mutated p53 cancer may have deacetylated p53 and may be characterized by increased resistance to treatment with an anti-cancer agent when compared to a cancer having mutated p53. The non-mutated p53 cancer may have increased HDAC8 expression and may be characterized by increased resistance to treatment with an anti-cancer agent when compared to a cancer having mutated p53.

The methods described herein may further include determining whether the non-mutated cancer has increased HDAC8 activity or HDAC8 expression. Increased HDAC8 activity or HDAC8 expression may be determined using techniques known in the art. Thus the level of HDAC8 activity may be measured from a sample taken from the subject and compared to the level of HDAC8 activity in a control sample (e.g. a healthy or non-cancerous cell). The level of HDAC8 expression may be determined using methods of quantifying a polypeptide (e.g. fluorometric or colorimetric assays, IHC, ELISA, or western blots). The level of HDAC8 expression may be determined using methods of quantifying a polynucleotide (e.g. fluorometric or colorimetric assays, PCR, or northern blots).

Also provided herein are methods of determining whether a subject has a non-mutated p53 cancer. Determining the presence or absence of non-mutated p53 in a cancer may allow for more effective treatment in the subject. The method may further include determining the expression or activity levels of HDAC8 in the non-mutated p53 cancer. When a non-mutated p53 cancer in the subject is determined to also have increased activity or expression of HDAC8, the cancer may be resistant to anti-cancer agents. When the non-mutated cancer in the subject is determined to also have increased activity or expression of HDAC8, p53 in the non-mutated cancer may be deacetylated.

The non-mutated p53 cancer may be leukemia where the cancer also has increased HDAC expression or activity. The non-mutated p53 cancer may be leukemia where the cancer also has increased HDAC expression. The non-mutated p53 cancer may be leukemia where the cancer also has increased HDAC activity.

In another aspect, the method is a method of treating cancer stem cells by administering to a subject in need thereof an effective amount of a HDAC8 inhibitor as described herein. The HDAC inhibitor is as described herein. The HDAC8 inhibitor may inhibit the leukemia-initiating capacity (e.g. population of cancer stem cells causing relapse). The cancer stem cells may be resistant to treatment with anti-cancer agents listed herein. Thus, treatments with an HDAC8 inhibitor described herein may target cancer stem cells resistant to such treatments and allow efficacy of previously resistant anti-cancer agents.

The HDAC8 inhibitor may be selective for HDAC8 over other HDAC isoforms (e.g. HDAC1, HDAC2, HDAC3, HDAC6, HDAC10, or HDAC 11). The HDAC8 inhibitor may be at least 1, 2, 5, 10, 15, 25, 50, 100, 200, 300, 400, or 500× more selective (e.g. by determining $K_i$ or $IC_{50}$ values for the compound for HDAC8 and other HDAC isoforms described herein).

Also provided herein are methods of treating cancer by modulating p53 activity. In one aspect, is a method of treating cancer by modulating p53 activity by administering to a subject in need thereof a HDAC8 inhibitor as described herein. The HDAC8 inhibitor may be a compound described herein. The cancer is as described herein. The cancer may overexpress HDAC8.

III. METHODS OF INHIBITING

Further provided herein are methods of inhibiting HDAC8 mediated deacetylation of p53. In one aspect, the method includes contacting HDAC8 with a HDAC8 inhibitor as described herein, thereby inhibiting HDAC8 mediated deacetylation of p53. The inhibition of HDAC8 may allow for acetylation and activation of p53, thereby mediating cell apoptosis.

The contacting may be performed in vitro or in vivo. The contacting may be performed in vitro. The contacting may be performed in vivo. The contacting may be performed in an organism.

The inhibition of HDAC8 mediated deacetylation of p53 may be monitored by techniques known in the art, including for example, fluorescent and colorimetric assays.

IV. METHODS OF ACTIVATING

Further provided herein are methods of activating p53. The method may be a method of activating p53 in vivo by contacting a cell with a HDAC8 inhibitor in the presence of HDAC8 and allowing the HDAC8 inhibitor to contact the HDAC8, thereby inhibiting the HDAC8 and activating p53. The contacting is performed as described herein. The HDAC8 inhibitor is as described herein. The HDAC8 inhibitor may be a compound described herein.

V. EXAMPLES

Example 1. Chemical Design

The synthesis of N-hydroxycinnamides 8a-f is illustrated in Scheme 1 following. 7-Hydroxycoumarin 3 reacted with the appropriate benzyl bromides gave corresponding coumarins 4a-f. Ethanolysis of compounds 4a-f using sodium ethoxide under anhydrous conditions provided (E)-ethyl cinnamates 5a-f,[26] respectively. Methylation of compounds 5a-f reacted with DMS gave corresponding cinnamic esters 6a-f. Saponification of compounds 6a-f in the presence of LiOH gave corresponding cinnamic acids 7a-f in quantitative yields. Compounds 7a-f reacted with ethyl chlorformate to produce the corresponding activated mixed anhydride in situ, and subsequent treatment of the prepared hydroxylamine gave N-hydroxycinnamides 8a-f, respectively. The synthesis of N-hydroxycinnamides 13a-e is described in Scheme 2. Ethanolysis of 7-methoxycoumarin 9 gave (E)-ethyl cinnamate 10. Reaction of (E)-ethyl cinnamate 10 with the appropriate benzyl bromides provided cinnamic esters 11 a-e, respectively. N-Hydroxycinnamides 13a-e were achieved starting from compounds 11 a-e through saponification followed by reaction with ethyl chloroformate and hydroxylamine according to the synthetic approach for 8a-f. The synthesis of N-hydroxycinnamides 18a-d is shown in Scheme 3.

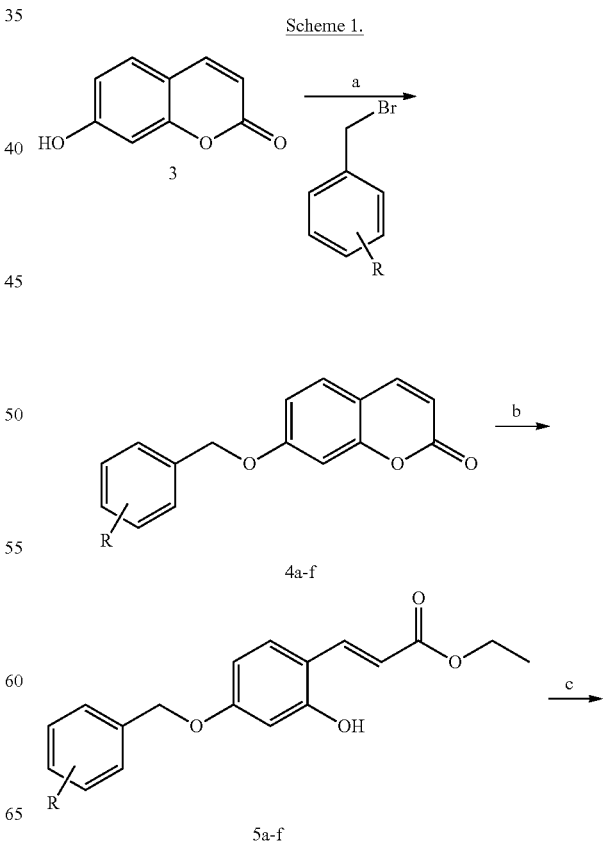

Scheme 1.

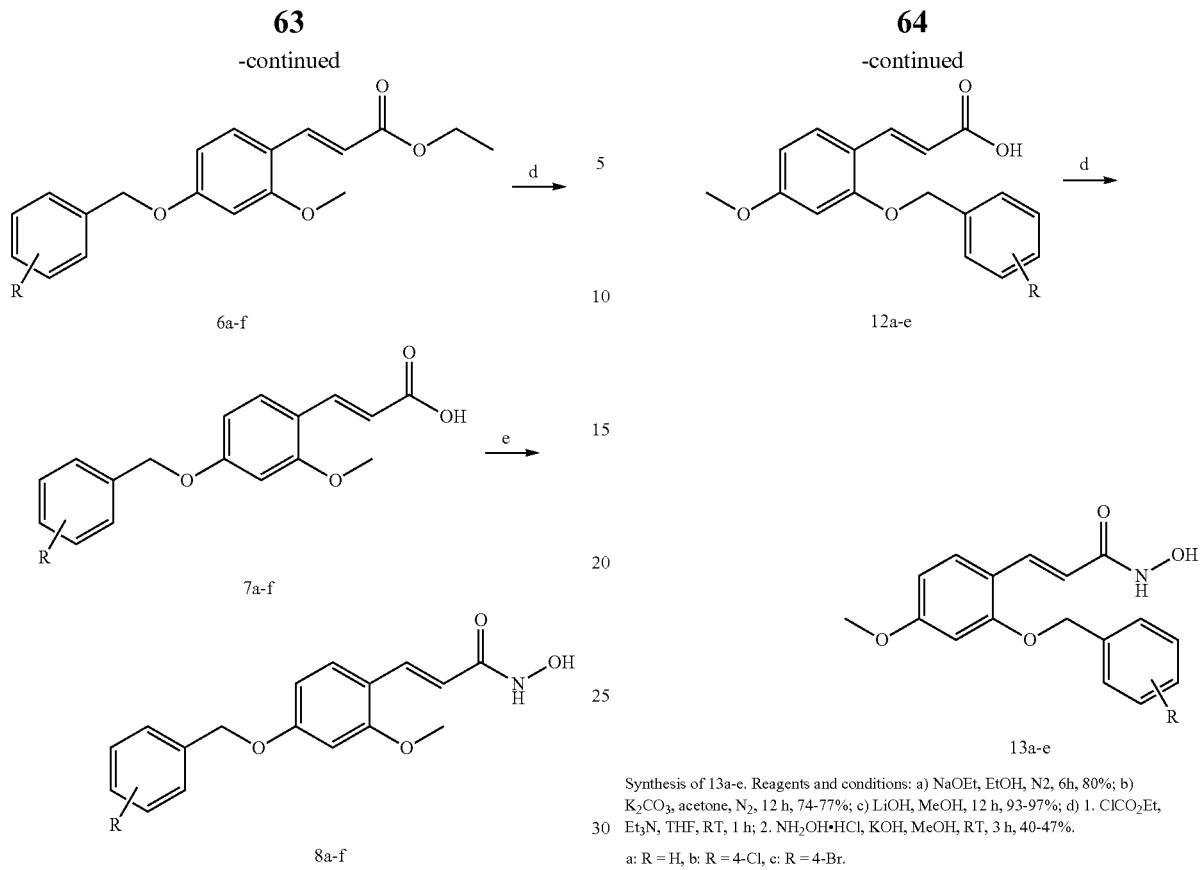

Synthesis of 8a-f. Reagents and conditions: a) K₂CO₃, acetone, N₂, 12 h, 75-85%; b) NaOEt, EtOH, N₂, 6 h, 72-79%; c) DMS, K₂CO₃, acetone, N₂, 12 h, 80-88%; d) LiOH, MeOH, 12 h, 92-96%; e) 1. ClCO₂Et, Et₃N, THF, RT, 1 h; 2. NH₂OH·HCl, KOH, MeOH, RT, 3 h, 51-58%.
a: R = H, b: R = 4-Cl, c: R = 4-Br, d: R = 4-OCH₃, e: R = 3,4-C₆H₄, f: R = 4-OCF₃

Synthesis of 13a-e. Reagents and conditions: a) NaOEt, EtOH, N2, 6h, 80%; b) K₂CO₃, acetone, N₂, 12 h, 74-77%; c) LiOH, MeOH, 12 h, 93-97%; d) 1. ClCO₂Et, Et₃N, THF, RT, 1 h; 2. NH₂OH·HCl, KOH, MeOH, RT, 3 h, 40-47%.

a: R = H, b: R = 4-Cl, c: R = 4-Br.
d: R = 4-OCH₃, e: R = 3,4-C₅H₄

Scheme 2.

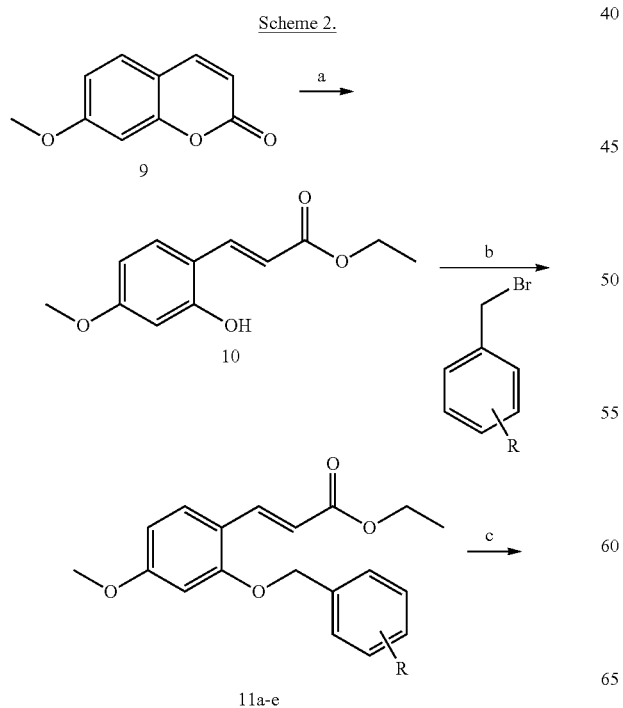

Scheme 3.

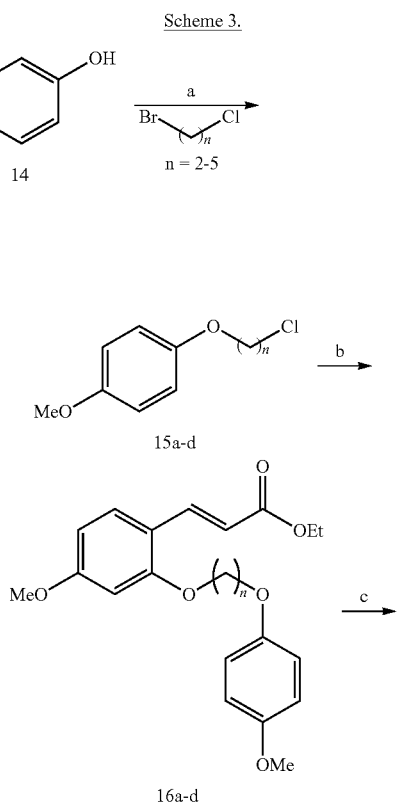

-continued

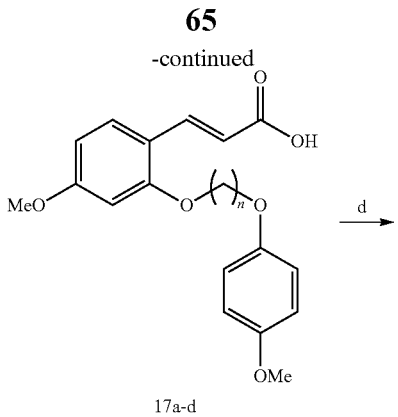

17a-d

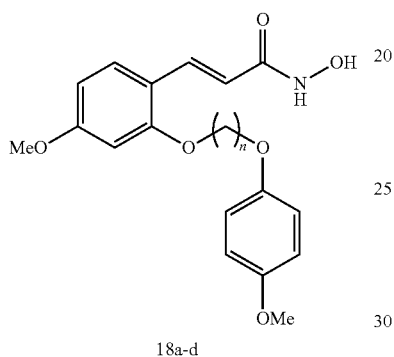

18a-d

Synthesis of 18-d. Reagents and conditions: a) K₂CO₃, MeCN, N₂, 12 h, 82-91%; b) 10, K₂CO₃, DMF, N₂, RT, 12 h, 43-54%; c) LiOH, MeOH, 12 h, 91-96%; d) 1. ClCO₂Et, Et₃N, THF, RT, 1 h; 2. NH2OH•HCl, KOH, MeOH, RT, 3 h, 53-64%.

Reaction of 4-methoxyphenol 14 with the appropriate chlorosubstituted alkyl bromides with chain lengths of two to five carbons yielded corresponding compounds 15a-d. Coupling of ethyl cinnamate 10 with 15a-d gave compounds 16a-d, respectively. Saponification of compounds 16a-d and subsequent reaction with ethyl chloroformate and hydroxylamine gave corresponding N-hydroxycinnamides 18a-d. The synthesis of ortho-aryl N-hydroxycinnamides 22a-g is described in Scheme 4. Reaction of ethyl cinnamate 10 with trifluoromethanesulfonyl (triflic) anhydride in the presence of pyridine gave compound 19. Suzuki coupling[27] of 19 with the appropriate aryl borates using catalytic tetrakis(triphenylphosphine) palladium yielded compounds 20a-g, respectively. Using compound 20a-g as the starting material, saponification followed by reaction with ethyl chloroformate and hydroxylamine gave corresponding the N-hydroxycinnamides 22a-g. The synthesis of ortho-phenyl N-hydroxycinnamides 27a-c with various chain lengths at the para position is achieved as described in Scheme 5. Reaction of 7-hydroxycoumarin 3 with the appropriate alkyl bromides with a three- to five-carbon chain length gave 23a-c, respectively. Ethanolysis of compounds 23a-c yielded corresponding (E)-ethyl cinnamates 24a-c. Reaction of compounds 24a-c with triflic anhydride provided 25a-c, respectively. Suzuki coupling of compounds 25a-c with phenyl borate gave corresponding compounds 26a-c. Ethyl cinnamates 26a-c was reacted directly with hydroxylamine in the presence of NaOH to yield N-hydroxycinnamides 27a-c, respectively. The synthesis of N-hydroxycinnamide 27d with a phenyl group at the ortho and para position was achieved as illustrated in Scheme 6. Reaction of 7-hydroxycoumarin 3 with triflic anhydride gave 28. Suzuki coupling of compound 28 with phenyl borate yielded phenyl coumarin 29. Methanolysis of compound 29 provided (E)-methyl cinnamate 30. Trifluoromethanesulfonylation of compound 30 and subsequent Suzuki coupling was repeated to give 32. Compound 32 was converted into N-hydroxycinnamide 27d using hydroxylamine and NaOH. Details on the synthesis, isolation, and characterization of reaction intermediates can be found in the Supporting Information.

Scheme 4.

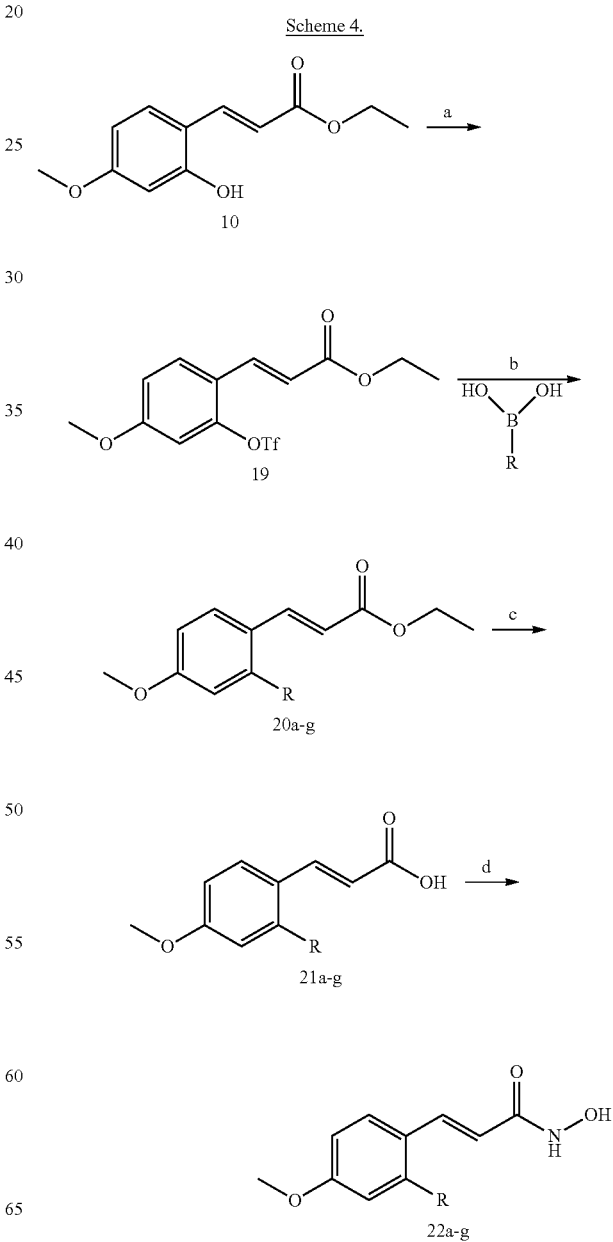

-continued
Synthesis of 22a-g. Reagents and conditions: a) Tf$_2$O, py, CH$_2$Cl$_2$, RT, 2 h, 62%; b) Pd(PPh$_3$)$_4$, K$_2$CO$_3$, DMF, 90 8C, 12 h, 38-99%; c) LiOH, MeOH, 89-99%; d) 1. ClCO$_2$Et, Et$_3$N, THF, RT, 1 h; 2. NH$_2$OH•HCl, KOH, MeOH, RT, 3 h, 39-59%.
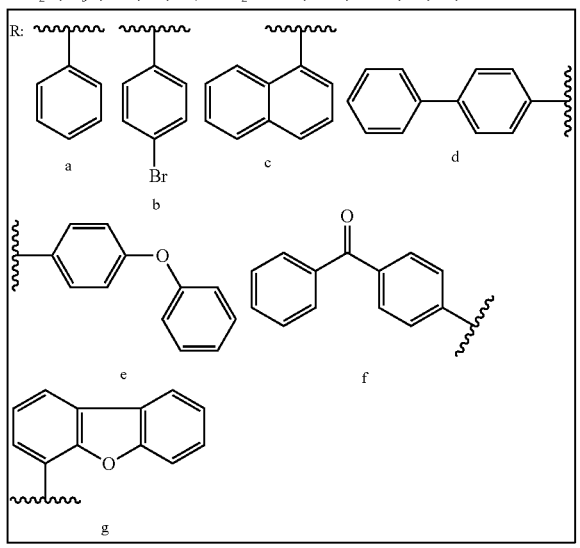
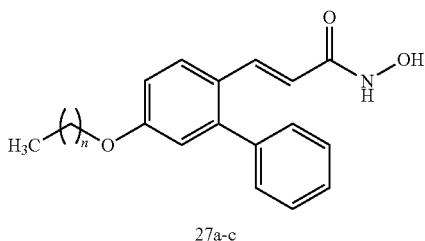
27a-c
Synthesis of 27a-c. Reagents and conditions: a) K$_2$CO$_3$, acetone, N$_2$, 12 h, 89-93%; b) NaOEt, EtOH, N$_2$, 6 h, 31-42%; c) Tf$_2$O, py, CH$_2$Cl$_2$, RT, 2 h, 62-92%; d) Ph(PPh$_3$)$_4$, K$_2$CO$_3$, DMF, 90° C., 12 h, 84-91%; e) 50% NH$_2$OH, NaOH, MeOH/THF, RT, 3 h, 51-57%.
Scheme 5.
Scheme 6.
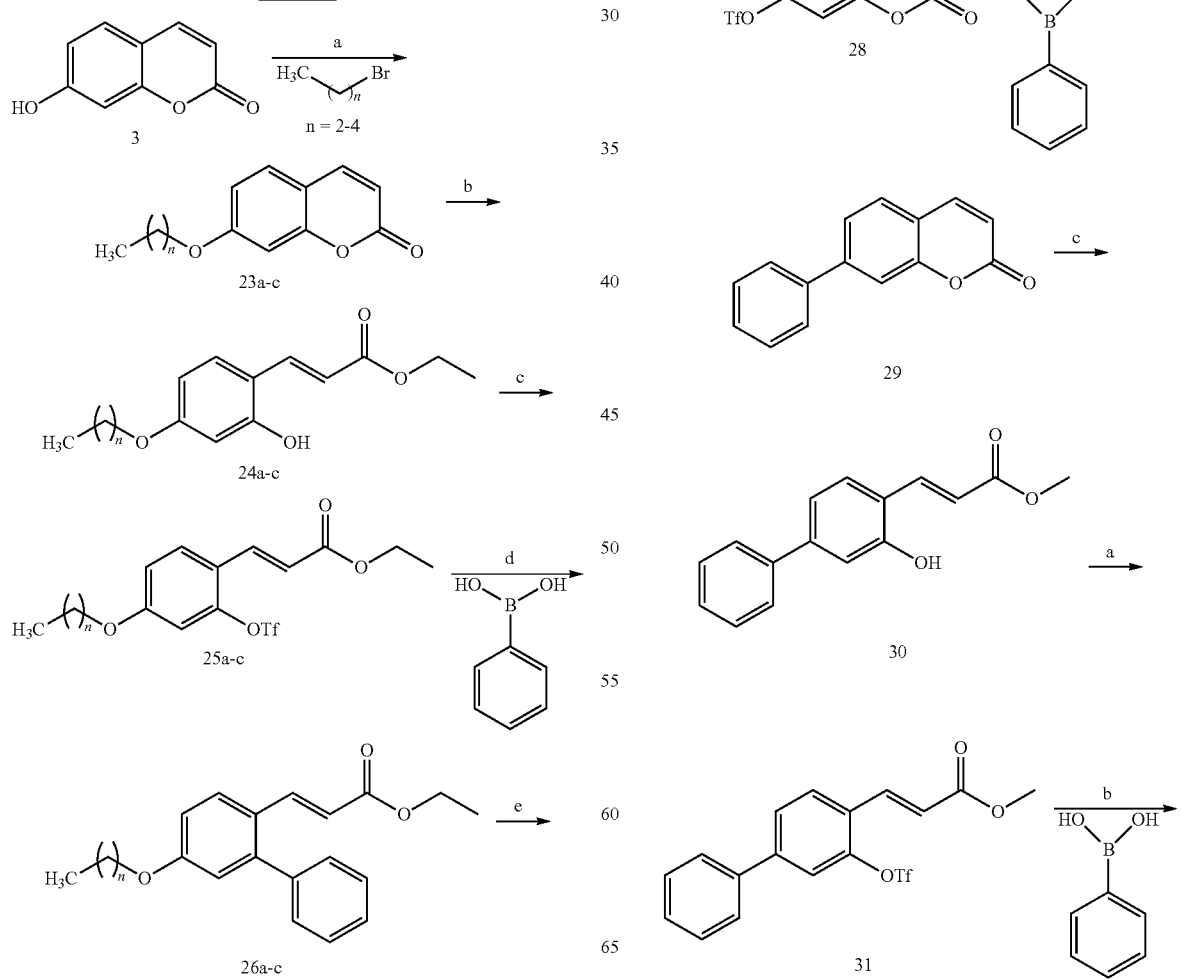

-continued

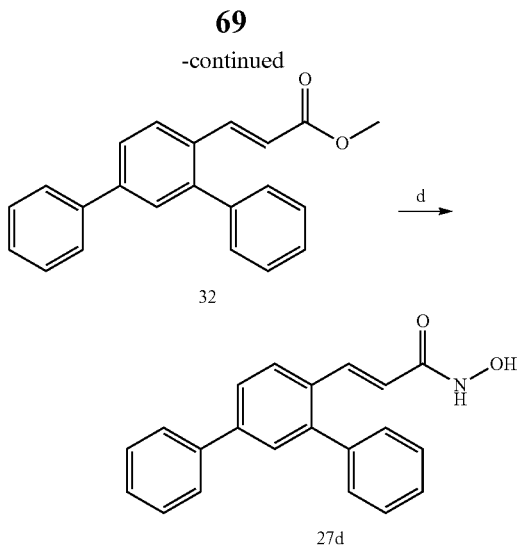

Synthesis of 27d. Reagents and conditions: a) Tf₂O, py, CH₂Cl₂, RT, 2 h, 27: 80%, 30: 68%; b) Pd(PPh₃)₄, K₂CO₃, DMF, 90°C, 12 h, 28: 75%, 31: 44%; c) NaOMe, MeOH, N₂, 6 h, 35%; d) 50% NH₂OH, NaOH, MeOH/THF, RT, 3 h, 44%.

Example 2. Compound Synthesis

General.

$^1$H NMR spectrum was obtained on a Bruker AV400 or AV500 spectrometer using standard pulse programs. Melting point was recorded on a Fisher-Johns apparatus (uncorrected). MS data were measured on a JEOL JMX-HX110 mass spectrometer (HREIMS and HRFABMS), a JMS-SX102A mass spectrometer (EIMS and FABMS), or a Finnigan Mat 95S mass spectrometer (HRESIMS and ESIMS). TLC analyses were carried out on silica gel plates (KG60-F254, Merck). The microplate spectrophotometer Victor 2X (PerkinElmer, Fremont, Calif., USA) was used for fluorometric analysis. Unless otherwise mentioned, all chemicals and materials were used as received from commercial suppliers without further purification. CH₂Cl₂ was distilled from CaH under N₂. THF was distilled from sodium and benzophenone under N₂. All test compounds were estimated to be at least 98% pure as judged by HPLC analysis, which was performed on an Ascentis C18 column (150×4.6 mm) using an L-2130 pump (Hitachi) and a UV/Vis L-2420 detector (Hitachi) with UV detection at 250 nm.

7-Benzyloxycoumarin (4a)

To a solution of 7-hydroxy-2H-chromen-2-one (4.86 g, 30.00 mmol) and K₂CO₃ (10.35 g, 75.00 mmol) in acetone (200 mL) was added benzyl chloride (6.90 mL, 60.00 mmol). The resulting was heated to 56 C under N₂ overnight. After filtration to remove K₂CO₃, the filtrate was concentrated in vacuo. The residue was diluted with distd H₂O (100 mL) and then extracted with EtOAc (50 mL×3). The organic layer was dried (Na₂SO₄), filtered and the solvent removed in vacuo. The residue was purified by silica gel chromatography (EtOAc: n-Hexane=1:4) to give 4a (6.43 g, 85%) as a white solid: mp: 135-140° C.; $^1$H NMR (500 MHz, CDCl₃): δ=7.62 (d, J=9.5 Hz, 1H), 7.42 (m, 3H), 7.37 (d, J=8.7 Hz, 1H), 7.34 (m, 2H), 6.91 (d, J=8.7 Hz, 1H), 6.89 (s, 1H), 6.25 (d, J=9.5 Hz, 1H), 5.13 ppm (s, 2H); MS (EI, 70 ev) m/z: 252 [M]₊.

7-(4-Chlorobenzyloxy)coumarin (4b)

To a solution of 7-hydroxy-2H-chromen-2-one (5.16 g, 31.85 mmol) and K₂CO₃ (10.99 g, 79.63 mmol) in acetone (200 mL) was added 4-chlorobenzyl chloride (10.29 g, 63.70 mmol). Following the procedure as described for 4a gave 4b (7.47 g, 82%) as a white solid: mp: 120-125° C.; $^1$H NMR (500 MHz, CDCl₃): δ=7.63 (d, J=9.5 Hz, 1H), 7.37 (m, 5H), 6.90 (dd, J=2.4, 8.6 Hz, 1H), 6.86 (d, J=2.4 Hz, 1H), 6.26 (d, J=9.5 Hz, 1H), 5.09 ppm (s, 2H); MS (EI, 70 ev) m/z: 286 [M]₊.

7-[(Naphthalen-4-yl)methoxyl]coumarin (4e)

To a solution of 7-hydroxy-2H-chromen-2-one (4.45 g, 27.47 mmol) and K₂CO₃ (9.48 g, 68.67 mmol) in acetone (220 mL) was added 1-(chloromethyl)naphthalene (8.30 mL, 54.94 mmol). Following the procedure as described for 4a gave 4e (6.22 g, 75%) as a white solid: mp: 135-150° C.; $^1$H NMR (500 MHz, CDCl₃): δ=8.03 (d, J=8.1 Hz, 1H), 7.91 (d, J=7.8 Hz, 1H), 7.88 (d, J=8.1 Hz, 1H), 7.63 (d, J=9.5 Hz, 1H), 7.60 (m, 1H), 7.56 (m, 2H), 7.48 (t, J=7.8 Hz, 1H), 7.39 (d, J=8.6 Hz, 1H), 7.00 (d, J2.2 Hz, 1H), 6.96 (dd, J2.2, 8.6 Hz, 1H), 6.26 (d, J=9.5 Hz, 1H), 5.56 ppm (s, 2H); MS (EI, 70 ev) m/z: 302 [M]₊.

(E)-Ethyl 4-benzyloxy-2-hydroxycinnamate (5a)

To a solution of 4a (5.54 g, 22.00 mmol) in anhydrous EtOH (50 mL) was added NaOEt (3.12 g, 44.00 mmol) in anhydrous EtOH (50 mL) dropwise during 1 h. The resulting solution was heated to 78° C. under N₂ at for 6 h. The reaction was diluted with distd H₂O (200 mL), acidified with 1N HCl(aq) to pH 4-5 and extracted with EtOAc (100 mL×3). The organic layer was dried (Na₂SO₄), filtered and the solvent removed in vacuo. The residue was purified by silica gel chromatography (EtOAc:n-Hexane=1:4) to give 5a (4.92 g, 75%) as a white solid: mp: 120-130° C.; $^1$H NMR (500 MHz, [D6] DMSO): δ 10.33 (s, 1H), 7.77 (d, J=16.2 Hz, 1H), 7.52 (d, J=9.3 Hz, 1H), 7.40 (m, 5H), 7.33 (d, J=9.3 Hz, 1H), 6.51 (s, 1H), 6.44 (d, J=16.2 Hz, 1H), 5.08 (s, 2H), 4.14 (q, J=7.1 Hz, 2H), 1.22 ppm (t, J7.2 Hz, 3H); MS (EI, 70 ev) m/z: 298 [M]+.

(E)-Ethyl 4-(4-chlorobenzyloxy)-2-hydroxycinnamate (5b)

To a solution of 4b (6.26 g, 21.89 mmol) in anhydrous EtOH (60 mL) was added NaOEt (3.10 g, 43.78 mmol) in anhydrous EtOH (50 mL) dropwise during 1 h. Following the procedure as described for 5a gave 5b (5.23 g, 72%) as a white solid: mp: 133-140° C.; $^1$H NMR (500 MHz, CDCl₃): δ 7.95 (d, J=16.2 Hz, 1H), 7.39 (d, J=8.7 Hz, 1H), 7.35 (dd, J=2.3, 9.0 Hz, 4H), 6.66 (s, 1H), 6.53 (dd, J=2.3, 8.7 Hz, 1H), 6.52 (d, J=16.2 Hz, 1H), 6.44 (d, J=2.3 Hz, 1H), 5.01 (s, 2H), 4.27 (q, J7.1 Hz, 2H), 1.34 ppm (t, J7.1 Hz, 3H); MS (EI, 70 ev) m/z: 332 [M]+.

(E)-Ethyl 2-hydroxy-4-[(naphthalen-4-yl)methoxy]cinnamate (5e)

To a solution of 4e (6.00 g, 19.87 mmol) in anhydrous EtOH (60 mL) was added NaOEt (2.81 g, 39.74 mmol) in anhydrous EtOH (50 mL) dropwise during 1 h. Following the procedure as described for 5a gave 5e (5.12 g, 74%) as a white solid: mp: 139-144° C.; $^1$H NMR (500 MHz, [D6]DMSO): δ=10.34 (s, 1H), 8.05 (d, J=8.0 Hz, 1H), 7.97

(d, J=7.6 Hz, 1H), 7.93 (d, J=8.7 Hz, 1H), 7.79 (d, J=16.1 Hz, 1H), 7.64 (t, J=6.9 Hz, 1H), 7.57 (m, 3H), 7.51 (t, J=7.6 Hz, 1H), 6.61 (dd, =2.1, 8.7 Hz, 1H), 6.57 (d, J=2.1 Hz, 1H), 6.46 (d, J=16.1 Hz, 1H), 5.53 (s, 2H), 4.14 (q, J=7.1 Hz, 2H), 1.23 ppm (t. J=7.1 Hz, 3H); MS (EI, 70 ev) m/z: 348 [M]+.

(E)-N-Hydroxy-4-benzyloxy-2-methxycinnamide (8a)

KOH (1.23 g, 22.00 mmol) was added to a solution of $NH_2OH$ (1.53 g, 22.00 mmol) in MeOH (20 mL). The resulting solution was stirred in an ice bath for 1 h. Filtration to remove the white salt gave a solution of $NH_2OH$ in MeOH. A solution of 7a (3.12 g, 11.00 mmol) in freshly distilled THF (30 mL) was treated with ethyl chloroformate (1.58 mL, 16.50 mmol) and $Et_3N$ (3.06 mL, 22.00 mmol) and was stirred at room temperature for 1 h. The prepared free $NH_2OH$ solution was then added to the reaction, and stirring was continued for 3 h. The reaction was diluted with distilled water (100 mL), acidified with 1n HCl(aq) to pH 2-3, and extracted with EtOAc (3×50 mL). The organic layer was dried ($Na_2SO_4$) and filtered, and the solvent was removed in vacuo. The residue was purified by silica gel chromatography (EtOAc/n-hexane, 1:2-1:1) to give 8a (1.81 g, 55%) as a white solid: mp: 128-135° C.; $^1$H NMR (500 MHz, [D6]DMSO): d=10.60 (s, 1H), 8.89 (s, 1H), 7.58 (d, J=15.9 Hz, 1H), 7.45 (t, J=7.4 Hz, 2H), 7.42 (d, J=8.5 Hz, 1H), 7.38 (t, J=7.4 Hz, 2H), 7.33 (d, J=7.4 Hz, 1H), 6.70 (d, J=1.9 Hz, 1H), 6.64 (dd, J=1.9, 8.5 Hz, 1H), 6.37 (d, J=15.9 Hz, 1H), 5.14 (s, 2H), 3.83 ppm (s, 3H); $^{13}$C NMR (125 MHZ, [D6]DMSO): d=161.6, 160.0, 137.2, 134.9, 129.6, 128.4, 127.9, 127.7, 116.9, 106.6, 99.2, 69.8, 55.2 ppm; HRMS-EI: m/z [M]+ calcd for $C_{17}H_{17}NO_4$: 299.1157, found: 299.1160.

(E)-N-Hydroxy-4-(4-chlorobenzyloxy)-2-methoxycinnamide (8b)

Following the procedure as described for 8a, reaction of 7b (3.50 g, 11.00 mmol) in THF (40 mL) with ethyl chloroformate (1.54 mL, 16.50 mmol) and $Et_3N$ (2.31 mL, 16.50 mmol) gave 8b (1.94 g, 53%) as a white solid: mp: 167-172° C.; $^1$H NMR (500 MHz, [D6]DMSO): d=7.57 (d, J=15.8 Hz, 1H), 7.47 (d, J=8.6 Hz, 2H), 7.44 (d, J=8.6 Hz, 2H), 7.42 (d, J=8.8 Hz, 1H), 6.68 (s, 1H), 6.62 (d, J=8.8 Hz, 1H), 6.36 (d, J=15.8 Hz, 1H), 5.14 (s, 2H), 3.82 ppm (s, 3H); $^{13}$C NMR (125 MHz, [D6]DMSO): d=164.1, 161.0, 159.4, 136.3, 133.0, 130.1, 129.7, 128.9, 117.4, 116.9, 107.1, 99.9, 69.1, 56.2 ppm; HRMS-ESI: m/z [M_H]_ calcd for $C_{17}H_{15}NO_4Cl$: 332.0690, found: 332.0693.

(E)-N-Hydroxy-4-(4-bromobenzyloxy)-2-methoxycinnamide (8c)

Following the procedure as described for 8a, reaction of 7c (3.80 g, 10.50 mmol) in THF (40 mL) with ethyl chloroformate (1.47 mL, 15.75 mmol) and $Et_3N$ (2.21 mL, 15.75 mmol) gave 8c (2.26 g, 57%) as a white solid: mp: 165-170° C.; $^1$H NMR (500 MHz, [D6]DMSO): d=10.60 (s, 1H), 8.89 (s, 1H), 7.59 (d, J=8.2 Hz, 2H), 7.56 (d, J=16.0 Hz, 1H), 7.42 (d, J=8.2 Hz, 3H), 6.69 (d, J=2.1 Hz, 1H), 6.63 (dd, J=2.1, 8.6 Hz, 1H), 6.37 (d, J=16.0 Hz, 1H), 5.13 (s, 2H), 3.84 ppm (s, 3H); $^{13}$C NMR (125 MHz, [D6]DMSO): d=164.1, 161.0, 159.4, 136.7, 133.7, 131.9, 130.4, 129.7, 121.5, 117.4, 116.9, 107.1, 99.9, 69.1, 56.2 ppm; HRMS-EI: m/z [M]+ calcd for $C_{17}H_{16}BrNO_4$: 377.0263, found: 377.0259.

(E)-N-Hydroxy-4-(4-methoxybenzyloxy)-2-methoxycinnamide (8d)

Following the procedure as described for 8a, reaction of 7d (3.50 g, 11.15 mmol) in THF (35 mL) with ethyl chloroformate (1.56 mL, 16.73 mmol) and $Et_3N$ (2.35 mL, 16.73 mmol) gave 8d (2.02 g, 55%) as a white solid: mp: 140-150° C.; $^1$H NMR (500 MHz, [D6]DMSO): d=10.60 (s, 1H), 8.89 (s, 1 H), 7.58 (d, J=15.9 Hz, 1H), 7.41 (d, J=8.5 Hz, 1H), 7.38 (d, J=8.3 Hz, 2H), 6.94 (d, J=8.3 Hz, 2H), 6.67 (s, 1H), 6.63 (d, J=8.5 Hz, 1H), 6.37 (d, J=15.9 Hz, 1H), 5.05 (s, 2H), 3.83 (s, 3H), 3.75 ppm (s, 3H); $^{13}$C NMR (125 MHz, [D6]DMSO): d=164.2, 161.3, 159.6, 159.4, 133.8, 130.1, 129.6, 129.1, 117.2, 116.7, 114.3, 107.2, 99.8, 69.7, 56.1, 55.6 ppm; HRMS-EI: m/z [M]+ calcd for $C_{18}H_{19}NO_5$: 329.1263, found: 329.1259.

(E)-N-Hydroxy-4-[(naphthalen-4-yl)methoxy]-2-methoxycinnamide (8e)

Following the procedure as described for 8a, reaction of 7e (3.15 g, 9.43 mmol) in THF (35 mL) with ethyl chloroformate (1.32 mL, 14.15 mmol) and $Et_3N$ (1.99 mL, 14.15 mmol) gave 8e (1.67 g, 51%) as a white solid: mp: 150-158° C.; $^1$H NMR (500 MHz, [D6]DMSO): d=10.61 (s, 1H), 8.91 (s, 1H), 8.09 (d, J=8.2 Hz, 1H), 7.97 (d, J=7.7 Hz, 1H), 7.94 (d, J=8.2 Hz, 1H), 7.69 (d, J=7.7 Hz, 1H), 7.61 (d, J=9.1 Hz, 1H), 7.56 (m, 3H), 7.52 (t, J=7.7 Hz, 1H), 7.46 (d, J=15.9 Hz, 1H), 6.78 (s, 1H), 6.75 (d, J=8.6 Hz, 1H), 6.39 (d, J=15.9 Hz, 1H), 5.59 (s, 2H), 3.84 ppm (s, 3H); $^{13}$C NMR (125 MHz, [D6]DMSO): d=164.2, 161.4, 159.4, 133.8, 132.7, 131.6, 129.7, 129.3, 129.0, 127.4, 127.0, 126.5, 125.9, 124.4, 117.3, 116.9, 107.3, 99.8, 68.5, 56.2 ppm; HRMS-ESI m/z [M_H]_ calcd for $C_{21}H_{18}NO_4Cl$: 348.1236, found: 348.1235.

(E)-N-Hydroxy-4-(trifluoromethoxy)-2-methoxycinnamide (8f)

Following the procedure as described for 8a, reaction of 7 f (4.50 g, 12.23 mmol) in THF (45 mL) with ethyl chloroformate (1.71 mL, 18.35 mmol) and $Et_3N$ (2.58 mL, 18.35 mmol) gave 8 f (2.72 g, 58%) as a white solid: mp: 155-160° C.; $^1$H NMR (500 MHz, [D6]DMSO): d=7.58 (d, J=8.5 Hz, 2H), 7.57 (d, J=16.6 Hz, 1H), 7.43 (d, J=8.5 Hz, 1H), 7.38 (d, J=8.5 Hz, 2H), 6.69 (d, J=1.9 Hz, 1H), 6.64 (d, J=8.5 Hz, 1H), 6.37 (d, J=16.6 Hz, 1H), 5.17 (s, 2H), 3.82 ppm (s, 3H); $^{13}$C NMR (125 MHz, [D6]DMSO): d=161.0, 159.4, 148.4, 136.8, 133.7, 130.1, 129.7, 121.5, 117.4, 117.0, 107.1, 99.9, 69.0, 56.2 ppm; HRMS-EI: m/z [M]+ calcd for $C_{11}H_{16}F_3NO_5$: 383.0980, found: 383.0981.

(E)-N-Hydroxy-2-benzyloxy-4-methoxycinnamide (13a)

KOH (1.46 g, 26.00 mmol) to a solution of $NH_2OH \cdot HCl$ (1.81 g, 26.00 mmol) in MeOH (20 mL). The resulting mixture was stirred in an ice bath for 1 h. Filtration to remove the white salt gave a solution of $NH_2OH$ in MeOH. A solution of 12a (3.69 g, 13.00 mmol) in freshly distilled THF (45 mL) was treated with ethyl chloroformate (1.29 mL, 20.97 mmol), $Et_3N$ (3.61 mL, 26.00 mmol) and the resulting solution was stirred at room temperature for 1 h. The prepared free $NH_2OH$ solution was then added to the reaction and stirring was continued for 3 h. The reaction was diluted with distilled water (100 mL), acidified with 1n HCl(aq) to pH 2-3, and extracted with EtOAc (3_50 mL).

The combined organic layer was dried (Na$_2$SO$_4$) and filtered, and the solvent was removed in vacuo. The residue was purified by silica gel chromatography (EtOAc/n-hexane, 1:1) to give 13a (1.55 g, 40%) as a white solid: mp: 134-140° C.; $^1$H NMR (500 MHz, [D6]acetone): d=8.02 (d, J=15.8 Hz, 1H), 7.62 (d, J=7.5 Hz, 3H) 7.52 (t, J=7.2 Hz, 2H), 7.45 (t, J=7.3 Hz, 1H), 6.80 (d, J=2.2 Hz, 1H), 6.68 (dd, J=8.6, 2.3 Hz, 1H), 6.66 (d, J=8.6 Hz, 1H), 6.52 (d, J=15.8 Hz, 1H), 5.36 (s, 2H), 3.92 ppm (s, 3H); $^{13}$C NMR (125 MHz, [D6]DMSO): d=164.1, 162.1, 158.1, 137.3, 133.5, 129.1, 129.0, 128.4, 128.0, 117.2, 117.0, 106.7, 100.4, 70.1, 55.9 ppm; HRMS-FAB: m/z [M+H]+ calcd for C$_{17}$H$_{18}$NO$_4$: 300.1235, found: 300.1234.

(E)-N-Hydroxy-2-(4-chlorobenzyloxy)-4-methoxycinnamide (13b)

Following the procedure as described for 13a, reaction of 12b (2.53 g, 7.86 mmol) in THF (40 mL) with ethyl chloroformate (1.10 mL, 11.79 mmol) and Et$_3$N (1.65 mL, 11.79 mmol) gave 13b (1.10 g, 42%) as a white solid: mp: 160-170° C.; $^1$H NMR (500 MHz, [D4]MeOH): d=11.04 (s, 1H), 9.69 (s, 1H), 8.44 (d, J=15.9 Hz, 1H), 8.27 (d, J=8.8 Hz, 1H), 8.25 (br s, 4H), 7.48 (d, J=1.9 Hz, 1H), 7.39 (dd, J=8.8, 1.9 Hz, 1H), 7.16 (d, J=15.9 Hz, 1H), 6.01 (s, 2H), 4.57 ppm (s, 3H); $^{13}$C NMR (125 MHz, [D6]DMSO): d=164.1, 162.0, 157.9, 136.3, 133.5, 133.0, 129.9, 129.3, 129.1, 117.3, 117.0, 106.8, 100.4, 69.3, 55.9 ppm; HRMS-ESI: m/z [M+H]+ calcd for C$_{17}$H$_{17}$ClNO$_4$: 334.0846, found: 334.0843.

(E)-N-Hydroxy-2-(4-bromobenzyloxy)-4-methoxycinnamide (13c)

Following the procedure as described for 13a, reaction of 12c (3.50 g, 9.67 mmol) in THF (40 mL) with ethyl chloroformate (1.35 mL, 14.51 mmol) and Et$_3$N (2.03 mL, 14.51 mmol) gave 13c (1.46 g, 40%) as a white solid: mp: 148-155° C.; $^1$H NMR (500 MHz, [D6]acetone): d=10.17 (s, 1H), 7.18 (d, J=16.1 Hz, 1H), 7.14 (d, J=8.3 Hz, 2H), 7.00 (d, J=8.6 Hz, 1H), 6.96 (d, J=8.3 Hz, 2H), 6.21 (s, 1H), 6.13 (d, J=8.6 Hz, 1H), 5.90 (d, J=16.1 Hz, 1H), 4.73 (s, 2H), 3.32 ppm (s, 3H); $^{13}$C NMR (125 MHz, [D6]DMSO): d=164.1, 162.0, 157.9, 136.7, 133.5, 132.0, 130.2, 129.3, 121.6, 117.3, 117.0, 106.8, 100.4, 69.3, 55.9 ppm; HRMS-ESI: m/z [M+H]+ calcd for C$_{17}$H$_{17}$BrNO$_4$: 378.0341, found: 378.0340.

(E)-N-Hydroxy-2-(4-methoxybenzyloxy)-4-methoxycinnamide (13d)

Following the procedure as described for 13a, reaction of 12d (2.20 g, 7.00 mmol) in THF (40 mL) with ethyl chloroformate (1.86 mL, 10.51 mmol) and Et$_3$N (2.80 mL, 10.51 mmol) gave 13d (1.04 g, 45%) as a white solid: mp: 145-150° C.; $^1$H NMR (500 MHz, [D6]acetone): d=7.98 (d, J=15.8 Hz, 1H), 7.61 (d, J=8.4 Hz, 1H), 7.55 (d, J=8.6 Hz, 2H), 7.07 (d, J=8.6 Hz, 2H), 6.81 (d, J=2.2 Hz, 1H), 6.67 (dd, J=8.6, 2.2 Hz, 1H), 6.64 (d, J=15.8 Hz, 1H), 5.27 (s, 2H), 3.93 (s, 3H), 3.92 ppm (s, 3H); $^{13}$C NMR (125 MHz, [D6]DMSO): d=162.5, 159.7, 158.6, 135.6, 129.0, 128.8, 116.8, 114.4, 113.6, 105.8, 99.5, 69.9, 54.5, 54.3 ppm; HRMS-ESI: m/z [M+H]+ calcd for C$_{18}$H$_{20}$NO$_5$: 330.1341, found: 330.1341.

(E)-N-Hydroxy-2-[(naphthalen-4-yl)methoxy]-4-methoxycinnamide (13e)

Following the procedure as described for 13a, reaction of 12e (2.82 g, 8.44 mmol) in THF (40 mL) with ethyl chloroformate (2.24 mL, 12.67 mmol) and Et$_3$N (3.38 mL, 12.67 mmol) gave 13e (1.38 g, 47%) as a white solid: mp: 152-165° C.; $^1$H NMR (500 MHz, [D6]DMSO): d=10.55 (s, 1H), 8.84 (s, 1H), 8.13 (d, J=8.2 Hz, 1H), 7.98 (m, 2H), 7.94 (d, J=8.2 Hz, 1H), 7.69 (d, J=6.7 Hz, 1H), 7.61 (d, J=16.1 Hz, 1H), 7.55 (m, 2H), 7.45 (d, J=8.5 Hz, 1H), 6.90 (s, 1H), 6.60 (d, J=8.5 Hz, 1H), 6.30 (d, J=16.1 Hz, 1H), 5.65 (s, 2H), 3.80 ppm (s, 3H); $^{13}$C NMR (125 MHz, [D6]DMSO): d=163.9, 162.2, 158.1, 133.8, 133.2, 132.7, 131.6, 129.3, 129.0, 128.7, 127.1, 127.0, 126.5, 125.9, 124.3, 117.0, 106.9, 100.4, 68.7, 55.9 ppm; HRMS-ESI: m/z [M+H]+ calcd for C$_{21}$H$_{20}$NO$_4$: 350.1392, found: 350.1390.

(E)-N-Hydroxy-2-(2-(4-methoxyphenoxyoxy)ethoxy)-4-methoxycinnamide (18a)

Following the procedure described for 8a, reaction of 17a (900 mg, 2.61 mmol) in THF (10 mL) with ethyl chloroformate (424 mg, 3.92 mmol) and Et3N (0.73 mL, 5.22 mmol) gave 18a (497 mg, 53%) as a white solid: mp: 110-115° C.; $^1$H NMR (500 MHz, [D6]acetone): d=10.12 (s, 1H), 8.63 (s, 1H), 7.85 (d, J=15.8 Hz, 1H), 7.49 (d, J=8.5 Hz, 1H), 6.95 (d, J=8.1 Hz, 2H), 6.86 (d, J=8.1 Hz, 2H), 6.68 (d, J=2.4 Hz, 1H), 6.57 (dd, J=2.4, 8.5 Hz, 1H), 6.54 (d, J=15.8 Hz, 1H), 4.42 (m, 2H), 4.38 (m, 2H), 3.83 (s, 3H), 3.73 ppm (s, 3H); $^{13}$C NMR (125 MHz, [D6]DMSO): d=162.1, 158.4, 158.3, 154.1, 152.8, 133.7, 129.4, 117.2, 116.9, 116.2, 115.1, 113.2, 107.0, 100.0, 67.7, 67.3, 60.4, 55.9, 55.8 ppm; HRMS-EI: m/z [M]+ calcd for C$_{19}$H$_{21}$NO$_6$: 359.1369, found: 359.1364.

(E)-N-Hydroxy-2-(2-(4-methoxyphenoxyoxy)propoxy)-4-methoxycinnamide (18b)

Following the procedure described for 8a, reaction of 17b (300 mg, 0.84 mmol) in THF (10 mL) with ethyl chloroformate (136 mg, 1.26 mmol) and Et$_3$N (0.23 mL, 1.68 mmol) gave 18b (191 mg, 61%) as a white solid: mp: 115-120° C.; $^1$H NMR (500 MHz, [D6]acetone): d=10.60 (s, 1H), 8.86 (s, 1H), 7.57 (d, J=15.9 Hz, 1H), 7.41 (d, J=8.6 Hz, 1H), 6.86 (d, J=9.2 Hz, 2H), 6.82 (d, J=9.2 Hz, 2H), 6.60 (d, J=2.3 Hz, 1H), 6.54 (dd, J=2.3, 8.6 Hz, 1H), 6.38 (d, J=15.9 Hz, 1H), 4.18 (t, J=6.2 Hz, 2H), 4.07 (t, J=6.2 Hz, 2H), 3.75 (s, 3H), 3.66 (s, 3H), 2.19 ppm (q, J=6.2 Hz, 2H); $^{13}$C NMR (125 MHz, [D6]DMSO): d=164.2, 162.1, 158.7, 153.9, 152.9, 134.0, 130.1, 117.3, 116.7, 115.9, 115.1, 106.6, 99.6, 65.5, 65.2, 55.9, 55.8, 29.1 ppm; HRMS-ESI: m/z [M+Na]+ calcd for C$_{20}$H$_{23}$NNaO$_6$: 396.1408, found: 396.1418.

(E)-N-Hydroxy-2-(2-(4-methoxyphenoxyoxy)butoxy)-4-methoxycinnamide (18c)

Following the procedure described for 8a, reaction of 17c (250 mg, 0.67 mmol) in THF (10 mL) was treated with ethyl chloroformate (109 mg, 1.00 mmol) and Et3N (0.19 mL, 1.34 mmol) gave 18c (166 mg, 64%) as a white solid: mp: 82-88° C.; $^1$H NMR (500 MHz, [D6]DMSO): d=10.62 (s, 1H), 9.46 (s, 1H), 7.57 (d, J=15.9 Hz, 1H), 7.40 (d, J=8.4 Hz, 1H), 6.83 (d, J=9.4 Hz, 2H), 6.79 (d, J=9.4 Hz, 2H), 6.56 (s, 1H), 6.52 (d, J=8.4 Hz, 1H), 6.35 (d, J=15.9 Hz, 1H), 4.06 (t, J=5.7 Hz, 2H), 3.93 (t, J=5.7 Hz, 2H), 3.74 (s, 3H), 3.64 (s, 3H), 1.86 ppm (m, 4H); $^{13}$C NMR (125 MHz, [D6]DMSO): d=164.2, 162.1, 158.8, 153.8, 153.1, 134.0, 129.9, 117.2, 116.7, 115.8, 115.1, 106.5, 99.6, 68.3, 68.0, 55.9, 55.8, 26.1, 25.8 ppm; HRMS-ESI: m/z [M_H]_ calcd for C$_{21}$H$_{24}$NO$_6$: 386.1604, found: 386.1609.

(E)-N-Hydroxy-2-(2-(4-methoxyphenoxyoxy)pentyloxy)-4-methoxycinnamide (18d)

Following the procedure described for 8a, reaction of 17d (200 mg, 0.52 mmol) in THF (10 mL) with ethyl chloroformate (85 mg, 0.78 mmol) and Et$_3$N (0.15 mL, 1.04 mmol) gave 18d (118 mg, 57%) as a colorless liquid: $^1$H NMR (500 MHz, [D6]acetone): d=7.82 (d, J=15.7 Hz, 1H), 7.47 (d, J=8.4 Hz, 1H), 6.86 (d, J=9.4 Hz, 2H), 6.84 (d, J=15.7 Hz, 1H), 6.82 (d, J=9.4 Hz, 2H), 6.60 (d, J=2.2 Hz, 1H), 6.54 (dd, J=2.2, 8.4 Hz, 1H), 4.12 (t, J=6.4 Hz, 2H), 3.97 (t, J=6.4 Hz, 2H), 3.82 (s, 3H), 3.71 (s, 3H), 1.93 (m, 2H), 1.84 (m, 2H), 1.69 ppm (m, 2H); $^{13}$C NMR (125 MHz, [D6]DMSO): d=162.4, 159.1, 153.9, 153.3, 135.1, 129.8, 116.8, 115.4, 114.5, 105.7, 99.0, 68.2, 68.1, 54.9, 28.9, 28.7, 22.6 ppm; HRMS-ESI: m/z [M_H]_calcd for C$_{22}$H$_{26}$NO$_6$: 400.1760, found: 400.1766.

(E)-N-Hydroxy-4-methoxy-2-phenylcinnamide (22a)

Following the procedure described for 8a, reaction of 21a (800 mg, 3.15 mmol) in THF (10 mL) with ethyl chloroformate (512 mg, 4.73 mmol) and Et$_3$N (0.88 mL, 6.30 mmol) gave 22a (355 mg, 42%) as a white solid: mp: 100-102° C.; $^1$H NMR (500 MHz, [D6]acetone): d=8.67 (br s, 1H), 7.66 (d, J=8.2 Hz, 1H), 7.55 (d, J=15.5 Hz, 1H), 7.47 (m, 2H), 7.39 (m, 1H), 7.33 (d, J=8.4 Hz, 2H), 6.98 (dd, J=2.5, 8.7 Hz, 1H), 6.88 (d, J=2.5 Hz, 1H), 6.41 (d, J=15.5 Hz, 1H), 3.89 ppm (s, 3H); $^{13}$C NMR (125 MHz, [D6]acetone): d=164.7, 161.3, 145.1, 141.1, 138.6, 130.5, 129.1, 128.8, 128.4, 128.1, 126.4, 117.3, 115.9, 114.9, 114.7, 55.8 ppm; HRMS-ESI: m/z [M+Na]+ calcd for C$_{16}$H$_{15}$NNaO$_3$: 292.0950, found: 292.0944.

(E)-N-Hydroxy-4-methoxy-2-(4-bromophenyl)cinnamide (22b)

Following the procedure described for 8a, reaction of 21b (500 mg, 1.51 mmol) in THF (10 mL) with ethyl chloroformate (245 mg, 2.27 mmol) and Et$_3$N (0.42 mL, 3.02 mmol) gave 22b (204 mg, 39%) as a white solid: mp: 141-144° C.; $^1$H NMR (500 MHz, [D6]DMSO): d=10.64 (s, 1H), 8.90 (s, 1H), 7.65 (d, J=8.2 Hz, 2H), 7.63 (d, J=8.7 Hz, 1H), 7.25 (d, J=8.2 Hz, 2H), 7.22 (d, J=15.6 Hz, 1H), 7.02 (dd, J=2.1, 8.7 Hz, 1H), 6.84 (d, J=2.1 Hz, 1H), 6.28 (d, J=15.6 Hz, 1H), 3.80 ppm (s, 3H); $^{13}$C NMR (125 MHz, [D6]DMSO): d=163.4, 160.3, 142.6, 139.4, 136.4, 132.1, 131.8, 128.3, 125.6, 121.7, 118.6, 115.4, 115.1, 55.9 ppm. HRMS-ESI: m/z [M+Na]+ calcd for C$_{16}$H$_{14}$BrNNaO$_3$: 370.0055, found: 370.0049.

(E)-N-Hydroxy-4-methoxy-2-(naphthalen-1-yl)cinnamide (22 c)

Following the procedure described for 8a, reaction of 21c (1.00 g, 3.29 mmol) in THF (15 mL) with ethyl chloroformate (533 mg, 4.93 mmol) and Et$_3$N (0.92 mL, 6.58 mmol) gave 22c (619 mg, 59%) as a white solid: mp: 125-127° C.; $^1$H NMR (500 MHz, [D6]DMSO): d=8.00 (d, J=8.2 Hz, 2H), 7.74 (d, J=8.8 Hz, 1H), 7.59 (t, J=7.9 Hz, 1H), 7.52 (t, J=7.2 Hz, 1H), 7.42 (t, J=7.9 Hz, 1H), 7.33 (d, J=6.8 Hz, 1H), 7.30 (d, J=8.4 Hz, 1H), 7.11 (dd, J=2.6, 8.8 Hz, 1H), 6.83 (d, J=2.6 Hz, 1H), 6.82 (d, J=2.5 Hz, 1H), 6.25 (d, J=15.6 Hz, 1H), 3.79 ppm (s, 3H); $^{13}$C NMR (125 MHz, [D6]DMSO): d=163.3, 160.3, 142.4, 137.9, 136.2, 133.6, 132.0, 128.8, 128.6, 127.7, 127.5, 127.0, 126.9, 126.6, 125.9, 118.0, 116.3, 115.1, 55.9 ppm; HRMS-ESI: m/z [M+Na]+ calcd for C$_{20}$H$_{17}$NNaO$_3$: 342.1106, found: 342.1101.

(E)-N-Hydroxy-4-methoxy-2-(biphenyl-4-yl)cinnamide (22d)

Following the procedure described for 8a, reaction of 21d (800 mg, 2.42 mmol) in THF (15 mL) with ethyl chloroformate (393 mg, 3.64 mmol) and Et$_3$N (0.68 mL, 4.84 mmol) gave 22d (326 mg, 39%) as a white solid: mp: 76-79° C.; $^1$H NMR (500 MHz, [D6]DMSO): d=7.76 (d, J=8.1 Hz, 1H), 7.73 (d, J=7.7 Hz, 2H), 7.65 (d, J=8.7 Hz, 1H), 7.48 (t, J=7.7 Hz, 2H), 7.39 (d, J=8.1 Hz, 3H), 7.35 (d, J=15.0 Hz, 1H), 7.02 (dd, J=2.6, 8.7 Hz, 1H), 6.90 (d, J=2.6 Hz, 1H), 6.32 (d, J=15.0 Hz, 1H), 3.82 ppm (s, 3H); $^{13}$C NMR (125 MHz, [D6]DMSO): d=163.5, 160.4, 143.5, 140.0, 139.9, 139.3, 136.9, 130.6, 129.5, 128.3, 128.1, 127.2, 127.1, 125.6, 118.3, 115.4, 114.9, 55.9 ppm; HRMS-ESI: m/z [M+Na]+ calcd for C$_{22}$H$_{19}$NNaO$_3$: 368.1263, found: 368.1257.

(E)-N-Hydroxy-4-methoxy-2-(4-phenoxyphenyl)cinnamide (22e)

Following the procedure described for 8a, reaction of 21e (800 mg, 2.31 mmol) in THF (15 mL) with ethyl chloroformate (374 mg, 3.47 mmol) and Et$_3$N (0.65 mL, 4.62 mmol) gave 22e (417 mg, 50%) as a white solid: mp: 75-78° C.; $^1$H NMR (500 MHz, [D6]DMSO): d=7.61 (d, J=8.7 Hz, 1H), 7.42 (t, J=8.1 Hz, 1H), 7.42 (d, J=15.8 Hz, 1H), 7.30 (d, J=8.5 Hz, 3H), 7.18 (t, J=7.4 Hz, 1H), 7.10 (d, J=8.0 Hz, 2H), 7.05 (d, J=8.5 Hz, 2H), 6.99 (dd, J=2.6, 8.7 Hz, 1H), 6.85 (d, J=2.6 Hz, 1H), 6.28 (d, J=15.8 Hz, 1H), 3.80 ppm (s, 3H); $^{13}$C NMR (125 MHz, [D6]DMSO): d=163.5, 160.3, 157.1, 156.5, 143.3, 136.9, 135.0, 131.6, 130.7, 128.3, 125.7, 124.5, 119.8, 118.3, 118.2, 115.5, 114.7, 55.8 ppm; HRMS-ESI: m/z [M+Na]+ calcd for C$_2$H$_{19}$NNaO$_4$: 384.1212, found: 384.1206.

(E)-N-Hydroxy-4-methoxy-2-(4-benzoylphenyl)cinnamide (22f)

Following the procedure described for 8a, reaction of 21 f (900 mg, 2.51 mmol) in THF (20 mL) with ethyl chloroformate (406 mg, 3.77 mmol) and Et$_3$N (0.71 mL, 5.02 mmol) gave 22 f (487 mg, 52%) as a white solid: mp: 71-73° C.; $^1$H NMR (500 MHz, [D6]DMSO): d=7.83 (d, J=8.0 Hz, 2H), 7.78 (d, J=7.6 Hz, 2H), 7.68 (d, J=7.3 Hz, 1H), 7.67 (d, J=7.6 Hz, 1H), 7.58 (t, J=7.6 Hz, 2H), 7.50 (d, J=8.0 Hz, 2H), 7.29 (d, J=15.6 Hz, 1H), 7.06 (dd, J=2.3, 8.6 Hz, 1H), 6.92 (d, J=2.3 Hz, 1H), 6.31 (d, J=15.6 Hz, 1H), 3.82 ppm (s, 3H); $^{13}$C NMR (125 MHz, [D6]DMSO): d=195.8, 163.4, 160.4, 144.5, 142.8, 137.5, 136.5, 136.4, 133.2, 130.3, 130.2, 130.1, 129.1, 128.5, 125.6, 118.8, 115.4, 55.9 ppm; HRMS-ESI: m/z [M+Na]+ calcd for C$_{23}$H$_{19}$NNaO$_4$: 396.1212, found: 396.1206.

(E)-N-Hydroxy-4-methoxy-2-(dibenzofuran-4-yl)cinnamide (22g)

Following the procedure described for 8a, reaction of 21g (1.00 g, 2.91 mmol) in THF (20 mL) with ethyl chloroformate (470 mg, 4.36 mmol) and Et$_3$N (0.82 mL, 5.82 mmol) gave 22g (532 mg, 51%) as a white solid: mp: 158-161° C.; $^1$H NMR (500 MHz, [D6]DMSO): d=8.21 (d, J=7.7 Hz, 1H), 8.19 (d, J=7.7 Hz, 1H), 7.74 (d, J=8.5 Hz, 1H), 7.60 (d, J=8.2 Hz, 1H), 7.49 (q, J=7.5 Hz, 2H), 7.41 (d, J=7.5 Hz, 1H), 7.38 (d, J=7.2 Hz, 1H), 7.11 (dd, J=2.5, 8.5 Hz, 1H), 7.10 (d, J=15.6 Hz, 1H), 7.01 (d, J=2.5 Hz, 1H), 6.30 (d, J=15.6 Hz, 1H), 3.82 ppm (s, 3H); $^{13}$C NMR (125 MHz, [D6]DMSO): d=163.3, 160.4, 156.0, 153.4, 138.5, 136.2, 129.2, 128.3, 127.9, 126.5, 124.5, 124.3, 124.0, 123.7, 121.8, 121.4, 118.3, 116.3, 115.4, 112.3, 55.9 ppm; HRMS-ESI: m/z [M+Na]+ calcd for $C_{22}H_{17}NNaO_4$: 382.1055, found: 382.1050.

(E)-N-Hydroxy-4-propoxy-2-phenylcinnamide (27a)

NaOH (120 mg, 3.01 mmol) in 50% $NH_2OH$(aq) (2 mL) in an ice bath was added to a solution of 26a (170 mg, 0.60 mmol) in MeOH/THF (1 mL: 1 mL). The resulting solution was then warmed to room temperature and stirred for an additional 3 h. The reaction was diluted with distilled water (50 mL), acidified with 1n HCl(aq) to pH 6-7, and extracted with EtOAc (25 mL×3). The organic layer was dried ($Na_2SO_4$) and filtered, and the solvent was removed in vacuo. The residue was purified by silica gel chromatography (MeOH/$CH_2Cl_2$, 3:97) to give 27a (90 mg, 51%) as a white solid: mp: 147-150° C.; $^1$H NMR (500 MHz, [D6]DMSO): d=10.22 (s, 1H), 7.69 (d, J=8.5 Hz, 1H), 7.54 (d, J=15.4 Hz, 1H), 7.42 (m, 3H), 7.33 (m, 2H), 6.97 (dd, J=2.5, 8.5 Hz, 1H), 6.87 (d, J=2.5 Hz, 1H), 6.39 (d, J=15.4 Hz, 1H), 4.03 (t, J=6.6 Hz, 2H), 1.78 (m, 2H), 1.01 ppm (t, J=7.5 Hz, 3H); $^{13}$C NMR (125 MHz, [D6]DMSO): d=163.5, 159.8, 140.0, 140.2, 136.9, 130.0, 128.8, 128.2, 128.1, 125.4, 118.0, 116.0, 115.1, 69.7, 22.5, 10.8 ppm; HRMS-ESI: m/z [M+Na]+ calcd for $C_{18}H_{19}NNaO_3$: 320.1263, found: 320.1257.

(E)-N-Hydroxy-4-butoxy-2-phenylcinnamide (27b)

NaOH (100 mg, 2.50 mmol) in 50% $NH_2OH$(aq) (2 mL) in an ice bath was added to a solution of 26b (162 mg, 0.50 mmol) in MeOH/THF (1 mL: 1 mL). Following the procedure as described for 27a gave 27b (88 mg, 57%) as a white solid: mp: 140-144° C.; $^1$H NMR (500 MHz, [D6]DMSO): d=10.61 (s, 1H), 8.87 (s, 1H), 7.61 (d, J=8.7 Hz, 1H), 7.45 (d, J=15.7 Hz, 1H), 7.42 (m, 2H), 7.28 (m, 3H), 6.99 (dd, J=2.3, 8.7 Hz, 1H), 6.82 (d, J=2.3 Hz, 1H), 6.28 (d, J=15.7 Hz, 1H), 4.02 (t, J=7.4 Hz, 2H), 1.69 (m, 2H), 1.41 (m, 2H), 0.91 ppm (t, J=7.4 Hz, 3H); $^{13}$C NMR (125 MHz, [D6]DMSO): d=163.5, 159.8, 144.0, 140.2, 136.9, 130.0, 128.8, 128.1, 125.4, 118.0, 115.9, 115.2, 67.9, 31.2, 19.2, 14.2 ppm; HRMS-ESI: m/z [M+Na]+ calcd for $C_{19}H_{21}NNaO_3$: 334.1419, found: 334.1414.

(E)-N-Hydroxy-4-pentoxy-2-phenylcinnamide (27c)

NaOH (100 mg, 2.50 mmol) in 50% $NH_2OH$(aq) (2 mL) in an ice bath was added to a solution of 26c (169 mg, 0.50 mmol) in MeOH/THF (1 mL: 1 mL). Following the procedure as described for 27a gave 27c (86 mg, 53%) as a white solid: mp: 121-124° C.; $^1$H NMR (500 MHz, [D6]DMSO): d=10.61 (s, 1H), 9.47 (s, 1H), 7.62 (d, J=8.7 Hz, 1H), 7.47 (d, J=15.6 Hz, 1H), 7.46 (m, 1H), 7.42 (m, 1H), 7.29 (m, 3H), 7.00 (dd, J=2.6, 8.7 Hz, 1H), 6.83 (d, J=2.6 Hz, 1H), 6.29 (d, J=15.6 Hz, 1H), 4.02 (t, J=6.5 Hz, 2H), 1.71 (m, 2H), 1.36 (m, 4H), 0.88 ppm (t, J=6.5 Hz, 3H); $^{13}$C NMR (125 MHz, [D6]DMSO): d=163.5, 159.8, 158.4, 144.0, 140.2, 136.9, 130.0, 128.8, 128.1, 128.0, 125.4, 118.0, 115.9, 115.2, 68.2, 28.8, 28.1, 22.3, 14.4 ppm; HRMS-ESI: m/z [M+Na]+ calcd for $C_{20}H_{23}NNaO_3$: 348.1576, found: 348.1570.

(E)-N-Hydroxy-2,4-diphenylcinnamide (27d)

NaOH (191 mg, 4.78 mmol) in 50% $NH_2OH$(aq) (4 mL) in an ice bath was added to a solution of 32 (300 mg, 0.96 mmol) in MeOH/THF (2 mL:2 mL) was added. Following the procedure as described for 27a gave 27d (133 mg, 44%) as a white solid: mp: 135-137° C.; $^1$H NMR (500 MHz, [D6]DMSO): d=7.64 (d, J=15.4 Hz, 1H), 7.74 (d, J=7.4 Hz, 2H), 7.71 (dd, J=1.5, 8.2 Hz, 1H), 7.63 (d, J=1.5 Hz, 1H), 7.49 (m, 3H), 7.45 (m, 1H), 7.42 (m, 3H), 7.32 (m, 1H), 6.58 ppm (d, J=15.4 Hz, 1H); $^{13}$C NMR (125 MHz, [D6]DMSO): d=163.1, 142.9, 141.4, 140.2, 139.6, 136.8, 132.2, 130.2, 129.5, 129.4, 128.9, 128.4, 128.1, 127.4, 127.3, 126.7, 120.5 ppm; HRMS-ESI: m/z [M+Na]+ calcd for $C_{21}H_{17}NNaO_2$: 338.1157, found: 338.1151.

Example 3. Initial Biological Evaluation

The para-benzyl N-hydroxycinnamides 8a-f and ortho-benzyl N-hydroxycinnamides 13a-e were screened for inhibitory activity against HDAC8 at a concentration of 1 μm, using SAHA as a reference compound. Ortho-substituted series 13a-e showed higher potency than parasubstituted 8a-f. Compounds 13a, 13c, and 13d were further evaluated for $IC_{50}$ values against HDAC8, as well as against HeLa nuclear extract that contained mainly HDACs1-3, to analyze isoform selectivity (Table 4).

TABLE 4

Inhibition of HDAC8 and HeLa nuclear HDAC by compounds 13a, 13c, and 13d.

| Compd | R | HDAC8 $IC_{50}$ [nM][a] | HeLa HDAC $IC_{50}$ [nM][a] |
|---|---|---|---|
| 13a | H | 206.5 ± 13.4 | >10000 |
| 13c | Br | 613.5 ± 60.8 | >10000 |
| 13d | $OCH_3$ | 397.2 ± 12.7 | >10000 |
| SAHA | | 1855.1 ± 0.1 | 41.7 ± 3.2 |

[a]Data are expressed as the mean _SD of three determinations.

These compounds appeared to prefer HDAC8 ($IC_{50}$=206-613 nm) over other class I isoforms ($IC_{50}$>10 000 nm), suggesting that the ortho-oriented benzyl group may exploit the secondary hydrophobic surface pocket of HDAC8.

Next, N-hydroxycinnamides 18a-d were synthesized with various linker chains added to the ortho-aryl groups, as well as ortho-phenyl N-hydroxycinnamide 22a with a shortened linker chain (Table 5, Table 6).

TABLE 5

Inhibition of HDAC8 and HeLa nuclear HDAC by compounds with varying chain length (n).

[Structure: MeO-substituted phenyl with N-hydroxycinnamide, linked via O-(CH2)n-O to 4-methoxyphenyl]

| Compound | n | IC$_{50}$ [nM][a] HDAC8 | HeLa HDAC |
|---|---|---|---|
| 18a | 2 | 122.5 ± 3.5 | >10000 |
| 18b | 3 | 191.3 ± 2.2 | >10000 |
| 18c | 4 | 112.1 ± 2.2 | >10000 |
| 18d | 5 | 200.3 ± 6.5 | >10000 |
| PCI450451 | — | 55.7 ± 0.7 | >10000 |

[a]Data are expressed as the mean SD of three determinations.

Although the enzyme inhibitory activity of compounds 18a-d (IC$_{50}$=112-191 nm) were all increased relative to the original benzyl-substituted series, compound 22a with no flexible linker showed the best HDAC8 inhibitory activity (IC50=72 nm), which was compatible to PCI34051 (IC$_{50}$=56 nm).

We further performed molecular docking for HDAC8 crystal structure with compound 22a and PCI34051, which showed that further hydrophobic incorporation into the ortho-phenyl moiety of compound 22a may potentially make additional contacts to the active site of HDAC8. To test the molecular modeling results, we synthesized compounds 22b-g and 27a-d and examined the resulting compounds for enzyme inhibitory activity. Compounds 22b, 22d, 22 f, and 22g showed inhibitory activities superior to PCI34051 for HDAC8; in particular, 22b and 22d were around ten- and two-fold more potent, respectively. Compound 22b was 13-fold more potent than 22a, suggesting that introduction of a para-bromo group results in a significant increase in binding affinity. Compounds 22d and 22 f-g were two- to threefold more potent than 22a, indicating that the introduction of additional coplanar phenyl group leads to an increase in activity. Compound 22e was three-fold less potent than 22a, suggesting that the dramatic loss of activity is perhaps due to the twisted phenyl conformation adopted in ether moiety. The para-alkyl-substituted phenyl N-hydroxycinnamides 27a-d were approximately two- to fourfold less potent than 22a, suggesting that increasing the carbon chain length attached to the para-oxygen position weakens binding affinity.

TABLE 6

Inhibition of HDAC8 and HeLa nuclear HDAC by compounds 22a-g and 27a-d.

[Structure: R1-substituted phenyl with R2 group and N-hydroxycinnamide]

| Compound | R$^1$ | R$^2$ | IC$_{50}$ [nM][a] HDAC8 | HeLa HDAC |
|---|---|---|---|---|
| 22a | OCH$_3$ | benzyl | 72.4 ± 0.1 | >10000 |
| 22b | OCH$_3$ | 4-bromobenzyl | 5.7 ± 0.1 | >10000 |
| 22c | OCH$_3$ | naphthalen-1-ylmethyl | 78.0 ± 4.3 | >10000 |
| 22d | OCH$_3$ | biphenyl-4-ylmethyl | 27.2 ± 3.1 | >10000 |
| 22e | OCH$_3$ | 4-phenoxybenzyl | 173.8 ± 5.9 | >10000 |
| 22f | OCH$_3$ | 4-benzoylbenzyl | 41.8 ± 3.3 | >10000 |
| 22g | OCH$_3$ | dibenzofuran-4-yl | 47.7 ± 0.7 | >10000 |
| 27a | OC$_3$H$_7$ | benzyl | 132.6 ± 12.6 | >10000 |
| 27b | OC$_4$H$_9$ | benzyl | 289.2 ± 30.1 | >10000 |

TABLE 6-continued

Inhibition of HDAC8 and HeLa nuclear
HDAC by compounds 22a-g and 27a-d.

[Structure: cinnamic acid hydroxamate with R¹ and R² substituents on phenyl ring]

| Compound | R¹ | R² | HDAC8 IC$_{50}$ [nM][a] | HeLa HDAC |
|---|---|---|---|---|
| 27c | OC$_5$H$_{11}$ | [benzyl] | 186.4 ± 59.8 | >10000 |
| 27d | C$_6$H$_5$ | [benzyl] | 174.9 ± 0.2 | >10000 |
| PCI34051 | — | — | 55.7 ± 0.7 | >10000 |

[a]Data are expressed as the mean SD of three determinations.

We evaluated the potent HDAC8 inhibitors 22b, 22d, 22 f, and 22g for anti-proliferative activity in human lung cancer cell lines, including A549 cells, H1299 cells, CL-1 cells, and CL1-5 cells using SAHA and PCI34051 as reference compounds (Table 7).

TABLE 7

Cytotoxicity of compounds 22b, 22d, 22 f, and 22g
against various lung cancer cell lines.

| Compound | A549 | H1299 | Cl1-1 | Cl1-5 |
|---|---|---|---|---|
| 22b | >10 | >10 | >10 | >10 |
| 22d | 7.9 ± 1.5 | 7.2 ± 0.7 | >10 | 7.0 ± 1.5 |
| 22f | >10 | 8.4 ± 0.2 | >10 | >10 |
| 22g | >10 | 6.6 ± 0.7 | 8.5 ± 1.2 | 8.7 ± 0.1 |
| SAHA | 1.5 ± 0.7 | 4.9 ± 0.3 | 2.9 ± 0.5 | 6.2 ± 0.6 |
| PCI34051 | >10 | >10 | >10 | >10 |

IC$_{50}$ [nM][a]

[a]Data are expressed as the mean _SD of three determinations.

Compound 22b exhibited low cytotoxicity in all four cancer cell lines. In addition, compounds 22d and 22g showed higher cytotoxicity than PCI34051 in three cancer cell lines. Although compound 22d showed moderate antiproliferative effects in human lung cancer A549 and H1299 cells, it exhibited activity similar to that of SAHA in CL1-5 cells with no significant cytotoxicity in normal IMR-90 cells. The HDAC8 level in CL1-5 is higher than that in H1299 and A549. To verify whether these compounds were HDAC8-selective, we tested inhibitory activities of compounds 22b and 22d against a panel of purified HDACs, including class I (HDAC1, 2, 3),[28] class II (HDAC4, 6, 10)[29] and class IV (HDAC11)[30] enzymes. Table 8 shows that these compounds were inactive toward most other HDACs and had limited activity against HDAC1 and 3.

TABLE 8

Inhibition of class I (1, 2, 3), II (4, 6, 10), and IV (11) HDACs by
compounds 22b, 22d, and PCI34051.

| Compound | IC$_{50}$ [nM][a] | | | | | | |
|---|---|---|---|---|---|---|---|
| | 1 | 2 | 3 | 4 | 6 | 10 | 11 |
| 22b | 4.5 ± 0.1 | >20 | 4.8 ± 0.5 | >20 | >20 | >20 | >20 |
| 22d | 3.0 ± 0.2 | >20 | 3.0 ± 0.1 | >20 | >20 | >20 | >20 |
| PCI34051 | 7.5 ± 0.4 | >20 | >20 | >20 | >20 | >20 | >20 |

[a]Data are expressed as the mean _SD of three determinations.

Example 4. Inhibition of HDAC8 Reactivates p53 and Abrogates Leukemia Stem Cell Activity in CBFβ-SMMHC Associated Acute Myeloid Leukemia Introduction.

Acute myeloid leukemia (AML) arises from disordered hematopoiesis as a consequence of multiple cooperative mutations or alternations disrupting differentiation, proliferation and survival programs in hematopoietic progenitors. Recurrent chromosomal abnormalities in AML involve transcription factor fusion proteins that contribute to unique etiology and prognosis [1]. The core-binding factor (CBF) transcription complex is a regulator of hematopoietic development and a frequent target of leukemia associated chromosomal translocation or inversion [2]. A functional CBF complex consists of a DNA-binding a subunit (RUNX1, RUNX2, RUNX3) and a non-DNA binding β subunit (CBFβ), which increases DNA-binding affinity and may be essential for transactivation activity [3-5]. Chromosomal 16 inversion, inv(16)(p13.1q22) or t(16;16)(p13.1;q22) is found in approximately 5-12% of AML patients and is associated with the FAB M4Eo AML subtype [6-11]. This inversion results in fusion of CBFB with the MYH11 gene, which encodes a smooth muscle myosin heavy chain (SMMHC) protein [12]. The CBFB-MYH11 fusion gene encodes a fusion protein CBFβ-SMMHC, which retains the RUNX1 binding interface of CBFβ and the coiled-coil rod region of SMMHC. A knock-in allele for Cbfb-MYH11 was previously generated in mice and resultant Cbfb-MYH11 heterozygotes showed a profound defect in definitive hematopoiesis and exhibited lethal hemorrhage at E12.5 [13]. These phenotypes are identical to those of Runx1- or Cbfb-null mice [14,15], suggesting that CBFβ-SMMHC is a dominant inhibitor of CBF function. Using a conditional Cbfb-MYH11 knock-in mouse model, we showed that CBFβ-SMMHC expression in adult hematopoietic stem cells (HSCs) leads to impaired differentiation of multiple hematopoietic lineages and produces pre-leukemic stem and progenitor populations at risk for acquiring cooperating alterations required for AML transformation [16].

Dominant inhibition of RUNX1 has been considered the main function of CBFβ-SMMHC. CBFβ-SMMHC was shown to contain an additional RUNX1 binding site within SMMHC near the inversion breakpoint, and thus binds to RUNX1 with a much higher affinity than CBFβ [17]. Therefore, it is proposed that CBFβ-SMMHC transdominantly inhibits RUNX1 function through high affinity binding and cytoplasmic sequestration [18,19]. Meanwhile, CBFβ-SMMHC was shown to interact with the mSin3A corepressor and histone deacetylase 8 (HDAC8), supporting an alternative model where CBFβ-SMMHC converts RUNX1 to a constitutive transcriptional repressor [20,21]. We showed that elevated levels of Runx2 expression enhances CBFβ-SMMHC-mediated leukemic transformation while loss of one Runx2 allele reduces and delays leukemogenesis [22]. This genetic evidence suggests that the leukemogenic function of CBFβ-SMMHC is in fact dependent on functional RUNX proteins rather than RUNX inhibition. Studies demonstrated that the high affinity RUNX1 binding domain of CBFβ-SMMHC is dispensable for leukemogenesis [23]. In addition, RUNX1 activity is required for the growth and maintenance of inv(16) AML cells [24,25].

The tumor suppressor p53 is a genomic guardian that centrally coordinates cellular responses including cell cycle progression, DNA repair, and apoptosis. Genetic mutations that inactivate p53 function occur in approximately half of all cases of human cancer; however, these TP53 mutations are relatively rare in de novo AML (approximately 10%). TP53 mutation in AML is correlated with complex karyotype, drug resistance and dismal outcome [26-28]. Loss of p53 is shown to promote AML pathogenesis in mice by enabling aberrant self-renewal [29]. Wide spectrum post-translational modifications including phosphorylation, acetylation, ubiquitination, methylation, sumoylation and neddylation act to coordinate and modulate specific functions of p53 [30]. Given the low TP53 mutation rate, alternative mechanisms affecting protein stability or modifications are expected to be involved in disrupting p53 function during AML pathogenesis.

HDACs are a family of enzymes that catalyze the removal of acetyl moieties from ε-amino groups of lysine residues in a variety of proteins, including histones and transcription factors, and thus play crucial roles in chromatin remodeling and regulation of gene expression. HDAC8 is a class I HDAC, maps to the X chromosome q13 [31-33], and is likely important for diverse biological functions, including smooth muscle contraction [34], telomere protection [35], skull morphogenesis [36], and regulation of cohesion dynamics [37]. HDAC8 is highly expressed in myeloid and lymphoid leukemia cell lines [33] and is likely overexpressed in multiple tumor types, including neuroblastoma, glioma [38] and childhood acute lymphoblastic leukemia [39]. Although HDAC8 has been shown to interact with CBFβ-SMMHC [21], its role in AML pathogenesis and maintenance remains unclear.

Without being bound by any particular theory, we hypothesized that p53 activity is disrupted by the leukemogenic CBFβ-SMMHC fusion protein. We demonstrate that CBFβ-SMMHC impairs p53 through a previously unknown mechanism involving post-translational modification by HDAC8. Our results provide new molecular insights into the leukemogenic mechanism driven by inv(16) and highlight the therapeutic opportunity of reactivating p53 by HDAC8 inhibition.

Experimental Methods

Mice.

All Cbfb$^{56M/+}$ [16] and the Mx1-Cre [58] mice used were backcrossed to C57BL/6 for more than 8 generations. Ai14 Cre reporter tdTomato mice on C57BL/6 background were obtained from the Jackson Laboratory. To induce CBFβ-SMMHC expression, 4-6 week old Mx1-Cre/Cbfb$^{56M/+}$ mice were injected with 250 μg of polyinosinic-polycytidylic acid (pIpC) (InvivoGen) every 2 days for 7 doses. Similarly treated Cbfb$^{56M/+}$ littermates without Cre were used as control. Pre-leukemic cells were isolated from mice 2 weeks after the last dose of pIpC treatment. For leukemia development, induced mice were monitored up to 6 months and analyzed when moribund. Transplantation of AML cells ($2 \times 10^6$ cells/mouse) was performed via tail vein injection into sub-lethally irradiated (6.5 Gy) 6-8-week-old congenic C57BL/6 mice (CD45.1$^+$/CD45.2$^+$). All mice were maintained in an AAALAC-accredited animal facility at City of Hope, and all experimental procedures involving mice were performed in accordance with federal and state government guidelines and established institutional guidelines and protocols approved by the Institutional Animal Care and Use Committee at Beckman Research Institute of City of Hope.

Human Samples.

Cord blood (CB) samples were provided by Stemcyte (Arcadia, Calif.). Mobilized peripheral blood stem cells (PBSC) were obtained from healthy donors (City of Hope). Inv(16)$^+$ AML samples were obtained from previously untreated patients at the City of Hope. See Table 6X following for characteristics of human samples for studies disclosed herein. CD34$^+$ cell isolation was performed using magnetic beads (StemCell Technologies, Vancouver, BC, Canada). Leukopheresis samples were processed for CD34$^+$ cell selection with CliniMACS (Miltenyi Biotech, Germany). All subjects signed an informed consent form. Sample acquisition was approved by the Institutional Review Boards at the City of Hope, in accordance with an assurance filed with and approved by the Department of Health and Human Services.

TABLE 9

Characteristics of patient samples

| ID | Sex | Age | Diag. | FAB Class. | Sample Type | Disease State at Collection | Risk Status | Cytogenetic | Other mutation | WBC | Blasts in PB | Blasts in BM |
|---|---|---|---|---|---|---|---|---|---|---|---|---|
| AML020 | F | 47 | AML | M4eo | PB | Untreated | Better-risk | inv(16) | FLT-3 ITD Neg | 50.8 | 67 | 90 |
| AML021 | F | 42 | AML | M4 | BM | Untreated | Better-risk | inv(16) | | 39.2 | 60 | 40 |
| AML033 | M | 69 | AML | non-classified | PB | Untreated | Intermediate risk | inv(16), trisomy 22 | | 6.3 | 30 | 98 |
| AML041 | F | 56 | AML | M2 | PB | Untreated | Better-risk | inv(16), trisomy 8 | | 38.8 | 63 | 44 |
| AML111 | M | 51 | AML | M2 | BM | Untreated | Intermediate-risk | Inv(16), trisomy 8, trisomy 21 | | 13.4 | 70 | 75 |
| AML163 | M | 57 | AML | M4 | PB | Relapsed | Intermediate-risk | t(16; 16), trisomy 21, trisomy 22 | | 82.8 | 94 | 67 |
| AML319 | F | 46 | AML | M4 | PB | Untreated | Better-risk | CBFB/16q22 rearrangement | | 1.4 | 0 | |
| AML987 | M | 50 | AML | M4 | PB | Relapsed | Intermediate-risk | t(16; 16), trisomy22, CBFB rearrangement | FLT-3 ITD Neg, FLT-3 D835 Pos., NPM1 Neg., C-KIT Neg | 64.1 | 90 | |

TABLE 9-continued

Characteristics of patient samples

| ID | Sex | Age | Diag. | FAB Class. | Sample Type | Disease State at Collection | Risk Status | Cytogenetic | Other mutation | WBC | Blasts in PB | Blasts in BM |
|---|---|---|---|---|---|---|---|---|---|---|---|---|
| AML1052 | F | 23 | AML | M4 | BM | Relapsed | Intermediate-risk | inv(16), trisomy 8, trisomy 22 | FLT-3 ITD Neg, FLT-3 D835 Neg | 9.9 | 64 | 87 |
| AML1070 | F | 37 | AML | M4Eo | BM | Relapsed | Better-risk | der(16) inv(16) (p13.1q22) del(16) (q22.1q22.?2) [16]/[22] 44% CBFB rearrangement by FISH | NPM1 neg | 2.7 | 3 | 30 |
| AML270 | M | 61 | AML | | PR | Untreated | Poor-risk | Complex abnormalities, including 11q23, MLL gain, loss of TP53/17p13.1, add(2), add(5), add(22), ider(11), del(11) | FLT-3 ITD Neg | 4.4 | 5 | 50 |
| AML467 | F | 61 | AML | | PB | Untreated | Poor-risk | Complex abnormalities with trisomy 8, trisomy 9 and trisomy 22 | FLT-3 ITD Neg, FLT-3 D835 Neg | 44.7 | 51 | 80 |
| AML578 | M | 38 | AML | M5b | PB | Refractory/Induction failure | Poor-risk | Trisomy 8, del(9q), t(2; 18), trisomy 13 | FLT-3 ITD Pos, FLT-3 D835 Neg, NPM1 Neg | 1.3 | 41 | 8 |
| AML865 | F | 60 | AML | | PB | Untreated | Poor-risk | Normal cytogenetics | FLT-3 ITD Pos, FLT-3 D835 Neg, JAK2 Neg | 86.3 | 90 | 90 |

Cell Transduction and Flow Cytometry.

Bone marrow cells were isolated as previously described [59]. Cell culture employed conditions well known in the art. Bone marrow cells or 32D cells were transduced with MSCV-ires-GFP (MIG) based retroviruses or lentiviruses (pLKO.1 or HIV-7) [40] by spinoculation in the presence of 5 ug/mL polybrene (American Bioanalytical, Natick, Mass.). Human CD34$^+$ cells were transduced with pLKO.1 lentivirus by two rounds of spinoculation. Cell sorting was performed on a 4-laser, 15-detector FACSAria-III or a 6-laser, 18-detector FACSAria II SORP (BD Bioscience, San Jose, Calif.). Cell proliferation and apoptosis assays were conducted as well known in the art.

Immunoprecipitation (IP) and Western Blotting.

Cells were lysed in RIPA buffer containing protease inhibitor cocktail (Roche) and MG132. Antibodies used for IP were conjugated with protein A/G beads using the antibody cross-linking kit (Pierce Biotechnology, Rockford, Ill.) following manufacturer's protocol. For Western blot, proteins were resolved in 10% SDS-PAGE. The antibodies used induced anti-FLAG (Sigma), anti-HDAC8, anti-CBFβ (Santa Cruz), anti-p53 (DO-1), anti-Ac-p53 (K379) (Cell Signaling), anti-p53 (Cell signaling) and anti-β-actin (Sigma). Horseradish peroxidase-conjugated anti-rabbit or anti-mouse secondary antibodies (Jackson ImmunoResearch, West Grove Pa.) were used, followed by detection using the SuperFemto kit (Pierce Biotechnology, Rockford, Ill.).

DUOLINK® In Situ Proximity Ligation Assay (PLA).

The DUOLINK® kit (Sigma, St. Louis, Mo.) was used to perform in situ proximity ligation assay (PLA) following manufacturer suggested procedures. Antibodies used included mouse anti-CBFβ (Santa Cruz), rabbit anti-Ac-p53 (K379) (Cell Signaling) and rabbit anti-p53 (Cell Signaling). Slides were mounted using in anti-fade media containing DAPI (Santa Cruz) and imaged using a Zeiss upright LSM 510 2-photon confocal microscope.

Statistics.

Statistical analyses were performed with Student's t test or analysis of variance (ANOVA) for normal distribution. Mann-Whitney U tests were performed when normal distribution was not satisfied. p value less than 0.05 was considered statistically significant (*p<0.05; p<0.01; *p<0.001).

Results and Discussion

CBFβ-SMMHC Expression Impairs Activation and Acetylation of p53.

Figure 1A:
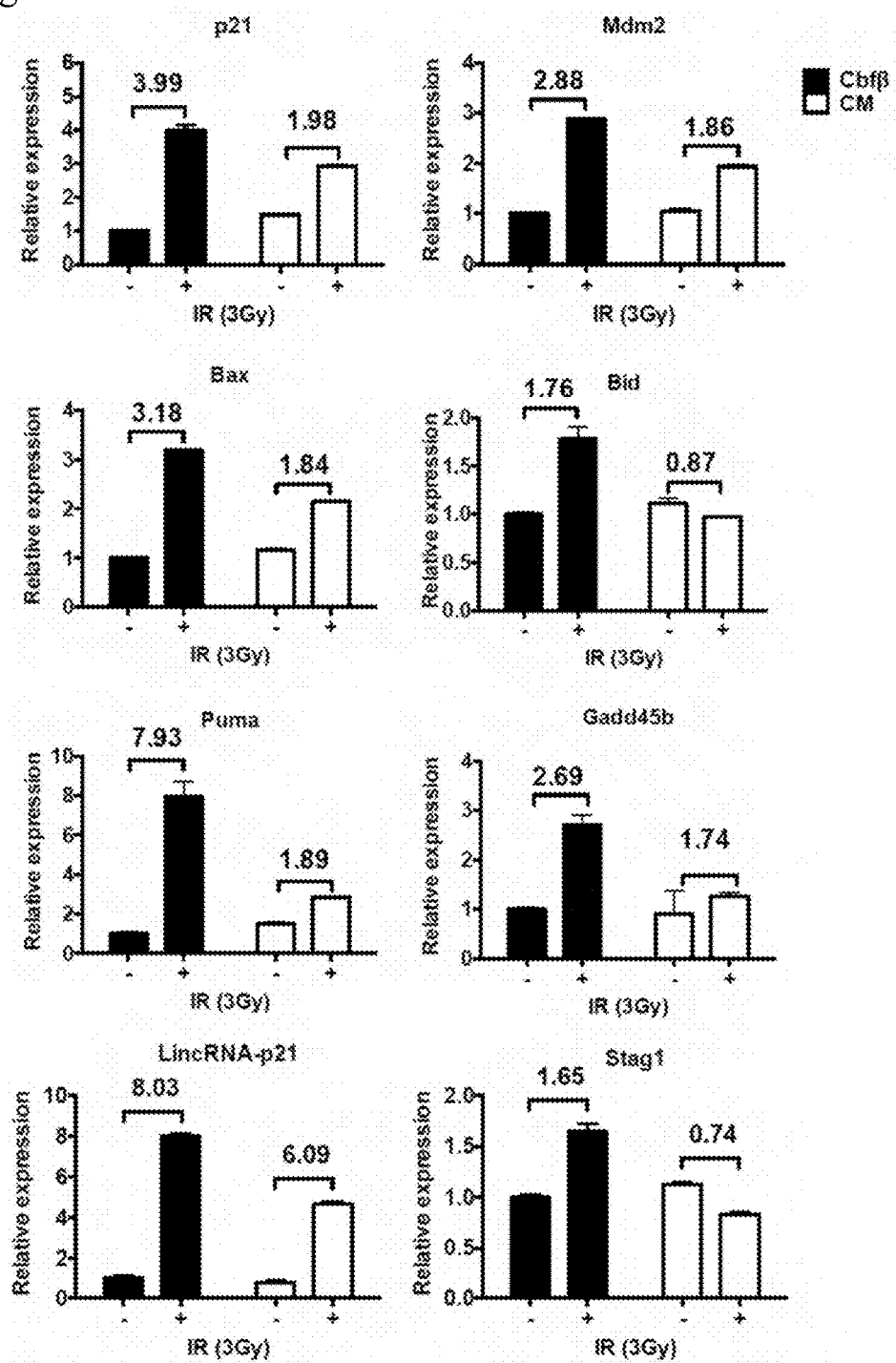
FIGS. 1A-1G. CBFβ-SMMHC expression impaired p53 target gene induction and reduced acetylation of p53.

Without being bound by any particular theory, we hypothesized that CBFβ-SMMHC exerts its leukemogenic function through affecting molecular and cellular processes operating to safeguard genome integrity. Since p53 represents the master genomic guardian, we tested whether CBFβ-SMMHC fusion protein impairs p53 function. We generated myeloid progenitor 32D cell lines (p53 wild type) expressing CBFβ-SMMHC (CM) or CBFβ (all FLAG-tagged) through MSCV-ires-GFP (MIG) retroviral transduction, and sorting of GFP$^+$ transduced cells. We performed quantitative RT-PCR analysis to analyze induction of p53 target genes including p21 Cdkn1a, Mdm2, Bid, Bax, and Gadd45b in 32D cells after γ-irradiation (IR) (3 Gy, 24 h). Compared to control cells expressing CBFβ, CM-expressing cells partially or completely inhibited induction of p53 targets (FIG. 1A).

Figure 1B:
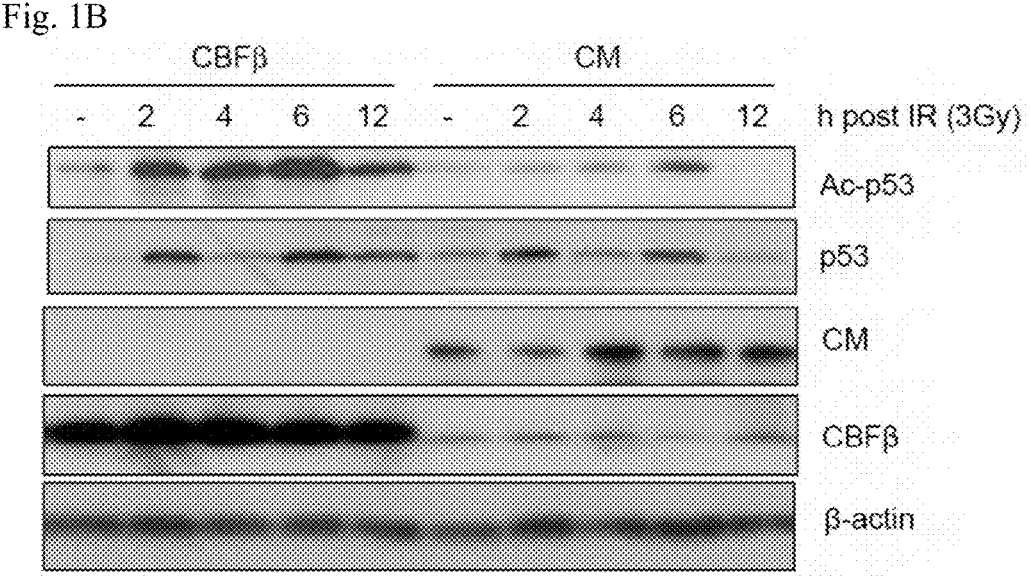
Figure 1C:
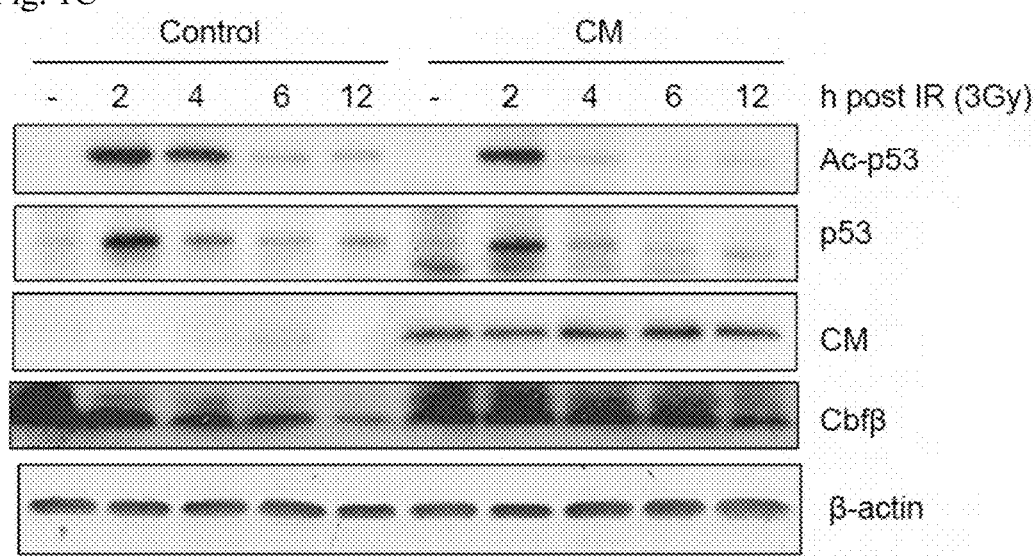
Figure 1D:
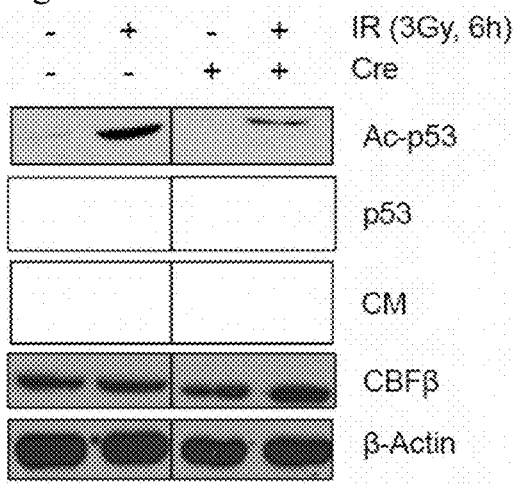
Figure 1E:
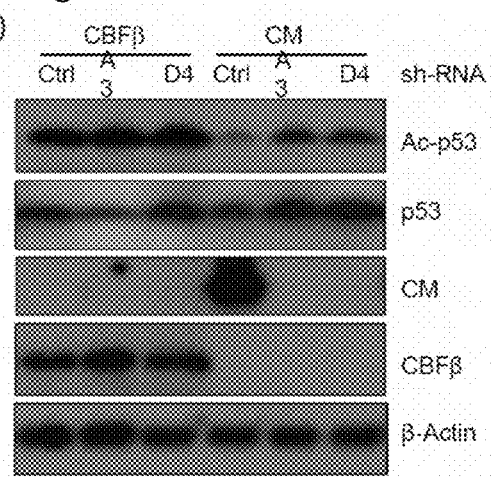
Figure 1F:
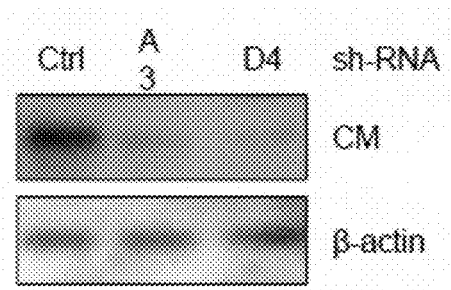
Figure 1G:
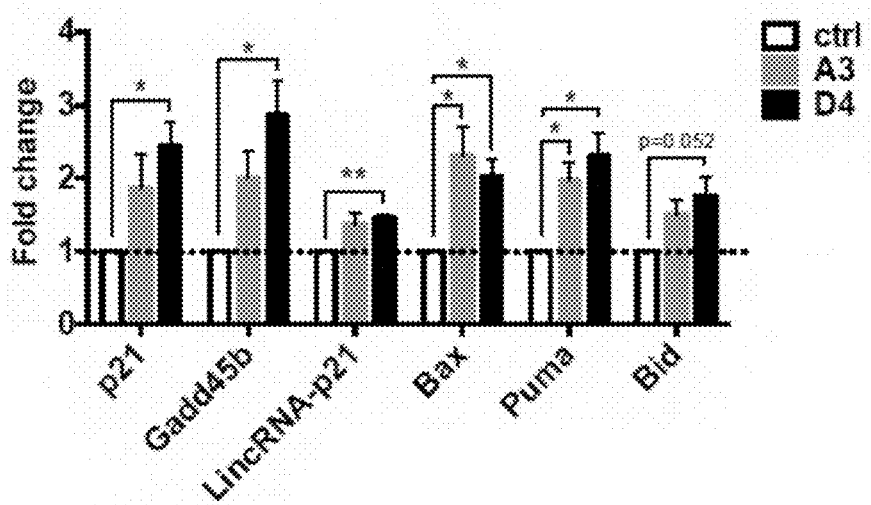

Acetylation of p53 protein is important for protein stabilization and its transcriptional activity. Using western blot analysis with an antibody against an acetylated (Ac)-form of p53 (K379), we tested the effect of CM on p53 acetylation in response to IR (3 Gy)-induced DNA damage. The level of Ac-p53 was markedly reduced in CM-expressing cells compared to control cells expressing CBFβ at all time points (2, 4, 6, 12 h) analyzed (FIG. 1B). We have established a conditional knock-in mouse model Cbfb$^{56M/+}$/Mx1-Cre can be efficiently induced to express CM by pIpC [16]. We examined total p53 and Ac-p53 levels in primary bone marrow (BM) progenitor cells isolated from pre-leukemic Cbfb$^{56M/+}$/Mx1-Cre or control Cbfb$^{56M/+}$ mice 2 weeks after pIpC induction. Likewise, we find that induction of Ac-p53 level is largely reduced in pre-leukemic progenitor cells expressing endogenous levels of CM (FIG. 1C). Time course analysis revealed that the initial acetylation of p53 can occur (2 h post-IR), however, p53 is rapidly deacetylated in CM-expressing progenitors (FIG. 1C). To rule out possible secondary pre-leukemic effects not directly caused by CM-expression, we introduced Cre through MIG retroviral transduction of BM progenitors from Cbfb$^{56M/+}$ mice. Transduced cells were sorted 48 h later and tested for IR (3 Gy)-induced p53 acetylation. CM expression was efficiently induced in MIG-Cre-transduced progenitor cells and readily led to marked reduction in the Ac-p53 level (FIG. 1D), suggesting this likely to be a primary effect of CM. Therefore, we tested whether knocking-down CM cells could restore p53 acetylation in CM-expressing. We transduced 32D-CM cells with lentiviral vectors (HIV-7) [40] expressing 2 independent shRNA (A3, D4) specifically against the CBFb-MYH11 sequence and analyzed Ac-p53 induced by IR (3 Gy) at 6 h. Knocking-down CM resulted in restoration of Ac-p53 to similar levels as the control cells (FIG. 1E). We further assessed changes in p53 target gene expression upon knocking-down CM (FIG. 1F) in primary leukemic cells isolated from induced Cbfb$^{56M/+}$/Mx1-Cre mice. We discovered that CM knock-down results in significant induction of p53 target expression even without additional stimulation (FIG. 1G). Taken together, these studies indicate that CM fusion protein expression impairs activation and acetylation of p53.

CBFβ-SMMHC Forms an Aberrant Protein Complex with p53 and HDAC8.

Figure 2A:
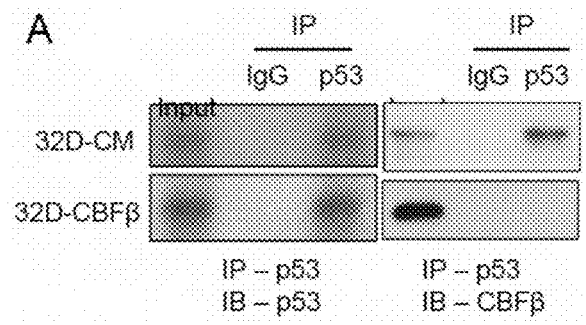
FIGS. 2A-2F. CBFβ-SMMHC fusion protein aberrantly interacts with p53.
Figure 2B:
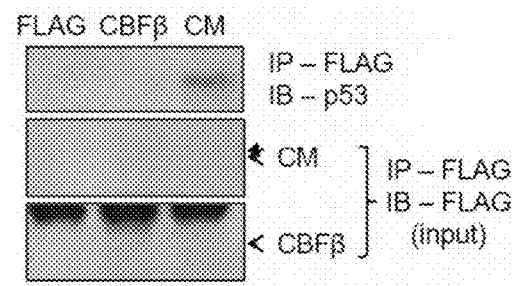
Figure 2C:
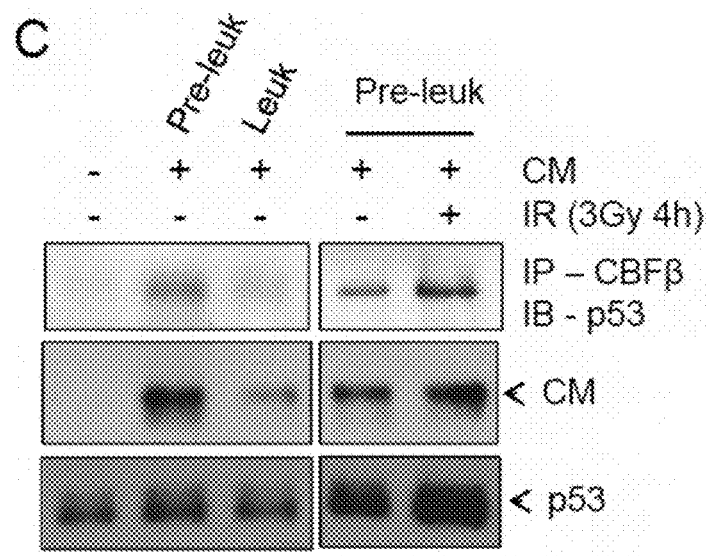
Figure 2D:
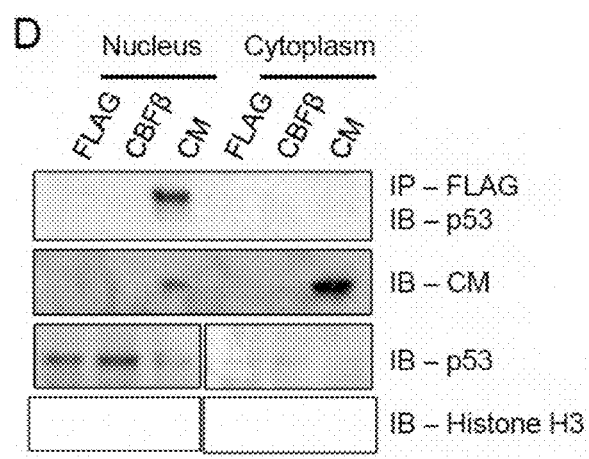
Figure 2E:
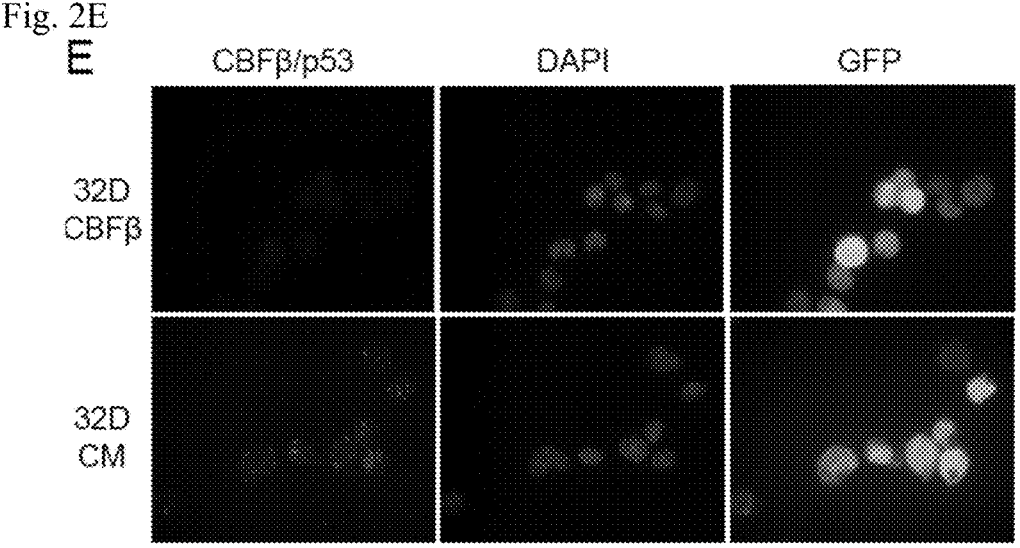
Figure 2F:
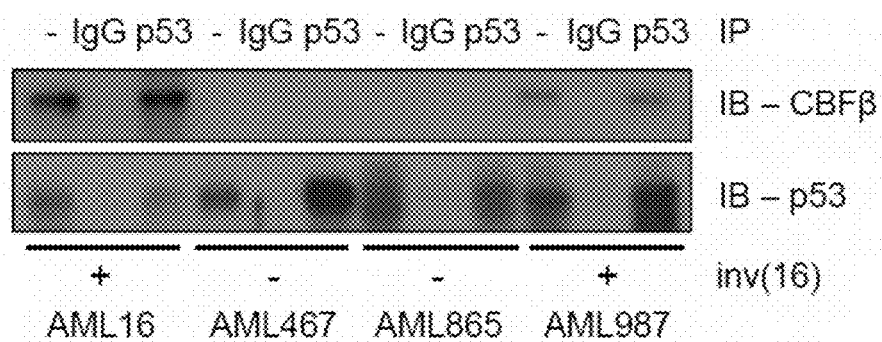
Figure 9:
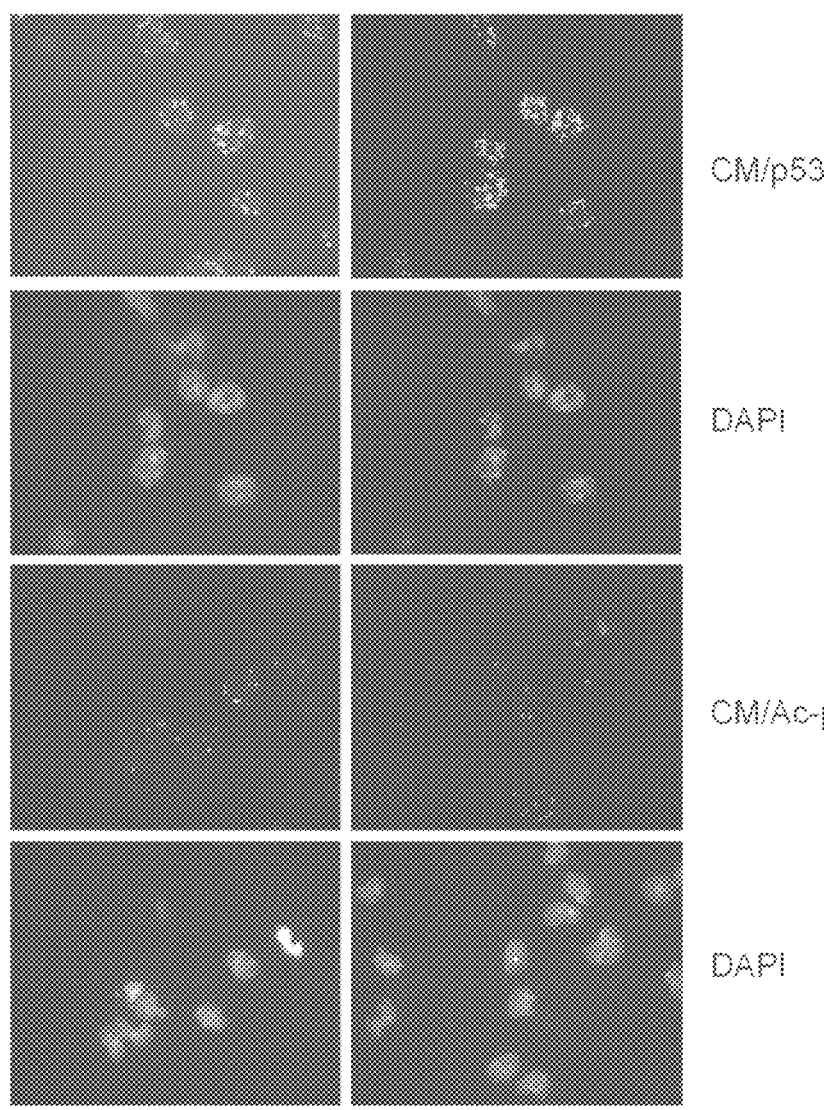
FIG. 9. CM interacts with mostly deacetylated p53 proteins. DUOLINK® in situ PLA in 32D-CM cells using mouse anti-CBFβ, rabbit anti-p53 or Ac-p53 (K379) and PLA probes. Red fluorescent spots indicate CM-p53 or CM-Ac-p53 protein interactions (top), DAPI-stained nucleus is in blue (center) and GFP reporter indicates transduced cells (bottom).

To determine how CM fusion protein impairs p53 activity, we tested whether the CM fusion protein interacts with the p53 protein. We performed co-immunoprecipitation (co-IP) with anti-p53 antibody followed by western blot analysis with anti-CBFβ antibody in 32D-CM cells compared to 32D-CBFβ cells. The results showed that anti-p53 is able to pull down CM fusion protein, but not CBFβ (FIG. 2A). Co-IP using anti-Flag or anti-CBFβ followed by western blot using anti-p53 revealed similar results (FIG. 2B, data not shown). To assess whether CM interacts with p53 in primary hematopoietic cells expressing CM at endogenous levels, we performed similar co-IP and western blot analysis using pre-leukemic or leukemic cells isolated from pIpC induced Cbfb$^{56M/+}$/Mx1-Cre or Cbfb$^{56M/+}$ control mice. Consistent with results from 32D cells, we found that p53 forms a protein complex with CM in pre-leukemic as well as leukemic progenitor cells with or without IR (FIG. 2C). To assess the cellular localization of this complex, we isolated nuclear and cytoplasmic fractions for co-IP using anti-Flag followed by western blot with anti-p53 antibodies. The CM fusion protein is present in both the nucleus and the cytoplasm, however, the complex with p53 is detected exclusively in the nucleus (FIG. 2D). As an alternative approach, we performed a Duolink in situ proximity ligation assay (PLA) to detect intermolecular interaction between CM fusion protein and p53. We observed punctuate red fluorescent spots in CM-expressing cells but not the CBFβ-expressing cells (FIG. 2E), again indicating aberrant protein-protein interaction between CM and p53. In contrast, similar Duolink in situ PLA using an Ac-p53 (K379) specific antibody showed very few interacting foci (FIG. 9), suggesting that CM interacts with mostly deacetylated p53 proteins. To test whether this aberrant interaction also occurs in primary human AML cells, we performed co-IP with anti-p53 antibody followed by western blot analysis with anti-CBFβ antibody in CD34$^+$ cells isolated from patients with inv(16)$^+$ AML compared to non-inv(16) AML. Interaction of CM with p53 is detected specifically in primary inv(16)$^+$ AML CD34$^+$ cells (FIG. 2F).

Figure 3A:
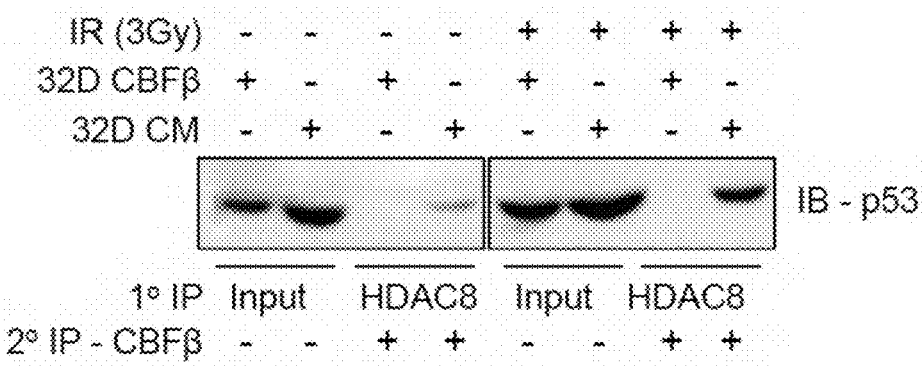
FIGS. 3A-3F. CBFβ-SMMHC recruits p53 and HDAC8 in a protein complex through distinct protein regions.
Figure 3B:
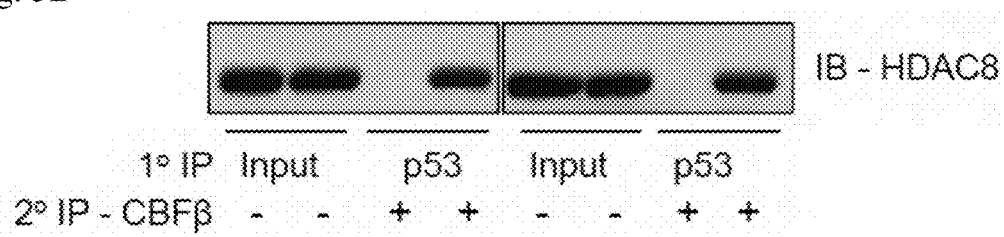
Figure 3C:
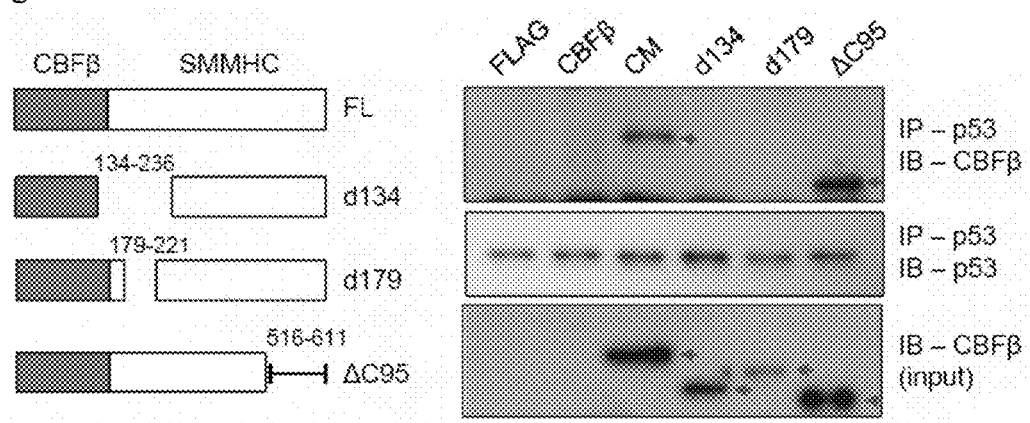
Figure 3D:
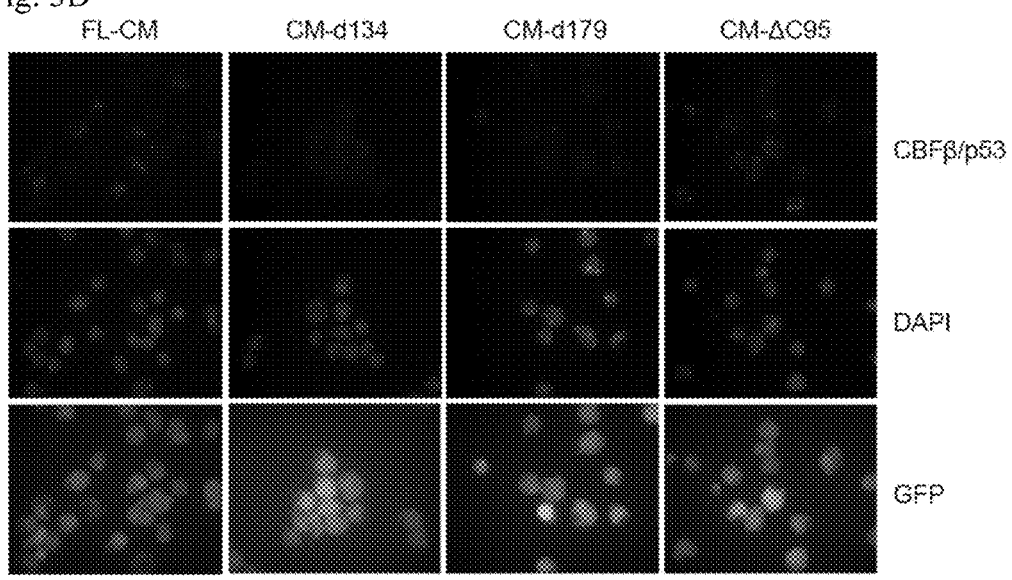
Figure 3E:
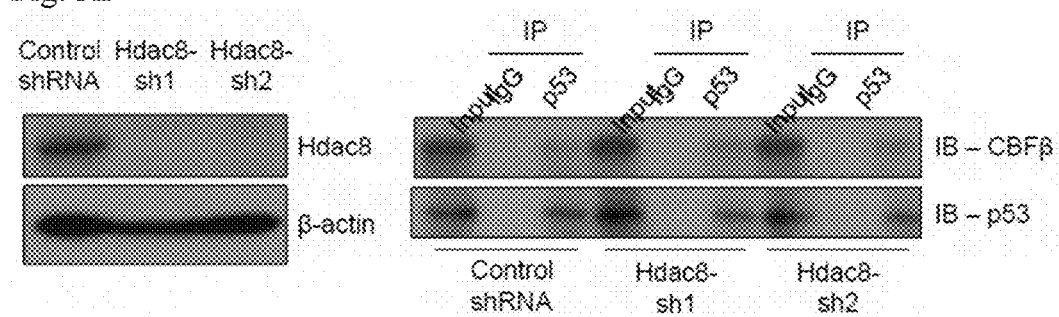
Figure 3F:
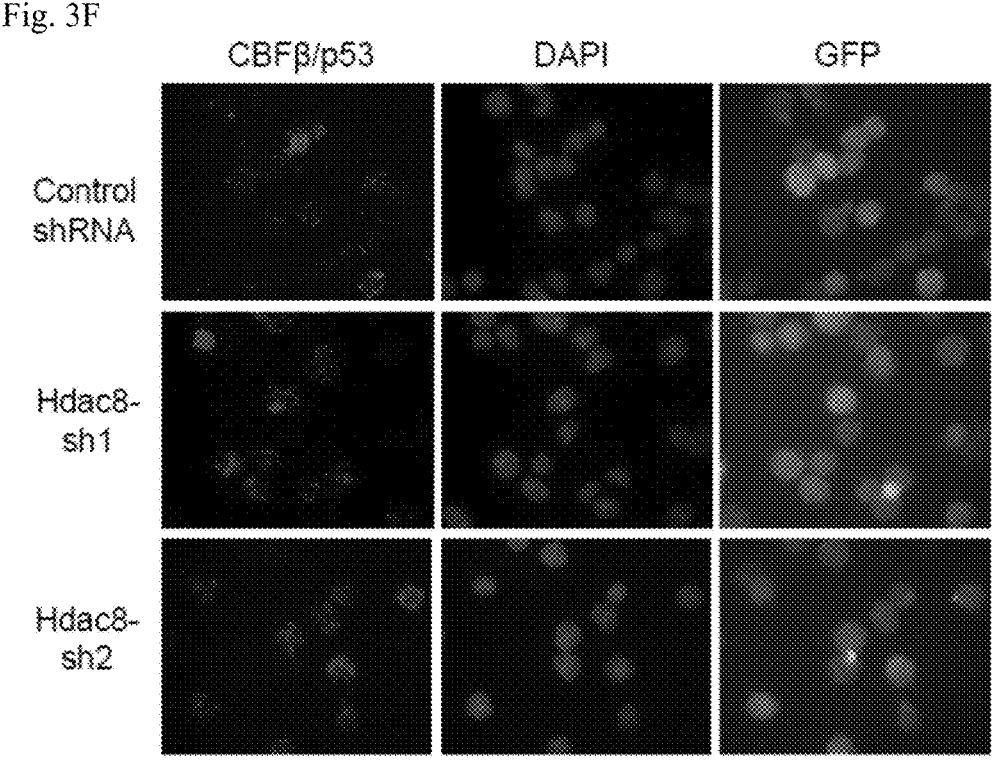
Figure 10:
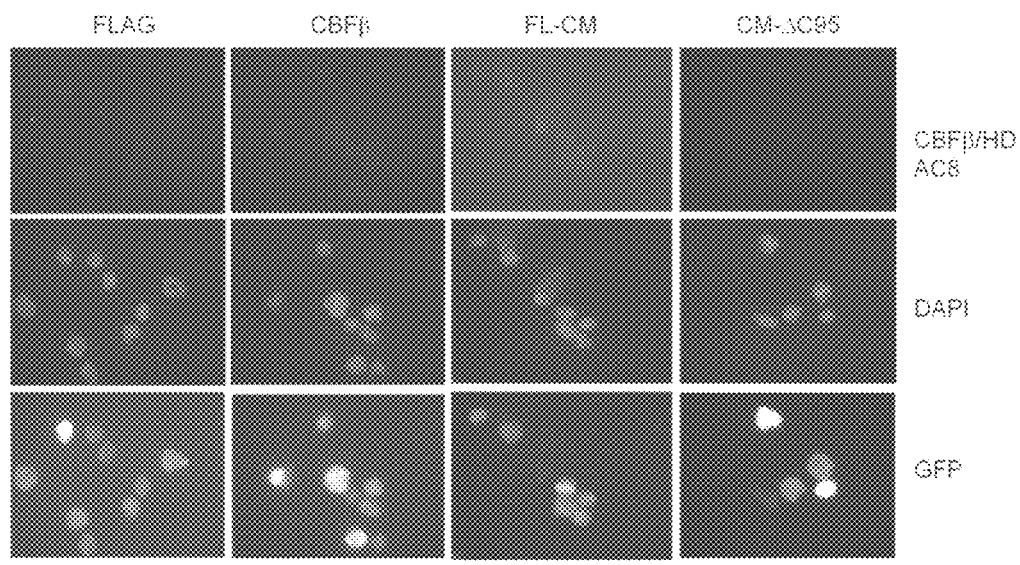
FIG. 10. HDAC8 interacts with CM C-terminal region. DUOLINK® in situ PLA in 32D cells expressing FL-CM, deletion mutant ΔC95 using mouse anti-CBFβ, xrabbit anti-HDAC8 and PLA probes. Fluorescent spots indicate CM-HDAC8 protein interactions (top), DAPI-stained nucleus is in center, and GFP reporter indicates transduced cells (bottom).

It has been reported that CBFβ-SMMHC interacts with HDAC8 through the C-terminal SMMHC region [21]. Therefore, we assessed whether CM forms a multimeric complex with HDAC8 and p53 by sequential IP followed by western blot analysis to detect co-immunoprecipitating proteins. We performed primary IP with either anti-HDAC8 or anti-p53 antibodies, and secondary IP with anti-CBFβ followed by western blot using anti-p53 (FIG. 3A) or anti-HDAC8 (FIG. 3B), respectively. We detected a multimeric protein complex containing CM, p53, and HDAC8 in CM-expressing cells. To further examine whether the interaction of CM fusion protein and p53 is dependent on HDAC8 binding, we generated a deletion mutant of CM lacking 95 amino acids at the C-terminal region (ΔC95). CM-ΔC95 deletion does not bind HDAC8 (FIG. 10), however, it was capable of binding to p53 as detected by co-IP and Duolink PLA (FIG. 3C, D). We also tested CM deletion mutants lacking regions containing the high affinity RUNX binding sites [18]. Both d134 (residues 134-236 deleted) and d179 (residues 179-221 deleted) deletion mutants were unable to bind p53 (FIG. 3C, D). The interaction of CM and p53 may be independent of HDAC8 binding. We further confirmed this by knocking-down Hdac8 in 32D-CM cells and performing co-IP and Duolink PLA assay. We used lentivirus (pLKO.1) mediated expression of 2 independent small-hairpin (sh)-RNA sequences against Hdac8 to specifically knock-down Hdac8 in 32D-CM cells (FIG. 3E, left). The binding of CM and p53 is unaffected in Hdac8 knocked-down cells (FIG. 3E right, F), confirming that the protein-protein interaction between CM and p53 is independent of HDAC8.

HDAC8 Mediates the Deacetylation of p53 Associated with CBFβ-SMMHC.

Figure 4A:
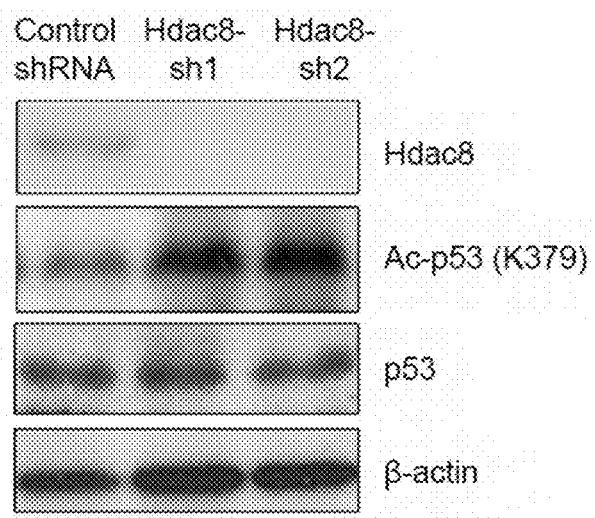
FIGS. 4A-4E. HDAC8 mediates the deacetylation of p53 in CBFβ-SMMHC-expressing cells.
Figure 4B:
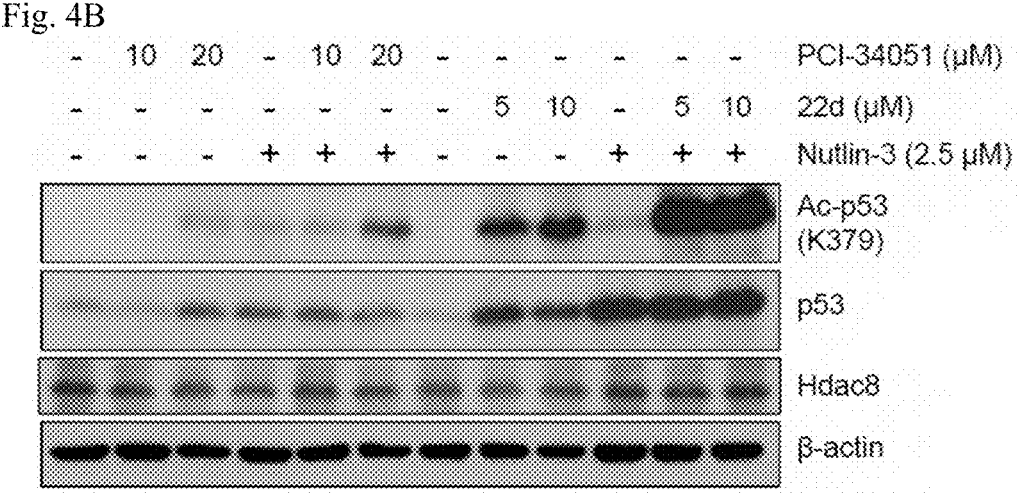
Figure 4C:
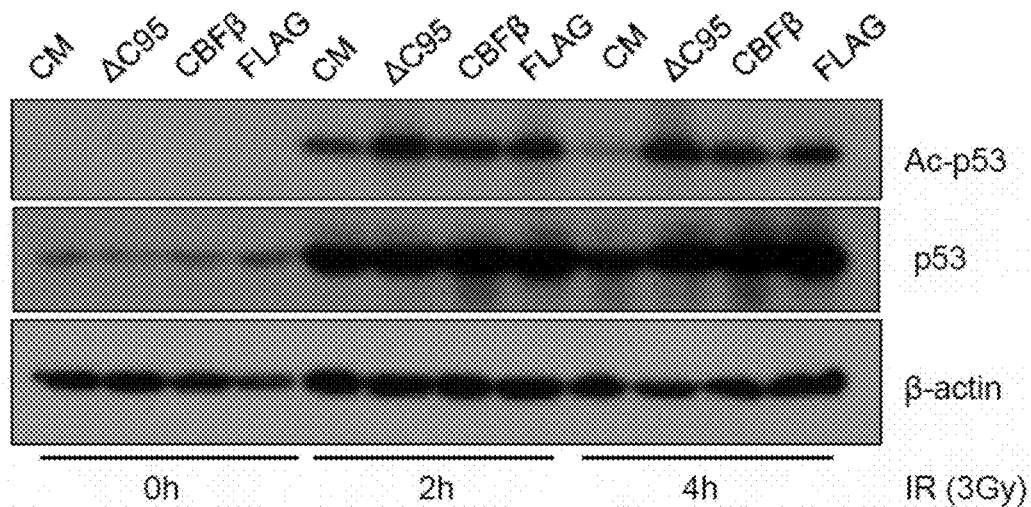
Figure 11:
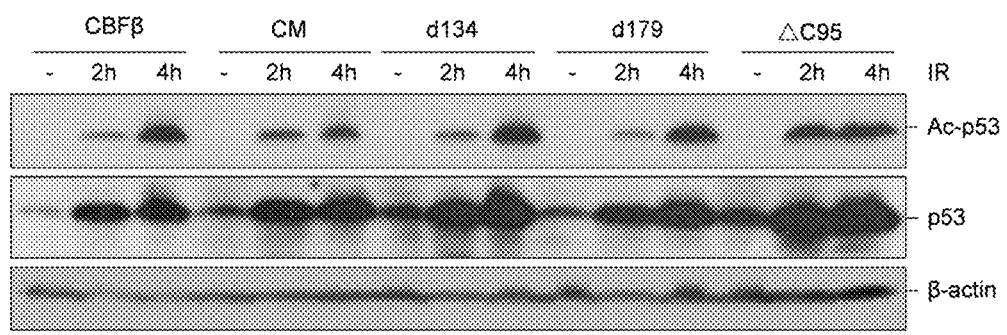
FIG. 11. Acetylation of p53 is not affected in CM deletion mutants unable to interact with p53 or HDAC8. Western blot analysis of Ac-p53 (K379), total p53 levels in 32D cells expressing CBFβ, CM, CM-d134, CM-d179 or CM-ΔC95 deletions. Cell lysate were isolated before, 2 h or 4 h after IR (3 Gy). Levels of β-actin were detected as loading control.

Class 1 HDACs, including HDAC1, HDAC2, and HDAC3, reportedly could inhibit p53 activity by deacetylating p53 [41-43]. Based on our observation that p53 acetylation is reduced and that CM forms a protein complex with HDAC8 and p53, without being bound by any particular theory, we hypothesized that HDAC8 mediates the aberrant deacetylation of p53 in CM-expressing cells. To test this, we used lentivirus (pLKO.1) mediated expression of 2 independent small-hairpin (sh)-RNA sequences against Hdac8 to specifically knock-down Hdac8 in 32D-CM cells. Cells were exposed to IR (3 Gy) and analyzed for levels of p53 acetylation 6 h after. Silencing of HDAC8 led to robust increase in Ac-p53 levels while total p53 levels were not affected (FIG. 4A). To test whether this effect is dependent on the deacetylase activity of HDAC8, we used HDAC8 isoform-selective inhibitors (HDAC8i) including PCI-34051 [44] or compound 22d [45] directed against its catalytic activity. Treatment with both HDAC8i remarkably increased Ac-p53 in CM-expressing cells (FIG. 4B). Since p53 protein levels were also increased upon HDAC8i treatment, we included Mdm2 inhibitor Nutlin-3 to stabilize p53 protein. HDAC8i treatment (PCI-34051 or 22d) in combination with Nutlin-3 enhanced Ac-p53 compared to Nutlin-3 alone (FIG. 4B), confirming that the effect of HDAC8i on Ac-p53 does not simply reflect p53 stabilization. We also confirmed that HDAC8i (22d) treatment did not disrupt the interaction of CM with p53, further supporting the involvement of deacetylase activity. In addition, expression of the CM-ΔC95 deletion mutant that was unable to bind HDAC8 (FIG. 9) had no effect on Ac-p53 induction compared to control (FLAG or CBFβ) 32D cells (FIG. 4C). Similarly, expression of CM-d134 or d179 deletions incapable of binding p53 (FIG. 3C, D) did not alter induction of Ac-p53 levels in response to 3 Gy IR (FIG. 11). Collectively, these results indicate that the CM fusion protein recruits HDAC8 and p53 in a protein complex, thereby facilitating the deacetylation of p53 by HDAC8.

Figure 4D:
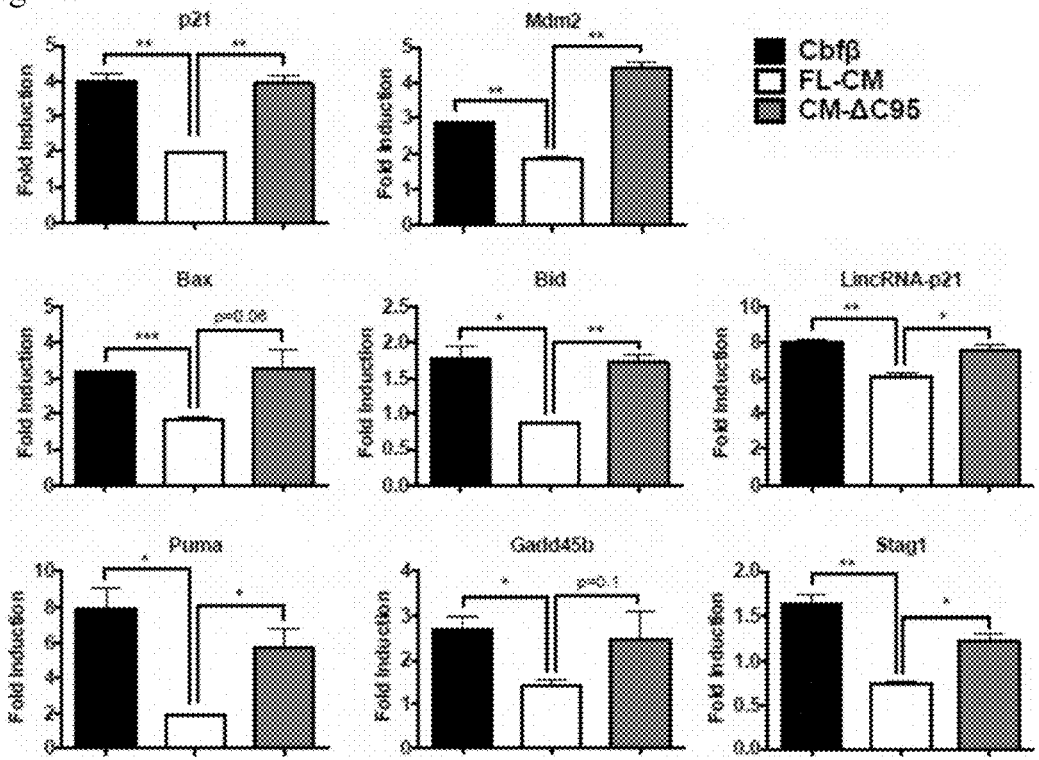
Figure 4E:
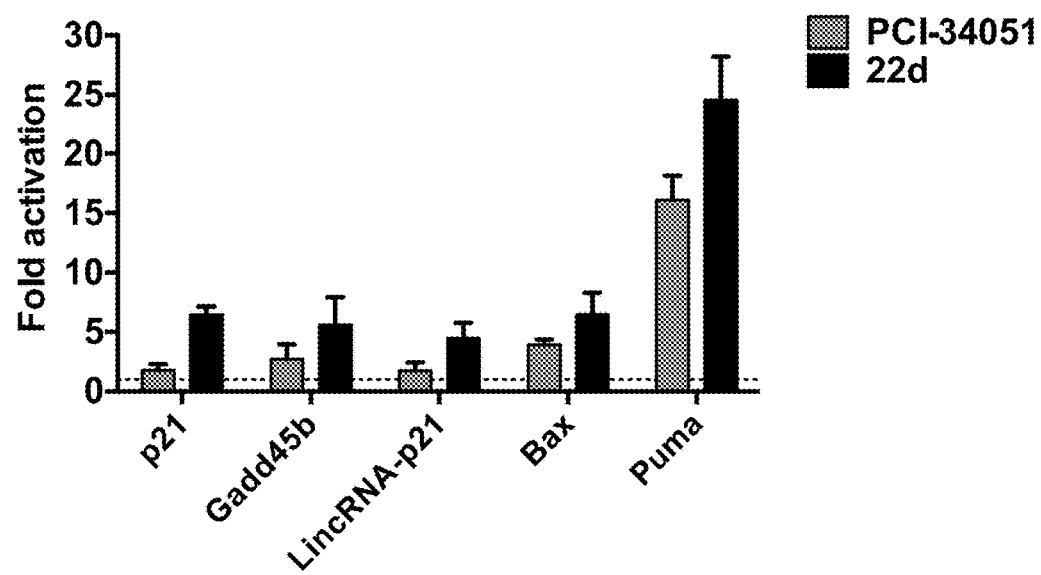

We next examined whether enhanced p53 acetylation translate into increased p53 transcriptional activity. Using qRT-PCR assay, we accessed induction of p53 target genes in CM-ΔC95, CM, and CBFβ expressing cells upon IR (3 Gy). For target genes assessed, we observed restored activation in CM-ΔC95 cells and a significant increase compared to full-length CM could be detected for most targets (FIG. 4D). Since HDAC8i treatment robustly increased Ac-p53 levels, we evaluated activation of p53 target genes upon treatment with HDAC8i PCI-34051 or 22d. Variable levels of activation in p53 targets (Bax, Puma, p21, Gadd45b and LincRNA-p21) were observed (FIG. 4E), consistent with the enhanced p53 acetylation. Similarly, we observed activation of subsets of p53 targets in pre-leukemic (FIG. 12A) or leukemic cells (FIG. 12B) expressing endogenous levels of CM. Together, these results support that HDAC8-p53 protein complex associated with CM leads to aberrant deacetylation of p53 mediated by HDAC8.

Pharmacologic Inhibition of HDAC8 Activates p53 and Selectively Induces Apoptosis of Inv(16)$^+$ AML Stem and Progenitor Cells.

Figure 5A:
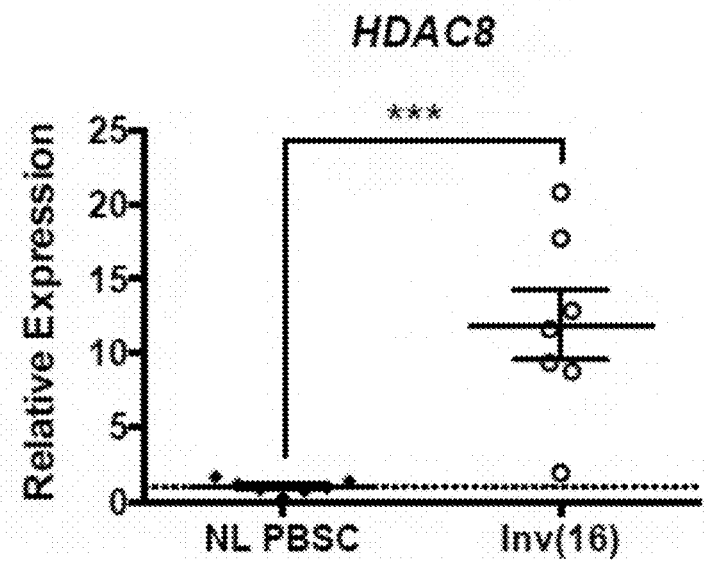
FIGS. 5A-5G. Pharmacological inhibition of HDAC8 selectively activates p53, reduces proliferation and induces p53-dependent apoptosis in inv(16)$^+$ AML CD34$^+$ cells.
Figure 5B:
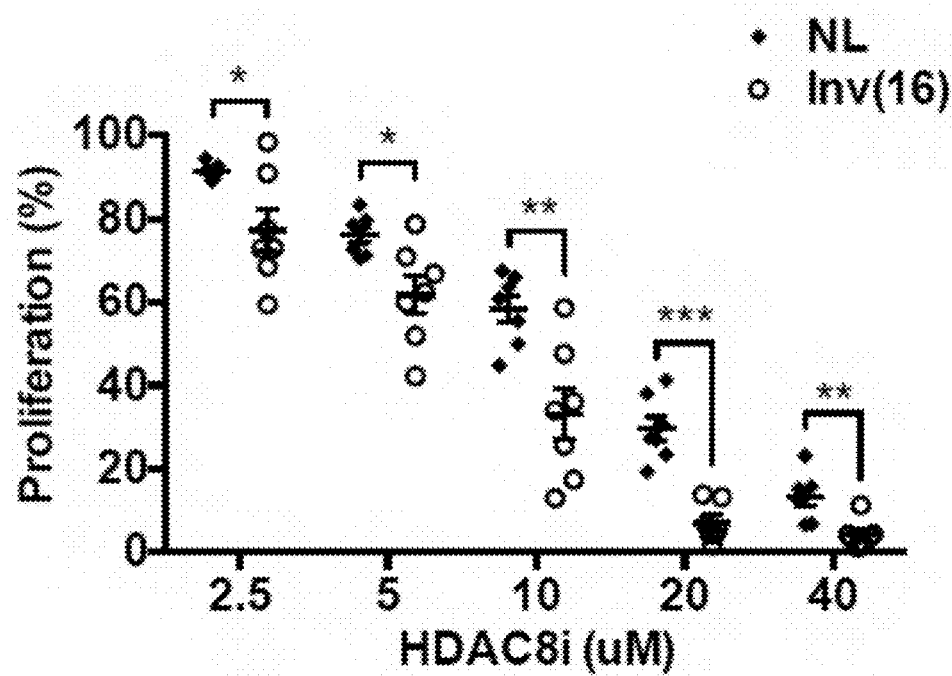

Given that the frequency of TP53 mutation is relatively low in AML, altered post-translational modification by HDAC8 could represent an alternative p53-inactivating mechanism and contribute to drug resistance of AML stem cells. We first examined the expression of HDAC8 in CD34$^+$ stem and progenitor cells isolated from patients with inv(16)$^+$ AML compared to normal mobilized peripheral blood stem cells (PBSC). Significant elevation in HDAC8 expression was observed in inv(16)$^+$ AML CD34$^+$ cells (n=7; p=0.0003) compared to normal CD34$^+$ cells (n=7) (FIG. 5A). Therefore, we reasoned that inv(16)$^+$ CD34$^+$ cells might selectively depend on HDAC8 for proliferation and/or survival. To test this, we treated inv(16)$^+$ AML CD34$^+$ cells and normal CD34$^+$ cells with HDAC8i 22d for 48 h. Dose responses to HDAC8i 22d (2.5 μM to 40 μM) were determined by an ATP-based cell viability assay and Annexin V staining. Indeed, HDAC8i (22d) treatment significantly reduced proliferation of inv(16)$^+$ CD34$^+$ cells compared to normal CD34$^+$ cells (FIG. 5B, inv(16)$^+$ AML n=9; normal n=7). Importantly, 22d HDAC8i selectively induced apoptosis of inv(16)$^+$ AML CD34$^+$ cells compared to normal CD34$^+$ cells (FIG. 5C) or non-inv(16) AML (FIG. 13A). Modest cytotoxicity in normal CD34$^+$ cells was observed with higher dose (40 μM) of 22d, however, inv(16)$^+$ AML CD34$^+$ cells were significantly more sensitive and were sensitive at a lower dose (2.5 μM to 10 μM). Analysis of CD34$^+$ cells from PBSC and CB showed no significant difference (data not shown).

Figure 5C:
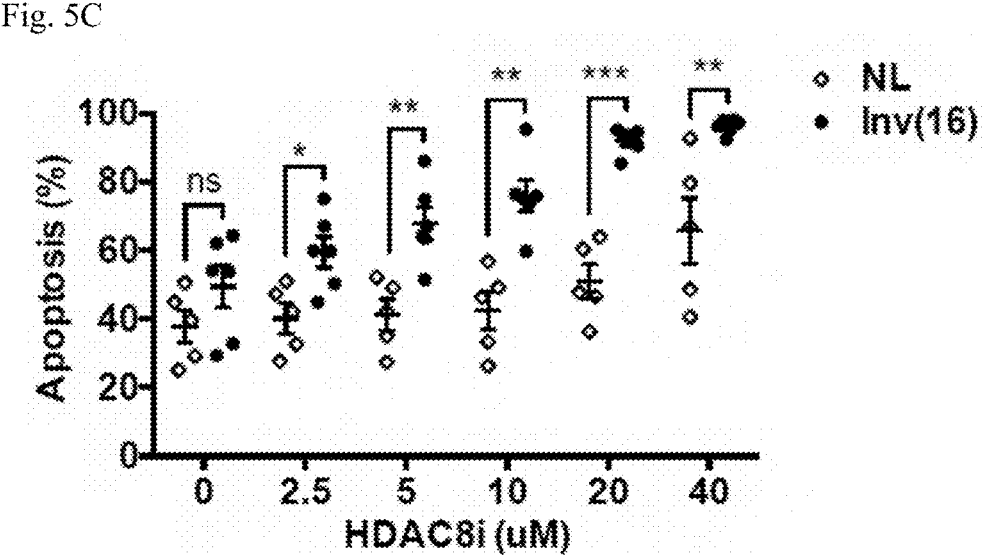
Figure 5D:
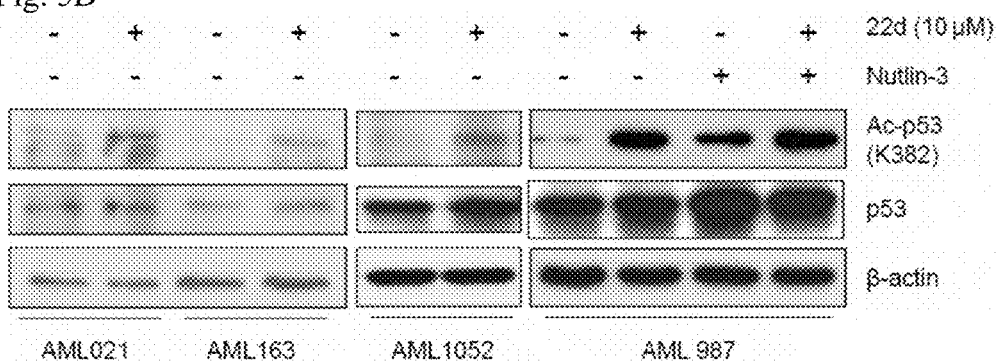

Similar to results obtained in mouse models, we detected protein-protein interaction between CM and p53 in CD34$^+$ cells isolated from inv(16)$^+$ AML patients (FIG. 2F). We therefore tested whether inhibiting HDAC8 deacetylase activity in inv(16)$^+$ AML CD34$^+$ cells could similarly lead to increased p53 acetylation and transcriptional activity. We purified inv(16)$^+$ AML CD34$^+$ cells and accessed changes in p53 acetylation levels upon HDAC8i (22d, 6h) treatment by western blot analysis. Indeed, elevated levels of Ac-p53 (K382) were consistently observed in all patients examined (FIG. 5D, data not shown). Similar treatments with 22d did not affect Ac-p53 in non-inv(16) AML (p53 non-mutated) CD34$^+$ cells (FIG. 13B). Together with the selective induction of apoptosis, these results support a CM-specific mechanism underlying p53 inactivation.

Figure 5E:
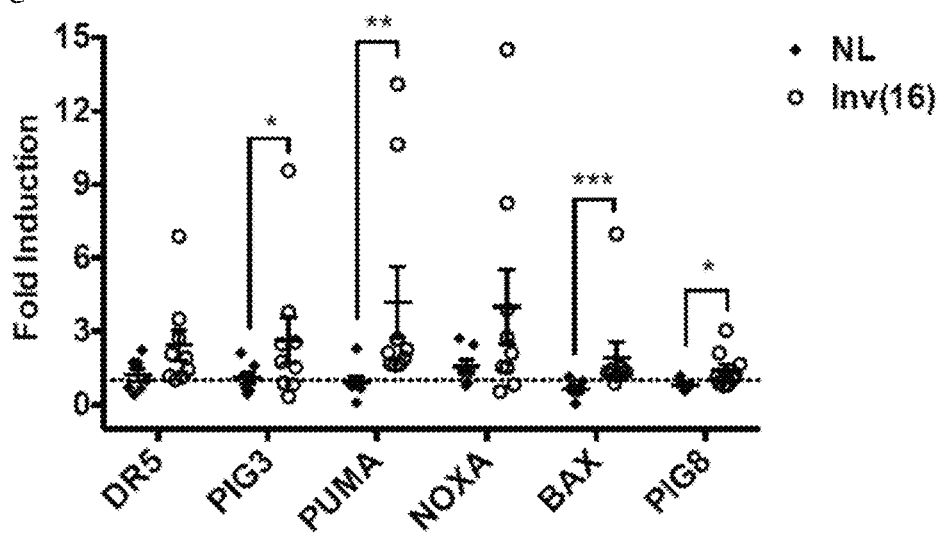
Figure 5F:
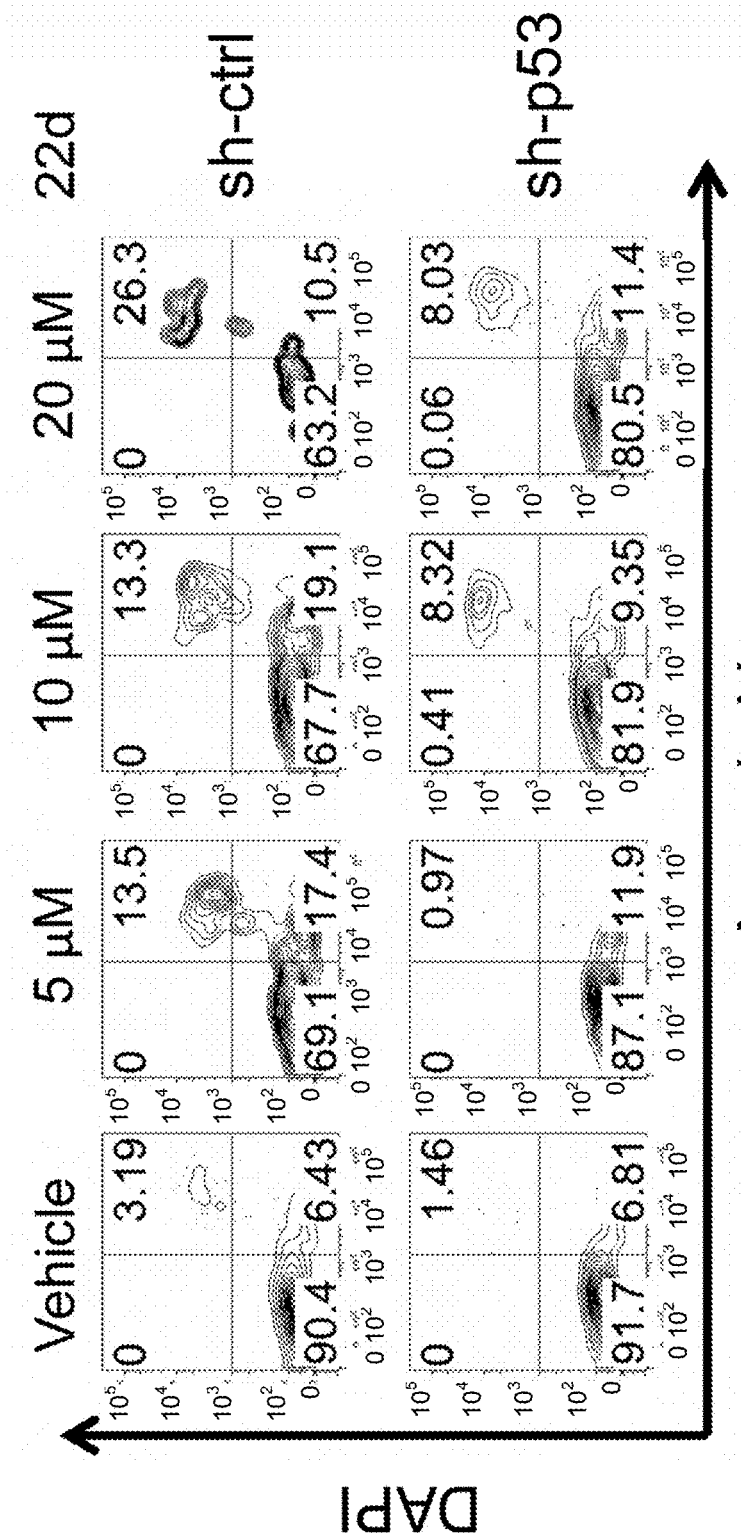
Figure 5G:
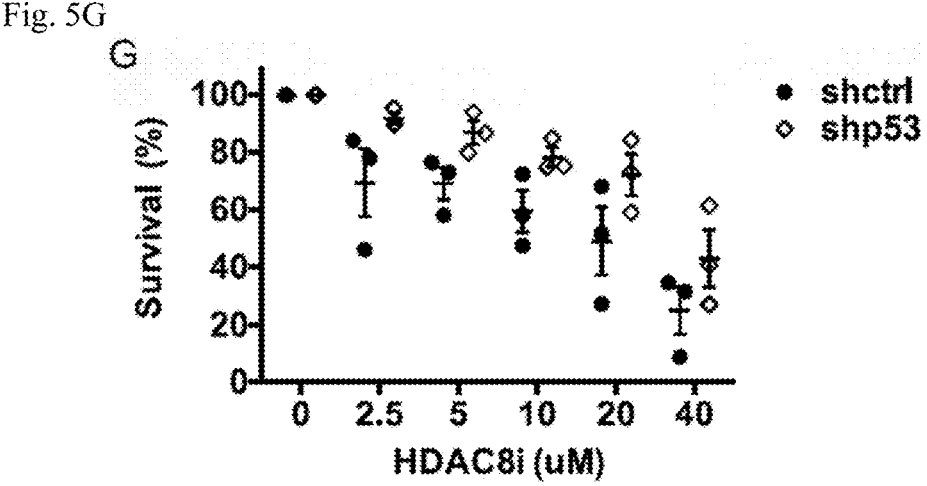

Consistent with the enhanced acetylation, 22d treatment also significantly induced expression of p53 target genes, particularly apoptosis related genes (FIG. 5E; n=9). Similar treatment of normal CD34$^+$ cells resulted in no or little change in p53 target expression (FIG. 5E, n=7). In order to determine whether HDAC8i-induced apoptosis is mediated by p53, we transduced inv(16)$^+$ AML CD34$^+$ cells with a lentiviral vector (pLKO.1-GFP) carrying an p53 shRNA we confirmed could effectively knock down p53 expression (FIGS. 14A,14B). Transduced GFP$^+$ cells were sorted and exposed to 22d (2.5-40 μM). Despite the inter-sample variability, knocking down p53 expression led to reduction of 22d-induced apoptosis compared to non-silencing shRNA control in all AML samples tested (n=3) (FIGS. 5F and 5G), suggesting that p53 contributes to the apoptosis effect induced by 22d HDAC8i in inv(16)$^+$ AML stem and progenitor cells.

Pharmacologic inhibition of HDAC8 abrogate leukemia initiating activity of CBFβ-SMMHC$^+$ LSCs.

Figure 6A:
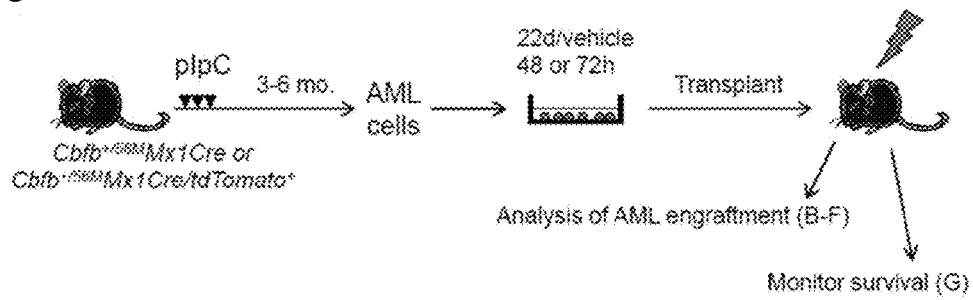
FIGS. 6A-6G. Inhibiting HDAC8 by pharmacological inhibitor 22d eliminates LSC engraftment and AML propagation.
Figure 6B:
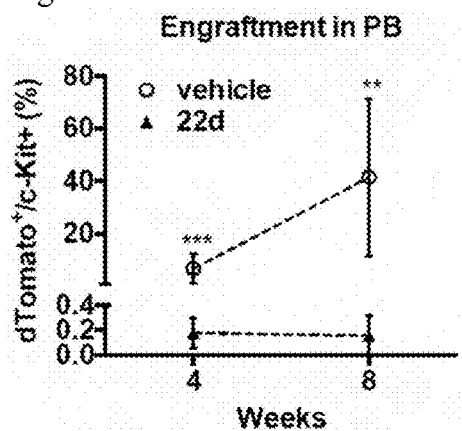
Figure 6C:
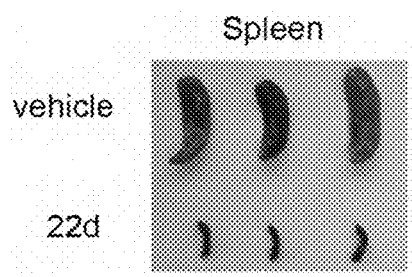
Figure 6D:
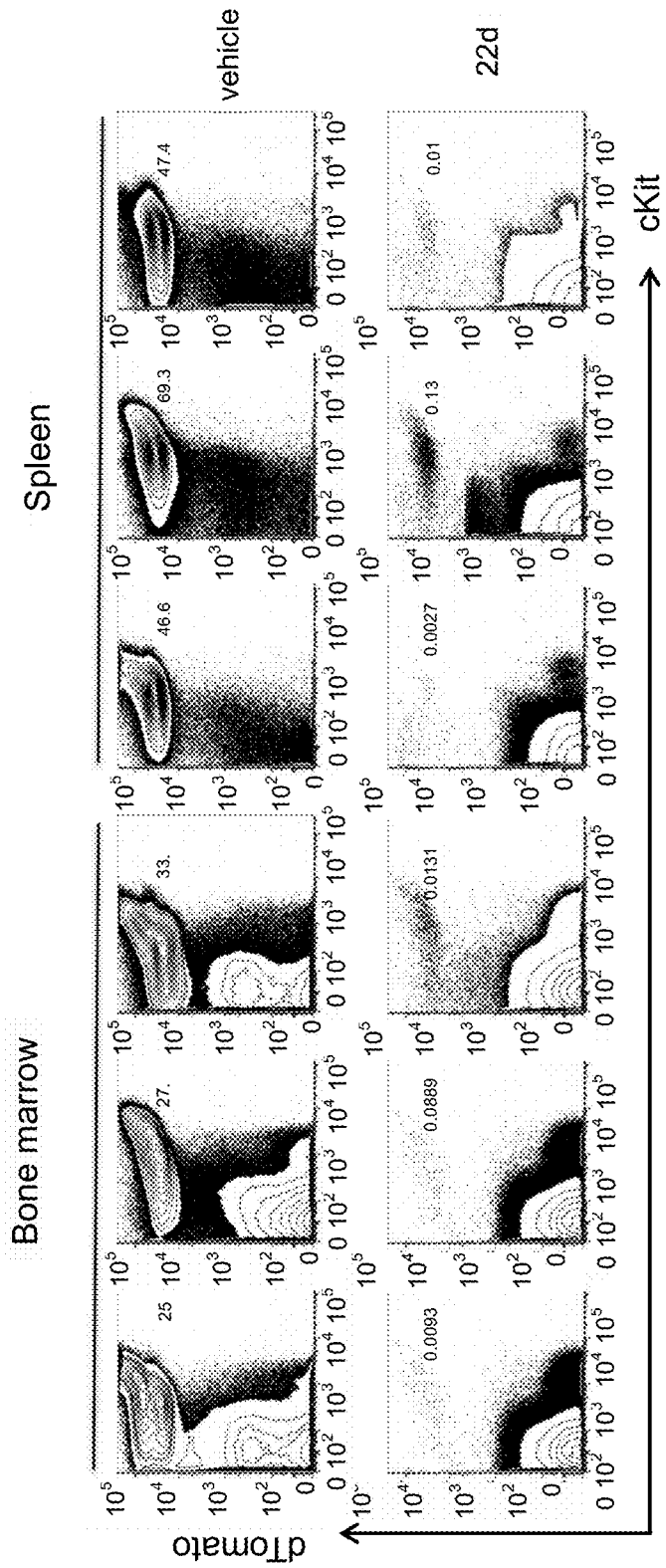
Figure 6E:
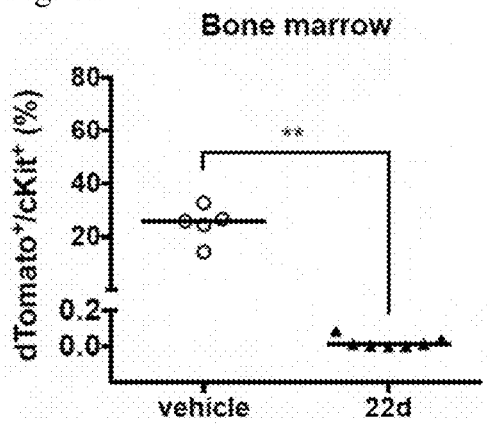
Figure 6F:
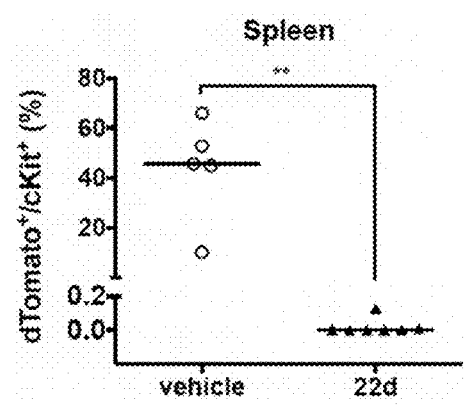
Figure 6G:
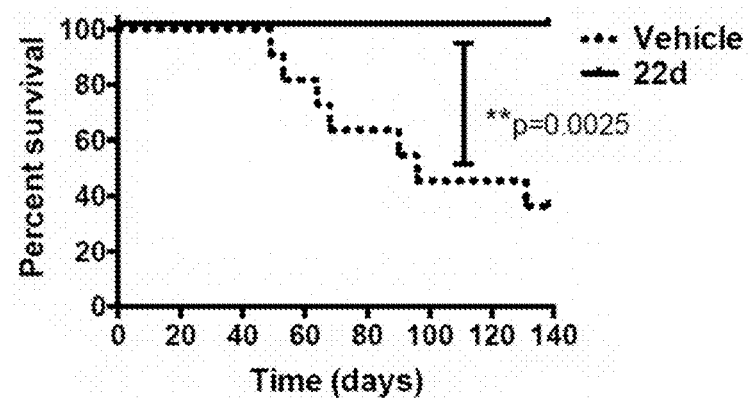

AML LSCs are functionally characterized by their capacity to engraft and reproduce AML disease in transplanted host. We reason that p53 activation induced by HDAC8i could reduce or eliminate LSC engraftment and leukemia-initiating capacity. To test this, we made use of our murine CM-induced AML model allowing for high-level engraftment and reproducible disease upon secondary transplantation. To facilitate tracking of CM-expressing AML cells, we created Cbfb$^{56M/+}$/Mx1-Cre mice with a Cre-reporter line expressing tdTomato fluorescence protein following Cre-mediated recombination. AML can be induced in Cbfb$^{56M/+}$/Mx1-Cre/tdTomato$^+$ mice 3-6 months following pIpC and the AML cells are predominately dTomato$^+$/cKit$^+$ (data not shown). Freshly isolated AML cells (2×10$^6$) from BM of moribund animals were treated with 22d (10 μM) or vehicle for 48 h before transplanting into sub-lethally irradiated congenic recipients (FIG. 6A). Progression of AML disease is evident by increasing frequencies of dTomato$^+$/cKit$^+$ cells in the peripheral blood of mice transplanted with vehicle-treated cells whereas these cells are barely detectable in mice receiving 22d-treated cells (FIG. 6B). At 8 weeks after transplantation, animals in the vehicle-treated group all showed enlarged spleens compared to the 22d-treated group (FIGS. 6C, 15A). In fact, 2 out of 7 mice in the vehicle-treated group succumbed to lethal AML 5-6 weeks after transplantation prior to analysis of BM and spleen engraftment (data not shown). Analysis of BM and spleen at 8 weeks show significantly (p=0.025) reduced frequencies of dTomato$^+$/cKit$^+$ AML cells in mice receiving 22d-treated cells compared to vehicle-treated cells (FIG. 6D-F). Likewise, the total numbers of dTomato$^+$/cKit$^+$ AML cells in the BM and spleen were also significantly (p=0.025) lower in 22d-treated compared to vehicle-treated group (FIGS. 15B, 15C). Finally, we monitored AML onset and survival in a separate cohort transplanted with AML cells from Cbfb$^{56M/+}$/Mx1-Cre mice and treated with 22d (10 μM) or vehicle for 72 h prior to transplantation. We observed that 22d treatment prevented AML reoccurrence in transplanted mice while more than 50% of vehicle treated transplants succumb to lethal AML disease within 4 months (FIG. 6G; p=0.0025). Transplantation of BM cells isolated from diseased mice reproduced similar leukemia in all secondary recipients within 4 weeks (data not shown), confirming robust LSC activity. To examine whether 22d treatment affects the engraftment capacity of surviving cells, we transplanted equal number ($2 \times 10^6$) of AML cells treated with either 22d or vehicle in another cohort of mice (n=4). Similarly, 22d treatment reduced the engraftment of dTomato$^+$ and dTomato$^+$/cKit$^+$ cells (FIGS. 15D, 15E) and enhanced survival (FIG. 15F), suggesting that the engraftment capacity is altered in addition to reducing AML cell survival.

Figure 7A:
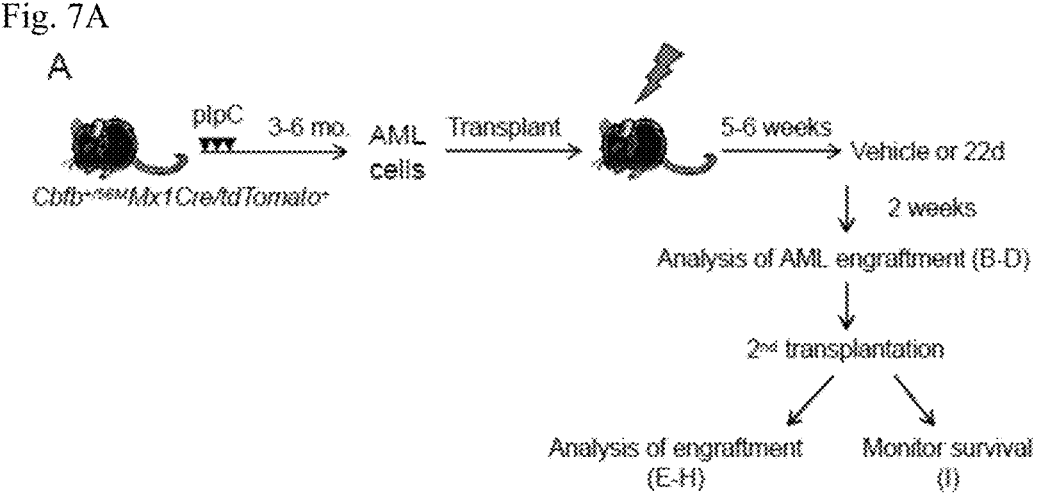
FIG. 7A-7I. In vivo administration of 22d significantly reduce AML burden and abrogate LSC activity.
Figure 7B:
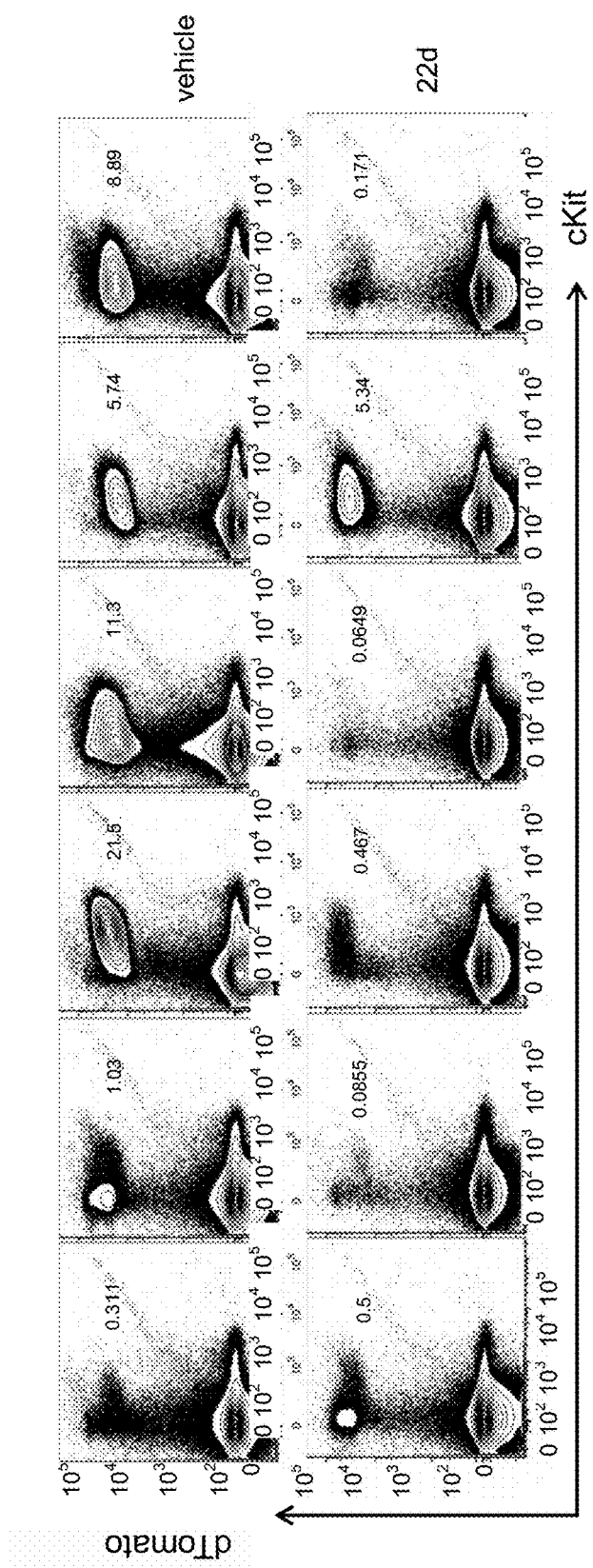
Figure 7C:
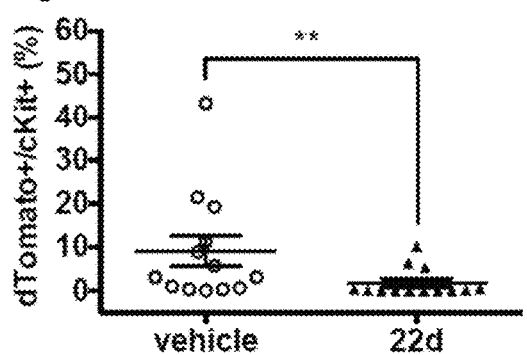
Figure 7D:
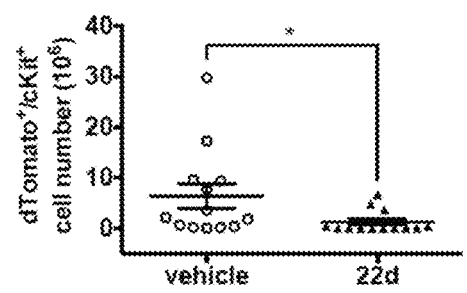
Figure 7E:
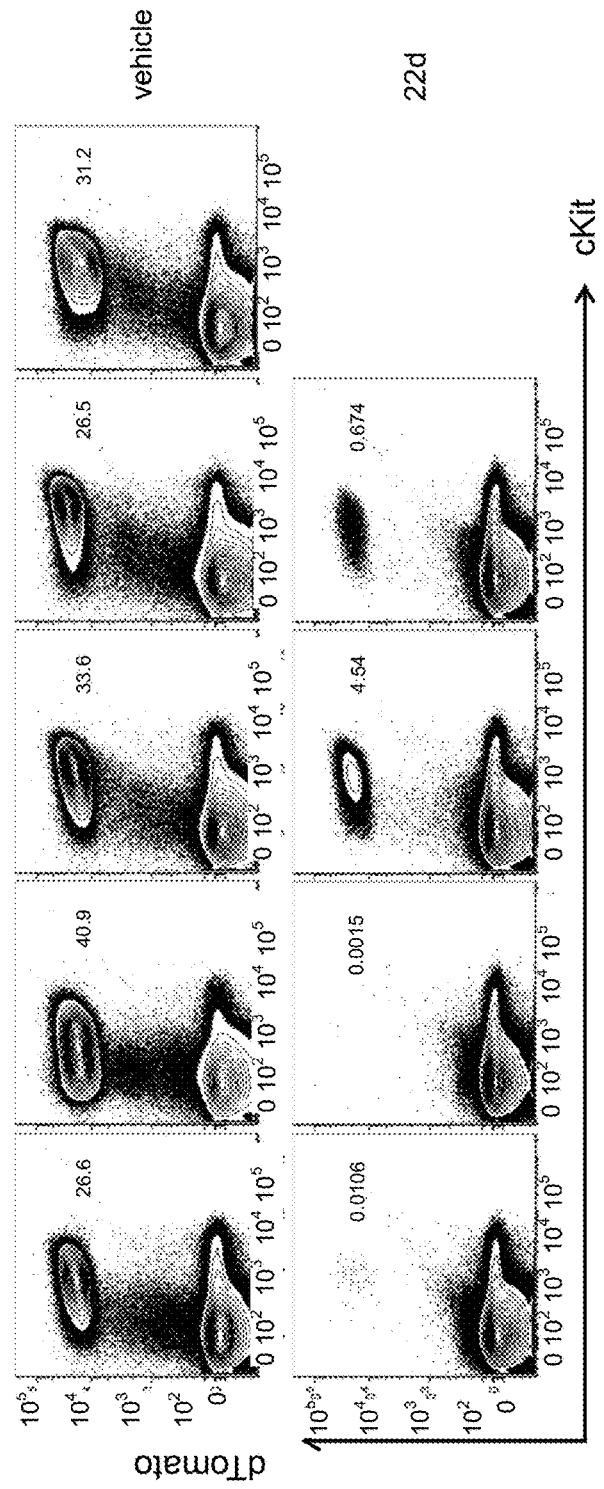
Figure 7F:
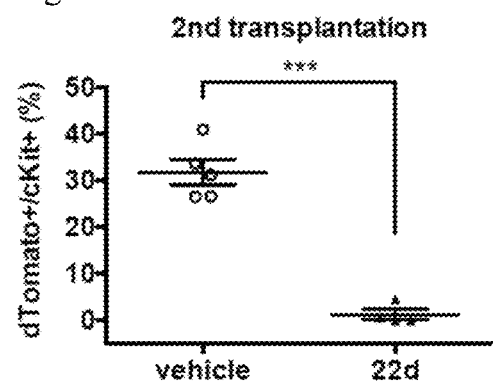
Figure 7G:
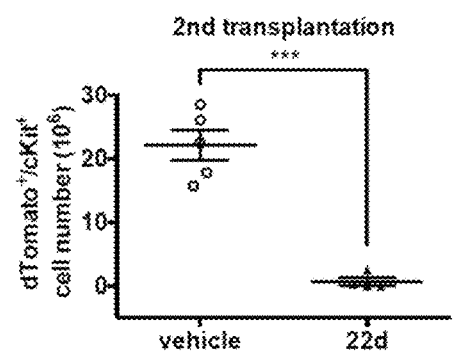
Figure 7H:
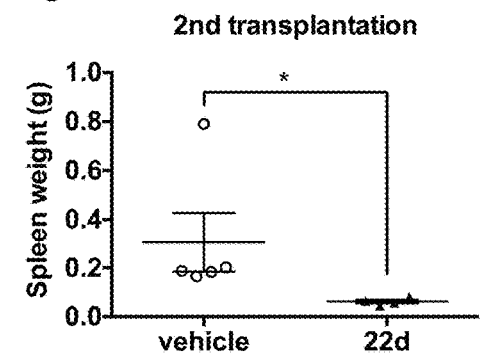
Figure 7I:
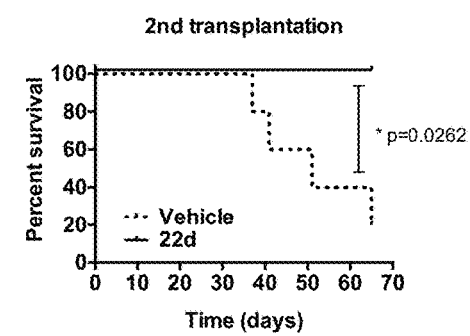

We performed preclinical studies to determine the efficacy of in vivo administration of 22d. AML cells ($1 \times 10^6$ or $2 \times 10^6$) were directly transplanted into sub-lethally irradiated congenic recipients. After 5-6 weeks, transplanted mice were randomized into two groups, one group treated with vehicle and the other treated with 22d by intraperitoneal injection (50 mg/kg/dose) twice a day for 2 weeks (FIG. 7A). Flow cytometry analysis revealed significantly reduced the frequency (p=0.0097) and the number (p=0.0101) of dTomato$^+$/cKit$^+$ AML cells in the bone marrow of 22d treated mice compared to vehicle treated group (FIG. 7B, C, D). To further assess the impact on LSC activity, we transplanted bone marrow cells ($2 \times 10^6$) from these treated mice into secondary recipients and analyzed for AML engraftment. Significant reduction in the frequency (p<0.0001) and the number (p=0.0006) of dTomato$^+$/cKit$^+$ AML cells was observed in the bone marrow 8 weeks after transplantation (FIG. 7E, F). Significant difference in spleen weight and AML cellularity is also evident (FIG. 7G, data not shown). We monitored leukemia onset and disease-free survival in another cohort of secondary recipients who received $5 \times 10^6$ BM cells from 22d or vehicle treated mice. At 5-7 weeks after transplant, 60% (3 out of 5) of vehicle treated transplants are moribund with aggressive AML whereas all 22d treated transplants show no signs of leukemia (FIG. 7I, data not shown). Collectively, these results indicate that HDAC8 inhibition by 22d treatment effectively reduces AML engraftment and eliminates the leukemia-initiating capacity of LSCs.

AML transformation requires multiple genetic and/or epigenetic alterations, which cooperatively impair differentiation, and confer proliferation and survival signals. Previous studies demonstrated that CBFβ-SMMHC expression dominantly inhibits CBF/RUNX1 function and disrupts hematopoietic differentiation [13,16,46,47]. It has been long thought that dominant inhibition of CBF/RUNX1 function underlies the leukemogenic function of CBFβ-SMMHC. However, recent genetic studies suggested that CBFβ-SMMHC-mediated leukemogenesis requires functional Runx proteins [22], and that RUNX1 dominant inhibition is not essential for transformation [23]. On the contrary, RUNX1 activity is now shown to be required for the growth and survival of AML cells, including RUNX1-ETO and CBFβ-SMMHC associated leukemia [24,25]. Recent genome wide binding analyses further revealed that CBFβ-SMMHC binds to target DNA in a RUNX1-dependent manner [48]. In this study, we show a novel mechanism of CBF-SMMHC-mediated transformation whereby CBFβ-SMMHC fusion protein disrupts p53 activity through aberrant post-translational modification. It has been previously reported that CBFβ-SMMHC reduces p53 mRNA transcription and slows apoptosis in Ba/F3 pro-B cell line [49]. We did not observe significant changes in p53 mRNA or protein levels by CBFβ-SMMHC expression in 32D myeloid progenitor cell line (FIGS. 1B, 16A) or in primary myeloid progenitor cells (FIGS. 1C, 16B). Since transcriptional activity of CBF is considerably context dependent, this possibly reflects context specific transcriptional regulation of p53. Although p53 expression levels are not affected, we showed that CBFβ-SMMHC notably reduced acetylated p53 levels (FIGS. 1 B and C) and forms an aberrant protein complex with p53 (FIG. 2 and FIG. 3). This is independent of p19Arf/p16 ink4a given that this locus is inactivated in 32D cells. We found that residues 179-221 of CBFβ-SMMHC are important for interaction with p53 (FIG. 3C, D), independent on the binding to HDAC8 at the C-terminus of SMMHC. RUNX1 has been shown to bind HDAC1, HDAC3, and HDAC9 whereas no binding to HDAC8 can be detected [16]. Given that normal CBFβ proteins do not interact with p53 (FIG. 2 and FIG. 3), the binding of p53 to CBFβ-SMMHC is unlikely to result from binding to RUNX1. Whether CBFβ-SMMHC residues 179-221 bind p53 directly or contribute to unique conformational properties of CBFβ-SMMHC chimeric protein requires further investigation.

Figure 8:
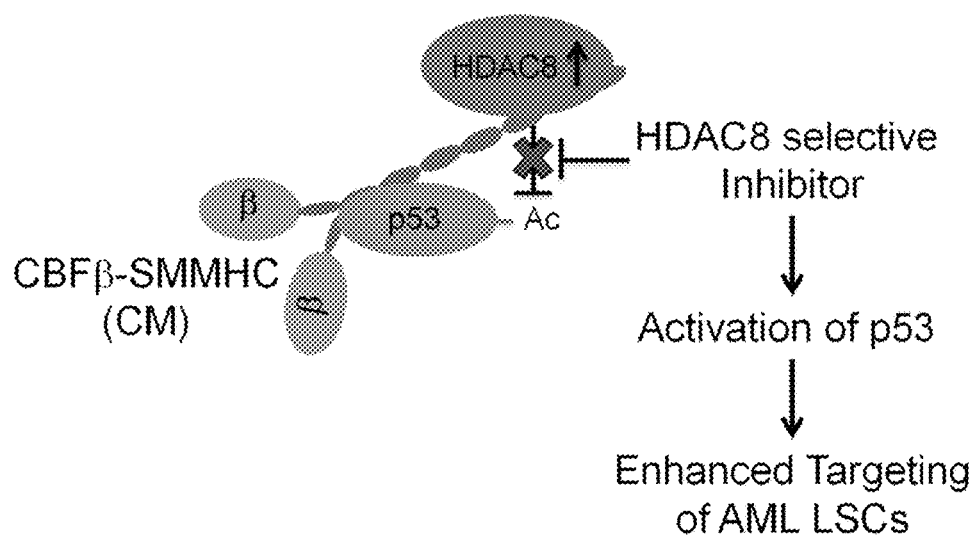
FIG. 8. Cartoon depicting proposed model illustrating HDAC8-mediated p53 inactivation contributes to CBFβ-SMMHC-associated AML LSC maintenance. The leukemogenic fusion protein CBFβ-SMMHC recruits p53 and HDAC8 into an aberrant protein complex, thereby inhibiting the tumor suppressor p53 activity is through aberrant deacetylation by HDAC8. Inhibiting HDAC8 deacetylase activity by HDAC8 selective pharmacological inhibitor leads to reactivation of p53 in AML LSCs. This novel p53-inactivating mechanism highlights a promising approach to restore p53 activity, and enhance targeting of AML LSCs.

The acetylation of p53 promotes p53 stabilization, inhibits formation of repressive complexes and recruits cofactors for transcriptional activity. Histone deacetylases, including HDAC1, 2, 3 and Sirtuin I (SIRT1) are known to modulate p53 activity through deacetylating p53 [41-43,50]. We found that CBFβ-SMMHC reduced acetylated p53 levels particularly at later time points after stimulation (FIG. 1B, C), suggesting that p53 is aberrantly deacetylated. We demonstrate that HDAC8, similar to other class I HDACs, can deacetylate p53 and modulate p53 activity. Based on our results, we propose a model whereby CBFβ-SMMHC impairs p53 function through protein-protein interaction resulting in recruitment of HDAC8 into a stable protein complex with p53, hence leading to aberrant deacetylation of p53 (FIG. 8). Remarkably, either knocking-down CBFβ-SMMHC or inhibition of HDAC8 deacetylase activity substantially enhances p53 acetylation and p53 target gene expression. The effect of HDAC8i on p53 targets is p53 dependent because significantly reduced effect was seen when p53 is knocked-down (FIGS. 17A-17C). Our results also reveal that HDAC8i led to activation of a distinct subset of p53 targets in pre-leukemic progenitors (FIG. 12A) compared to leukemic cells (FIG. 12B), likely reflecting the context-dependent and disease-stage specific activity of p53.

AML is maintained by LSCs that are relatively resistant to chemotherapy and can persist as potential sources of relapse. Even though AML with CBF translocations are considered to have favorable prognosis, the incidence of relapse is still 25-58% with chemotherapy [51-53]. Novel strategies directed to eradicate LSCs are required to improve treatment outcome. We show that inhibiting HDAC8 by an isotype-selective inhibitor, 22d, leads to restoration of p53 acetylation and activity, induction of apoptosis, and abrogates engraftment and leukemia-initiating activity of inv (16)$^+$ AML LSCs. Whether additional mechanisms besides increased apoptosis contribute to the reduced engraftment capacity remains to be examined. Importantly, this effect is selective for LSCs as normal HSCs display relatively low levels of p53 target activation (FIG. 5E) and induction of apoptosis (FIG. 5C). Treatment of 22d also had no impact on short-term or long-term engraftment activity of normal HSCs (FIG. 18). This selectivity is likely due to the combined effect of elevated HDAC8 expression and the recruitment of HDAC8 and p53 into a stable protein complex in inv(16)$^+$ AML CD34$^+$ cells. The increase in HDAC8 expression does not appear to be directly caused by CM expression since we did not observe changes of HDAC8 levels in 32D cells expressing CM (FIG. 19). The impact of CM-associated protein complex on HDAC8 activity requires further investigation.

Given that TP53 is rarely mutated in inv(16)+ AML, our results not only provide insights into an alternative p53 inactivating mechanism but also highlight the potential therapeutic opportunity. Inhibition of MDM2 by Nutlins and other inhibitors has been explored as an approach to activate p53 in AML [54,55]. Various degrees of sensitivity and resistance influenced by multiple distinct mechanisms have been observed, underscoring the need to further dissect the heterogeneity and distinct pathogenic pathways amongst AML subtypes. Many broad-spectrum HDAC inhibitors have potent anticancer activities, however, considerable toxicity and lack of selectivity related to the pleiotropic biological effects have greatly hampered their clinical application and efficacy. More selective inhibition of mechanistically defined HDAC targets is needed to efficaciously eliminate cancer cells while minimizing toxicity. It has been recently shown that selective inhibition of a class III HDAC, SIRT1, enhances elimination of chronic myelogenous leukemia LSCs while preserving normal HSC function [56]. Herein, we discovered that HDAC8 function can potentially be exploited to modulate p53 activity in AML and other cancers overexpressing HDAC8. Indeed, inhibition of HDAC8 results in reduced clonogenic growth and enhanced differentiation in neuroblastoma where high HDAC8 expression is associated with poor prognosis [38]. Most broad-spectrum HDAC inhibitors currently used or being tested in clinical trails display low activity against HDAC8 [57]. Besides the selective hydroxamic acid inhibitor PCI-34051 previously reported [44], our team developed a series of ortho-aryl N-hydroxycinnamides as potent HDAC8 selective inhibitors with anti-HDAC8 activity superior to PCI-34051 [45]. Herein, we tested several HDAC8i in parallel and have found similar biological effects consistent with their HDAC8 inhibitory activities. In addition, inhibiting HDAC8 using 22d show a differential activity in enhancing p53 acetylation in CBFβ-SMMHC expressing cells compared to other class I HDAC (MS-275), class III HDAC (TV6) or broad-spectrum (PCI-24781) inhibitors (FIG. 20). Together, these results suggest that the p53 activating effects of 22d are not likely caused by off-target effects and further support the selectivity of 22d towards HDAC8.

Without being bound by any particular theory, we propose a model that CBFβ-SMMHC impairs p53 function through aberrant protein interaction with p53 and HDAC8, and that HDAC8-mediated deacetylation of p53 contributes to CBF 3-SMMHC-associated AML LSC maintenance (FIG. 8). Our studies reveal a novel p53-inactivating mechanism by the CBFβ-SMMHC leukemogenic fusion protein. The mechanisms underlying p53 inactivation is likely dependent on the context of oncogenic lesions and should be separately defined in order to select optimal targets for intervention. Herein we have demonstrated methods for designing HDAC8-targeted therapies to enhance eradication of inv (16)+ AML LSCs and which are expected to be useful for other cancers. Our in vivo treatment studies using 22d show remarkable effectiveness in abrogating AML burden and LSC capacity.

Example 5. Primers

Primers used in the experimental procedures disclosed herein are set forth in Table 10 following.

TABLE 10

Listing of primers

| Gene | Cells | Primer type | Sequence | SEQ ID NO: |
|---|---|---|---|---|
| p21 | Mouse | Forward | GCGGCTGTTTTTCTTGGTAG | 1 |
|  | Mouse | Reverse | AGACGAGGAAAGCAGTTCCA | 2 |
| Mdm2 | Mouse | Forward | TTAGTGGCTGTAAGTCAGCAAGA | 3 |
|  | Mouse | Reverse | CCTTCAGATCACTCCCACCT | 4 |
| Bax | Mouse | Forward | GTGAGCGGCTGCTTGTCT | 5 |
|  | Mouse | Reverse | GGTCCCGAAGTAGGAGAGGA | 6 |
| Bid | Mouse | Forward | GACAGCTAGCCGCACAGTT | 7 |
|  | Mouse | Reverse | GGCCAGGCAGTTCCTTTT | 8 |
| Puma | Mouse | Forward | TTCTCCGGAGTGTTCATGC | 9 |
|  | Mouse | Reverse | TACAGCGGAGGGCATCAG | 10 |
| Hprt | Mouse | Forward | TCCTCCTCAGACCGCTTTT | 11 |
|  | Mouse | Reverse | CCTGGTTCATCATCGCTAATC | 12 |
| HDAC8 | Human | Forward | GGTGACGTGTCTGATGTTGG | 13 |
|  | Human | Reverse | GACACTTGCCAATTCCCACT | 14 |
| p21 | Human | Forward | TACCCTTGTGCCTCGCTCAG | 15 |
|  | Human | Reverse | CGGCGTTTGGAGTGGTAGA | 16 |
| HDM2 | Human | Forward | CCTTCGTGAGAATTGGCTTC | 17 |
|  | Human | Reverse | CAACACATGACTCTCTGGAATCA | 18 |
| 14-3-3σ | Human | Forward | CTCTCCTGCGAAGAGCGAAAC | 19 |
|  | Human | Reverse | CCTCGTTGCTTTTCTGCTCAA | 20 |
| PUMA | Human | Forward | GACCTCAACGCACAGTACGAG | 21 |
|  | Human | Reverse | AGGAGTCCCATGATGAGATTGT | 22 |
| ACTB | Human | Forward | GTGGATCAGCAAGCAGGAG | 23 |
|  | Human | Reverse | TTTGTCAAGAAAGGGTGTAACG | 24 |

Example 6. Inhibition of HDAC8 and HeLa Nuclear HDACs

Results of inhibition studies of HDAC8 and HeLA nuclear HDACs by compounds disclosed herein are tabulated in Table 11 following.

TABLE 11

Inhibition of HDAC8 (A) and HeLa nuclear HDACs ($IC_{50}$, nM) by compounds 5a-h

| Compound | R | A (relative potency to PCI34051)[a] | HeLa HDAC |
|---|---|---|---|
| 5a | MeO-, MeO-, OMe (3,4,5-trimethoxyphenyl) | 0.29 | >10000 |

TABLE 11-continued

Inhibition of HDAC8 (A) and HeLa nuclear HDACs ($IC_{50}$, nM) by compounds 5a-h

[Structure: MeO-phenyl with CH=CH-C(O)-NH-OH and R substituent]

| Compound | R | A (relative potency to PCI34051)[a] | HeLa HDAC |
|---|---|---|---|
| 5b | thiophen-2-yl | 1.43 | >10000 |
| 5c | 3-chlorophenyl | 1.17 | >10000 |
| 5d | 4-fluorophenyl | 1.90 | >10000 |
| 5e | benzo[1,3]dioxol-5-yl | 1.86 | 8550 ± 0.12 |
| 5f | 1H-indol-4-yl | 0.64 | >10000 |
| 5g | isoquinolin-4-yl | 0.28 | 798.4 ± 0.3 |
| 5h | quinolin-3-yl | 0.63 | 836.0 ± 9.1 |
| PCI34051 | | 1 | >10000 |

[a]Calculated from dividing the $IC_{50}$ value of each compound by that of PCI34051.

Example 7. Inhibition of HDAC8 and HeLa Nuclear HDACs and Cytotoxicity for Compounds 6a-6f Results of inhibitions studies of Cmpds 6a-6f and PCI-34051 are tabulated in Table 12 following.

TABLE 12

Inhibition of HDAC8 (A) and HeLa nuclear HDACs ($IC_{50}$, nM) and cytotoxicity ($IC_{50}$, µM) by compounds 6a-f

[Structure with methoxy-phenyl, acrylamide hydroxamate, and NH-phenyl-R]

| Compound | R | A (relative potency to PCI34051)[a] | HeLa HDAC |
|---|---|---|---|
| 6a | H | 0.40 | >10000 |
| 6b | 2-OMe | 0.17 | >10000 |
| 6c | 3-OMe | 0.44 | >10000 |
| 6d | 4-OMe | 0.30 | >10000 |
| 6e | 3,4-diOMe | 0.44 | >10000 |
| 6f | 3,4,5-triOMe | 0.24 | >10000 |
| PCI34051 | | 1 | >10000 |

[a]Calculated from dividing the $IC_{50}$ value of each compound by that of PCI34051.

Example 8. Inhibition of HDAC8 and HeLa Nuclear HDACs by Cmpds 15a-15e, 21 and 25.

Results of inhibition studies on HDAC8 and HeLa nuclear HDAC8 by Cmpds 15a-15e, 21 and 25 are tabulated in Table 13 following.

TABLE 13

Inhibition of HDAC 8 (A) and HeLa nuclear HDACs ($IC_{50}$, nM) by compounds 15a-e, 21 and 25.

[Structure 15a-e: R-phenyl with acrylamide hydroxamate and NH-(3,4,5-trimethoxyphenyl)]

15a-e

TABLE 13-continued

Inhibition of HDAC 8 (A) and HeLa nuclear HDACs (IC$_{50}$, nM) by compounds 15a-e, 21 and 25.

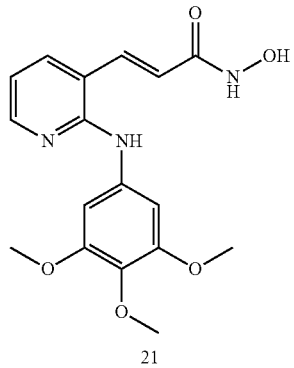 [SMILES: COc1cc(Nc2ncccc2/C=C/C(=O)NO)cc(OC)c1OC]

21

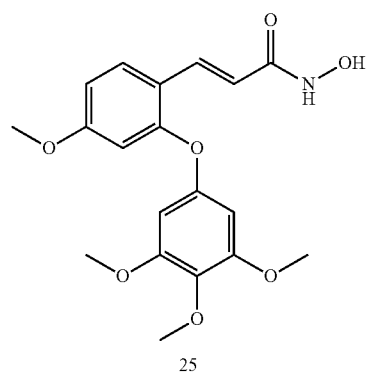 [SMILES: COc1ccc(/C=C/C(=O)NO)c(Oc2cc(OC)c(OC)c(OC)c2)c1]

25

| Compound | R | A (relative potency to PCI34051)[a] | HeLa HDAC |
|---|---|---|---|
| 15a | 4-F | 0.38 | >10000 |
| 15b | 4-CF$_3$ | 0.55 | >10000 |
| 15c | 5-OMe | 0.06 | >10000 |
| 15d | 3,4-OMe | 0.44 | >10000 |
| 15e | 3,4,5-OMe | 0.02 | >10000 |
| 21 | | 0.68 | >10000 |
| 25 | | 0.49 | >10000 |
| PCI-34051 | | 1 | |

[a]Calculated from dividing the IC$_{50}$ value of each compound by that of PCI34051.

Example 9. HDAC8 Inhibition Activates p53 and Induces p53-Dependent Apoptosis in Human AML Cells Survival of human AML cell lines upon contact with an HDAC8i (e.g. Cmpd 22d) was investigated. As shown in the FIG. 21A, survival of each cell line (MV4-11, MOLM13, OCI-AML3 and KG1a) decreases with increased HDAC8i concentration.

FIG. 21B demonstrates that increased HDAC8i concentration results in greater signal for Ac-p53 and p53 by western blot analysis to assay the effects of administration of HDAC8i (e.g. 22d) for 6-hr for Ac-p53, p53, Ac-H3, Ac-H4 and β-actin.

The fold change in mRNA levels of p53 targets after treatment with PCI-48012 for 16-hrs is depicted in FIG. 21C.

Western blot analysis of p53, b-actin and MV4-11 cells transduced with control or sh-p53 is provided in FIG. 21D.

Example 10. Activity of HDAC8i Compounds on AML Cell Proliferation and Survival Relative survival of non-p53 mutated AML cell lines (MV4-11, MOLM13, and OCI-AML3) treated with HDAC8i compounds (Cmp[ds 22d, 5b, 5e, 5h) for 48-hr was determined by Annexin V labeling and normalization to vehicle-treated controls. See FIGS. 22A-22C.

Relative proliferation of AML cell lines (MV4-11 and MOLM13) treated with HDAC8i (Cmpds 22d, 5b, 5e, 5h) for 48-hr was determined by luminescent cell viability assay, normalized to vehicle treated control. See FIGS. 22D-22E.

Resulting inhibitory activity of HDAC8i compounds is tabulated in Table 14 following.

TABLE 14

Inhibitory activity of HDAC8i compounds on AML cell growth and survival.

| | IC$_{50}$ (uM) | | | | |
|---|---|---|---|---|---|
| Compound | MV4-11 Apoptosis | MOLM13 Apoptosis | OCI-AML3 Apoptosis | MV4-11 Proliferation | MOLM13 Proliferation |
| 22d | 2.713 | 3.615 | 8.115 | 2.484 | 2.421 |
| 5b | 0.5243 | 0.3453 | 2.352 | 0.0825 | 0.05327 |
| 5e | 11.92 | 11.7 | 12.48 | 7.494 | 3.358 |
| 5h | ~22733 | 90.87 | ~170501 | 16.59 | 7.174 |

Example 11. Apoptosis Studies, Cmpd 22D

Analysis of CD34$^+$ cells from PBSC and CB showed no significant difference based on cell origin upon contact with Cmpd 22d. See FIG. 23.

Example 12. Changes in p53 mRNA or Protein Levels by CBFb-SMMHC Expression

It has been previously reported that CBFβ-SMMHC reduces p53 mRNA transcription and slows apoptosis in Ba/F3 pro-B cell line. We did not observe significant changes in p53 mRNA or protein levels by CBFβ-SMMHC expression in 32D myeloid progenitor cell line (FIG. 24A) or in primary myeloid progenitor cells (FIG. 24B). Since transcriptional activity of CBF is considerably context dependent, this possibly reflects context specific transcriptional regulation of p53.

Example 13. Gel Analyses of p53 and Ac-p53

The effect of agents PCI-24781, PCI-48012 and Nutlin on protein express employing Ac-p53, p53 and β-actin is depicts in FIG. 25.

Example 14. Effects of HDAC8 Inhibitors on Interaction Between p53 and CM

The effects of Cmpd 22d on IgG and IP expression were investigated. See FIG. 26A. Expression of after contact with Cmpd 22d on Ac-p53, p53 and β-actin under various timing and wash conditions are depicted in FIG. 26B. The survival rate with and without wash of Cmpd 22d is depicted in FIG. 26C, showing that washing of Cmpd 22d results in increased survival.

Example 15. Inhibition of HDAC8 Selectively Activate p53 in Inv(16)+ AML CD34+ Cells Western blotting of Ac-p53, (K382), and p53 levels was conducted in inv(16)+ AML CD34+ cells upon contact with Cmpd 22d. Results are depicted in FIG. 27A. The fold activation of the indicated p53 target genes in inv(16)+AML CD34+ and normal CD34+ cells is depicted in the histogram of FIG. 27B.

VI. REFERENCES

1. Look, A. T. 1997, Science 278:1059-1064.
2. Speck, N. A., and Gilliland, D. G. 2002, Nat Rev Cancer 2:502-513.
3. Wang, S., et al., 1993, Mol Cell Biol 13:3324-3339.
4. Ogawa, E., et al., 1993, Virology 194:314-331.
5. Huang, G., et al., 2001, Embo J 20:723-733.
6. Liu, P. P., et al., 1995, Blood 85:2289-302.
7. Grimwade, D., and Hills, R. K. 2009, Hematology Am Soc Hematol Educ Program: 385-395.
8. Grimwade, et al., 2010, Blood 116:354-365.
9. Mrózek, K., et al., 2004, Blood Rev 18:115-136.
10. Mrózek, K., et al., 2012, J Clin Oncol 30:4515-4523.
11. von Neuhoff, C., et al., 2010, J Clin Oncol 28:2682-2689.
12. Liu, P., et al., 1993, Science 261:1041-1044.
13. Castilla, L. H., et al., 1996, Cell 87:687-696.
14. Okuda, T., et al., 1996, Cell 84:321-30.
15. Wang, Q., et al., 1996, Cell 87:697-708.
16. Kuo, Y.-H., et al., 2006, Cancer Cell 9:57-68.
17. Lukasik, S. M., et al., 2002, Nat Struct Biol 9:674-679.
18. Adya, N., et al., 1998, Mol Cell Biol 18:7432-7443.
19. Kanno, Y., et al., 1998, Mol Cell Biol 18:4252-4261.
20. Lutterbach, B., et al., 1999, Proc Natl Acad Sci USA 96:12822-12827.
21. Durst, K. L., et al., 2003m, Mol Cell Biol 23:607-619.
22. Kuo, Y.-H., et al., L. H. 2009. Blood 113(14):3323-32.
23. Kamikubo, Y., et al., P. P. 2010. Cancer Cell 17:455-468.
24. Ben-Ami, O., et al., Y. 2013. Cell Rep 4:1131-1143.
25. Goyama, S., et al., 2013. J Clin Invest.
26. Rilcker, F. G., et al., 2012. Blood 119:2114-2121.
27. Haferlach, C., et al., 2008. Leukemia 22:1539-1541.
28. Nahi, H et al., 2008. Leuk Lymphoma 49:508-516.
29. Zhao, Z., et al., 2010. p5 Genes Dev 24:1389-1402.
30. Dai, C., and Gu, W. 2010. Trends Mol Med 16:528-536.
31. Buggy, J. J., et al., 2000. Biochem J 350 Pt 1:199-205.
32. Hu, E., et al., 2000. J Biol Chem 275:15254-15264.
33. Van den Wyngaert, I., et al., 2000. FEBS Lett 478:77-83.
34. Waltregny, D., et al., 2005. FASEB J 19:966-968.
35. Lee, H., et al., 2006. Mol Cell Biol 26:5259-5269.
36. Haberland, M., et al., 2009. Genes Dev 23:1625-1630.
37. Deardorff, M. A., et al., 2012. Nature.
38. Oehme, I., et al., 2009. Clin Cancer Res 15:91-99.
39. Moreno, D. A., et al., 2010. Br J Haematol 150:665-673.
40. Lo, H.-L., et al., 2007. Gene Ther 14:1503-1512.
41. Luo, J., et al., 2000. Nature 408:377-381.
42. Juan, L. J., et al., 2000. J Biol Chem 275:20436-20443.
43. Ito, A., et al., 2002. EMBO J 21:6236-6245.
44. Balasubramanian, S., et al., 2008 Leukemia 22:1026-1034.
45. Huang, W.-J., et al., 2012. ChemMedChem.
46. Kuo, Y.-H., et al., 2008. Blood 111:1543-1551.
47. Zhao, L., et al., 2007. Blood 109:3432-3440.
48. Mandoli, A., et al., 2013. Leukemia.
49. Britos-Bray, M., et al., 1998. Blood 92:4344-4352.
50. Luo, J., et al., 2001. Cell 107:137-148.
51. Appelbaum, F. R, et al., 2006. Br J Haematol 135:165-173.
52. Prébet, T et al., 2009. J Clin Oncol 27:4747-4753.
53. Kurosawa, S., et al., 2013. Haematologica 98:1525-1531.
54. Kojima, K., et al., 2005. Blood 106:3150-3159.
55. Long, J., et al., 2010. Blood 116:71-80.
56. Li, L., et al., 2012. Cancer Cell 21:266-281.
57. Khan, N., et al., 2008. Biochem J 409:581-589.
58. Khn, R., et al., 1995. Science 269:1427-1429.
59. Jeannet, R., et al., 2012. Alcam Regulates Long-term Hematopoietic Stem Cell Engraftment and Self-Renewal. Stem Cells.

VII. EMBODIMENTS

Embodiment P1 A compound having formula:

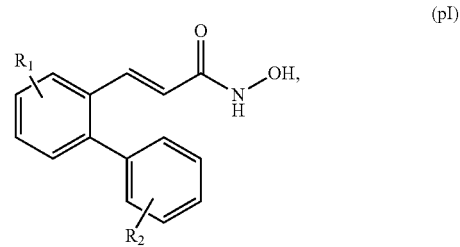

(pI)

$R^1$ is substituted or unsubstituted $C_1$-$C_{20}$ alkyl, substituted or unsubstituted 2 to 20 membered heteroalkyl, substituted or unsubstituted 3 to 7 membered cycloalkyl, substituted or unsubstituted 3 to 7 membered heterocycloalkyl, substituted or unsubstituted 3 to 7 membered aryl, or substituted or unsubstituted 3 to 7 membered heteroaryl; and $R^2$ is substituted or unsubstituted $C_1$-$C_{20}$ alkyl, substituted or unsubstituted 2 to 20 membered heteroalkyl, substituted or unsubstituted 3 to 7 membered cycloalkyl, substituted or unsubstituted 3 to 7 membered heterocycloalkyl, substituted or unsubstituted 3 to 7 membered aryl, or substituted or unsubstituted 3 to 7 membered heteroaryl.

Embodiment P2 The compound of embodiment P1 having the formula:

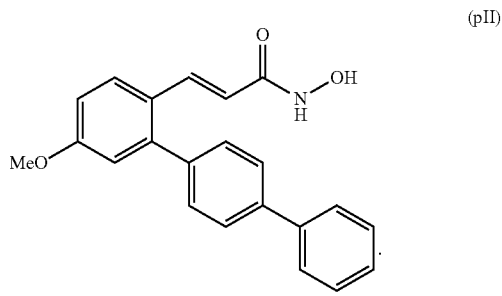 [SMILES: COc1ccc(/C=C/C(=O)NO)c(-c2ccc(-c3ccccc3)cc2)c1]

(pII)

Embodiment P3 The compound of any one of embodiments P1 to P2, wherein said compound is a HDAC8 inhibitor.

Embodiment P4 A method of treating cancer, the method comprising administering to a subject in need thereof a therapeutically effective amount the compound of any one of embodiments P1 to P3.

Embodiment P5 The method of embodiment P4, wherein said cancer is a hematological cancer.

Embodiment P6 The method of any one of embodiments P4 to P5, wherein said cancer is acute myeloid leukemia.

Embodiment 1 A compound having the formula:

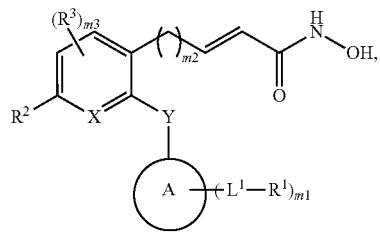

A is cycloalkyl, heterocycloalkyl, aryl, or heteroaryl. X is —C($R^4$)— or —N═. Y is a bond, —N($R^5$)—, —O—, or —S—. $L^1$ is a bond, —C(O)—, —C(O)O—, —O—, —S—, —N($R^6$)—, —C(O)N($R^6$)—, —S(O)$_6$—, —S(O)N($R^6$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is halogen, —$N_3$, —$CF_3$, —$CCl_3$, —$CBr_3$, —$CI_3$, —CN, —$OR^{1A}$, —C(O)$R^{1A}$, —$NR^{1A}R^{1B}$, —C(O)$OR^{1A}$, —C(O)$NR^{1A}R^{1B}$, —$NO_2$, —$SR^{1A}$, —S(O)$_{n1}R^{1A}$, —S(O)$_{n1}OR^{1A}$, —S(O)$_{n1}NR^{1A}R^{1B}$, —NHN$R^{1A}R^{1B}$, —ON$R^{1A}R^{1B}$, —NHC(O)NHN$R^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is halogen, —$N_3$, —$CF_3$, —$CCl_3$, —$CBr_3$, —$CI_3$, —CN, —$OR^{2A}$, —C(O)$R^{2A}$, —$NR^{2A}R^{2B}$, —C(O)$OR^{2A}$, —C(O)$NR^{2A}R^{2B}$, —$NO_2$, —$SR^{2A}$, —S(O)$_{n2}R^{2A}$, —S(O)$_{n2}OR^{2A}$, —S(O)$_{n2}NR^{2A}R^{2B}$, —NHN$R^{2A}R^{2B}$, —ON$R^{2A}R^{2B}$, —NHC(O)NHN$R^{2A}R^{2B}$, substituted or unsubstituted $C_1$-$C_5$ alkyl, or substituted or unsubstituted 2 to 5 membered heteroalkyl. $R^3$ is independently hydrogen, halogen, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —S(O)$_2$H, —$NHNH_2$, —$ONH_2$, —NHC(O)$NHNH_2$, substituted or unsubstituted $C_1$-$C_5$ alkyl, or substituted or unsubstituted 2 to 5 membered heteroalkyl. $R^4$ is hydrogen, halogen, —$N_3$, —$CF_3$, —$CCl_3$, —$CBr_3$, —$CI_3$, —CN, —$OR^{4A}$, —C(O)$R^{4A}$, —$NR^{4A}R^{4B}$, —C(O)$OR^{4A}$, —C(O)$NR^{4A}R^{4B}$, —$NO_2$, —$SR^{4A}$, —S(O)$_{n4}R^{4A}$, —S(O)$_{n4}OR^{4A}$, —S(O)$_{n4}NR^{4A}R^{4B}$, —NHN$R^{4A}R^{4B}$, —ON$R^{4A}R^{4B}$, —NHC(O)NHN$R^{4A}R^{4B}$, substituted or unsubstituted $C_1$-$C_5$ alkyl, or substituted or unsubstituted 2 to 5 membered heteroalkyl. $R^5$ is hydrogen, halogen, —$N_3$, —$CF_3$, —$CCl_3$, —$CBr_3$, —$CI_3$, —CN, —$OR^{5A}$, —C(O)$R^{5A}$, —$NR^{5A}R^{5B}$, —C(O)$OR^{5A}$, —C(O)$NR^{5A}R^{5B}$, —$NO_2$, —$SR^{5A}$, —S(O)$_{n5}R^{5A}$, —S(O)$_{n5}OR^{5A}$, —S(O)$_{n5}NR^{5A}R^{5B}$, —NHN$R^{5A}R^{5B}$, —ON$R^{5A}R^{5B}$, —NHC(O)NHN$R^{5A}R^{5B}$, substituted or unsubstituted $C_1$-$C_5$ alkyl, or substituted or unsubstituted 2 to 5 membered heteroalkyl. $R^6$ is hydrogen, halogen, —$N_3$, —$CF_3$, —$CCl_3$, —$CBr_3$, —$CI_3$, —CN, —$OR^{6A}$, —C(O)$R^{6A}$, —$NR^{6A}R^{6B}$, —C(O)$OR^{6A}$, —C(O)$NR^{6A}R^{6B}$, —$NO_2$, —$SR^{6A}$, —S(O)$_{n6}R^{6A}$, —S(O)$_{n6}OR^{6A}$, —S(O)$NR^{6A}R^{6B}$, —NHN$R^{6A}R^{6B}$, —ON$R^{6A}R^{6B}$, —NHC(O)NHN$R^{6A}R^{6B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{2A}$, $R^{2B}$, $R^{4A}$, $R^{4B}$, $R^{5A}$, $R^{5B}$, $R^{6A}$, and $R^{6B}$ are independently hydrogen, oxo, halogen, —$CF_3$, —CN, —OH, —$NH_2$, —COOH, —$CONH_2$, —$NO_2$, —SH, —S(O)$_2$Cl, —S(O)$_3$H, —S(O)$_4$H, —S(O)$_2NH_2$, —$NHNH_2$, —$ONH_2$, —NHC(O)$NHNH_2$, —NHC(O)$NH_2$, —NHS(O)$_2$H, —NHC(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n1, n2, n4, n5, and n6 are independently 1, 2, or 3. m1 is 0, 1, 2, 3, or 4. m2 is 0, 1, 2, 3, 4, 5, or 6. m3 is 0, 1, or 2.

Embodiment 2 The compound of embodiment 1, wherein X is —C($R^4$)—.

Embodiment 3 The compound of any one of embodiments 1 to 2, wherein $R^2$ is halogen, —$CF_3$, —$OR^{2A}$, —$NO_2$, substituted or unsubstituted $C_1$-$C_5$ alkyl, or substituted or unsubstituted 2 to 5 membered heteroalkyl.

Embodiment 4 The compound of one of embodiments 1 to 3, wherein $R^2$ is $OR^{2A}$, wherein $R^{2A}$ is substituted or unsubstituted $C_1$-$C_3$ alkyl.

Embodiment 5 The compound of one of embodiments 1 to 4, wherein $R^3$ is hydrogen, halogen, or —$OR^{3A}$.

Embodiment 6 The compound of embodiment 5, wherein $R^3$ is hydrogen.

Embodiment 7 The compound of one of embodiments 1 to 6, wherein m2 is 0.

Embodiment 8 The compound of one of embodiments 1 to 7, wherein Y is a bond or —N($R^5$)—.

Embodiment 9 The compound of embodiment 8, wherein Y is a bond or —NH—.

Embodiment 10 The compound of one of embodiments 1 to 9, wherein $L^1$ is a bond, —C(O)—, —O—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 11 The compound of one of embodiments 1 to 10, wherein $R^1$ is halogen, —$CF_3$, —$NO_2$, —$NH_2$, —$OR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 12 The compound of one of embodiments 1 to 11, wherein $R^1$ is halogen, —$CF_3$, —$NO_2$, —$NH_2$, —$OR^{1A}$.

Embodiment 13 The compound of one of embodiments 1 to 12, wherein $R^1$ is —$OR^{1A}$, wherein $R^{1A}$ is substituted or unsubstituted $C_1$-$C_5$ alkyl, substituted or unsubstituted 2 to 5 membered heteroalkyl, substituted or unsubstituted 3 to 6 membered cycloalkyl, substituted or unsubstituted 3 to 6 membered heterocycloalkyl, substituted or unsubstituted 5 or 6 membered aryl, or substituted or unsubstituted 5 or 6 membered heteroaryl.

Embodiment 14 The compound of one of embodiments 1 to 13, wherein $R^1$ is $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl, wherein $R^{10}$ is hydrogen, halogen, —$N_3$, —$CF_3$, —$CCl_3$, —$CBr_3$, —$CI_3$, —CN, —C(O)H, —$OCH_3$, —$OCH_2CH_3$, —$NH_2$, —COOH, —$CONH_2$, —$NO_2$, —SH, —S(O)$_2$H, —$NHNH_2$, —ONH₂, —NHC(O)NHNH₂, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 15 The compound of one of embodiments 1 to 14, wherein m1 is 1, 2, or 3.

Embodiment 16 The compound of one of embodiments 1 to 15, wherein A is aryl or heteroaryl.

Embodiment 17 The compound of one of embodiments 1 to 16, wherein said compound has the formula:

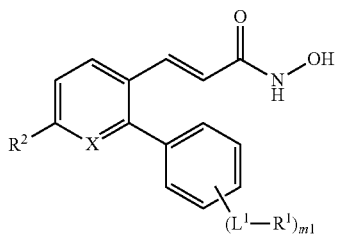

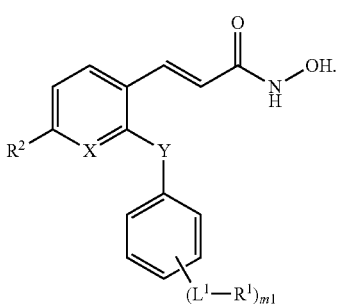

Embodiment 18 The compound of embodiment 17, wherein
$R^2$ is halogen or —$OR^{2A}$, wherein $R^{2A}$ is hydrogen or unsubstituted $C_1$-$C_5$ alkyl;
X is —$CH_2$— or —N—;
Y is —NH— or —O—;
$L^1$ is a bond;
$R^1$ is halogen, —$NO_2$, —$NH_2$, —$OR^{1A}$, wherein $R^{1A}$ is hydrogen or unsubstituted $C_1$-$C_5$ alkyl; and
m1 is 1, 2, or 3.

Embodiment 19 The compound of one of embodiments 1 to 16, wherein A is aryl, 5,6-fused ring heteroaryl, 6,5-fused ring heteroaryl, or 6,6-fused ring heteroaryl.

Embodiment 20 The compound of embodiment 19, wherein said compound has the formula:

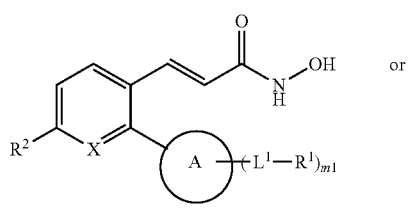 or

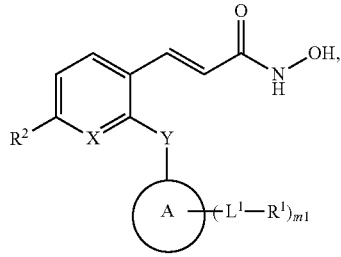

wherein A is 5,6-fused ring heteroaryl, 6,5-fused ring heteroaryl, or 6,6-fused ring heteroaryl.

Embodiment 21 The compound of embodiment 20, wherein
$R^2$ is halogen or —$OR^{2A}$, wherein $R^{2A}$ is hydrogen or unsubstituted $C_1$-$C_5$ alkyl;
X is —$CH_2$— or —N—;
Y is —NH— or —O—;
$L^1$ is a bond;
$R^1$ is halogen, —$NO_2$, —$NH_2$, —$OR^{1A}$, wherein $R^{1A}$ is hydrogen or unsubstituted $C_1$-$C_5$ alkyl; and
m1 is 1, 2, or 3.

Embodiment 22 A method of treating cancer in a subject in need thereof, said method comprising administering an effective amount of an HDAC8 inhibitor to said subject.

Embodiment 23 The method of embodiment 22, wherein said cancer is a non-mutated p53 cancer.

Embodiment 24 The method of any one of embodiments 22 to 23, wherein said non-mutated p53 cancer is acute myeloid leukemia (AML), acute lymphoblastic leukemia (ALL), lymphoma, neuroblastoma, glioma, bladder cancer, lung cancer, non-small cell lung cancer, breast cancer, or triple-negative breast cancer.

Embodiment 25 The method of any one of embodiments 22 to 24, wherein said non-mutated p53 cancer is acute myeloid leukemia (AML).

Embodiment 26 The method of any one of embodiments 22 to 25, wherein said non-mutated p53 cancer has increased HDAC8 activity or HDAC8 expression compared to a mutated p53 cancer.

Embodiment 27 The method of any one of embodiments 22 to 26, wherein said method further comprises prior to said treating, determining whether said cancer in said subject is a non-mutated p53 cancer.

Embodiment 28 The method of any one of embodiments 22 to 27, further comprising determining whether said non-mutated p53 cancer has increased HDAC8 activity or HDAC8 expression.

Embodiment 29 The method of any one of embodiments 22 to 28, wherein said HDAC8 inhibitor is a HDAC8 inhibitor compound.

Embodiment 30 The method of any one of embodiments 22 to 29, wherein said HDAC8 inhibitor is a compound described herein.

Embodiment 31 The method of any one of embodiments 22 to 28, wherein said HDAC8 inhibitor is a HDAC8 inhibitor antibody, a HDAC8 inhibitor siRNA, a HDAC8 inhibitor shRNA, or a HDAC8 inhibitor protein.

Embodiment 32 A method of inhibiting HDAC8 mediated deacetylation of p53, said method comprising contacting HDAC8 with a HDAC8 inhibitor in the presence of p53, thereby inhibiting HDAC8 deacetylation of p53.

Embodiment 33 The method of embodiment 31, wherein said contacting is performed in vitro.

Embodiment 34 The method of embodiment 31, wherein said contacting is performed in vivo.

Embodiment 35 The method of embodiment 31, wherein said contacting is performed in an organism.

Embodiment 36 The method of any one of embodiments 32 to 35, wherein said HDAC8 inhibitor is a compound described herein.

Embodiment 37 A method of activating p53 in vivo, said method comprising contacting a cell with a HDAC8 inhibitor in the presence of HDAC8 and allowing said HDAC8 inhibitor to contact said HDAC8, thereby inhibiting said HDAC8 and activating p53.

Embodiment 38 The method of embodiment 36, wherein said contacting is performed in an organism.

Embodiment 39 The method of any one of embodiments 37 to 38, wherein said HDAC8 inhibitor is a compound described herein.

What is claimed is:

1. A compound having the formula (I):

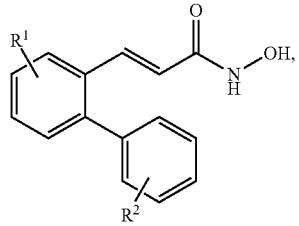

wherein:
R¹ is substituted or unsubstituted 2 to 20 membered heteroalkyl, substituted or unsubstituted $C_3$-$C_7$ cycloalkyl, substituted or unsubstituted 3 to 7 membered heterocycloalkyl, substituted or unsubstituted $C_3$-$C_7$ aryl, or substituted or unsubstituted 3 to 7 membered heteroaryl; and R² is substituted or unsubstituted $C_1$-$C_{20}$ alkyl, substituted or unsubstituted 2 to 20 membered heteroalkyl, substituted or unsubstituted $C_3$-$C_7$ cycloalkyl, substituted or unsubstituted 3 to 7 membered heterocycloalkyl, substituted or unsubstituted $C_3$-$C_7$ aryl, or substituted or unsubstituted 3 to 7 membered heteroaryl.

2. The compound of claim 1, wherein R¹ is substituted or unsubstituted $C_1$-$C_4$ alkoxy and R² is a substituted or unsubstituted $C_4$-$C_6$ aryl.

3. The compound of claim 2, wherein R¹ is unsubstituted $C_1$-$C_2$ alkoxy and R² is unsubstituted C6 aryl.

4. The compound of claim 1, wherein the compound has formula (II):

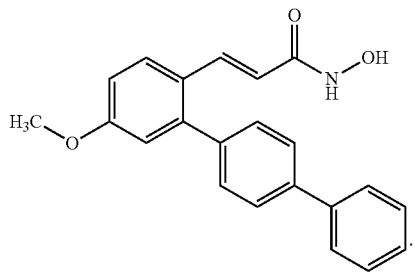

5. A compound selected from the group consisting of:

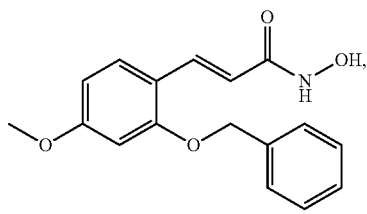

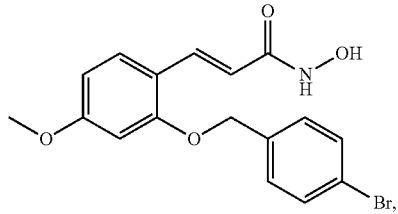

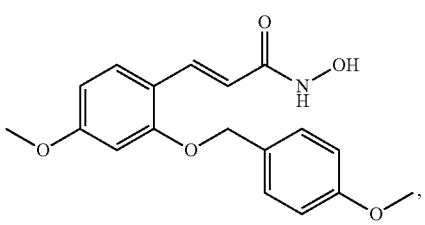

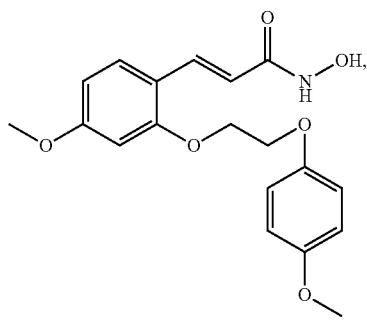

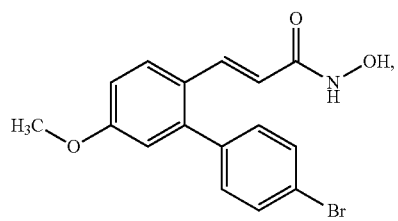

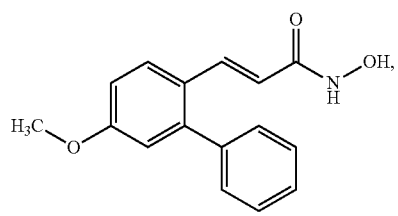

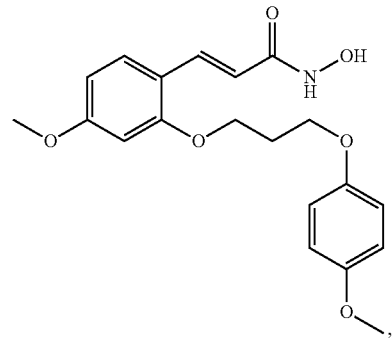

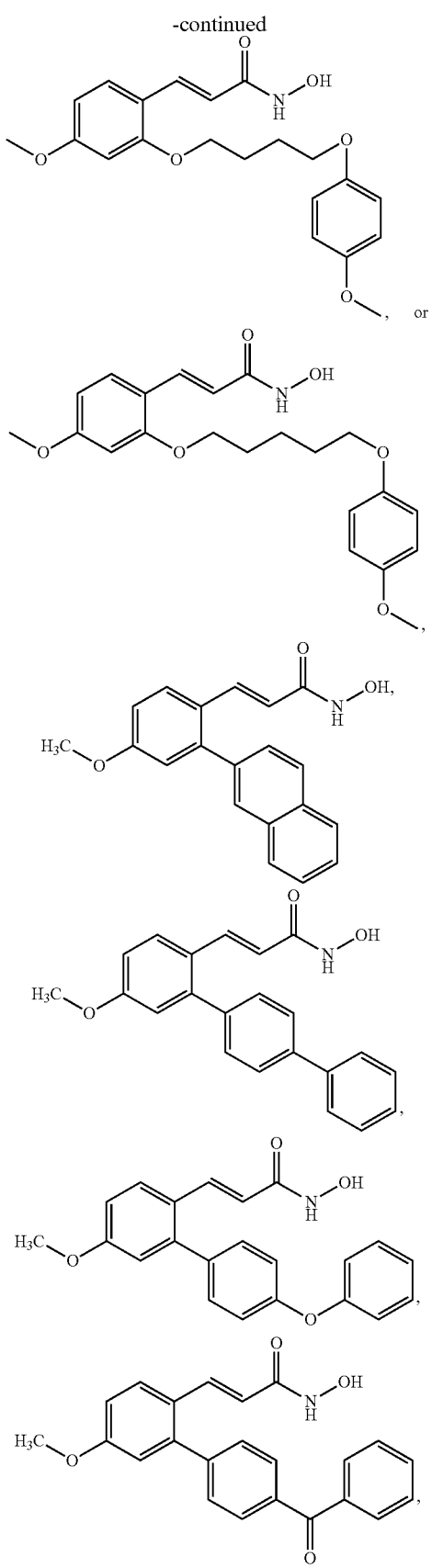

6. A method of inhibiting HDAC8 mediated deacetylation of p53, the method comprising contacting HDAC8 with the compound of claim 1 in the presence of p53, thereby inhibiting HDAC8 deacetylation of p53.

7. A method of activating p53 in vivo, the method comprising contacting a cell with the compound of claim 1 in the presence of HDAC8; wherein the cell is an AML cell.

8. The method of claim 7, wherein the AML cell is an AML stem cell.

9. The compound of claim 1, wherein:

$R^1$ is substituted or unsubstituted 2 to 20 membered heteroalkyl, substituted or unsubstituted $C_3$-$C_7$ cycloalkyl, substituted or unsubstituted 3 to 7 membered heterocycloalkyl, substituted or unsubstituted $C_6$-$C_7$ aryl, or substituted or unsubstituted 3 to 7 membered heteroaryl; and $R^2$ is substituted or unsubstituted $C_1$-$C_{20}$ alkyl, substituted or unsubstituted 2 to 20 membered heteroalkyl, substituted or unsubstituted $C_3$-$C_7$ cycloalkyl, substituted or unsubstituted 3 to 7 membered heterocycloalkyl, substituted or unsubstituted $C_6$-$C_7$ aryl, or substituted or unsubstituted 3 to 7 membered heteroaryl.

* * * * *

UNITED STATES PATENT AND TRADEMARK OFFICE
CERTIFICATE OF CORRECTION

PATENT NO.         : 10,308,596 B2
APPLICATION NO.    : 15/042012
DATED              : June 4, 2019
INVENTOR(S)        : Ya-Huei Kuo et al.

It is certified that error appears in the above-identified patent and that said Letters Patent is hereby corrected as shown below:

In the Specification

At Column 1, Line numbers 17-20, should be changed to:
-- This invention was made with Government support under grant number P30 CA033572 awarded by the National Institutes of Health. The Government has certain rights in the invention. --

Signed and Sealed this
Third Day of September, 2019

Andrei Iancu
*Director of the United States Patent and Trademark Office*